US008076370B2

(12) United States Patent
Das et al.

(10) Patent No.: US 8,076,370 B2
(45) Date of Patent: Dec. 13, 2011

(54) ANTIMICROBIAL AGENTS

(75) Inventors: Biswajit Das, Haryana (IN); Jasbir Singh Arora, Haryana (IN); Shahadat Ahmed, Haryana (IN); Anish Bandyopadhyay, Haryana (IN); Rita Katoch, Chandigarh (IN); Santosh Haribhau Kurhade, Haryana (IN); Sujata Rathy, Delhi (IN); Soma Ghosh, Punjab (IN); Abhijit Datta Khoje, Haryana (IN); Arti Gujrati, Haryana (IN); Dilip J. Upadhyay, Maharashtra (IN)

(73) Assignee: Ranbaxy Laboratories Limited, New Delhi (IN)

( * ) Notice: Subject to any disclaimer, the term of this patent is extended or adjusted under 35 U.S.C. 154(b) by 754 days.

(21) Appl. No.: 11/913,380

(22) PCT Filed: May 3, 2006

(86) PCT No.: PCT/IB2006/051397
§ 371 (c)(1),
(2), (4) Date: May 27, 2008

(87) PCT Pub. No.: WO2006/117762
PCT Pub. Date: Nov. 9, 2006

(65) Prior Publication Data
US 2009/0215764 A1 Aug. 27, 2009

(30) Foreign Application Priority Data

May 3, 2005 (IN) .......................... 1102/DEL/2005
Jul. 22, 2005 (IN) .......................... 1936/DEL/2005
Apr. 10, 2006 (IN) ............................ 978/DEL/2006

(51) Int. Cl.
*A61K 31/27* (2006.01)
*A61K 31/18* (2006.01)
*A61K 31/155* (2006.01)
*A61K 31/44* (2006.01)
*A61K 31/501* (2006.01)
*C07D 213/72* (2006.01)
*C07C 333/00* (2006.01)
*C07C 303/00* (2006.01)
*C07C 277/00* (2006.01)

(52) U.S. Cl. ........ 514/478; 514/602; 514/634; 514/352; 514/252.01; 546/304; 558/242; 564/80; 564/230

(58) Field of Classification Search ................ 514/478, 514/602, 634, 352, 252.01; 546/304; 558/242; 564/80, 230
See application file for complete search history.

(56) References Cited

U.S. PATENT DOCUMENTS

| 4,916,155 | A | 4/1990 | Baker et al. .................... 514/460 |
| 5,059,602 | A | 10/1991 | Effland et al. ................. 514/258 |
| 5,191,093 | A | 3/1993 | Baker et al. .................... 549/414 |
| 2003/0013724 | A1 | 1/2003 | Hammond et al. ....... 514/255.05 |
| 2004/0224981 | A1 | 11/2004 | Janjic et al. .................... 514/312 |

FOREIGN PATENT DOCUMENTS

| FR | 2 518 544 | 6/1983 |
| JP | 57-085346 | 5/1982 |
| WO | WO 00/18772 | 4/2000 |
| WO | WO 01/26654 | 4/2001 |
| WO | WO 2004/056816 | 7/2004 |

OTHER PUBLICATIONS

H. Bundgaard, ed., 1985. *Design of Prodrugs.* Elsevier.
Humber, "Agents Affecting Lipid Metabolism. XII. N,N' -Disubstituted Cyclohexane-1,4-bis(methylamines)," *Journal of Medicinal Chemistry*, 7(6):826-830 (1964).
Mayer et al., "New Substituted 1-(2,3-Dihydrobenzo[1,4]dioxin-2-ylmethyl)piperidin-4-yl Derivatives with $\alpha_2$-Adrenoceptor Antagonist Activity", *Journal of Medicinal Chemistry*, 43(20):3653-3664 (2000).
Bar-Haim and Kol, "Regioselective N-Alkylation of 2-Aminobenzylamine via Chelation to 9-BBN", *Tetrahedron Letters*, 39(17):2643-2644 (1998).
Phillips et al., "Synthesis and Antibacterial Activity of 5-Substituted Oxazolidinones", *Bioorganic & Medicinal Chemistry*, 11(1):35-41 (2003).

*Primary Examiner* — Shengjun Wang

(57) ABSTRACT

Provided herein are substituted aromatic compounds, which are tRNA synthetase inhibitors, and hence can be used as antimicrobial agents. Compounds described herein can be used for the treatment or prevention of a condition caused by or contributed to by gram positive, gram negative, anaerobic bacteria or fungal organisms, more particularly against bacterium, for example, *Staphylococci, Enterococci, Streptococci, Haemophilus, Moraxalla, Escherichia, Chlamydia, Mycoplasm, Legionella, Mycobacterium, Helicobacter, Clostridium, Bacteroides, Corynebacterium, Bacillus* or Enterobactericeae, and fungal organisms, for example, *Aspergillus, Blastomyces, Candida, Coccidiodes, Cryptococcus, Epidermophyton, Hendersonula, Histoplasma, Microsporum, Paecilomyces, Paracoccidiodes, Pneumocystis, Trichophyton,* or *Trichosporium.* Processes for the preparation of these compounds, pharmaceutical compositions thereof, and methods of treating microbial infections are also provided.

6 Claims, No Drawings

ANTIMICROBIAL AGENTS

FIELD OF THE INVENTION

Provided herein are substituted aromatic compounds, which are tRNA synthetase inhibitors, and hence can be used as antimicrobial agents. Compounds described herein can be used for the treatment or prevention of a condition caused by or contributed to by gram positive, gram negative, anaerobic bacteria or fungal organisms, more particularly against bacterium, for example, Staphylococci, Enterococci, Streptococci, *Haemophilus, Moraxalla, Escherichia, Chlamydia, Rickettsiae, Mycoplasm, Legionella, Mycobacterium, Helicobacter, Clostridium, Bacteroides, Corynebacterium, Bacillus* or Enterobactericeae, and fungal organisms, for example, *Aspergillus, Blastomyces, Candida, Coccidiodes, Cryptococcus, Epidermophyton, Hendersonula, Histoplasma, Microsporum, Paecilomyces, Paracoccidiodes, Pneumocystis, Trichophyton,* or *Trichosporium*. Processes for the preparation of these compounds, pharmaceutical compositions thereof, and methods of treating microbial infections are also provided.

BACKGROUND OF THE INVENTION

Antibiotics are of immense value for combating infectious diseases. In recent decades, the effectiveness of antibiotics has been threatened by an inexorable rise in the prevalence of microbial drug resistance. Some important pathogens have serious resistance problems. *Staphylococcus aureus* is perhaps the most significant of these pathogens. It causes community and hospital acquired infections and is associated with high morbidity and mortality rates. Vancomycin has been used as the antibiotic of last resort to treat methicillin-resistance *staphylococcus aureus* infections (MRSA) with multiple resistance. Strains with some level of resistance to vancomycin (Vancomycin-intermediates-resistant *S. aureus*, VISA) have been known since 1996, but the newly identified highly resistant strain (VRSA) heralds a new stage in the battle with this pathogen. Other serious treatment problems include multidrug resistance in tuberculosis, vancomycin resistant enterococci (VRE), resistance owing to extended spectrum β-lactamases (ESBLs) in Enterobacteriaceae and *Pseudomonas aeruginosa*, and penicillin resistance in *Streptococcus pneumoniae*.

A nation wide epidemic of multi drug resistant *Salmonella typhi* occurred in 1990 and has not yet fully subsided. Antimicrobial resistance among respiratory pathogens has become a common clinical problem, currently over 90% of *Morexella catarrhalis* and 25% of *Haemophilus influenzae* produce β lactamases, requiring treatment with a β lactamase stable cephalosporin or combination drugs. In the last several years, there has been a rapid increase in the number of strains resistant to penicillin, cephalosporins, macrolides and fluoroquinolones.

These circumstances have prompted efforts to develop new antibiotics that overcome the emerging antibiotic resistance bacteria. The amino acyl tRNA synthetases are essential enzymes found in all living organisms. These enzymes have emerged as an attractive target for the development of new antibiotics. Amino acyl tRNA synthetases charge tRNA molecules with their corresponding amino acid, an essential step in protein synthesis. There are 20 tRNA synthetases, most of which correspond to attractive broad-spectrum antibacterial targets. This is a validated target class in that pseudomonic acid A, also known as mupirocin, a natural product from *Pseudominas fluorescens*, inhibits isoleucyl tRNA synthase and is marketed as a topical antibiotic Bactropan. Other known natural products directed against amino acyl tRNA synthetases include borrelidin, furanomycin, granaticin, indolmycin, ochartoxin A, and cispentacin, none of them has been developed as antibiotic compounds.

U.S. Patent Application Nos. 2004/0224981 and 2003/0013724 disclose tRNA synthetase inhibitors. WO 00/18772 discloses condensed imidazolidinone as tRNA synthetase inhibitors. U.S. Pat. Nos. 5,191,093 and 4,916,155 disclose crystalline pseudomonate, processes for its production and its use in human and veterinary medicines. U.S. Pat. No. 4,916,155 discloses crystalline calcium pseudomonate or the hydrate thereof, and their use in human and veterinary medicine.

Novel synthetic compounds, which target tRNA synthetases, offer clear advantages as useful therapeutic agents to curb the threat of drug resistance.

SUMMARY OF THE INVENTION

Accordingly, this invention provides substituted aromatic compounds, which are tRNA synthetase inhibitors, and hence can be used for the treatment of microbial infections, and processes for the synthesis of these compounds. Pharmaceutically acceptable salts, pharmaceutically acceptable solvates, stereoisomers, prodrugs, metabolites, polymorphs and N-oxides of these compounds having same type of activity are also provided. Pharmaceutical compositions containing the described compounds (Formula I) together with pharmaceutically acceptable carriers, excipients or diluents, which can be used for the treatment of microbial infections. Other aspects will be set forth in the accompanying description which follows and in part will be apparent from the description or may be learnt by the practice of the invention.

In one aspect, provided herein are compounds having the structure of Formula I,

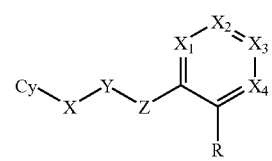

Formula I pharmaceutically acceptable salts, pharmaceutically acceptable solvates, stereoisomers, prodrugs, metabolites, polymorphs, or N-oxide thereof, wherein:
Cy can be cycloalkyl or heterocyclyl;
X and Z can be alkylene;
Y can be $NR_1$ (wherein $R_1$ can be hydrogen, alkyl or OCOalkyl);
$X_1$, $X_2$, $X_3$ and $X_4$ can be CH or N; and
R can be $OR_2$, $OCONHR_2$, $OCONHSO_2R_2$, $SR_3$ or $NR_4R_5$ {wherein $R_2$ can be aryl or heteroaryl, $R_3$ can be hydrogen, alkyl, cycloalkyl, heterocyclyl, heteroaryl or aryl, $R_4$ and $R_5$ can be independently hydrogen, $SO_2R_6$, $COR_6$, $CSR_6$, or $COOR_6$ [wherein $R_6$ can be alkyl, aryl, heteroaryl, heterocyclyl, aralkyl, heteroarylalkyl, heterocycloalkyl, $OR_7$, $NHR_7$, $NHSO_2R_7$, $NHCOR_7$, $NHCSR_7$ or $NH_2C\!=\!NHSO_2R_7$ (wherein $R_7$ can be alkyl, aryl, heteroaryl or heterocyclyl)] or $R_4$ and $R_5$ can, together with the nitrogen to which they are attached, form a heterocyclic ring}.

The compounds can include one or more of the following embodiments. For example, the compounds can be:

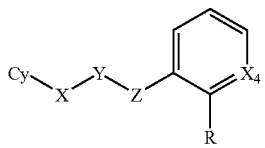

Formula Ia pharmaceutically acceptable salts, pharmaceutically acceptable solvates, stereoisomers, prodrugs, metabolites, polymorphs or N-oxide thereof, wherein:

Cy can be cyclopentyl or cyclohexyl;
X can be $CH_2C(CH_3)$ or $CH(OH)C(CH_3)$;
Z can be $CH_2$;
Y can be NH or $NSO_2CH_3$;
$X_4$ can be CH or N; and
R can be $NR_4R_5$ [wherein $R_4$ and $R_5$ can be independently hydrogen, $SO_2R_6$, $COR_6$, $CONHR_6$, $CONHSO_2R_6$ or $COOCH_2R_6$ (wherein $R_6$ can be $N(CH_3)_2$, $NH_2$, $CH=CHCOOC_2H_5$, $(CH_2)_3COOC_2H_5$, phenyl, 1,2,3,4-tetrahydroisoquinolinyl, 2,2,2-trifluoroacetyl-1-(3,4-dihydro-1H-isoquinolin-2-yl), morpholinyl or heteroaryl)].

In another example, the compounds can be:

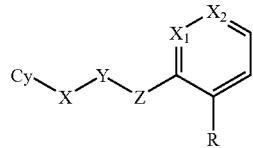

Formula Ib pharmaceutically acceptable salts, pharmaceutically acceptable solvates, stereoisomers, prodrugs, metabolites, polymorphs, or N-oxides thereof, wherein:

Cy can be cyclohexyl or cyclopentyl;
X can be $—CH_2CH(CH_3)—$, $—CH(F)CH(CH_3)—$, $—CH(OH)CH(CH_3)—$ or $—CH_2CH(F)CH_2—$;
Y can be NH;
Z can be $—CH_2—$;
$X_1$ and $X_2$ can be CH or N; and
R can be $NHC(NH)NH_2$, $NHCOOCH_2R_6$ or $NHSO_2R_6$ (wherein $R_6$ can be aryl, heteroaryl or heterocyclyl).

In another aspect, provided herein are methods for treating or preventing a condition caused by or contributed to by Gram-positive, Gram-negative, anaerobic bacteria or fungal organisms, comprising administering to the subject in need thereof therapeutically effective amounts of one or more compounds or pharmaceutical composition described herein.

Bacterium, for example, Staphylococci, Enterococci, Streptococci, *Haemophilus, Moraxalla, Escherichia, Chlamydia, Rickettsiae, Mycoplasm, Legionella, Mycobacterium, Helicobacter, Clostridium, Bacteroides, Propionibacterium* acnes, *Corynebacterium, Bacillus* or Enterobactericeae may cause the bacterial infections.

Organisms, for example, *Aspergillus, Blastomyces, Candida, Coccidiodes, Cryptococcus, Epidermophyton, Hendersonula, Histoplasma, Microsporum, Paecilomyces, Paracoccidiodes, Pneumocystis, Trichophyton,* or *Trichosporium,* Enterobactericeae may cause the fungal infections.

The conditions may be, for example, community acquired pneumonia, upper and lower respiratory tract infections, skin and soft tissue infections, hospital-acquired lung infections or bone and joint infections, and other bacterial infections, for example, mastitis, catheter infection, foreign body, acne vulgaris, prosthesis infections or peptic ulcer disease.

In another aspect, provided herein are processes for the preparation of compounds as described herein.

In yet another aspect, provided herein are methods for treating or preventing a condition caused by or contributed to by gram positive, gram negative, anaerobic bacteria or fungal organisms, comprising administering to the subject in need thereof therapeutically effective amounts of one or more compounds or pharmaceutical composition described herein in combination with one or more aminoacyl tRNA synthetase (i.e., mupirocin) inhibitors, antibacterial agents or mixture thereof.

The following definitions apply to terms as used herein:

The term "alkyl," unless otherwise specified, refers to a monoradical branched or unbranched saturated hydrocarbon chain having from 1 to 20 carbon atoms. This term can be exemplified by groups such as methyl, ethyl, n-propyl, isopropyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, aryl, heterocyclyl, heteroaryl, arylthio, thiol, alkylthio, aryloxy, nitro, aminosulfonyl, aminocarbonylamino, $—NHC(=O)R_f$, $NR_fR_q$, $—C(=O)NR_fR_q$, $—NHC(=O)NR_fR_q$, $—C(=O)$heteroaryl, $C(=O)$heterocyclyl, $—O—C(=O)NR_fR_q$ {wherein $R_f$ and $R_q$ are independently selected from alkyl, alkenyl, cycloalkyl, cycloalkenyl, aryl, aralkyl, heterocyclyl, heteroaryl, heterocyclylalkyl, heteroarylalkyl}, nitro, or $—SO_2R_6$ (wherein $R_6$ is alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, carboxy, $—NR_fR_q$, $—C(=O)NR_fR_q$, $—OC(=O)NR_fR_q$, $—NHC(=O)NR_fR_q$ (wherein $R_f$ and $R_q$ are the same as defined earlier), hydroxy, alkoxy, halogen, $CF_3$, cyano, and $—SO_2R_6$, (wherein $R_6$ are the same as defined earlier); or an alkyl group also may be interrupted by 1-5 atoms of groups independently selected from oxygen, sulfur or $—NR_a—$ {wherein $R_a$ is selected from hydrogen, alkyl, cycloalkyl, alkenyl, cycloalkenyl, alkynyl, aryl, acyl, aralkyl, $—C(=O)OR_f$ (wherein $R_f$ is the same as defined earlier), $SO_2R_6$ (where $R_6$ is as defined earlier), or $—C(=O)NR_fR_q$ (wherein $R_f$ and $R_q$ are as defined earlier)}. Unless otherwise constrained by the definition, all substituents may be substituted further by 1-3 substituents selected from alkyl, carboxy, $—NR_fR_q$, $—C(=O)NR_fR_q$, $—O—C(=O)NR_fR_q$ (wherein $R_f$ and $R_q$ are the same as defined earlier) hydroxy, alkoxy, halogen, $CF_3$, cyano, and $—SO_2R_6$ (where $R_6$ is same as defined earlier); or an alkyl group as defined above that has both substituents as defined above and is also interrupted by 1-5 atoms or groups as defined above.

The term "alkylene" herein refers to $—(CH)_n—$ wherein n can be an integer of from 0 to 4 and one or more hydrogen can optionally be substituted with alkyl, hydroxy, halogen or oximes. Alkylene can also be optionally interrupted by $—CONH—$, $—C=O$ or $—C=NOH$.

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like, or multiple ring structures, including adamantanyl, and bicyclo[2.2.1]heptane, or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —$NR_fR_q$, —NHC(=O)$NR_fR_q$, —NHC(=O)$R_f$, —C(=O)$NR_fR_q$, —O—C(=O)$NR_fR_q$ (wherein $R_f$ and $R_q$ are the same as defined earlier), nitro, heterocyclyl, heteroaryl, heterocyclylalkyl, heteroarylalkyl, or $SO_2$—$R_6$ (wherein $R_6$ is same as defined earlier). Unless otherwise constrained by the definition, cycloalkyl substituents optionally may be substituted further by 1-3 substituents selected from alkyl, carboxy, hydroxy, alkoxy, halogen, $CF_3$, —$NR_fR_q$, —C(=O)$NR_fR_q$, —NHC(=O)$NR_fR_q$, —OC(=O)$NR_fR_q$ (wherein $R_f$ and $R_q$ are the same as defined earlier), cyano or —$SO_2R_6$ (where $R_6$ is same as defined earlier). "Cycloalkylalkyl" refers to alkyl-cycloalkyl group linked through alkyl portion, wherein the alkyl and cycloalkyl are the same as defined earlier.

The term "aryl," unless otherwise specified, refers to carbocyclic aromatic groups, for example, phenyl, biphenyl or napthyl ring and the like, optionally substituted with 1 to 3 substituents selected from halogen (e.g., F, Cl, Br, I), hydroxy, thiol, alkyl, alkenyl, alkynyl, cycloalkyl, alkoxy, acyl, aryloxy, $CF_3$, cyano, nitro, $COOR_e$ (wherein $R_e$ is hydrogen, alkyl, alkenyl, cycloalkyl, aralkyl, heterocyclylalkyl, heteroarylalkyl), NHC(=O)$R_f$, —$NR_fR_q$, —C(=O)$NR_fR_q$, —NHC(=O)$NR_fR_q$, —O—C(=O)$NR_fR_q$ (wherein $R_f$ and $R_q$ are the same as defined earlier), —$SO_2R_6$ (wherein $R_6$ is same as defined earlier), carboxy, heterocyclyl, heteroaryl, heterocyclylalkyl, heteroarylalkyl or amino carbonyl amino. The aryl group optionally may be fused with a cycloalkyl group, wherein the cycloalkyl group may optionally contain heteroatoms selected from O, N or S. The aryl group can also be substituted with substituents selected from Cl, Br, $NH_2$, $OCH_3$, $CONH_2$, $NHCOCH_3$, $CH(OH)CH_3$, $C(CH_3)$=NOH, $C(CH_3)$=$NOCH_3$, NH—N(=NH)$NH_2$, oxazolyl, pyrrolyl, pyrazolyl, pyridinyl, morpholinyl, pyrimidinyl, triazinyl, N-methyl-pyrazolyl, 2-oxo-oxazolidinyl, isoindolyl-1,3-dione, thiadiazolyl, pyrrolyl-3-carbaldehyde oxime, pyrrolyl-3-carbaldehyde, $NHSO_2R_z$ or $NHCOR_6$ [(wherein $R_5$ can be selected from $C_1$-$C_4$ alkyl, thienyl, 3,5-dimethyl-isooxazolyl, N-methyl-imidazolyl, p-acetylphenyl, 2,4-dimethyl-thiazolyl, 5-chloro-1,3-dimethyl-pyrazolyl, 2,5-dimethyl-furan-3-carboxylic acid methyl ester, 3-methyl-thiophene-2-carboxylic acid methyl ester, furan-2-carboxylic acid methyl ester, 1-(3,4-dihydro-1H-isoquinolin-2-yl)-2,2,2-trifluoroethanone, indole-2-yl-carbamic acid methyl ester or phenylcarbaldehyde oxime), $R_6$ can be methyl, $(CH_2)_3COOC_2H_5$, $NHC(CH_3)_2$ or isoxazolyl)], F, OH, $NHSO_2CH_3$, NHC(O)$OCH_3$, 5-oxo-1,5-dihydro-4H-1,2,4-triazol-4-yl; 5-methyl-1,3,4-oxadiazol-2-yl; 1-methyl-1H-pyrazol-4-yl; 3,5-dimethylisoxazol-4-yl; 1H-pyrrol-1-yl; thiophene-3-sulfonamido; 1H-tetrazol-1-yl; 1H-pyrrol-1-yl; 1,3-oxazol-5-yl; 1H-1,2,4-triazol-1-yl; 1H-1,2,3-triazol-1-yl; 1-methyl-1H-imidazole-4-sulfonamido; 1,2,3-thiadiazol-4-yl; 2-methyl-2H-tetrazol-5-yl; 5-methyl-1,3,4-oxadiazol-2-yl; 2-methyl-1,3-thiazol-4-yl; thiophene-2-sulfonamido; 2-oxo-1,3-oxazolidin-3-yl; 1,2,4-oxadiazol-3-yl; 1H-pyrazol-1-yl or [(alkyl or dialkylamino)sulfonyl]amino.

The term "heteroaryl," unless otherwise specified, refers to an aromatic ring structure containing 5 or 6 ring atoms, or a bicyclic aromatic group having from 8 to 10 ring atoms, with one or more heteroatom(s) independently selected from N, O or S optionally substituted with 1 to 4 substituent(s) selected from halogen (e.g., F, Cl, Br, I), hydroxy, thiol, alkyl, alkenyl, alkynyl, cycloalkyl, acyl, carboxy, aryl, alkoxy, aralkyl, cyano, nitro, heterocyclyl, heteroaryl, —$NR_fR_q$, CH=NOH, —$(CH_2)_wC(=O)R_g$ {wherein w is an integer from 0-4 and $R_g$ is hydrogen, hydroxy, $OR_f$, $NR_fR_q$, —$NHOR_z$ or —NHOH}, —C(=O)$NR_fR_q$ and —NHC(=O)$NR_fR_q$, —$SO_2R_6$, —OC(=O)$NR_fR_q$, —O—C(=O)$R_f$, —O—C(=O)$OR_f$ (wherein $R_6$, $R_f$ and $R_q$ are as defined earlier, and $R_z$ is alkyl, cycloalkyl, aryl, heteroaryl, heterocyclyl, heteroarylalkyl or heterocyclylalkyl). Heteroaryl can also be substituted with substituents selected from Cl, $CH_3$, $OCH_3$, $NHCOCH_3$, $NHCOOCH_3$, $C_6H_4COOC_2H_5$, $SO_2$thienyl, furanyl, phenyl, thienyl, trimethoxyphenyl, pyrazinyl or isoxazolyl. Unless otherwise constrained by the definition, the substituents are attached to a ring atom, i.e., carbon or heteroatom in the ring. Examples of heteroaryl groups include oxazolyl, imidazolyl, pyrazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzothiazolyl, or benzoxazolyl, isoquinolinyl, benzoisoxazolyl, benzothienyl, pyrazolyl-3-one, and the like. The term "heteroaryl" also include 5-bromo-1,3-thiazole-2-yl; 2-amino-pyrimidine-5-yl; 1-benzofuran-2-yl; 1-benzothiophene-2-yl; 5-methyl-1H-benzimidazole-2-yl; 5-fluoro-3-methyl-1-benzothiophene-2-yl; 5-chloro-1,3-benzothiazole-2-yl; 2-amino-H-benzimidazole-5-yl; 2-amino-1,3-benzothiazole-4-yl; 2-amino-1,3-benzothiazole-6-yl; 1,3-benzothiazol-2-acetamide-6-yl; 5-chloro-2,1,3-benzoxadiazole-4-yl; 2,1,3-benzothiadiazole-5-yl; 2-(dimethylamino)-1,3-benzothiazole-6-yl; 1,3-benzothiazol-2-L-alaninamide-6-yl; optionally substituted thiophene (wherein substituents are selected from 3,5-dimethylisoxazol-4-yl or isoxazol-5-yl); pyridine substituted with 1H-1,2,4-triazol-1-yl; 1H-pyrrol-1-yl; 2-furyl; 3-furyl; 1H-tetrazol-1-yl; 2-thienyl; 1H-imidazol-1yl; pyrrolidine-1-yl; morpholine-N-yl; Br; NH2; NHC(NH)$NH_2$ or $NHSO_2R_x$ (wherein $R_x$ is methyl, 2-thiophenyl or N-methylimidazolyl).

The term "heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, thiol, alkyl, alkenyl, alkynyl, cycloalkyl, acyl, aryl, alkoxy, alkaryl, cyano, nitro, oxo, carboxy, heterocyclyl, heteroaryl, —O—C(=O)$R_f$, —O—C(=O)$OR_f$, —C(=O)$NR_fR_q$, $SO_2R_6$, —O—C(=O)$NR_fR_q$, —NHC(=O)$NR_fR_q$, —$NR_fR_q$ (wherein $R_6$, $R_f$ and $R_q$ are as defined earlier) or guanidine. Heterocyclyl can optionally include rings having one or more double bonds. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include oxazolidinyl, tetrahydrofuranyl, dihydrofuranyl, dihydropyridinyl, dihydroisoxazolyl, dihydrobenzofuryl, azabicyclohexyl, dihydroindolyl, pyridinyl, isoindole 1,3-dione, piperidinyl or piperazinyl. The term "heterocyclyl" also includes 2-(trifluoroacetyl)-1,2,3,4-tetrahydroisoquinoline-7-yl; 1,2,3,4-tetrahydroisoquinoline-7-yl; 1-(trifluoroacetyl)indoline-5-yl; indoline-5-yl; 4-oxo-3,4-dihydroquinazoline-2-yl; 2-oxo-1,2-dihydroquinoline-6-yl; 1-methyl-2-oxo-1,2-dihydroquinoline-6-yl; 1-ethyl-2-oxo-1,2-dihydroquinoline-6-yl or 2-oxo-2,3-dihydro-1,3-benzoxazole-6-yl.

The groups "aryl, heteroaryl and heterocyclyl" can optionally be substituted with substituent(s) selected from alkyl, haloalkyl, cycloalkyl, aryl, heterocyclyl, heteroaryl, aralkyl, heteroarylalkyl, heterocycloalkyl, halogen, hydroxy, alkoxy, cyano, nitro, aryloxy, haloalkoxy, $COR_b$, $CSR_b$, $COOR_b$, $S(O)_aR_b$, $OCOOR_b$, $NHSO_2R_b$, $NHCOR_b$, $NHCSR_b$, $(CH)_{0-2}C(\!=\!O)NR_cR_d$ or $NR_cR_d$ (wherein $R_b$, $R_c$ and $R_d$ are independently selected from hydrogen, alkyl, aryl, heteroaryl, heterocyclyl and a is an integer of from 0-2. Unless otherwise constrained, all substituents may optionally be further substituted by substituent(s) defined earlier.

The term "antibacterial agents" as used herein refers to agent, which destroys bacteria or inhibits their growth, for example, penicillins, cephalosporins, aminoglycosides, tetracyclines, macrolides, lincosamides, streptogramins, fluoroquinolones, polypeptides, rifampicin, cycloserine, aminocyclitols, glycopeptides or oxazolidinones. Aminoacyl tRNA synthetase inhibitors and the antibacterial agents may be widely chosen from among those known in the prior art or subsequently discovered and/or hereafter discovered and/or hereafter developed.

The term "pharmaceutically acceptable solvates" refers to solvates with either water (e.g., hydrates, hemihydrate or sesquihydrate), or pharmaceutically acceptable solvents, for example solvates with common organic solvents as ethanol and the like. Such solvates are also encompassed within the scope of the disclosure.

The present invention also includes within its scope prodrugs of these agents. In general, such prodrugs will be functional derivatives of these compounds, which are readily convertible in vivo into the required compound. Conventional procedure for the selection and preparation of suitable prodrug derivatives are described, for example, in "Design of Prodrugs", ed. H Bundgaard and, Elsevier, 1985. As used herein the term "prodrugs" refers to the compounds that are rapidly transformed in vivo to yield the parent compound of Formula I, for example by hydrolysis in blood.

The described compounds may get metabolized in vivo and these metabolites are also encompassed within the scope of this invention.

The term "polymorphs" includes all crystalline form as well as amorphous forms for compounds described herein and as such are included in the present invention.

The phrase "pharmaceutically acceptable carriers" is intended to include non-toxic, inert solid, semi-solid or liquid filler, diluent, encapsulating material or formulation auxiliary of any type.

The term "pharmaceutically acceptable salts" refer to a salt prepared from pharmaceutically acceptable monovalent, divalent or trivalent non-toxic metal or organic base. Examples of such metal salts include, but are not limited to, lithium, sodium, potassium, calcium, magnesium, zinc, aluminum and the like. Examples of such organic bases include, but are not limited to, amino acid, ammonia, mono-alkyl ammonium, dialkyl ammonium, trialkyl ammonium and N-methyl glucamine and the like. The free acid forms of compounds of the present invention may be prepared from the salt forms, if desired, by contacting the salt with dilute aqueous solution of an acid, such as hydrochloric acid. The base addition salts may differ from the free acid forms of the compounds of this invention in such physical characteristics as solubility and melting point.

The term "pharmaceutically acceptable salts" can further refer to salts prepared from pharmaceutically acceptable non-toxic inorganic or organic acids. Examples of such inorganic acids include, but are not limited to, hydrochloric, hydrobromic, hydroiodic, nitrous, nitric, carbonic, sulfuric, phosphoric acid, and the like. Appropriate organic acids include, but are not limited to aliphatic, cycloaliphatic, aromatic, heterocyclic, carboxylic and sulfonic classes of organic acids, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic, methanesulfonic, ethanesulfonic, benzenesulfonic, panthenic, toluenesulfonic, 2-hydroxyethanesulfonic acid and the like.

The compounds of present invention include stereoisomers. The term "stereoisomer" refers to compounds, which have identical chemical composition, but differ with regard to arrangement of the atoms and the groups in space. These include enantiomers, diastereomers, geometrical isomers, atropisomer and conformational isomers as defined by the IUPAC 1974 Recommendations for Section E. All these stereoisomers are included within the scope of this invention.

The term "subject" as used herein refers to human or lower mammal.

The term "treatment", as used herein, unless otherwise indicated, includes the treatment or prevention of a bacterial or fungal infection as provided in the method of the present invention The term "pharmaceutically acceptable" means approved by regulatory agency of the federal or a state government or listed in the U.S. Pharmacopoeia or other generally recognized pharmacopoeia for use in animals, and more particularly in humans.

DETAILED DESCRIPTION OF THE INVENTION

The compounds described herein may be prepared by techniques well known in the art and familiar to the average synthetic organic chemist. In addition, the compounds of the present invention may be prepared by the following reaction sequences as depicted in Schemes I, Ia-Ie, Ia', II, IIa-IIe, III, IV, V, VI, VIa, VIb, VII, VIII, VIIIa, IX, X and XI.

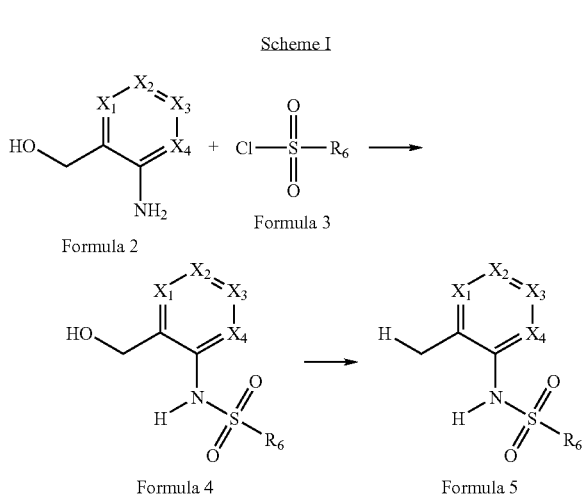

The sulfonamide of Formula 5 can be prepared according to, for example, Scheme I. Thus, a compound of Formula 2 can be reacted with a compound of Formula 3 to give a compound of Formula 4, which on oxidation can give sulfonamides of Formula 5 (wherein $X_1$-$X_4$ and $R_6$ are the same as defined earlier).

The reaction of a compound of Formula 2 with a compound of Formula 3 can be carried out in presence of one or more organic bases, for example, pyridine, triethylamine, trimethylamine, tributylamine or 4-N-dimethylaminopyridine. The oxidation of a compound of Formula 4 can be carried out in the presence of one or more oxidizing agents, for example, Dess-Martin periodinane, 2-iodoxybenzoic acid, N-chloro succinimide, pyridinium chlorochromate, Swern Oxidation reagent (oxalyl chloride and dimethylsulfoxide), Pfitzner-Moffatt Oxidation reagent (dicyclohexylcarbodiimide and dimethylsulfoxide), Jones Oxidation reagent (chromic acid, aqueous sulfuric acid and acetone), pyridinium dichromate, 1-ethyl-3-(3-dimethylaminopropyl) carbodiimide hydrochloride or in mixtures thereof, in one or more solvents, for example, chlorinated solvents (e.g., chloroform, dichloromethane, carbon tetrachloride or dichloroethane), polar aprotic solvents (e.g., dimethylsulfoxide, dimethylformamide, acetone, tetrahydrofuran or acetonitrile) or mixtures thereof. N-Chlorosuccinamide can be used in combination with dimethyl sulphide and 1-ethyl-3(3-dimethylaminopropyl) carbodiimide hydrochloride can be used in combination with dimethylsulfoxide.

Scheme Ia

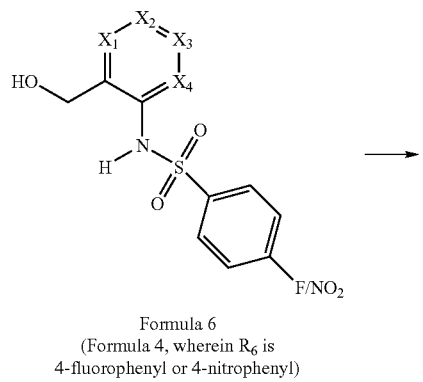

Formula 6
(Formula 4, wherein $R_6$ is
4-fluorophenyl or 4-nitrophenyl)

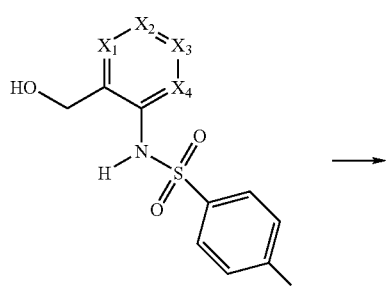

Formula 7

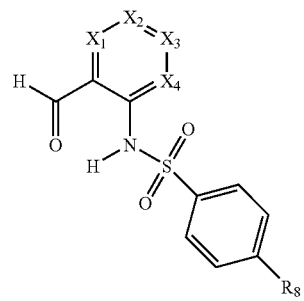

Formula 8

(Formula 5, wherein $R_6$ is 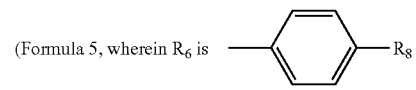 )

The compound of Formula 8 can be prepared according to, for example, Scheme Ia. Thus, (a) the compound of Formula 6 (when $R_6$ is 4-fluorophenyl) can be reacted with compounds of Formula $R_8H$ to give compounds of Formula 7, which on oxidation can give compound of Formula 8 (wherein $R_8$ is optionally substituted aryl, heteroaryl or heterocyclyl).

(b) the compound of Formula 6 (when $R_6$ is 4-nitrophenyl) reacted with a reducing agent can give the corresponding amine, which on reaction with a compound of Formula 2,5-dimethoxytetrahydrofuran or 2,5-dimethoxy-3-formyltetrahydrofuran can give a compound of Formula 7, which can be oxidized to give a compound of Formula 8 (wherein $R_8$ is 5-membered nitrogen containing heteroaryl).

The reaction of a compound of Formula 6 (wherein $R_6$ is 4-fluorophenyl) with a compound of Formula $R_8H$ can be carried out in the presence of one or more inorganic bases, for example, potassium carbonate, sodium carbonate, sodium hydrogen carbonate, sodium acetate or cesium carbonate, in one or more polar aprotic solvents, for example, N-methyl-2-pyrrolidinone, dimethylformamide or dimethylsulfoxide. The reduction of a compound of Formula 6 (when $R_6$ is 4-nitrophenyl) to give an amine compound can be carried out in the presence of one or more reducing agents, for example, Raney Nickel in hydrazine hydrate, zinc, tin or iron in the presence of hydrochloric acid or lithium aluminium hydride. The amine compound thus formed can be converted to a compound of Formula 7 by reaction with 2,5-dimethoxytetrahydrofuran in one or more polar protic solvents, for example, water, methanol, ethanol or acetic acid. The oxidation of a compound of Formula 7 to give a compound of Formula 8 can be carried out using the procedures described in, for example, Scheme I.

Scheme Ia'

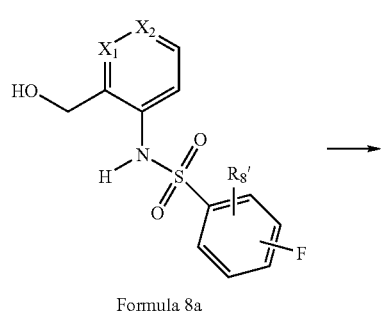

Formula 8a

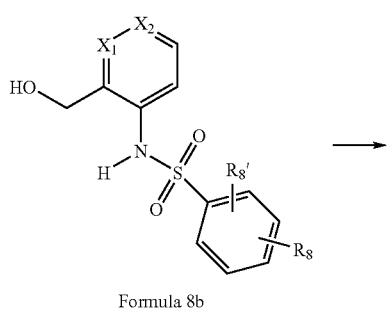

Formula 8b

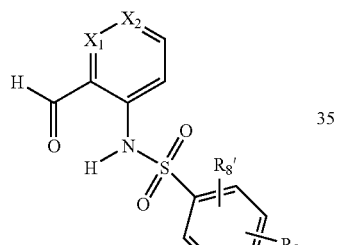

Formula 8c

The compound of Formula 8c (wherein $X_1$ and $X_2$ are the same as defined earlier; $R_8'$ is H or F; $R_8$ is 5-membered heteroaryl or 5-membered heterocyclyl) can be prepared, for example, according to Scheme Ia' following the procedure described in, for example, Scheme Ia.

Scheme Ib

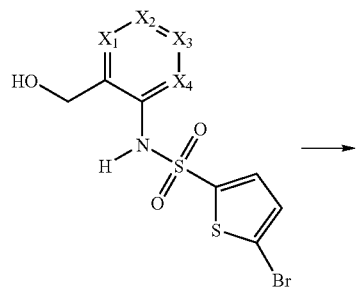

Formula 9
(Formula 4, wherein R6 is 5-bromothiopene)

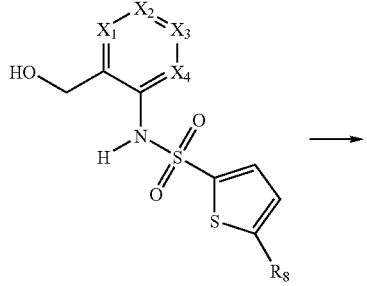

Formula 9a

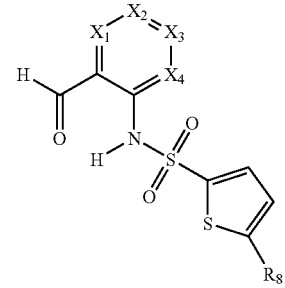

Formula 10

(Formula 5, wherein $R_6$ is 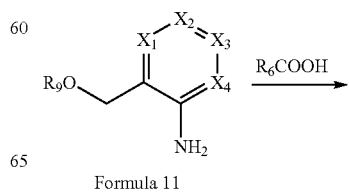)

The compound of Formula 10 can be prepared according to, for example, Scheme Ib. Thus, reaction of a compound of Formula 9 with a compound of Formula $R_8B(OH)_2$ can give a compound of Formula 9a, which on oxidation can give a compound of Formula 10 (wherein $R_8$ is H, optionally substituted aryl, heteroaryl or heterocyclyl and $X_1$-$X_4$ are the same as defined earlier).

The reaction of a compound of Formula 9 with a compound of Formula $R_8B(OH)_2$ can be carried out in one or more polar protic solvents, for example, methanol, ethanol, propanol, isopropanol, t-butanol or water. The reaction of a compound of Formula 9 can also be carried out in the presence of copper (I) iodide, palladium catalyst, for example, palladium (II) acetate, palladium (II) trifluoroacetate, palladium (II) propionate, tetra kis(triphenylphosphine) palladium (0), tris (dibenzylidineacetone) palladium (0) or bis(triphenylphosphine) palladium (II) chloride in the presence of one or more inorganic bases, for example, potassium carbonate, sodium carbonate, sodium hydrogen carbonate, sodium acetate or cesium carbonate. The oxidation of a compound of Formula 9a to give a compound of Formula 10 can be carried out using the procedures described in, for example, Scheme I.

Scheme Ic

R9O — [ring with $X_1, X_2, X_3, X_4$] — NH₂  →  $R_6COOH$

Formula 11

-continued

Formula 12

Formula 13  Formula 14

The compound of Formula 14 can be prepared, for example, according to Scheme Ic. Thus, reacting a compound of Formula 11 with a compound of Formula $R_6COOH$ to give a compound of Formula 12 (wherein $R_9$ is a protecting group, for example, tert-butyldimethylsilyl, trimethylsilyl, 4-benzyloxybutyryl, 1,4-diazabicyclo[2.2.1]octane, tertiary butoxycarbonyl or tert-butyldiphenylsilyl), which on deprotection can give a compound of Formula 13, which can be oxidized to give a compound of Formula 14 (wherein $X_1$-$X_4$ and $R_6$ are the same as defined earlier).

The reaction of a compound of Formula 11 with a compound of Formula $R_6COOH$ can be carried out in the presence of one or coupling agents, for example, 1-hydroxybenzotriazole, 1-(3-dimethylaminopropyl)-3-ethyl carbodiimide hydrochloride, N,N'-dicyclohexylcarbodiimodazole or N,N'-carbonyldiimidazole in one or more aprotic solvents, for example, N-methyl-2-pyrrolidinone, dimethylformamide or dimethylformamide. The deprotection of a compound of Formula 12 to give a compound of Formula 13 can be carried out in the presence of tetra-n-butylammonium fluoride in one or more solvents, for example, ethers (e.g., tetrahydrofuran, dioxane or ether) or aprotic solvents (e.g., dimethylsulfoxide, dimethylformamide), ketones (acetone or ethylmethyl ketone) or mixture thereof. The oxidation of a compound of Formula 13 to give a compound of Formula 14 can be carried out using the procedures described, for example, in Scheme I.

Scheme Id

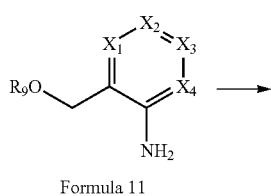

Formula 11

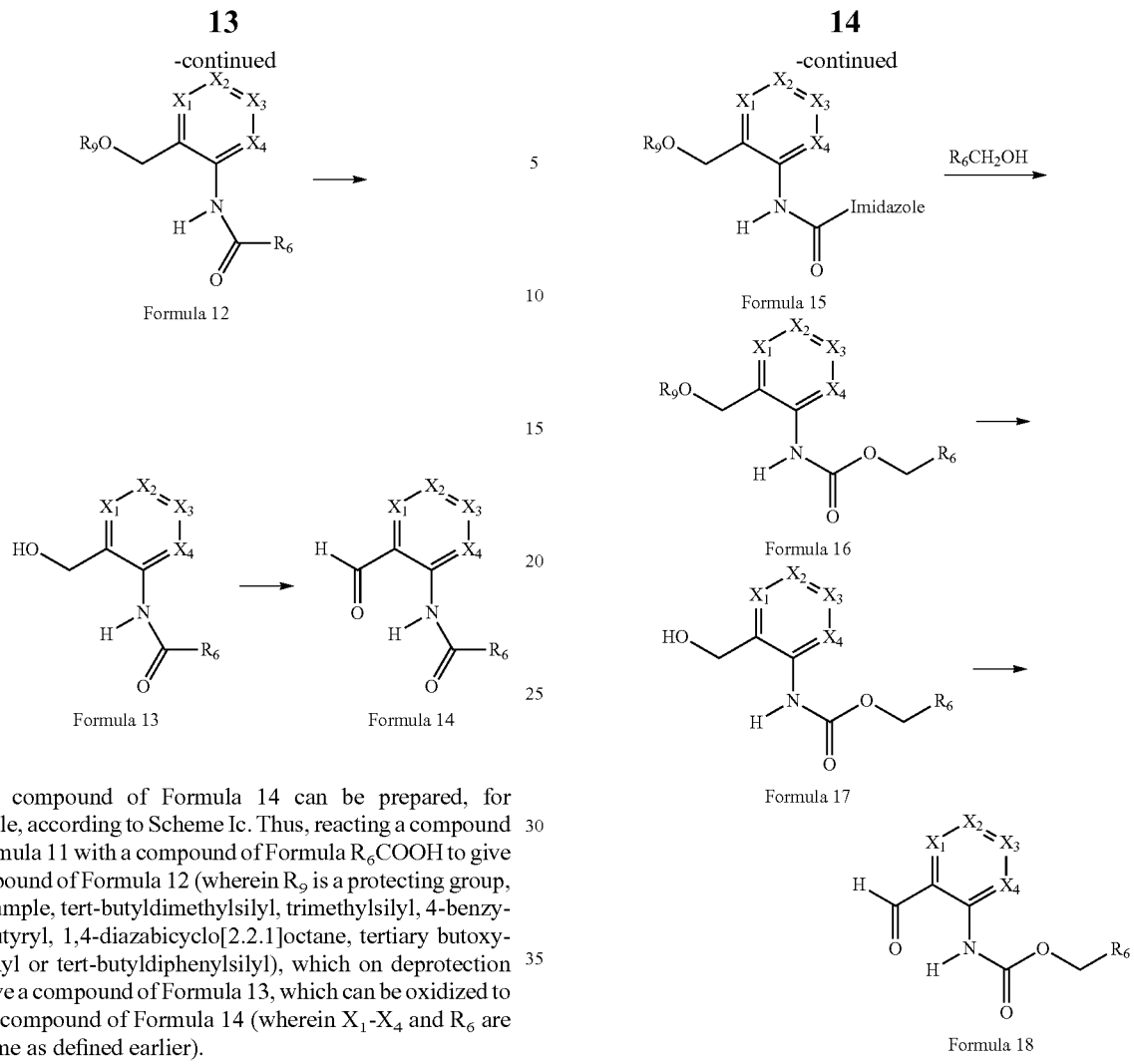

Formula 15

Formula 16

Formula 17

Formula 18

The compound of Formula 18 can be prepared according to, for example, Scheme 1d. Thus, reaction of a compound of Formula 11 with imidazole can give a compound of Formula 15, which on treatment with a compound of Formula $R_6CH_2OH$ can give a compound of Formula 16 (wherein $R_9$ is a protecting group, for example, tert-butyldimethylsilyl, trimethylsilyl, 4-benzyloxybutyryl, 1,4-diazabicyclo[2.2.1] octane, tertiary butoxycarbonyl or tert-butyldiphenylsilyl), which on deprotection can give a compound of Formula 17, which can be oxidized to give a compound of Formula 18 (wherein $X_1$-$X_4$ and $R_6$ are the same as defined earlier).

The reaction of a compound of Formula 11 with imidazole can be carried out in the presence of one or more coupling agents, for example, N,N-carbonyldiimidazole, N,N-dicyclohexylcarbodiimide or 1-(3-dimethylaminopropyl)-3-ethyl carbodiimide hydrochloride in one or more solvents, for example, chlorinated solvent (e.g., chloroform, dichloromethane, dichloroethane or tetrachloromethane), polar aprotic solvents (e.g., dimethylformamide, dimethylformamide), ketones (e.g., acetone or ethylmethylketone) or in mixtures thereof. The reaction of a compound of Formula 15 with a compound of Formula $R_6CH_2OH$ can be carried out in one or more solvents, for example, chlorinated solvent (e.g., dichloromethane, dichloroethane, chloroform or tetrachloromethane), aprotic solvents (e.g., dimethylformamide or dimethylformamide) or in mixtures thereof. The deprotection of a compound of Formula 16 to give a compound of Formula 17 can be carried out in the presence of tetra-n-butylammonium fluoride in one or more solvents, for example, ethers (e.g., tetrahydrofuran, dioxane or ether), polar aprotic solvents (e.g., dimethylsulfoxide, dimethylformamide), ketones (e.g., acetone or ethylmethylketone) or in mixtures thereof. The oxidation of a compound of Formula 17 to give a compound of Formula 18 can be carried out using the procedures described in, for example, Scheme I.

The compound of Formula 24 can be prepared according to, for example, Scheme II. Thus, reaction of a compound of Formula 19 with a compound of Formula 20 to give a compound of Formula 21, which on treatment with tosyl chloride gives a compound of Formula 22, which on reaction with a compound of Formula Cy-Ha gives a compound of Formula 23 (wherein Ha is halogen), which is finally deprotected to

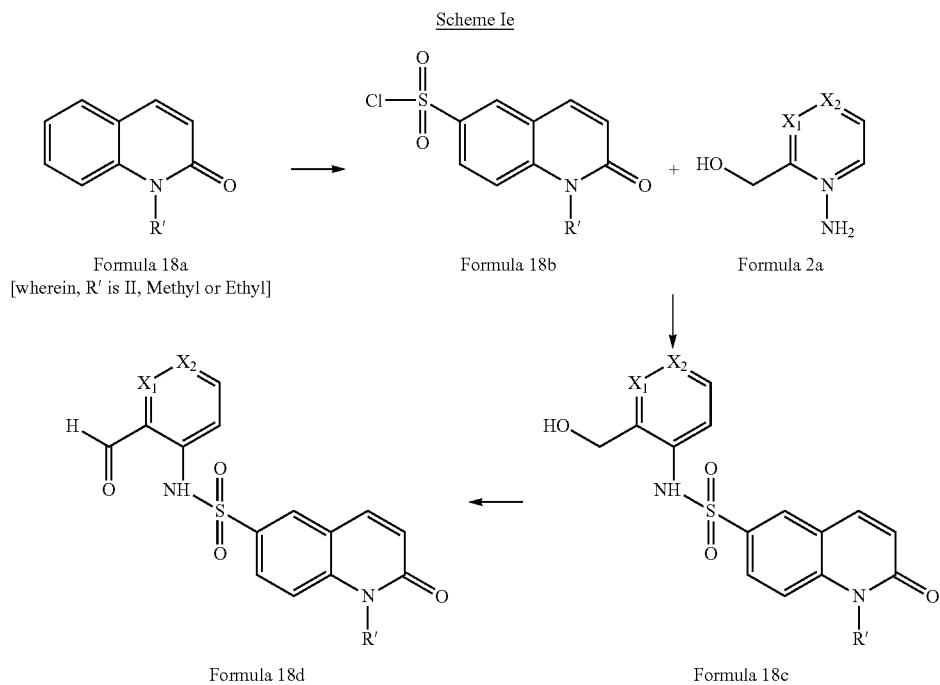

The compound of Formula 18d can be prepared according to, for example, Scheme 1e. Thus, reaction of a compound of Formula 18a with chlorosulfonic acid can give a compound of Formula 18b, which on treatment with a compound of Formula 2a can give a compound of Formula 18c, which can be oxidized to give a compound of Formula 18d.

The reaction of a compound of Formula 18b with a compound of Formula 2a can be carried out in one or more organic bases, for example, pyridine, triethylamine, trimethylamine, tributylamine or 4-N-dimethylaminopyridine. The oxidation of a compound of Formula 18c can be carried out using the procedure described in, for example, Scheme I.

give a compound of Formula 24 (S isomer, wherein Cy is the same as defined earlier). Similarly, the R isomers can be prepared.

The reaction of a compound of Formula 19 with a compound of Formula 20 can be carried out in one or more solvents, for example, chlorinated solvent (e.g., chloroform, dichloromethane, carbon tetrachloride or dichloroethane), polar aprotic solvents (e.g., dimethylsulfoxide or dimethylformamide) or in mixtures thereof. The reaction of a compound of Formula 21 with tosyl chloride can be carried out in one or more solvents, for example, ethers (e.g., ether, dioxane, or tetrahydrofuran), chlorinated solvents (e.g., dichlo-

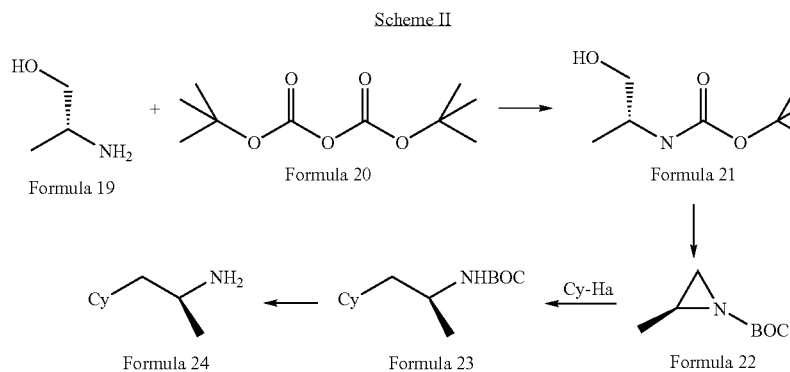

romethane, dichloroethane or chloroform) or in mixtures thereof. The reaction of a compound of Formula 21 with tosyl chloride can also be carried out in the presence of one or more metal hydroxide, for example, alkali metal hydroxides (e.g., potassium hydroxide, sodium hydroxide or lithium hydroxide), alkaline earth metal hydroxides (calcium hydroxide or magnesium hydroxide) or in mixtures thereof. The reaction of a compound of Formula 22 with a compound of Formula Cy-Ha can be carried out in the presence of magnesium (in dry ether) in one or more solvents, for example, ethers (e.g., ether, dioxane or tetrahydrofuran), chlorinated solvents (e.g., dichloromethane or chloroform) or in mixture thereof. The deprotection of a compound of Formula 23 to give a compound of Formula 24 can be carried out in the presence of one or more mineral acids, for example, hydrochloric, hydrobromic or hydroiodic acid in one or more solvents, for example, a polar protic solvent, for example, water, methanol, ethanol, propanol, isopropanol or tert-butanol).

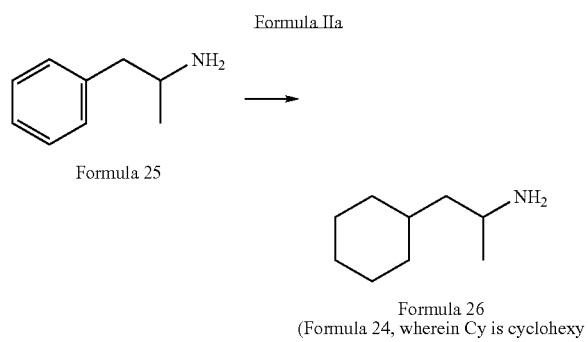

Formula IIa

Formula 25

Formula 26
(Formula 24, wherein Cy is cyclohexy

The compound of Formula 26 (Formula 24, wherein Cy is cyclohexyl) can also be prepared according to, for example, Scheme Ia. Thus, a compound of Formula 25 can be reduced to give a compound of Formula 26.

The reduction of a compound of Formula 25 to give a compound of Formula 26 can be carried out in one or more reducing agents, for example, platinum oxide in the presence of one or more organic acids, for example, acetic or trifluoroacetic acid.

The compound of Formula 31 (Formula 24, wherein Cy is piperidine) can also be prepared according to, for example, Scheme IIb. Thus, reaction of a compound of Formula 27 with nitroethane can give a compound of Formula 28, which on dehydration can give a compound of Formula 29, which on hydrogenation can give a compound of Formula 30, which can be protected to give a compound of Formula 31.

The reaction of a compound of Formula 27 with nitroethane can be carried out in the presence of one or more inorganic base, for example, sodium hydroxide, potassium hydroxide, cesium hydroxide, calcium hydroxide or sodium hydrogen carbonate. The dehydration of a compound of Formula 28 to give a compound of Formula 29 can be carried out in the presence of acetic anhydride and sodium acetate. The hydrogenation of a compound of Formula 29 to give a compound of Formula 30 can be carried out in the presence of a hydrogenating agent, for example, sodium, platinum/hydrogen or palladium-carbon/hydrogen in one or more protic polar solvents, for example, methanol, ethanol, isopropanol or water. The protection of a compound of Formula 30 to give a compound of Formula 31 can be carried out in the presence of an N-protecting agent, for example, di-tert-butyl dicarbonate in one or more solvents, for example, polar aprotic solvents (e.g., dimethylformamide or dimethylsulfoxide), ketones (e.g., ethylmethyl ketone, methyl isobutyl ketone or acetone) or in mixture thereof, in the presence of one or more inorganic bases, for example, sodium carbonate, sodium hydrogen carbonate, potassium carbonate, cesium carbonate or calcium carbonate.

Scheme IIc

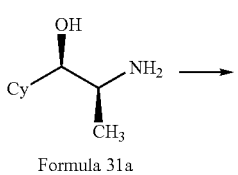

Formula 31a

Scheme IIb

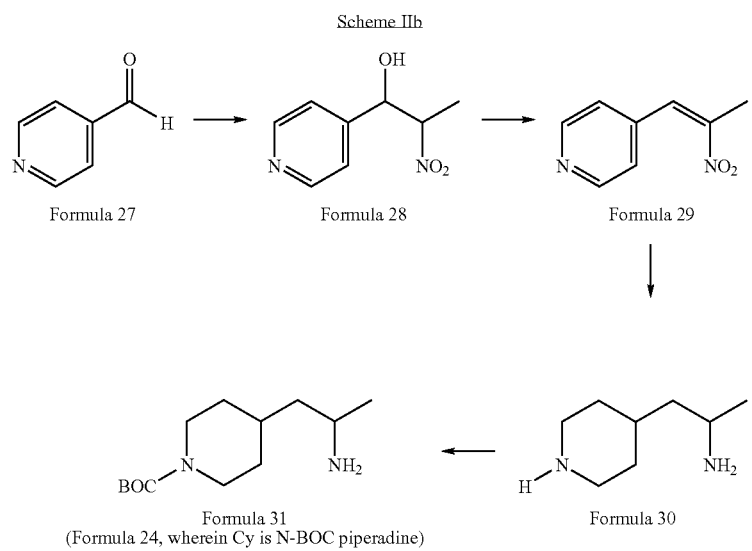

Formula 27    Formula 28    Formula 29

Formula 31
(Formula 24, wherein Cy is N-BOC piperadine)

Formula 30

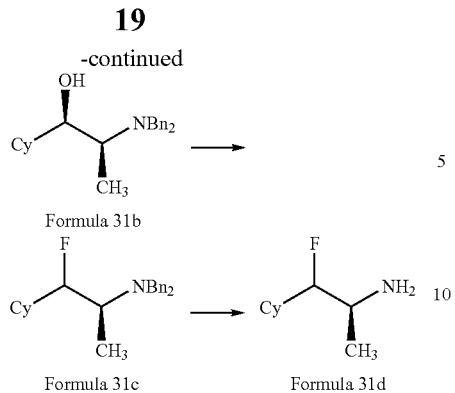

The compound of Formula 31d can be prepared according to, for example, Scheme IIc. Thus, reaction of a compound of Formula 31a with benzylbromide can give a compound of Formula 31b, which on fluorination can give a compound of Formula 31c, which can be deprotected to give a compound of Formula 31d.

The reaction of a compound of Formula 31a with benzylbromide can be carried out in one or more solvents, for example, chlorinated solvents (e.g., chloroform, dichloromethane, carbon tetrachloride or dichloroethane), polar aprotic solvents (e.g., dimethylsulfoxide or dimethylformamide), ketones (e.g., acetone or ethylmethyl ketone) or in mixtures thereof. The fluorination of a compound of Formula 31b with (Diethylamino) sulfur trifluoride (DAST) can be carried out in one or more solvents, for example, chlorinated solvents (e.g., dichloromethane, dichloroethane or chloroform), ethers (e.g., ether, dioxane, or tetrahydrofuran) or in mixtures thereof. The deprotection of a compound of Formula 31c can be carried out in the presence of reducing agents (e.g., palladium hydroxide or raney nickel) or one or more mineral acids (e.g., hydrochloric, hydrobromic or hydroiodic acid) in one or more polar protic solvents, for example, water, methanol, ethanol, propanol, isopropanol or tert-butanol.

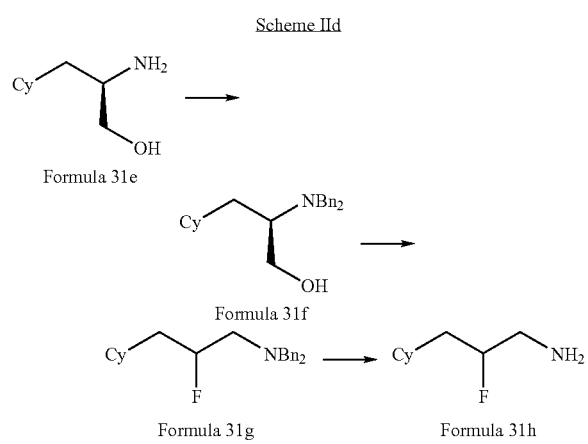

The compound of Formula 31h can be prepared according to, for example, Scheme IId. Thus, reaction of a compound of Formula 31e with benzyl bromide can give a compound of Formula 31f, which on fluorination can give a compound of Formula 31g, which can be deprotected to give a compound of Formula 31h.

The reaction of a compound of Formula 31e with benzyl bromide can be carried out in one or more solvents, for example, chlorinated solvents (e.g., chloroform, dichloromethane, carbon tetrachloride or dichloroethane), polar aprotic solvents (e.g., dimethylsulfoxide, dimethylformamide), ketones (e.g., acetone, methylethyl ketone or methyl isobutyl ketone) or in mixtures thereof. The fluorination of a compound of Formula 31f with (diethylamino) sulfur trifluoride (DAST) can be carried out in one or more solvents, for example, chlorinated solvents (e.g., dichloromethane, dichloroethane, carbon tetrachloride or chloroform), ethers (e.g., ether, dioxane, or tetrahydrofuran) or in mixtures thereof. The deprotection of a compound of Formula 31g can be carried out in the presence of reducing agents (e.g., palladium hydroxide or raney nickel) or one or more mineral acids, for example, hydrochloric, hydrobromic or hydroiodic acid, in one or more solvents, for example, nitriles (e.g., acetonitrile or propionitrile), chlorinated solvents (e.g., dichloromethane, dichloroethane, carbon tetrachloride or chloroform), polar protic solvents (e.g., water, methanol, ethanol, propanol, isopropanol or tert-butanol) or in mixtures thereof.

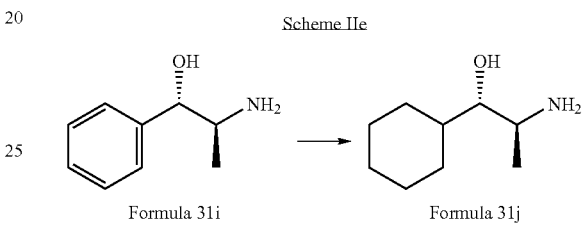

The compound of Formula 31j can be prepared according to, for example, Scheme IIe. Thus, reduction of the compound of Formula 31i can give a compound of Formula 31j (RS isomer). Similarly, the SS isomer can be prepared.

The reduction of a compound of Formula 31i can be carried out in one or more reducing agents (e.g., platinum oxide, palladium hydroxide or raney nickel) in the presence of one or more organic acids, for example, acetic acid or trifluoroacetic acid.

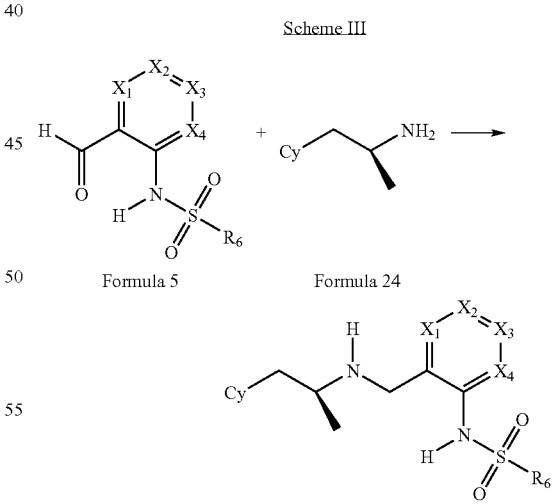

(Formula 1, wherein X = CH$_2$CH(CH3), Y = NH, Z = CH$_2$)

The compound of Formula 32 can be prepared according to, for example, Scheme III. Thus, reaction of a compound of Formula 5 with a compound of Formula 24 can give a compound of Formula 33 (wherein Cy, $X_1$-$X_4$ and $R_6$ are the same as defined earlier).

The reaction of a compound of Formula 5 with a compound of Formula 24 can be carried out in the presence of one or more reducing agents, for example, sodium cyanoborohydride, sodium borohydride or sodium triacetoxyborohydride in one or more polar protic solvents, for example, methanol, ethanol, propanol, isopropanol or water.

Scheme IV

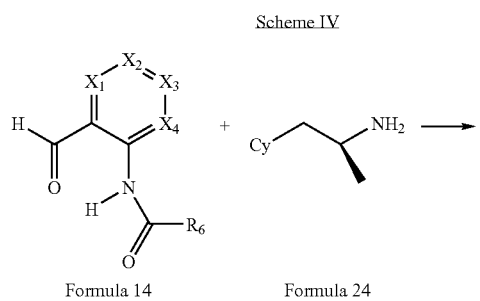

Formula 14     Formula 24

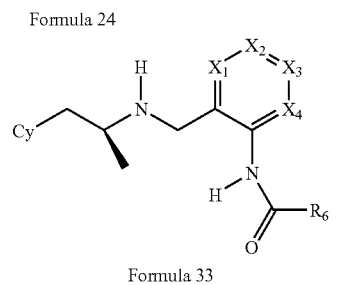

Formula 33

The compound of Formula 33 can be prepared according to, for example, Scheme IV using the procedures described in, for example, Scheme III.

Scheme V

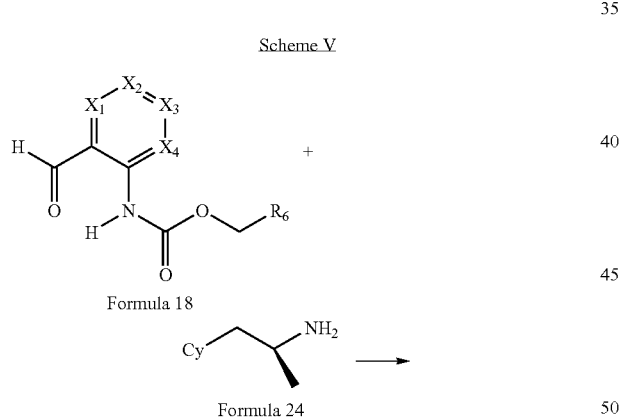

Formula 18

Formula 24

Formula 34

The compound of Formula 34 can be prepared according to, for example, Scheme V using the procedure described in, for example, Scheme III. In Schemes III-V, the compound of Formula 24 can be replaced by a compound of Formula 26, 31, 31d, 31h or 31j to form their respective sulfonamide, amide and carbamate compounds.

Scheme VI

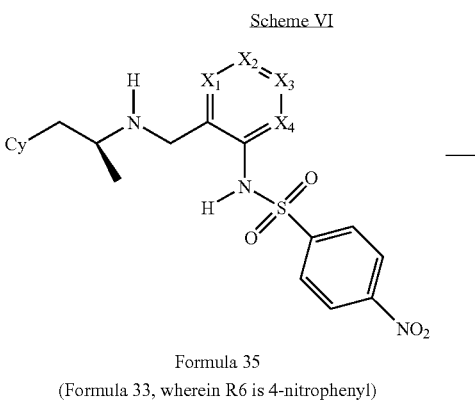

Formula 35
(Formula 33, wherein R6 is 4-nitrophenyl)

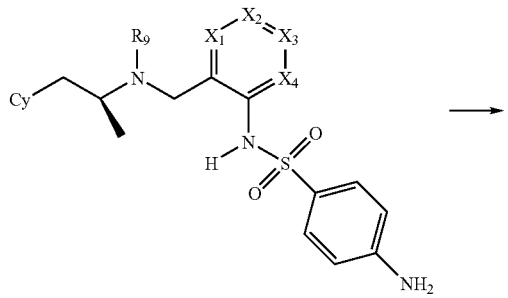

Formula 36

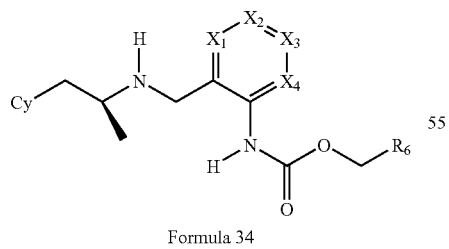

Formula 37

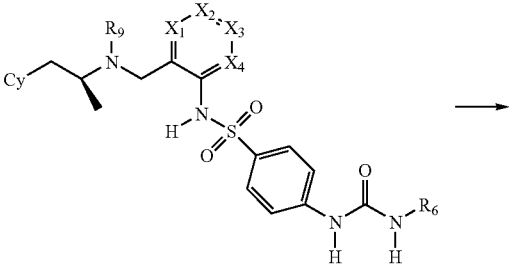

Formula 38

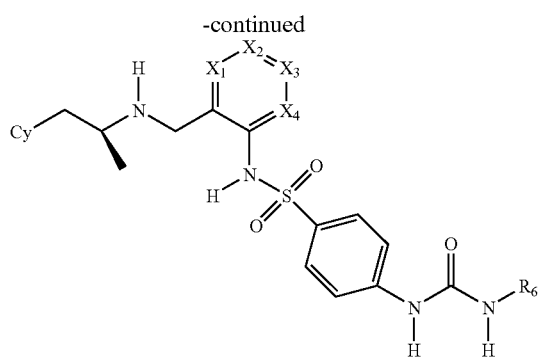

Formula 39

The compound of Formula 39 can be prepared according to, for example, Scheme VI. Thus, protection of a compound of Formula 35 with a protecting agent $R_9$Hal (wherein Hal is halogen) can give a compound of Formula 36 (wherein $R_9$ is tert-butyldimethylsilyl, trimethylsilyl, di-tert-Butyl dicarbonate, 4-benzyloxybutyryl, 1,4-diazabicyclo[2.2.1]octane, tertiary butoxycarbonyl or tert-butyldiphenylsilyl), which on reduction can give a compound of Formula 37, which on reaction with a compound of Formula $R_6$NCO can give a compound of Formula 38, which on deprotection can give a compound of Formula 39.

The protection of a compound of Formula 35 to give a compound of Formula 36 can be carried out in the presence of one or more organic bases, for example, triethylamine, trimethylamine, pyridine or tert-butylamine, in one or more chlorinated solvents, for example, dichloromethane, dichloroethane, chloroform or tetrachloromethane. The reduction of a compound of Formula 36 to give a compound of Formula 37 can be carried out in the presence of one or more reducing agents, for example, raney nickel in hydrazine hydrate, zinc, tin or iron in the presence of hydrochloric acid or lithium aluminium hydride. The reaction of a compound of Formula 37 with a compound of Formula $R_6$NCO can be carried out in one or more chlorinated solvents, for example, dichloromethane dichloroethane, chloroform or tetrachloromethane. The deprotection of a compound of Formula 38 to give a compound of Formula 39 can be carried out in the presence of one or more mineral acids, for example, hydrochloric, hydrobromic or hydroiodic acid in one or more polar protic solvents, for example, water, methanol, ethanol, propanol or isopropanol.

Scheme VIa

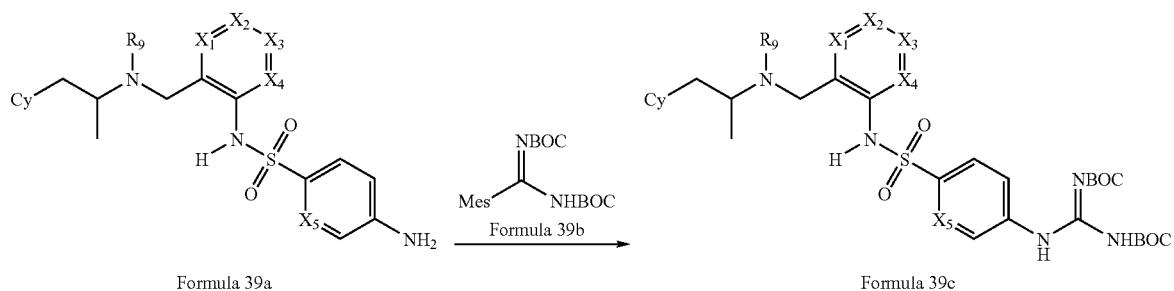

Formula 39a
[$X_5$ is CH, C(OH), C(CH$_3$) or N]

Formula 39c

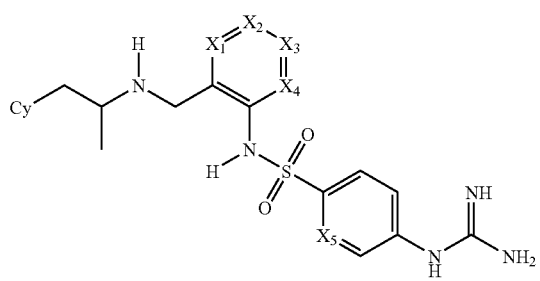

Formula 39d

The compound of Formula 39d can be prepared according to, for example, Scheme VIa. Thus, reaction of a compound of Formula 39a with a compound of Formula 39b can give a compound of Formula 39c, which on deprotection can give a compound of Formula 39d (wherein $X_1$-$X_4$ are the same as defined earlier).

The reaction of a compound of Formula 39a with a compound of Formula 39b can be carried out in the presence of one or more coupling agents, for example, N,N-carbonyldiimidazole, N,N-dicyclohexylcarbodiimide or 1-(3-dimethylaminopropyl)-3-ethyl carbodiimide hydrochloride, in one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethyl sulfoxide or dimethylformamide), ketones (e.g., acetone, ethylmethyl ketone or methyl isobutyl ketone) or in mixtures thereof. The deprotection of a compound of Formula 39c can be carried out in the presence of one or more acids, for example, mineral acids (e.g., hydrochloric, hydrobromic or hydroiodic acid), organic acids (e.g., trifluoro acetic acid or paratoluene sulfonic acid) or in mixture thereof, in one or more polar protic solvents, for example, water, methanol, ethanol, propanol or isopropanol.

The compound of Formula 39g can be prepared according to, for example, Scheme VIb. Thus, reaction of a compound of Formula 39a with a compound of Formula 39e can give a compound of Formula 39f, which on deprotection can give a compound of Formula 39 g (wherein $X_1$-$X_4$ are the same as defined earlier, Rb is methyl, methoxy or aminoethyl).

The reaction of a compound of Formula 39a with a compound of Formula 39e can be carried out in the presence of one or more coupling agents, for example, N,N-carbonyldiimidazole, N,N-dicyclohexylcarbodiimide or 1-(3-dimethylaminopropyl)-3-ethyl carbodiimide hydrochloride, in one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethyl sulfoxide, dimethylformamide), ketones (e.g., acetone, ethylmethyl ketone or methyl isobutyl ketone) or mixtures thereof. The deprotection of a compound of Formula 39f can be carried out in the presence of one or more acids, for example, mineral acids (e.g., hydrochloric, hydrobromic or hydroiodic acid), organic acids (e.g., trifluoro acetic acid or paratoluene sulfonic acid) or mixture thereof, in one or more polar protic solvents, for example, water, methanol, ethanol, propanol or isopropanol.

Scheme VIb

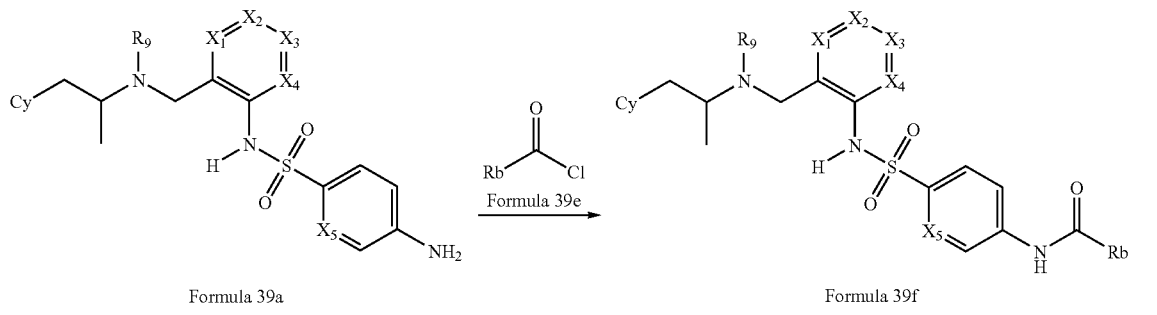

Formula 39a
[$X_5$ is CH, C(OH), C(CH$_3$) or N]

Formula 39f

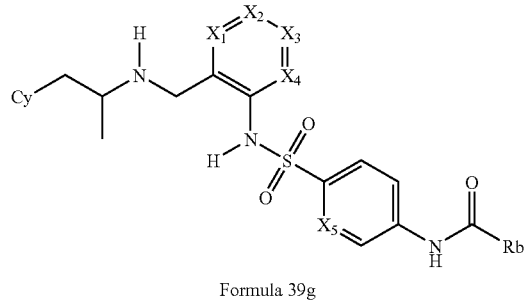

Formula 39g

Scheme VII

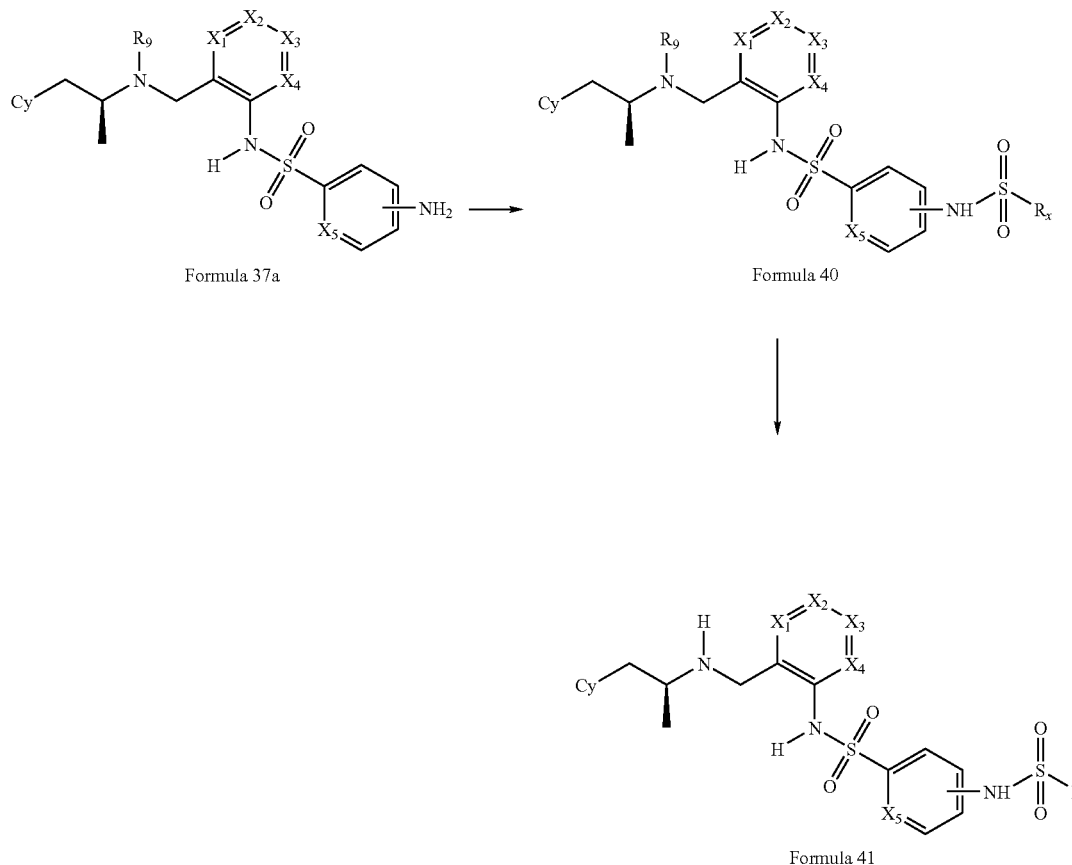

Formula 37a

Formula 40

Formula 41

The compound of Formula 41 can be prepared according to, for example, Scheme VII. Thus, reaction of a compound of Formula 37a with RxSO$_2$Cl can give a compound of Formula 40, which on deprotection can give a compound of Formula 41 (wherein Cy and X$_1$-X$_4$ are the same as defined earlier, Rx is methyl, N(CH$_3$)$_2$, NH$_2$, CH=CHCOOC$_2$H$_5$, (CH$_2$)$_3$COOC$_2$H$_5$, phenyl, 1,2,3,4-tetrahydroisoquinolinyl, 2,2,2-trifluoroacetyl-1-(3,4-dihydro-1H-isoquinolin-2-yl), morpholinyl or heteroaryl).

The reaction of a compound of Formula 37a with RxSO$_2$Cl can be carried out in the presence of one or more organic bases, for example, pyridine, triethylamine or trimethylamine. The deprotection of a compound of Formula 40 to give a compound of Formula 41 can be carried out in the presence of one or more mineral acids, for example, hydrochloric, hydrobromic or hydroiodic acid, in one or more polar protic solvents, for example, water, methanol, ethanol, propanol or isopropanol.

Scheme VIII

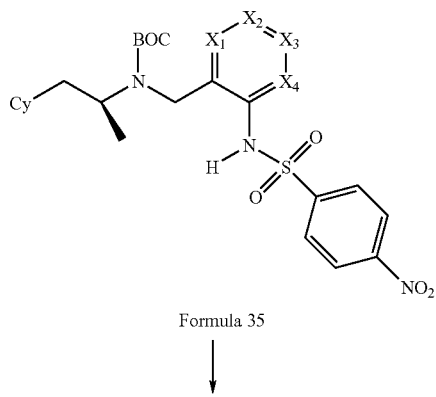

Formula 35

-continued

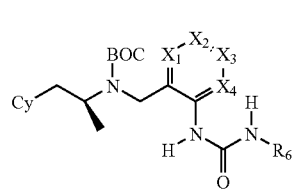

Formula 45

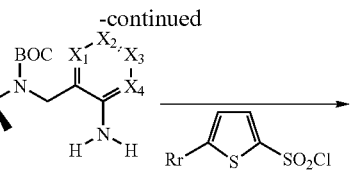

Formula 42

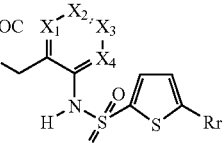

Formula 43

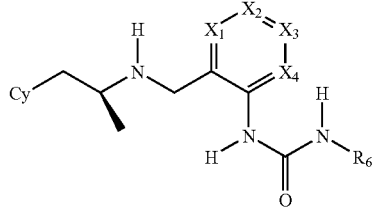

Formula 46

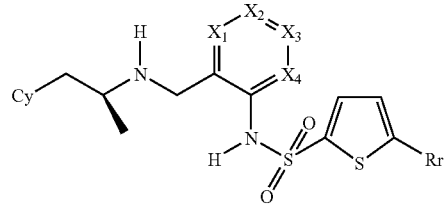

Formula 44

The compounds of Formula 44 and 46 can be prepared according to, for example, Scheme VIII. Thus, deprotection of a compound of Formula 35 with thiophenol or thioglycolic acid in the presence of a base, for example, potassium carbonate, sodium carbonate or cesium carbonate can give a compound of Formula 42, which on (1) reaction with a compound of Formula 42a can give a compound of Formula 43, which on deprotection can give a compound of Formula 44, or on (2) reaction with a compound of Formula $R_6$NCO can give a compound of Formula 45, which on deprotection can give a compound of Formula 46.

The deprotection of a compound of Formula 35 to give a compound of Formula 42 can be carried out in the presence of one or more inorganic bases, for example, cesium carbonate, sodium carbonate, sodium hydrogen carbonate, potassium carbonate or calcium carbonate in one or more solvents, for example, nitrites (e.g., acetonitrile or propionitrile), acetates (e.g., ethyl acetate or methyl acetate), polar aprotic solvents (e.g., dimethylsulfoxide or dimethylformamide), ketones (e.g., acetone or ethylmethyl ketone) or in mixtures thereof. The reaction of a compound of Formula 42 with a compound of Formula 42a can be carried out in the presence of one or more organic bases, for example, pyridine, triethylamine or trimethylamine. The reaction of a compound of Formula 42 with a compound of Formula $R_6$NCO can be carried out in one or more chlorinated solvents, for example, dichloromethane, dichloroethane, chloroform or tetrachloromethane. The deprotection of compounds of Formula 43 and 45 to give compounds of Formula 44 and 46, respectively, can be carried out in the presence of one or more mineral acids, for example, hydrochloric, hydrobromic or hydroiodic acid, in one or more polar protic solvents, for example, methanol, ethanol, propanol, isopropanol or butanol.

Scheme VIIIa

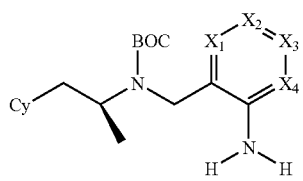

Formula 42

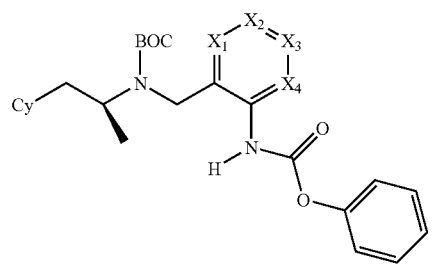

Formula 42b

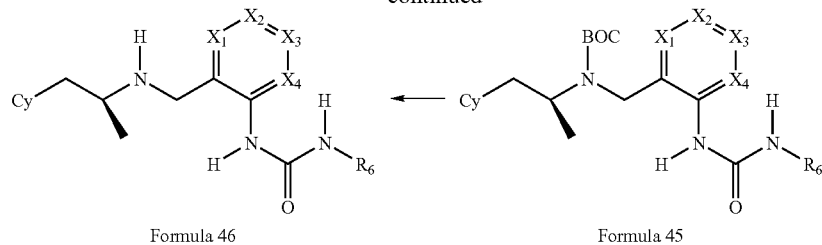

Formula 46                 Formula 45

The compound of Formula 46 can also be prepared according to, for example, Scheme VIIIa. Thus, reaction of a compound of Formula 42 with phenyl chloroformate can give a compound of Formula 42b, which on reaction with an amine of Formula $R_6NH_2$ can give a compound of Formula 45, which can be deprotected to give a compound of Formula 46.

The reaction of a compound of Formula 42 with phenyl chloroformate can be carried out in one or more solvents, for example, chlorinated solvents (e.g., dichloromethane, dichloroethane, chloroform or tetrachloromethane), nitriles (e.g., acetonitrile or propionitrile) or in mixture thereof. The compound of Formula 42b can be reacted in the presence of one or more bases, for example, triethylamine, trimethylamine or pyridine, in one or more chlorinated solvents, for example, dichloromethane, dichloroethane, chloroform or carbon tetrachloride. The compound of Formula 45 can be deprotected in the presence of one or more acids, for example, organic acids (e.g., trifluoro acetic or acetic acid), mineral acids (e.g., hydrochloric, hydrobromic or hydroiodic acid) or in mixture thereof, in one or more polar protic solvents, for example, methanol, ethanol, propanol, isopropanol, butanol or water.

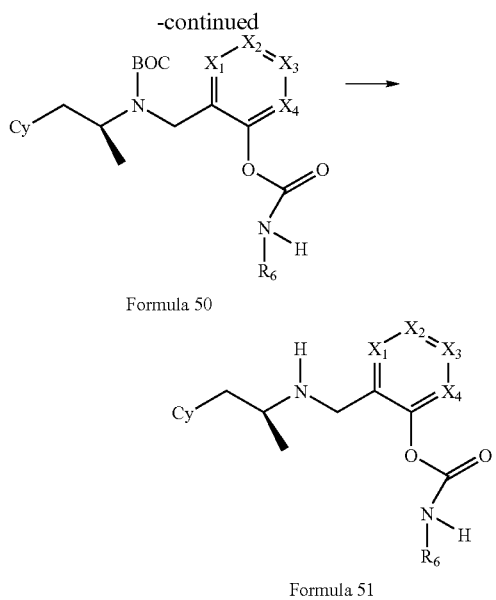

Formula 50

Formula 51

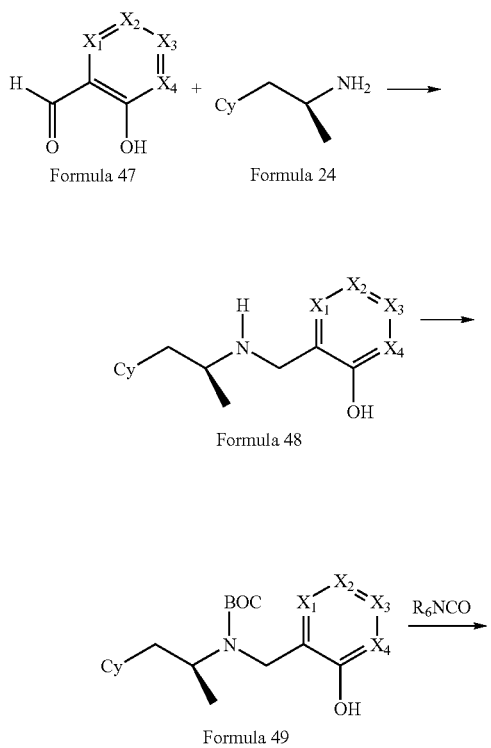

Scheme IX

Formula 47    Formula 24

Formula 48

Formula 49

The compound of Formula 51 can be prepared according to, for example, Scheme IX. Thus, reaction of a compound of Formula 47 with a compound of Formula 24 can give a compound of Formula 48, which on protection can give a compound of Formula 49, which on reaction with a compound of Formula $R_6NCO$ can give a compound of Formula 50, which can be deprotected to give a compound of Formula 51.

The reaction of a compound of Formula 47 with a compound of Formula 24 can be carried out in the presence of one or more reducing agents, for example, sodium cyanoborohydride or sodium borohydride, one or more organic acids, for example, acetic or trifluoroacetic acid in one or more polar protic solvents, for example, methanol, ethanol, propanol, isopropanol or butanol. The protection of a compound of Formula 48 with a protecting agent, for example, di-tert-butyl dicarbonate can be carried out in one or more chlorinated solvents, for example, dichloromethane, dichloroethane, chloroform or tetrachloromethane. The reaction of a compound of Formula 49 with a compound of Formula $R_6NCO$ can be carried out in the presence of one or more organic bases, for example, triethylamine, trimethylamine or pyridine in one or more chlorinated solvents, for example, dichloromethane, dichloroethane or chloroform. The deprotection of a compound of Formula 50 to give a compound of Formula 51 can be carried out in the presence of one or more mineral acids, for example, hydrochloric, hydrobromic or hydroiodic acid in one or more polar protic solvents, for example, water, methanol, ethanol, propanol or isopropanol.

Scheme X

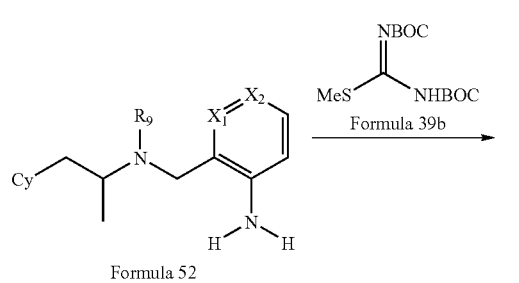

Formula 52

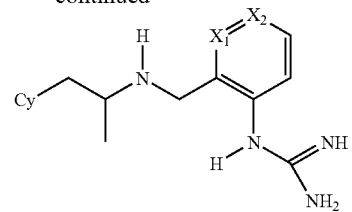

Formula 54

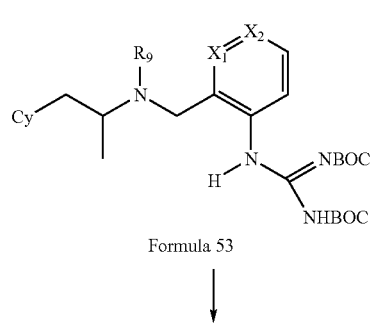

Formula 53

The compound of Formula 54 can be prepared according to, for example, Scheme X. Thus, reaction of a compound of Formula 52 with a compound of Formula 39b can give a compound of Formula 53, which on deprotection can give a compound of Formula 54.

The reaction of a compound of Formula 52 can be carried out in the presence of one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethyl sulfoxide or dimethylformamide), ketones (e.g., acetone, ethylmethyl ketone or methyl isobutyl ketone) or mixtures thereof. The deprotection of a compound of Formula 53 can be carried out in the presence of one or more organic acids (e.g., trifluoro acetic acid or paratoluene sulfonic acid), mineral acids (e.g., hydrochloric, hydrobromic or hydroiodic acid) in one or more solvents, for example, nitriles (e.g., acetonitrile or propionitrile), polar protic solvents (e.g., water, methanol, ethanol, propanol or isopropanol) or in mixtures thereof.

Scheme XI

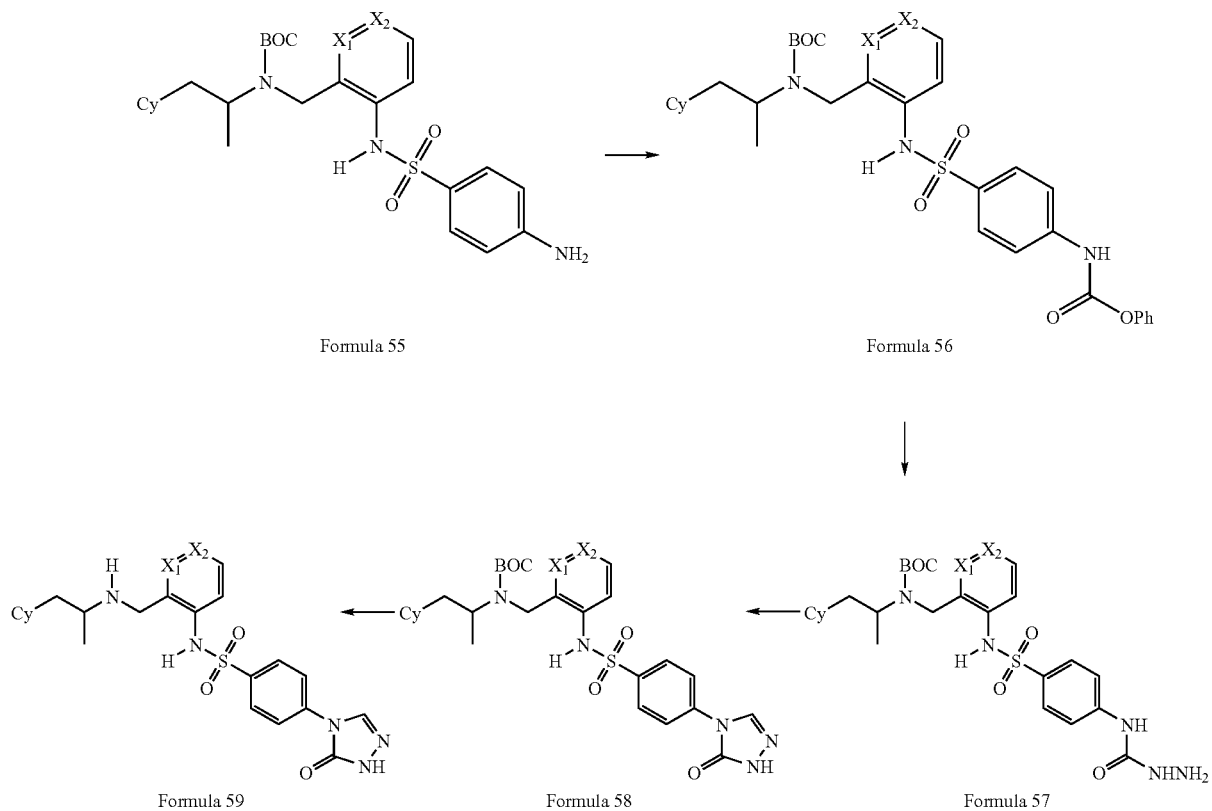

The compound of Formula 59 can be prepared according to, for example, Scheme XI. Thus, reaction of a compound of Formula 55 with phenyl chloroformate can give a compound of Formula 56, which on reaction with hydrazine hydrate can give a compound of Formula 57, which on cyclisation can give a compound of Formula 58, which can be deprotected to give a compound of Formula 59.

The reaction of a compound of Formula 55 with phenyl chloroformate can be carried out in one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethylsulfoxide or dimethylformamide), ketones (e.g., acetone, ethyl methylketone or methyl isobutyl ketone) or in mixtures thereof. The reaction of a compound of Formula 56 can be carried out in the presence of one or more coupling agents, for example, N,N-carbonyldiimidazole, N,N-dicyclohexylcarbodiimide or 1-(3-dimethylaminopropyl)-3-ethyl carbodiimide hydrochloride, in one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethylsulfoxide or dimethylformamide), ketones (e.g., acetone or ethyl methylketone) or in mixtures thereof. The reaction of a compound of Formula 57 with formamidine acetate can be carried out in the presence of acids, for example, acetic acid hydrochloride in one or more solvents, for example, nitriles (e.g., acetonitrile or propionitrile), chlorinated solvents (e.g., chloroform, dichloromethane, dichloroethane or tetrachloromethane), polar aprotic solvents (e.g., dimethylsulfoxide or dimethylformamide), ketones (e.g., acetone or ethyl methyl ketone) or in mixtures thereof. The deprotection of a compound of Formula 58 can be carried out in the presence of one or more organic acids (e.g., trifluoroacetic acid or paratoluene sulfonic acid), mineral acids (e.g., hydrochloric, hydrobromic or hydroiodic acid) or in mixture thereof, in one or more solvents, for example, nitriles (e.g., acetonitrile or propionitrile), polar protic solvents (e.g., water, methanol, ethanol, propanol or isopropanol) or in mixtures thereof.

In the above schemes, where the specific bases, oxidizing agents, reducing agents, coupling agents, solvents, etc., are mentioned, it is to be understood that other bases, oxidizing agents, reducing agents, coupling agents, solvents, etc., known to those skilled in the art may be used. Similarly, the reaction temperature and duration may be adjusted according to the desired needs.

The compounds described herein possess antimicrobial activity against Gram-positive, Gram-negative, anaerobic bacteria and fungal infections. They are useful as antimicrobial agents for the treatment of infections diseases in human and animal.

Particular exemplary compounds useful for such purpose include those listed below:

N-[2-({[(1S)-2-cyclohexyl-1-methylethyl]amino}methyl)phenyl]-2,3,4,5,6-pentafluoro benzenesulfonamide (Compound No. 1), N-[2-({[(1S)-2-cyclohexyl-1-methylethyl]amino}methyl)phenyl]-5-(3-methoxyphenyl)thiophene-2-sulfonamide (Compound No. 2), 5-(1-benzothien-2-yl)-N-[2-({[(1S)-2-cyclohexyl-1-methylethyl]amino}methyl)phenyl]thiophene-2-sulfonamide (Compound No. 3), N-[2-({[(1S)-2-cyclohexyl-1-methylethyl]amino}methyl)phenyl]-5-(3,4-dimethoxyphenyl)thiophene-2-sulfonamide (Compound No. 4), N-[2-({[(1S)-2-cyclohexyl-1-methylethyl]amino}methyl)phenyl]-1-benzothiophene-2-sulfonamide (Compound No. 5), N-[2-({[(1S)-2-cyclopentyl-1-methylethyl]amino}methyl)phenyl]-5-(2,5-dimethoxyphenyl)thiophene-2-sulfonamide (Compound No. 6), N-[2-({[(1S)-2-cycloheptyl-1-methylethyl]amino}methyl)phenyl]-5-(2,5-dimethoxyphenyl)thiophene-2-sulfonamide (Compound No. 7), 5-(3-acetylphenyl)-N-[2-({[(1S)-2-cyclopentyl-1-methylethyl]amino}methyl)phenyl]thiophene-2-sulfonamide (Compound No. 8), N-[2-({[(1S)-2-cyclohexyl-1-methylethyl]amino}methyl)phenyl]-5-[3-(1-hydroxyethyl)phenyl]thiophene-2-sulfonamide (Compound No. 9), 5-(3-acetylphenyl)-N-[2-({[(1S)-2-cycloheptyl-1-methylethyl]amino}methyl)phenyl]thiophene-2-sulfonamide (Compound No. 10), N-[2-({[(1S)-2-cyclohexyl-1-methylethyl]amino}methyl)phenyl]-5-(2,5-dimethoxyphenyl)thiophene-2-sulfonamide (Compound No. 11), N-[2-({[(1S)-2-cyclopentyl-1-methylethyl]amino}methyl)phenyl]-1-benzothiophene-2-sulfonamide (Compound No. 12), N-[2-({[(1S)-2-cycloheptyl-1-methylethyl]amino}methyl)phenyl]-1-benzothiophene-2-sulfonamide (Compound No. 13), N-[2-({[(1S)-2-cyclopentyl-1-methylethyl]amino}methyl)phenyl]-5-(3,4-dimethoxyphenyl)thiophene-2-sulfonamide (Compound No. 14), 6-chloro-N-[2-({[(1S)-2-cyclohexyl-1-methylethyl]amino}methyl)phenyl]imidazo[2,1-b][1,3]thiazole-5-sulfonamide (Compound No. 15), N-[2-({[(1S)-2-cyclohexyl-1-methylethyl]amino}methyl)phenyl]-5-[3-(trifluoromethyl)phenyl]thiophene-2-sulfonamide (Compound No. 16), N-[2-({[(1S)-2-cyclohexyl-1-methylethyl]amino}methyl)phenyl]-5-[1-methyl-5-(trifluoromethyl)-1H-pyrazol-3-yl]thiophene-2-sulfonamide (Compound No. 17), N-[2-({[(1S)-2-cyclohexyl-1-methylethyl]amino}methyl)phenyl]-5-[5-(trifluoromethyl)isoxazol-3-yl]thiophene-2-sulfonamide (Compound No. 18), N-[2-({[(1S)-2-cyclohexyl-1-methylethyl]amino}methyl)phenyl]-5-[1-methyl-3-(trifluoromethyl)-1H-pyrazol-5-yl]thiophene-2-sulfonamide (Compound No. 19), N-[2-({[(1S)-2-cyclopentyl-1-methylethyl]amino}methyl)phenyl]-5-[4-(trifluoromethoxy)phenyl]thiophene-2-sulfonamide (Compound No. 20), N-[2-({[(1S)-2-cyclopentyl-1-methylethyl]amino}methyl)phenyl]-5-[5-(trifluoromethyl)isoxazol-3-yl]thiophene-2-sulfonamide (Compound No. 21), N-[2-({[(1S)-2-cycloheptyl-1-methylethyl]amino}methyl)phenyl]-5-[5-(trifluoromethyl)isoxazol-3-yl]thiophene-2-sulfonamide (Compound No. 22), N-[2-({[(1S)-2-cycloheptyl-1-methylethyl]amino}methyl)phenyl]-5-[1-methyl-3-(trifluoromethyl)-1H-pyrazol-5-yl]thiophene-2-sulfonamide (Compound No. 23), N-[2-({[(1S)-2-cyclopentyl-1-methylethyl]amino}methyl)phenyl]-5-[1-methyl-3-(trifluoromethyl)-1H-pyrazol-5-yl]thiophene-2-sulfonamide (Compound No. 24), N-[2-({[(1S)-2-cycloheptyl-1-methylethyl]amino}methyl)phenyl]-5-[1-methyl-5-(trifluoromethyl)-1H-pyrazol-3-yl]thiophene-2-sulfonamide (Compound No. 25), N-[2-({[(1S)-2-cyclohexyl-1-methylethyl]amino}methyl)phenyl]-5-[4-(trifluoromethoxy)phenyl]thiophene-2-sulfonamide (Compound No. 26), 5-chloro-N-[2-({[(1S)-2-cyclohexyl-1-methylethyl]amino}methyl)phenyl]-3-methyl-1-benzothiophene-2-sulfonamide (Compound No. 27), methyl 5-({[2-({[(1S)-2-cyclohexyl-1-methylethyl]amino}methyl)phenyl]amino}sulfonyl)-4-methylthiophene-2-carboxylate (Compound No. 28), methyl 4-({[2-({[(1S)-2-cyclohexyl-1-methylethyl]amino}methyl)phenyl]amino}sulfonyl)-2,5-dimethyl-3-furoate (Compound No. 29), 5-chloro-N-[2-({[(1S)-2-cyclohexyl-1-methylethyl]amino}methyl)phenyl]-1,3-dimethyl-1H-pyrazole-4-sulfonamide (Compound No. 30), N-[2-({[(1S)-2-cyclohexyl-1-methylethyl]amino}methyl)phenyl]-2,2'-bithiophene-5-sulfonamide (Compound No. 31), N-[2-({[(1S)-2-cyclohexyl-1-methylethyl]amino}methyl)phenyl]-5-(3-furyl)thiophene-2-sulfonamide (Compound No. 32), N-[2-({[(1S)-2-cyclohexyl-1-methylethyl]amino}methyl)phenyl]-5-phenylthiophene-2-sulfonamide (Compound No. 33), N-[2-({[(1R)-2-cyclohexyl-1-(hydroxymethyl)ethyl]amino}methyl)phenyl]thiophene-2-sulfonamide (Compound No. 34), methyl 5-({[2-({[(1S)-2-cycloheptyl-1-methylethyl]amino}methyl)phenyl]amino}sulfonyl)-4-methylthiophene-2-carboxylate (Compound No. 35), 5-chloro-N-[2-({[(1S)-2-cycloheptyl-1-methylethyl]amino}methyl)phenyl]-3-methyl-1-benzothiophene-2-sulfonamide (Compound No. 36), 5-chloro-N-[2-({[(1S)-2-cycloheptyl-1-methylethyl]amino}methyl)phenyl]-1,3-dimethyl-1H-pyrazole-4-sulfonamide (Compound No. 37), N-[2-({[(1S)-2-cycloheptyl-1-methylethyl]amino}methyl)phenyl]-2,2'-bithiophene-5-sulfonamide (Compound No. 38), N-[2-({[(1S)-2-cyclopentyl-1-methylethyl]amino}methyl)phenyl]-5-(3-furyl)thiophene-2-sulfonamide (Compound No. 39), N-[2-({[(1S)-2-cycloheptyl-1-methylethyl]amino}methyl)phenyl]-5-(3-furyl)thiophene-2-sulfonamide (Compound No. 40), N-[2-({[(1S)-2-cyclopentyl-1-methylethyl]amino}methyl)phenyl]-5-phenylthiophene-2-sulfonamide (Compound No. 41), 5-bromo-N-[2-({[(1S)-2-cyclopentyl-1-methylethyl]amino}methyl)phenyl]thiophene-2-sulfonamide (Compound No. 42), N-[2-({[(1S)-2-cyclopentyl-1-methylethyl]amino}methyl)phenyl]thiophene-2-sulfonamide (Compound No. 43), N-[2-({[(1S)-2-cycloheptyl-1-methylethyl]amino}methyl)phenyl]thiophene-2-sulfonamide (Compound No. 44), N-[2-({[(1S)-2-cyclohexyl-1-methylethyl]amino}methyl)phenyl]isonicotinamide (Compound No. 45), N-[2-({[(1S)-2-cyclohexyl-1-methylethyl]amino}methyl)phenyl]nicotinamide (Compound No. 46), N-[2-({[(1S)-2-cyclopentyl-1-methylethyl]amino}methyl)phenyl]-2,2'-bithiophene-5-sulfonamide (Compound No. 47), N-[2-({[(1S)-2-cyclohexyl-1-methylethyl]amino}methyl)phenyl]-3,5-bis(trifluoromethyl)benzenesulfonamide (Compound No. 48), 2-({[(1S)-2-cyclohexyl-1-methylethyl]amino}methyl)phenyl[(2-methylphenyl)sulfonyl]carbamate hydrochloride salt (Compound No. 49), N-[2-({[(1S)-2-cyclohexyl-1-methylethyl]amino}methyl)phenyl]-6-phenoxypyridine-3-sulfonamide (Compound No. 50), 5-bromo-N-[2-({[(1S)-2-cyclohexyl-1-methylethyl]amino}methyl)phenyl]-2-furamide (Compound No. 51), N-[2-({[(1S)-2-cyclohexyl-1-methylethyl]amino}methyl)phenyl]-2-furamide (Compound No. 52), N-[2-({[(1S)-2-cyclohexyl-1-methylethyl]amino}methyl)phenyl]-1-benzothiophene-3-sulfonamide (Compound No. 53), N-[2-({[(1S)-2-cyclohexyl-1-methylethyl]amino}methyl)phenyl]thiophene-2-carboxamide (Compound No. 54), N-[2-({[(1S)-2-cycloheptyl-1-methylethyl]amino}methyl)phenyl]thiophene-2-carboxamide hydrochloride salt (Compound No. 55), N-[2-({[(1S)-2-cyclopentyl-1-methylethyl]amino}methyl)phenyl]-2-furamide hydrochloride salt (Compound No. 56), 5-bromo-N-[2-({[(1S)-2-cyclopentyl-1-methylethyl]amino}methyl)phenyl]-2-furamide hydrochloride salt (Compound No. 57), 5-(3-acetylphenyl)-N-[2-({[(1S)-2-cyclohexyl-1-methylethyl]amino}methyl)phenyl]thiophene-2-sulfonamide (Compound No. 58), 5-(1,3-benzodioxol-5-yl)-N-[2-({[(1S)-2-cyclohexyl-1-methylethyl]amino}methyl)phenyl]thiophene-2-sulfonamide (Compound No. 59), N-[2-({[(1S)-2-cyclohexyl-1-methylethyl]amino}methyl)phenyl]-3,3'-bithiophene-5-sulfonamide (Compound No. 60), N-[2-({[(1S)-2-cycloheptyl-1-methylethyl]amino}methyl)phenyl]-5-(3-methoxyphenyl)thiophene-2-sulfonamide (Compound No. 61), methyl 3-({[2-({[(1S)-2-cyclohexyl-1-methylethyl]amino}methyl)phenyl]amino}sulfonyl)-4-(isopropylsulfonyl)thiophene-2-carboxylate (Compound No. 62), N-[2-({[(1S)-2-cyclohexyl-1-methylethyl]amino}methyl)phenyl]-5-(3-fluorophenyl)thiophene-2-sulfonamide (Compound No. 63), N-[2-({[(1S)-2-cyclohexyl-1-methylethyl]amino}methyl)phenyl]-5-[3-(hydroxymethyl)phenyl]thiophene-2-sulfonamide (Compound No. 64), N-[2-({[(1S)-2-cyclohexyl-1-methylethyl]amino}methyl)phenyl]-5-[4-(hydroxymethyl)phenyl]thiophene-2-sulfonamide (Compound No. 65), methyl 5-({[2-({[(1S)-2-cyclopentyl-1-methylethyl]amino}methyl)phenyl]amino}sulfonyl)-4-methylthiophene-2-carboxylate (Compound No. 66), methyl 4-({[2-({[(1S)-2-cycloheptyl-1-methylethyl]amino}methyl)phenyl]amino}sulfonyl)-2,5-dimethyl-3-furoate (Compound No. 67), N-[2-({[(1S)-2-cycloheptyl-1-methylethyl]amino}methyl)phenyl]-5-[3-(trifluoromethyl)phenyl]thiophene-2-sulfonamide (Compound No. 68), N-[2-({[(1S)-2-cyclopentyl-1-methylethyl]amino}methyl)phenyl]-5-(3-fluorophenyl)thiophene-2-sulfonamide (Compound No. 69), N-[2-({[(1S)-2-cycloheptyl-1-methylethyl]amino}methyl)phenyl]-5-(3-fluorophenyl)thiophene-2-sulfonamide (Compound No. 70), N-[2-({[(1S)-2-cyclopentyl-1-methylethyl]amino}methyl)phenyl]-5-isoxazol-3-ylthiophene-2-sulfonamide (Compound No. 71), N-[2-({[(1S)-2-cyclohexyl-1-methylethyl]amino}methyl)phenyl]-5-methylthiophene-2-carboxamide (Compound No. 72), N-[2-({[(1S)-2-cycloheptyl-1-methylethyl]amino}methyl)phenyl]-5-methylthiophene-2-carboxamide (Compound No. 73), N-[2-({[(1S)-2-cyclopentyl-1-methylethyl]amino}methyl)phenyl]nicotinamide (Compound No. 74), N-[2-({[(1S)-2-cycloheptyl-1-methylethyl]amino}methyl)phenyl]nicotinamide (Compound No. 75), N-[3-({[(1S)-2-cycloheptyl-1-methylethyl]amino}methyl)pyridin-2-yl]thiophene-2-sulfonamide (Compound No. 76), N-[3-({[(1S)-2-cyclohexyl-1-methylethyl]amino}methyl)pyridin-2-yl]thiophene-2-sulfonamide (Compound No. 77), N-[3-({[(1S)-2-cyclohexyl-1-methylethyl]amino}methyl)pyridin-2-yl]-4-fluorobenzene sulfonamide (Compound No. 78), N-[2-({[(1S)-2-cyclohexyl-1-methylethyl]amino}methyl)phenyl]-2-(trifluoroacetyl)-1,2,3,4-tetrahydroisoquinoline-6-sulfonamide (Compound No. 79), N-[2-({[(1S)-2-cyclohexyl-1-methylethyl]amino}methyl)phenyl]-1,2,3,4-tetrahydroisoquinoline-6-sulfonamide (Compound No. 80), methyl 5-({[2-({[(1S)-2-cycloheptyl-1-methylethyl]amino}methyl)phenyl]amino}sulfonyl)-1-methyl-1H-pyrrole-2-carboxylate (Compound No. 81), methyl 5-({[2-({[(1S)-2-cyclopentyl-1-methylethyl]amino}methyl)phenyl]amino}sulfonyl)-1-methyl-1H-pyrrole-2-carboxylate (Compound No. 82), N-[2-({[(1S)-2-cyclopentyl-1-methylethyl]amino}methyl)phenyl]-1-methyl-1H-imidazole-4-sulfonamide (Compound No. 83), N-[2-({[(1S)-2-cycloheptyl-1-methylethyl]amino}methyl)phenyl]-1-methyl-1H-imidazole-4-sulfonamide (Compound No. 84), 5-bromo-N-[2-({[(1S)-2-cycloheptyl-1-methylethyl]amino}methyl)phenyl]-2-furamide (Compound No. 85), N-[2-({[(1S)-2-cyclopentyl-1-methylethyl]amino}methyl)phenyl]-3,5-bis(trifluoromethyl)benzenesulfonamide (Compound No. 86), N-[2-({[(1S)-2-cyclohexyl-1-methylethyl]amino}methyl)phenyl]-5-isoxazol-3-ylthiophene-2-sulfonamide (Compound No. 87), N-[2-({[(1S)-2-cycloheptyl-1-methylethyl]amino}methyl)phenyl]isonicotinamide (Compound No. 88), 5-chloro-N-[2-({[(1S)-2-cyclopentyl-1-methylethyl]amino}methyl)phenyl]-1,3-dimethyl-1H-pyrazole-4-sulfonamide (Compound No. 89), (1-benzothien-2-yl)-N-[2-({[(1S)-2-cycloheptyl-1-methylethyl]amino}methyl)phenyl]thiophene-2-sulfonamide (Compound No. 90), 5-(1-benzothien-2-yl)-N-[2-({[(1S)-2-cyclopentyl-1-methylethyl]amino}methyl)phenyl]thiophene-2-sulfonamide (Compound No. 91), N-[2-({[(1S)-2-cycloheptyl-1-methylethyl]amino}methyl)phenyl]-5-(3,4-dimethoxyphenyl)thiophene-2-sulfonamide (Compound No. 92), N-[2-({[(1S)-2-cyclopentyl-1-methylethyl]amino}methyl)phenyl]-5-(4-methoxyphenyl)thiophene-2-sulfonamide (Compound No. 93), N-[2-({[(1S)-2-cyclopentyl-1-methylethyl]amino}methyl)phenyl]-3,3'-bithiophene-5-sulfonamide (Compound No. 94), N-[2-({[(1S)-2-cycloheptyl-1-methylethyl]amino}methyl)phenyl]-3,3'-bithiophene-5-sulfonamide (Compound No. 95), N-[2-({[(1S)-2-cyclopentyl-1-methylethyl]amino}methyl)phenyl]-2-(trifluoroacetyl)-1,2,3,4-tetrahydroisoquinoline-6-sulfonamide (Compound No. 96), N-[2-({[(1S)-2-cyclopentyl-1-methylethyl]amino}methyl)phenyl]-1,2,3,4-tetrahydroisoquinoline-6-sulfonamide (Compound No. 97), 5-(1,3-benzodioxol-5-yl)-N-[2-({[(1S)-2-cyclopentyl-1-methylethyl]amino}methyl)phenyl]thiophene-2-sulfonamide (Compound No. 98), N-[2-({[(1S)-2-cyclohexyl-1-methylethyl]amino}methyl)phenyl]-2-[4-(4-methoxyphenyl)piperazin-1-yl]acetamide (Compound No. 99), 5-chloro-N-[2-({[(1S)-2-cyclopentyl-1-methylethyl]amino}methyl)phenyl]-3-methyl-1-benzothiophene-2-sulfonamide (Compound No. 100), N-[2-({[(1S)-2-cycloheptyl-1-methylethyl]amino}methyl)phenyl]-5-isoxazol-3-ylthiophene-2-sulfonamide (Compound No. 101), N-[2-({[(1S)-2-cyclopentyl-1-methylethyl]amino}methyl)phenyl]-5-(2-methyl-1,3-thiazol-4-yl)thiophene-2-sulfonamide (Compound No. 102), N-[2-({[(1S)-2-cycloheptyl-1-methylethyl]amino}methyl)phenyl]-5-(2-methyl-1,3-thiazol-4-yl)thiophene-2-sulfonamide (Compound No. 103), ethyl 3-[5-({[2-({[(1S)-2-cyclohexyl-1-methylethyl]amino}methyl)phenyl]amino}sulfonyl)-2-thienyl]-1,2,4-oxadiazole-5-carboxylate (Compound No. 104), ethyl 3-[5-({[2-({[(1S)-2-cyclopentyl-1-methylethyl]amino}methyl)phenyl]amino}sulfonyl)-2-thienyl]-1,2,4-oxadiazole-5-carboxylate (Compound No. 105), ethyl 3-[5-({[2-({[(1S)-2-cycloheptyl-1-methylethyl]amino}methyl)phenyl]amino}sulfonyl)-2-thienyl]-1,2,4-oxadiazole-5-carboxylate (Compound No. 106), N-[2-({[(1S)-2-cyclohexyl-1-methylethyl]amino}methyl)phenyl]-2,4-dimethyl-1,3-thiazole-5-sulfonamide (Compound No. 107), N-[2-({[(1S)-2-cyclopentyl-1-methylethyl]amino}methyl)phenyl]-2,4-dimethyl-1,3-thiazole-5-sulfonamide (Compound No. 108), N-[2-({[(1S)-2-cycloheptyl-1-methylethyl]amino}methyl)phenyl]-2,4-dimethyl-1,3-thiazole-5-sulfonamide (Compound No. 109), N-[2-({[(1S)-2-cyclopentyl-1-methylethyl]amino}methyl)phenyl]-5-methylthiophene-2-carboxamide (Compound No. 110), N-[2-({[(1S)-2-cyclopentyl-1-methylethyl]amino}methyl)phenyl]isonicotinamide (Compound No. 111), N-[2-({[(1S)-2-cyclohexyl-1-methylethyl]amino}methyl)phenyl]-2-(4-pyrimidin-2-ylpiperazin-1-yl)acetamide (Compound No. 112), methyl 3-({[2-({[(1S)-2-cyclopentyl-1-methylethyl]amino}methyl)phenyl]amino}sulfonyl)thiophene-2-carboxylate (Compound No. 113), methyl 3-({[2-({[(1S)-2-cycloheptyl-1-methylethyl]amino}methyl)phenyl]amino}sulfonyl)thiophene-2-carboxylate (Compound No. 114), N-[2-({[(1S)-2-cycloheptyl-1-methylethyl]amino}methyl)phenyl]-4-(1H-imidazol-1-yl)benzenesulfonamide (Compound No. 115), N-[2-({[(1S)-2-cyclohexyl-1-methylethyl]amino}methyl)phenyl]-2-(2-thienylsulfonyl)-1,2,3,4-tetrahydroisoquinoline-6-sulfonamide (Compound No. 116), N-[2-({[(1S)-2-cycloheptyl-1-methylethyl]amino}methyl)phenyl]-6-phenoxypyridine-3-sulfonamide (Compound No. 117), N-[2-({[(1S)-2-cyclopentyl-1-methylethyl]amino}methyl)phenyl]-6-phenoxypyridine-3-sulfonamide (Compound No. 118), N-[2-({[(1S)-2-cyclohexyl-1-methylethyl]amino}methyl)phenyl]-4-(1H-pyrrol-1-yl)benzenesulfonamide (Compound No. 119), N-[2-({[(1S)-2-cyclopentyl-1-methylethyl]amino}methyl)phenyl]-4-(1H-pyrrol-1-yl)benzenesulfonamide (Compound No. 120), N-[2-({[(1S)-2-cyclohexyl-1-methylethyl]amino}methyl)phenyl]-4-(1H-1,2,4-triazol-1-yl)benzenesulfonamide (Compound No. 121), N-[2-({[(1S)-2-cyclohexyl-1-methylethyl]amino}methyl)phenyl]-1H-imidazole-4-sulfonamide (Compound No. 122), N-[2-({[(1S)-2-cycloheptyl-1-methylethyl]amino}methyl)phenyl]-1H-imidazole-4-sulfonamide (Compound No. 123), N-[2-({[(1S)-2-cyclopentyl-1-methylethyl]amino}methyl)phenyl]-2-(4-pyrimidin-2-ylpiperazin-1-yl)acetamide (Compound No. 124), N-[2-({[(1S)-2-cycloheptyl-1-methylethyl]amino}methyl)phenyl]-2-(4-pyrimidin-2-ylpiperazin-1-yl)acetamide (Compound No. 125), N-[2-({[(1S)-2-cyclohexyl-1-methylethyl]amino}methyl)phenyl]-5-{3-[(1E)-N-hydroxy ethanimidoyl]phenyl}thiophene-2-sulfonamide (Compound No. 126), N-[2-({[(1S)-2-cyclohexyl-1-methylethyl]amino}methyl)phenyl]-5-{3-[(1E)-N-methoxy ethanimidoyl]phenyl}thiophene-2-sulfonamide (Compound No. 127), N-[2-({[(1S)-2-cycloheptyl-1-methylethyl]amino}methyl)phenyl]-2-furamide (Compound No. 128), 2-({[(1S)-2-cyclohexyl-1-methylethyl]amino}methyl)phenyl (4-methoxyphenyl)carbamate (Compound No. 129), N-[2-({[(1S)-2-cycloheptyl-1-methylethyl]amino}methyl)phenyl]-5-(phenylsulfonyl)thiophene-2-sulfonamide (Compound No. 130), N-[2-({[(1S)-2-cyclopentyl-1-methylethyl]amino}methyl)phenyl]-5-(phenylsulfonyl)thiophene-2-sulfonamide (Compound No. 131), N-[2-({[(1S)-2-cyclohexyl-1-methylethyl]amino}methyl)phenyl]-5-(phenylsulfonyl)thiophene-2-sulfonamide (Compound No. 132), N-[2-({[(1S)-2-cyclohexyl-1-methylethyl][(2,2-dimethylpropanoyl)oxy]amino}methyl)phenyl]-2-(2-thienylsulfonyl)-1,2,3,4-tetrahydroisoquinoline-6-sulfonamide (Compound No. 133), N-[2-({[(1S)-2-cyclohexyl-1-methylethyl][(2,2-dimethylpropanoyl)oxy]amino}methyl)phenyl]-2-(trifluoroacetyl)-1,2,3,4-tetrahydroisoquinoline-6-sulfonamide (Compound No. 134), N-[2-({[(1S)-2-cyclohexyl-1-methylethyl][(2,2-dimethylpropanoyl)oxy]amino}methyl)phenyl]-1,2,3,4-tetrahydroisoquinoline-6-sulfonamide (Compound No. 135), 5-(1,3-benzodioxol-5-yl)-N-[2-({[(1S)-2-cycloheptyl-1-methylethyl]amino}methyl)phenyl]thiophene-2-sulfonamide (Compound No. 136), N-[2-({[(1S)-2-cyclohexyl-1-methylethyl]amino}methyl)phenyl]-4-(1H-imidazol-1-yl)benzenesulfonamide (Compound No. 137), N-[2-({[(1S)-2-cyclopentyl-1-methylethyl]amino}methyl)phenyl]-4-(1H-imidazol-1-yl)benzenesulfonamide (Compound No. 138), N-[2-({[(1S)-2-cycloheptyl-1-methylethyl]amino}methyl)phenyl]-5-(1,3-oxazol-2-yl)thiophene-2-sulfonamide (Compound No. 139), N-[2-({[(1S)-2-cyclopentyl-1-methylethyl]amino}methyl)phenyl]thiophene-2-carboxamide (Compound No. 140), N-(4-acetylphenyl)-N'-[2-({[(1S)-2-cyclohexyl-1-methylethyl]amino}methyl)phenyl]urea (Compound No. 141), N-[2-({[(1S)-2-cyclopentyl-1-methylethyl]amino}methyl)phenyl]-1-benzothiophene-2-sulfonamide (Compound No. 142), N-[2-({[(1S)-2-cyclohexyl-1-methylethyl]amino}methyl)phenyl]-5-pyridin-4-ylthiophene-2-sulfonamide (Compound No. 143), N-[2-({[(1S)-2-cyclopentyl-1-methylethyl]amino}methyl)phenyl]-5-pyridin-3-ylthiophene-2-sulfonamide (Compound No. 144), 2-({[(1S)-2-cyclohexyl-1-methylethyl]amino}methyl)phenyl (4-acetylphenyl)carbamate (Compound No. 145), N-[2-({[(1S)-2-cyclopentyl-1-methylethyl]amino}methyl)phenyl]-4-(1H-1,2,4-triazol-1-yl)benzenesulfonamide (Compound No. 146), N-[2-({[(1S)-2-cycloheptyl-1-methylethyl]amino}methyl)phenyl]-4-(1H-1,2,4-triazol-1-yl)benzenesulfonamide (Compound No. 147), N-[2-({[(1S)-2-cyclopentyl-1-methylethyl]amino}methyl)phenyl]-2-(4-pyrimidin-2-ylpiperazin-1-yl)acetamide (Compound No. 148), 6-({[2-({[(1S)-2-cyclopentyl-1-methylethyl]amino}methyl)phenyl]amino}sulfonyl)-N-(4-methoxyphenyl)-3,4-dihydroisoquinoline-2(1H)-carboxamide (Compound No. 149), 6-({[2-({[(1S)-2-cyclopentyl-1-methylethyl]amino}methyl)phenyl]amino}sulfonyl)-N-isopropyl-3,4-dihydroisoquinoline-2(1H)-carboxamide (Compound No. 150), N-[2-({[(1S)-2-cyclopentyl-1-methylethyl]amino}methyl)phenyl]-2-(1H-imidazol-1-ylcarbonyl)-1,2,3,4-tetrahydroisoquinoline-6-sulfonamide (Compound No. 151), N-[2-({[(1S)-2-cyclohexyl-1-methylethyl]amino}methyl)phenyl]-4-({[(4-methoxyphenyl)amino]carbonyl}amino)benzenesulfonamide (Compound No. 152), 4-({[(4-acetylphenyl)amino]carbonyl}amino)-N-[2-({[(1S)-2-cyclohexyl-1-methylethyl]amino}methyl)phenyl]benzenesulfonamide (Compound No. 153), N-[4-({[2-({[(1S)-2-cyclohexyl-1-methylethyl]amino}methyl)phenyl]amino}sulfonyl)phenyl]thiophene-2-sulfonamide (Compound No. 154), N-[2-({[(1S)-2-cyclohexyl-1-methylethyl]amino}methyl)phenyl]-1-pyrimidin-2-yl-1H-imidazole-4-sulfonamide (Compound No. 155), N-[2-({[(1S)-2-cyclohexyl-1-methylethyl]amino}methyl)phenyl]-1-benzofuran-2-carboxamide (Compound No. 156), N-[2-({[(1S)-2-cyclopentyl-1-methylethyl]amino}methyl)phenyl]-1-benzofuran-2-carboxamide (Compound No. 157), N-[2-({[(1S)-2-cycloheptyl-1-methylethyl]amino}methyl)phenyl]-1-benzofuran-2-carboxamide (Compound No. 158), N-{3-[5-({[2-({[(1S)-2-cyclohexyl-1-methylethyl]amino}methyl)phenyl]amino}sulfonyl)-2-thienyl]phenyl}acetamide (Compound No. 159), N-{3-[5-({[2-({[(1S)-2-cyclopentyl-1-methylethyl]amino}methyl)phenyl]amino}sulfonyl)-2-thienyl]phenyl}acetamide (Compound No. 160), N-[2-({[(1S)-2-cyclohexyl-1-methylethyl]amino}methyl)phenyl]-5-(2,3,4-trimethoxy phenyl)thiophene-2-sulfonamide (Compound No. 161), N-[2-({[(1S)-2-cyclopentyl-1-methylethyl]amino}methyl)phenyl]-5-(2,3,4-trimethoxy phenyl)thiophene-2-sulfonamide (Compound No. 162), N-[2-({[(1S)-2-cyclopentyl-1-methylethyl]amino}methyl)phenyl]-4-fluorobenzamide (Compound No. 163),
N-[2-({[(1S)-2-cyclohexyl-1-methylethyl]amino}methyl)phenyl]-4-fluorobenzamide (Compound No. 164),
4-amino-N-[2-({[(1S)-2-cyclohexyl-1-methylethyl]amino}methyl)phenyl]benzamide (Compound No. 165),
N-[2-({[(1S)-2-cyclohexyl-1-methylethyl]amino}methyl)phenyl]-N'-isopropylurea (Compound No. 166),
N-[2-({[(1S)-2-cyclohexyl-1-methylethyl]amino}methyl)phenyl]-N'-isopropylthiourea (Compound No. 167),
N-[2-({[(1S)-2-cyclohexyl-1-methylethyl]amino}methyl)phenyl]-N'-(4-methoxyphenyl)urea (Compound No. 168),
N-(4-acetylphenyl)-6-({[2-({[(1S)-2-cyclopentyl-1-methylethyl]amino}methyl)phenyl]amino}sulfonyl)-3,4-dihydroisoquinoline-2(1H)-carboxamide (Compound No. 169),
N-[2-({[(1S)-2-cycloheptyl-1-methylethyl]amino}methyl)phenyl]-1,2,3,4-tetrahydro isoquinoline-6-sulfonamide (Compound No. 170),
N-[2-({[(1S)-2-cycloheptyl-1-methylethyl]amino}methyl)phenyl]-N'-isopropylurea (Compound No. 171),
N-[2-({[(1S)-2-cyclohexyl-1-methylethyl]amino}methyl)phenyl]isoxazole-5-carboxamide (Compound No. 172),
N-[2-({[(1S)-2-cyclohexyl-1-methylethyl]amino}methyl)phenyl]-5-isoxazol-5-ylthiophene-2-carboxamide (Compound No. 173),
N-[2-({[(1S)-2-cycloheptyl-1-methylethyl]amino}methyl)phenyl]-4-fluorobenzamide (Compound No. 174),
tert-butyl 4-(2-{[2-(2-furoylamino)benzyl]amino}propyl)piperidine-1-carboxylate (Compound No. 175),
N-[2-({[(1S)-2-cyclohexyl-1-methylethyl]amino}methyl)phenyl]-4-nitrobenzamide (Compound No. 176),
tert-butyl 4-[2-({2-[(4-fluorobenzoyl)amino]benzyl}amino)propyl]piperidine-1-carboxylate (Compound No. 177),
tert-butyl 4-[2-({2-[(2-thienylcarbonyl)amino]benzyl}amino)propyl]piperidine-1-carboxylate (Compound No. 178),
N-[2-({[(1S)-2-cyclohexyl-1-methylethyl]amino}methyl)phenyl]-1-pyrazin-2-yl-1H-imidazole-4-sulfonamide (Compound No. 179),
N-[2-({[(1S,2R)-2-cyclohexyl-2-hydroxy-1-methylethyl]amino}methyl)phenyl]thiophene-2-sulfonamide (Compound No. 180),
N-[2-({[(1S,2R)-2-cyclohexyl-2-hydroxy-1-methylethyl]amino}methyl)phenyl]-1-benzofuran-2-carboxamide (Compound No. 181),
tert-butyl 4-{2-[(2-{[(5-isoxazol-5-yl-2-thienyl)carbonyl]amino}benzyl)amino]propyl}piperidine-1-carboxylate (Compound No. 182),
N-[2-({[(1S)-2-cyclopentyl-1-methylethyl]amino}methyl)phenyl]-5-isoxazol-5-ylthiophene-2-sulfonamide (Compound No. 183),
N-(2-{[(2-cyclohexyl-1-methylethyl)amino]methyl}phenyl)-N'-[4-(1,3-oxazol-5-yl)phenyl]urea (Compound No. 183a),
N-(2-{[(2-cyclohexyl-1-methylethyl)amino]methyl}phenyl)-4-[(methylsulfonyl)amino]benzenesulfonamide (Compound No. 183b),
N-(4-chlorophenyl)-N'-(2-{[(2-cyclohexyl-1-methylethyl)amino]methyl}phenyl)urea (Compound No. 184),
N-(2-{[(2-cyclohexyl-1-methylethyl)amino]methyl}phenyl)-N'-phenylurea (Compound No. 185),
N-(2-{[(2-cyclohexyl-1-methylethyl)amino]methyl}phenyl)-N'-(3,4-dichlorophenyl)urea (Compound No. 186),
N-(2-{[(2-cyclohexyl-1-methylethyl)amino]methyl}phenyl)-N'-(3,4,5-trichlorophenyl)urea (Compound No. 187),
N-(2-{[(2-cyclohexyl-1-methylethyl)amino]methyl}phenyl)-N'-(2,4-dichlorophenyl)urea (Compound No. 188),
N-(2-{[(2-cyclohexyl-1-methylethyl)amino]methyl}phenyl)-N'-(4-fluorophenyl)urea (Compound No. 189),
N-(2-{[(2-cyclohexyl-1-methylethyl)amino]methyl}phenyl)-N'-1-naphthylurea (Compound No. 190),
N-(2-{[(2-cyclohexyl-1-methylethyl)amino]methyl}phenyl)-N'-isopropyl urea (Compound No. 191),
N-(2-{[(2-cyclohexyl-1-methylethyl)amino]methyl}phenyl)-N'-isopropylthiourea (Compound No. 192),
N-(2-{[(2-cyclohexyl-1-methylethyl)amino]methyl}phenyl)-N'-1-naphthylthiourea (Compound No. 193),
N-(2-{[(2-cyclohexyl-1-methylethyl)amino]methyl}phenyl)-N'-(trichloromethyl)thiourea (Compound No. 194),
N-(2-{[(2-cyclohexyl-1-methylethyl)amino]methyl}phenyl)-4-phenylpiperazine-1-carboxamide (Compound No. 195),
4-benzyl-N-(2-{[(2-cyclohexyl-1-methylethyl)amino]methyl}phenyl)piperazine-1-carboxamide (Compound No. 196),
N-(2-{[(2-cyclohexyl-1-methylethyl)amino]methyl}phenyl)piperazine-1-carboxamide (Compound No. 197),
4-(4-chlorophenyl)-N-(2-{[(2-cyclohexyl-1-methylethyl)amino]methyl}phenyl)piperazine-1-carboxamide (Compound No. 198),
N-(2-{[(2-cyclohexyl-1-methylethyl)amino]methyl}phenyl)-4-methylpiperazine-1-carboxamide (Compound No. 199),
N-(2-{[(2-cyclohexyl-1-methylethyl)amino]methyl}phenyl)morpholine-4-carboxamide (Compound No. 200),
N-(2-{[(2-cyclohexyl-1-methylethyl)amino]methyl}phenyl)-4-pyrimidin-4-ylpiperazine-1-carboxamide (Compound No. 201),
4-chloro-N-{[(2-{[(2-cyclohexyl-1-methylethyl)amino]methyl}phenyl)amino]carbonyl}benzenesulfonamide (Compound No. 202),
N-{[(2-{[(2-cyclohexyl-1-methylethyl)amino]methyl}phenyl)amino]carbonyl}-4-methyl benzenesulfonamide (Compound No. 203),
N-{[(2-{[(2-cyclohexyl-1-methylethyl)amino]methyl}phenyl)amino]carbonyl}benzamide (Compound No. 204),
N-{[(2-{[(2-cyclohexyl-1-methylethyl)amino]methyl}phenyl)amino]carbonyl}benzene carbothioamide (Compound No. 205),
4-[(4-chlorophenyl)sulfonyl]-N-(2-{[(2-cyclohexyl-1-methylethyl)amino]methyl}phenyl)piperazine-1-carboxamide (Compound No. 206),
N-(2-{[(2-cyclohexyl-1-methylethyl)amino]methyl}phenyl)-4-(phenylsulfonyl)piperazine-1-carboxamide (Compound No. 207),
N-(2-{[(2-cyclohexyl-1-methylethyl)amino]methyl}phenyl)-4-[(4-methylphenyl)sulfonyl]piperazine-1-carboxamide (Compound No. 208),
N-(2-{[(2-cyclohexyl-1-methylethyl)amino]methyl}phenyl)-4-(2-thienylsulfonyl)piperazine-1-carboxamide (Compound No. 209), N-{(1E)-amino[(2-{[(2-cyclohexyl-1-methylethyl)amino]methyl}phenyl)amino]methylene}-4-chlorobenzenesulfonamide (Compound No. 210), N-{(1E)-amino[(2-{[(2-cyclohexyl-1-methylethyl)amino]methyl}phenyl)amino]methylene}-4-methylbenzenesulfonamide (Compound No. 211), N-{(1E)-amino[(2-{[(2-cyclohexyl-1-methylethyl)amino]methyl}phenyl)amino]methylene}methanesulfonamide (Compound No. 212), N-{(1E)-amino[(2-{[(2-cyclohexyl-1-methylethyl)amino]methyl}phenyl)amino]methylene}thiophene-2-sulfonamide (Compound No. 213), N-(2-{[(1-methyl-2-piperazin-1-ylethyl)amino]methyl}phenyl)benzenesulfonamide (Compound No. 214), 4-methyl-N-(2-{[(1-methyl-2-piperazin-1-ylethyl)amino]methyl}phenyl)benzenesulfonamide (Compound No. 215), 4-chloro-N-(2-{[(1-methyl-2-piperazin-1-ylethyl)amino]methyl}phenyl)benzenesulfonamide (Compound No. 216), N-(2-{[(1-methyl-2-piperazin-1-ylethyl)amino]methyl}phenyl)thiophene-2-sulfonamide (Compound No. 217), 5-bromo-N-(2-{[(1-methyl-2-piperazin-1-ylethyl)amino]methyl}phenyl)thiophene-2-sulfonamide (Compound No. 218), 4-methyl-N-[2-({[1-methyl-2-(4-phenylpiperazin-1-yl)ethyl]amino}methyl)phenyl]benzenesulfonamide (Compound No. 219), N-[2-({[1-methyl-2-(4-phenylpiperazin-1-yl)ethyl]amino}methyl)phenyl]benzenesulfonamide (Compound No. 220), N-[2-({[1-methyl-2-(4-phenylpiperazin-1-yl)ethyl]amino}methyl)phenyl]thiophene-2-sulfonamide (Compound No. 221), 5-bromo-N-[2-({[1-methyl-2-(4-phenylpiperazin-1-yl)ethyl]amino}methyl)phenyl]thiophene-2-sulfonamide (Compound No. 222), 4-methyl-N-[2-({[1-methyl-2-(4-methylpiperazin-1-yl)ethyl]amino}methyl)phenyl]benzenesulfonamide (Compound No. 223), 4-chloro-N-[2-({[1-methyl-2-(4-methylpiperazin-1-yl)ethyl]amino}methyl)phenyl]benzenesulfonamide (Compound No. 224), N-[2-({[1-methyl-2-(4-methylpiperazin-1-yl)ethyl]amino}methyl)phenyl]thiophene-2-sulfonamide (Compound No. 225), N-(4-chlorophenyl)-N'-[2-({[1-methyl-2-(4-methylpiperazin-1-yl)ethyl]amino}methyl)phenyl]urea (Compound No. 226), N-(4-chlorophenyl)-N'-[2-({[1-methyl-2-(4-phenylpiperazin-1-yl)ethyl]amino}methyl)phenyl]urea (Compound No. 227), N-{2-[({[(2-cyclohexyl-1-methylethyl)amino]carbonyl}amino)methyl]phenyl}methanesulfonamide (Compound No. 228), N-{2-[({[(2-cyclohexyl-1-methylethyl)amino]carbonyl}amino)methyl]phenyl}benzenesulfonamide (Compound No. 229), N-{2-[({[(2-cyclohexyl-1-methylethyl)amino]carbonyl}amino)methyl]phenyl}-4-methylbenzenesulfonamide (Compound No. 230), N-{2-[({[(2-cyclohexyl-1-methylethyl)amino]carbonyl}amino)methyl]phenyl}thiophene-2-sulfonamide (Compound No. 231), 5-bromo-N-{2-[({[(2-cyclohexyl-1-methylethyl)amino]carbonyl}amino)methyl]phenyl}thiophene-2-sulfonamide (Compound No. 232), 4-chloro-N-{2-[({[(2-cyclohexyl-1-methylethyl)amino]carbonyl}amino)methyl]phenyl}benzenesulfonamide (Compound No. 233), N-(2-{[(2-cyclohexyl-1-methylethyl)amino]methyl}phenyl)-3-methoxy-4-piperazin-1-ylbenzenesulfonamide (Compound No. 234), N-(2-{[(2-cycloheptyl-1-methylethyl)amino]methyl}phenyl)-5-(phenylsulfonyl)thiophene-2-sulfonamide (Compound No. 235), N-(2-{[(2-cyclohexyl-1-methylethyl)amino]methyl}phenyl)-1-benzofuran-2-carboxamide (Compound No. 236), N-(2-{[(2-cyclopentyl-1-methylethyl)amino]methyl}phenyl)-2-(1,3-dioxo-1,3-dihydro-2H-isoindol-2-yl)acetamide (Compound No. 237), 2-{[(2-cyclohexyl-1-methylethyl)amino]methyl}phenyl (4-methoxyphenyl)carbamate (Compound No. 238), N-(2-{[(2-cycloheptyl-1-methylethyl)amino]methyl}phenyl)-6-(1H-imidazol-1-yl)nicotinamide (Compound No. 239), N-(4-{[(2-{[(2-cyclopropyl-1-methylethyl)amino]methyl}phenyl)amino]sulfonyl}phenyl)thiophene-2-sulfonamide (Compound No. 240), N-(2-{[(2-cyclopentyl-1-methylethyl)amino]methyl}phenyl)-2-(1H-1,2,4-triazol-1-yl)acetamide (Compound No. 241), N-(2-{[(2-cycloheptyl-1-methylethyl)amino]methyl}phenyl)-2-(4-pyrimidin-2-ylpiperazin-1-yl)acetamide (Compound No. 242), 2-{[(2-cyclopentyl-1-methylethyl)amino]methyl}phenyl (4-acetylphenyl)carbamate (Compound No. 243), N-(2-{[(2-cycloheptyl-1-methylethyl)amino]methyl}phenyl)isonicotinamide (Compound No. 244), N-(2-{[(2-cycloheptyl-1-methylethyl)amino]methyl}phenyl)-4-fluorobenzenesulfonamide (Compound No. 245), N-(2-{[(2-cyclohexyl-1-methylethyl)amino]methyl}phenyl)-6-(3-furyl)nicotinamide (Compound No. 246), N-(2-{[(2-cyclopentyl-1-methylethyl)amino]methyl}phenyl)-4-(1H-1,2,3-triazol-1-yl)benzenesulfonamide (Compound No. 247), N-(3-{[(2-cycloheptyl-1-methylethyl)amino]methyl}pyridin-2-yl)-2-furamide (Compound No. 248), N-(2-{[(2-cyclopentyl-1-methylethyl)amino]methyl}phenyl)isonicotinamide (Compound No. 249), N-(2-{[(2-cyclohex-1-en-1-yl-1-methylethyl)amino]methyl}phenyl)-5-(1,3-oxazol-5-yl)furan-2-sulfonamide (Compound No. 250), N-(2-{[(2-cyclopropyl-1-methylethyl)amino]methyl}phenyl)-N'-(3-methylisoxazol-5-yl)urea (Compound No. 251), 2-{[(2-cyclohexyl-1-methylethyl)amino]methyl}phenyl[4-(1H-imidazol-1-yl)phenyl]carbamate (Compound No. 252), N-(2-{[(2-cyclohexyl-1-methylethyl)amino]methyl}phenyl)-5-(3-furyl)nicotinamide (Compound No. 253), 1-benzofuran-2-ylmethyl (2-{[(2-cyclohexyl-1-methylethyl)amino]methyl}phenyl)carbamate (Compound No. 254), N-[2-({[1-methyl-2-(4-methylpiperazin-1-yl)ethyl]amino}methyl)phenyl]thiophene-2-sulfonamide (Compound No. 255), N-1-benzothien-2-yl-N'-[2-({[1-methyl-2-(tetrahydro-2H-pyran-4-yl)ethyl]amino}methyl)phenyl]urea (Compound No. 256),
2-{[(2-cyclohexyl-1-methylethyl)amino]methyl}phenyl[4-(1H-pyrazol-1-yl)phenyl]carbamate (Compound No. 257),
2-{[(2-cyclohexyl-1-methylethyl)amino]methyl}phenyl[4-(2-furyl)phenyl]carbamate (Compound No. 258),
3,3'-bipyridin-6-yl (2-{[(2-cyclohexyl-1-methylethyl)amino]methyl}phenyl)carbamate (Compound No. 259),
Pyridin-4-yl (2-{[(2-cyclohexyl-1-methylethyl)amino]methyl}phenyl)carbamate (Compound No. 260),
N-1-benzothien-2-yl-N'-(4-{[(2-cyclohexyl-1-methylethyl)amino]methyl}pyridin-3-yl)urea (Compound No. 261),
N-1-benzothien-2-yl-N'-(2-{[(2-cyclohexyl-1-methylethyl)amino]methyl}pyridin-3-yl)urea (Compound No. 262),
3-{[(2-cyclohexyl-1-methylethyl)amino]methyl}pyridin-4-yl 1-benzothien-2-ylcarbamate (Compound No. 263),
3-{[(2-cyclohexyl-1-methylethyl)amino]methyl}pyridin-2-yl 1-benzothien-2-ylcarbamate (Compound No. 264),
N-1-benzothien-2-yl-N'-(3-{[(2-cyclohexyl-1-methylethyl)amino]methyl}pyridin-2-yl)urea (Compound No. 265),
N-1-benzothien-2-yl-N'-(3-{[(2-cyclohexyl-1-methylethyl)amino]methyl}pyridin-4-yl)urea (Compound No. 266),
2-{[(2-cyclohexyl-1-methylethyl)amino]methyl}pyridin-3-yl 1-benzothien-2-ylcarbamate (Compound No. 267),
4-{[(2-cyclohexyl-1-methylethyl)amino]methyl}pyridin-3-yl 1-benzothien-2-ylcarbamate (Compound No. 268),
1-benzothien-2-yl (3-{[(2-cyclohexyl-1-methylethyl)amino]methyl}pyridin-2-yl)carbamate (Compound No. 269),
1-benzothien-2-yl (4-{[(2-cyclohexyl-1-methylethyl)amino]methyl}pyridin-3-yl)carbamate (Compound No. 270),
1-benzothien-2-yl (2-{[(2-cyclohexyl-1-methylethyl)amino]methyl}pyridin-3-yl)carbamate (Compound No. 271),
2-{[(2-cyclopropyl-1-methylethyl)amino]methyl}phenyl[4-(2-furyl)phenyl]carbamate (Compound No. 272),
2-{[(2-cyclopropyl-1-methylethyl)amino]methyl}phenyl 1-benzothien-2-ylcarbamate (Compound No. 273),
1-benzothien-2-yl[2-({[1-methyl-2-(tetrahydro-2H-pyran-4-yl)ethyl]amino}methyl)phenyl]carbamate (Compound No. 274),
1-benzothien-2-yl (3-{[(2-cyclohexyl-1-methylethyl)amino]methyl}pyridin-4-yl)carbamate (Compound No. 275),
1-benzothien-2-yl (2-{[(2-cyclopropyl-1-methylethyl)amino]methyl}phenyl)carbamate (Compound No. 276),
N-(2-{[(2-cyclopropyl-1-methylethyl)amino]methyl}phenyl)-2-(1,3-dioxo-1,3-dihydro-2H-isoindol-2-yl)acetamide (Compound No. 277),
1-benzothien-2-yl[2-({[1-methyl-2-(tetrahydro-2H-pyran-4-yl)ethyl]amino}methyl)pyridin-3-yl]carbamate (Compound No. 278),
N-(2-{[(2-cyclopentyl-1-methylethyl)amino]methyl}phenyl)-2-(1H-1,2,4-triazol-1-yl)acetamide (Compound No. 279),
1-benzothien-2-yl (2-{[(1-methyl-2-piperidin-4-ylethyl)amino]methyl}phenyl)carbamate (Compound No. 280),
3-{[(1-methyl-2-piperidin-4-ylethyl)amino]methyl}pyridin-4-yl 1-benzothien-2-ylcarbamate (Compound No. 281),
N-1-benzothien-2-yl-N'-(2-{[(1-methyl-2-piperidin-4-ylethyl)amino]methyl}phenyl)urea (Compound No. 282),
N-(2-{[(1-methyl-2-piperidin-4-ylethyl)amino]methyl}phenyl)thiophene-2-sulfonamide (Compound No. 283),
N-(2-{[(1-methyl-2-piperidin-4-ylethyl)amino]methyl}phenyl)-2-(1H-pyrazol-1-yl)acetamide (Compound No. 284),
N-(2-{[(1-methyl-2-piperidin-4-ylethyl)amino]methyl}phenyl)isonicotinamide (Compound No. 285),
4-chloro-N-({[2-({[(1S)-2-cyclohexyl-1-methylethyl]amino}methyl)phenyl]amino}carbonyl)benzenesulfonamide (Compound No. 286),
N-[2-({[(1S)-2-cyclohexyl-1-methylethyl]amino}methyl)phenyl]-N'-(4-morpholin-4-ylphenyl)urea (Compound No. 287),
N-[2-({[(1S)-2-cyclohexyl-1-methylethyl]amino}methyl)phenyl]-N'-[3-(2-furyl)-1H-pyrazol-5-yl]urea (Compound No. 288),
N-[2-({[(1S)-2-cyclohexyl-1-methylethyl]amino}methyl)phenyl]-N'-(5-oxo-1-phenyl-4,5-dihydro-1H-pyrazol-3-yl)urea (Compound No. 289),
N-[2-({[(1S)-2-cyclohexyl-1-methylethyl]amino}methyl)phenyl]-N'-(4-methoxy-1,2-benzisoxazol-3-yl)urea (Compound No. 290),
N-[2-({[(1S)-2-cyclohexyl-1-methylethyl]amino}methyl)phenyl]-N'-(3,4-dimethylisoxazol-5-yl)urea (Compound No. 291),
N-[2-({[(1S)-2-cyclohexyl-1-methylethyl]amino}methyl)phenyl]-N'-[1-methyl-3-(2-thienyl)-1H-pyrazol-5-yl]urea (Compound No. 292),
N-[2-({[(1S)-2-cyclohexyl-1-methylethyl]amino}methyl)phenyl]-1H-imidazole-4-sulfonamide (Compound No. 293),
N-[2-({[(1S)-2-cyclopentyl-1-methylethyl]amino}methyl)phenyl]-1H-imidazole-4-sulfonamide (Compound No. 294),
N-[4-({[2-({[(1S)-2-cyclohexyl-1-methylethyl]amino}methyl)phenyl]amino}sulfonyl)phenyl]acetamide (Compound No. 295),
4-amino-N-[2-({[(1S)-2-cyclohexyl-1-methylethyl]amino}methyl)phenyl]benzenesulfonamide (Compound No. 296),
N-[4-({[2-({[(1S)-2-cyclopentyl-1-methylethyl]amino}methyl)phenyl]amino}sulfonyl)phenyl]thiophene-2-sulfonamide (Compound No. 297),
2-thienylmethyl[2-({[(1S)-2-cyclohexyl-1-methylethyl]amino}methyl)phenyl]carbamate (Compound No. 298),
2-thienylmethyl[2-({[(1S)-2-cyclopentyl-1-methylethyl]amino}methyl)phenyl]carbamate (Compound No. 299),
N-[2-({[(1S)-2-cyclopentyl-1-methylethyl]amino}methyl)phenyl]-5-(2,3,4-trimethoxyphenyl)thiophene-2-sulfonamide (Compound No. 300),
N-[2-({[(1S)-2-cyclohexyl-1-methylethyl]amino}methyl)phenyl]-4-{3-[(E)-(hydroxyimino)methyl]-1H-pyrrol-1-yl}benzenesulfonamide (Compound No. 301),
N-[2-({[(1S)-2-cyclohexyl-1-methylethyl]amino}methyl)phenyl]-4-(3-formyl-1H-pyrrol-1-yl)benzamide (Compound No. 302),
N-[2-({[(1S)-2-cyclohexyl-1-methylethyl]amino}methyl)phenyl]-N'-[4-(1,2,3-thiadiazol-4-yl)phenyl]urea (Compound No. 303),
N-[2-({[(1S)-2-cyclohexyl-1-methylethyl]amino}methyl)phenyl]-1-benzofuran-6-carboxamide (Compound No. 304),
N-[2-({[(1S)-2-cyclohexyl-1-methylethyl]amino}methyl)phenyl]-3,5-dimethylisoxazole-4-sulfonamide (Compound No. 305),
N-[4-({[2-({[(1S)-2-cyclohexyl-1-methylethyl]amino}methyl)phenyl]amino}sulfonyl)phenyl]isoxazole-5-carboxamide (Compound No. 306),
N-[4-({[2-({[(1S)-2-cyclohexyl-1-methylethyl]amino}methyl)phenyl]amino}sulfonyl)phenyl]-3,5-dimethylisoxazole-4-sulfonamide (Compound No. 307), N-[4-({2-({[(1S)-2-cyclohexyl-1-methylethyl] amino}methyl)phenyl]amino}sulfonyl)phenyl]-1-methyl-1H-imidazole-4-sulfonamide (Compound No. 308), N-[2-({[(1S)-2-cyclohexyl-1-methylethyl]amino}methyl) phenyl]-4-(1-hydroxyethyl)Benzenesulfonamide (Compound No. 309), pyridin-3-ylmethyl[2-({[(1S)-2-cyclohexyl-1-methylethyl] amino}methyl)phenyl]carbamate (Compound No. 310), pyridin-3-ylmethyl[2-({[(1S)-2-cyclopentyl-1-methylethyl] amino}methyl)phenyl]carbamate (Compound No. 311), pyridin-3-ylmethyl[2-({[(1S,2R)-2-cyclohexyl-2-hydroxy-1-methylethyl]amino}methyl)phenyl]carbamate (Compound No. 312), N-[2-({[(1S)-2-cyclopentyl-1-methylethyl]amino}methyl) phenyl]-1-pyrazin-2-yl-1H-imidazole-4-sulfonamide (Compound No. 313), 5-chloro-N-[2-({[(1S,2R)-2-cyclohexyl-2-hydroxy-1-methylethyl]amino}methyl)phenyl]-3-methyl-1-benzothiophene-2-sulfonamide (Compound No. 314), ethyl 3-[5-({2-({[(1S)-2-cyclopentyl-1-methylethyl] amino}methyl)phenyl]amino}sulfonyl)-2-thienyl]benzoate (Compound No. 315), 4-acetyl-N-[4-({2-({[(1S)-2-cyclohexyl-1-methylethyl] amino}methyl)phenyl]amino}sulfonyl)phenyl]benzenesulfonamide (Compound No. 316), N-[4-({2-({[(1S)-2-cyclohexyl-1-methylethyl] amino}methyl)phenyl]amino}sulfonyl)phenyl]-2,4-dimethyl-1,3-thiazole-5-sulfonamide (Compound No. 317), N-1,3-benzothiazol-2-yl-N'-[2-({[(1S)-2-cyclohexyl-1-methylethyl]amino}methyl)phenyl]Urea (Compound No. 318), N-[2-({[(1S)-2-cyclohexyl-1-methylethyl]amino}methyl) phenyl]-N'-[4-(1,3-oxazol-5-yl)phenyl]urea (Compound No. 319), N-[2-({[(1S)-2-cyclohexyl-1-methylethyl]amino}methyl) phenyl]-4-(1,3-dioxo-1,3-dihydro-2H-isoindol-2-yl)benzenesulfonamide (Compound No. 320), N-[2-({[(1S,2S)-2-cyclohexyl-2-hydroxy-1-methylethyl] amino}methyl)phenyl]-1,2,3,4-tetrahydroisoquinoline-6-sulfonamide (Compound No. 321), N-[2-({[(1S,2S)-2-cyclohexyl-2-hydroxy-1-methylethyl] amino}methyl)phenyl]-1-benzothiophene-2-sulfonamide (Compound No. 322), N-[2-({[(1S,2S)-2-cyclohexyl-2-hydroxy-1-methylethyl] amino}methyl)phenyl]-5-isoxazol-5-ylthiophene-2-sulfonamide (Compound No. 323), N-[2-({[(1S,2S)-2-cyclohexyl-2-hydroxy-1-methylethyl] amino}methyl)phenyl]-2-(trifluoroacetyl)-1,2,3,4-tetrahydroisoquinoline-6-sulfonamide (Compound No. 324), N-[2-({[(1S)-2-cyclohexyl-1-methylethyl]amino}methyl) phenyl]-4-(3-formyl-1H-pyrrol-1-yl)benzenesulfonamide (Compound No. 325), N-[3-({[(1S)-2-cyclohexyl-1-methylethyl]amino}methyl) pyridin-2-yl]-5-isoxazol-5-ylthiophene-2-sulfonamide (Compound No. 326), N-[3-({[(1S)-2-cyclopentyl-1-methylethyl]amino}methyl) pyridin-2-yl]-5-isoxazol-3-ylthiophene-2-sulfonamide (Compound No. 327), N-[3-({[(1S)-2-cyclohexyl-1-methylethyl]amino}methyl) pyridin-2-yl]-4-(1H-pyrrol-1-yl)benzenesulfonamide (Compound No. 328), N-[2-({[(1S)-2-cyclopentyl-1-methylethyl]amino}methyl) phenyl]-4-(3-formyl-1H-pyrrol-1-yl)benzenesulfonamide (Compound No. 329), N-[2-({[(1S)-2-cyclohexyl-1-methylethyl]amino}methyl) phenyl]-4-(2-oxo-1,3-oxazolidin-3-yl)benzenesulfonamide (Compound No. 330), N-[4-({2-({[(1S)-2-cyclohexyl-1-methylethyl] amino}methyl)phenyl]amino}sulfonyl)phenyl] thiophene-3-sulfonamide (Compound No. 331), N-[2-({[(1S)-2-cyclohexyl-1-methylethyl]amino}methyl) phenyl]-5-(1-methyl-1H-pyrazol-4-yl)thiophene-2-sulfonamide (Compound No. 332), N-[2-({[(1S)-2-cyclohexyl-1-methylethyl]amino}methyl) phenyl]-1-(2-thienylsulfonyl)-1H-imidazole-4-sulfonamide (Compound No. 333), N-[2-({[(1S)-2-cyclopentyl-1-methylethyl]amino}methyl) phenyl]-2,1,3-benzothiadiazole-4-sulfonamide (Compound No. 334), N-[4-({2-({[(1S)-2-cyclopentyl-1-methylethyl] amino}methyl)phenyl]amino}sulfonyl)phenyl]-1-methyl-1H-imidazole-4-sulfonamide (Compound No. 335), N-[2-({[(1S)-2-cyclopentyl-1-methylethyl]amino}methyl) phenyl]-4-[(methylsulfonyl)amino]Benzenesulfonamide (Compound No. 336), 4-[(butylsulfonyl)amino]-N-[2-({[(1S)-2-cyclohexyl-1-methylethyl]amino}methyl)phenyl]benzenesulfonamide (Compound No. 337), N-[2-({[(1S)-2-cyclohexyl-1-methylethyl]amino}methyl) phenyl]-4-[(ethylsulfonyl)amino]Benzenesulfonamide (Compound No. 338), 5-chloro-N-[4-({2-({[(1S)-2-cyclohexyl-1-methylethyl] amino}methyl)phenyl]amino}sulfonyl)phenyl]-1,3-dimethyl-1H-pyrazole-4-sulfonamide (Compound No. 339), methyl 4-({[4-({2-({[(1S)-2-cyclohexyl-1-methylethyl] amino}methyl)phenyl]amino}sulfonyl)phenyl] amino}sulfonyl)-2,5-dimethyl-3-furoate (Compound No. 340), methyl 5-({[4-({2-({[(1S)-2-cyclohexyl-1-methylethyl] amino}methyl)phenyl]amino}sulfonyl)phenyl] amino}sulfonyl)-3-methylthiophene-2-carboxylate (Compound No. 341), methyl 5-({[4-({2-({[(1S)-2-cyclohexyl-1-methylethyl] amino}methyl)phenyl]amino}sulfonyl)phenyl] amino}sulfonyl)-2-furoate (Compound No. 342), N-[2-({[(1S)-2-cyclohexyl-1-methylethyl]amino}methyl) phenyl]-N'-(3-oxo-1,3-dihydro-2-benzofuran-5-yl)urea (Compound No. 343), 2-[({[2-({[(1S)-2-cyclohexyl-1-methylethyl]amino}methyl) phenyl]amino}carbonyl)amino]benzamide (Compound No. 344), N-[2-({[(1S)-2-cyclohexyl-1-methylethyl]amino}methyl) phenyl]-N'-isoquinolin-5-ylurea (Compound No. 345), N-[2-({[(1S)-2-cyclohexyl-1-methylethyl]amino}methyl) phenyl]-N'-morpholin-4-ylurea (Compound No. 346), N-1,3-benzothiazol-6-yl-N'-[2-({[(1S)-2-cyclohexyl-1-methylethyl]amino}methyl)phenyl]urea (Compound No. 347), N-[2-({[(1S)-2-cyclohexyl-1-methylethyl]amino}methyl) phenyl]-N'-1,3-thiazol-2-ylurea (Compound No. 348), ethyl 3-[5-({2-({[(1S)-2-cyclohexyl-1-methylethyl] amino}methyl)phenyl]amino}sulfonyl)-2-thienyl]benzoate (Compound No. 349), N-[2-({[(1S)-2-cyclohexyl-1-methylethyl]amino}methyl) phenyl]-1,3-benzothiazole-2-sulfonamide (Compound No. 350), N-[2-({[(1S,2R)-2-cyclohexyl-2-hydroxy-1-methylethyl] amino}methyl)phenyl]-4-(1H-1,2,4-triazol-1-yl)benzenesulfonamide (Compound No. 351), N-[2-({[(1S,2R)-2-cyclohexyl-2-hydroxy-1-methylethyl] amino}methyl)phenyl]-4-(1H-pyrrol-1-yl)benzenesulfonamide (Compound No. 352), N-[4-({[2-({[(1S)-2-cyclohexyl-1-methylethyl]amino}methyl)phenyl]amino}sulfonyl)phenyl]-2-(trifluoroacetyl)-1,2,3,4-tetrahydroisoquinoline-7-sulfonamide (Compound No. 353), N-[2-({[(1S)-2-cyclohexyl-1-methylethyl]amino}methyl)phenyl]-4-pyridin-3-ylbenzenesulfonamide (Compound No. 354), N-[2-({[(1S)-2-cyclopentyl-1-methylethyl]amino}methyl)phenyl]-4-pyridin-3-ylbenzenesulfonamide (Compound No. 355), N-[2-({[(1S)-2-cyclohexyl-1-methylethyl]amino}methyl)phenyl]-4-pyrimidin-5-ylbenzenesulfonamide (Compound No. 356), N-[2-({[(1S)-2-cyclopentyl-1-methylethyl]amino}methyl)phenyl]-4-pyrimidin-5-ylbenzenesulfonamide (Compound No. 357), N-[2-({[(1S)-2-cyclohexyl-1-methylethyl]amino}methyl)phenyl]-4-(1-methyl-1H-pyrazol-4-yl)benzenesulfonamide (Compound No. 358), N-[2-({[(1S)-2-cyclopentyl-1-methylethyl]amino}methyl)phenyl]-4-(1-methyl-1H-pyrazol-4-yl)benzenesulfonamide (Compound No. 359), N-[2-({[(1S,2R)-2-cyclohexyl-2-hydroxy-1-methylethyl]amino}methyl)phenyl]-1,2,3,4-tetrahydroisoquinoline-6-sulfonamide (Compound No. 360), N-[2-({[(1S,2R)-2-cyclohexyl-2-hydroxy-1-methylethyl]amino}methyl)phenyl]-5-isoxazol-5-ylthiophene-2-sulfonamide (Compound No. 361), N-[2-({[(1S,2R)-2-cyclohexyl-2-hydroxy-1-methylethyl]amino}methyl)phenyl]-1-benzothiophene-2-sulfonamide (Compound No. 362), N-[2-({[2-({[(1S)-2-cyclohexyl-1-methylethyl]amino}methyl)phenyl]amino}sulfonyl)phenyl]-1-methyl-1H-imidazole-4-sulfonamide (Compound No. 363), N-[3-({[2-({[(1S)-2-cyclohexyl-1-methylethyl]amino}methyl)phenyl]amino}sulfonyl)phenyl]-1-methyl-1H-imidazole-4-sulfonamide (Compound No. 364), 5-chloro-N-[4-({[2-({[(1S)-2-cyclopentyl-1-methylethyl]amino}methyl)phenyl]amino}sulfonyl)phenyl]-1,3-dimethyl-1H-pyrazole-4-sulfonamide (Compound No. 365), N-[2-({[(1S)-2-cyclohexyl-1-methylethyl]amino}methyl)phenyl]-N,N-dimethylsulfamide (Compound No. 366), N-[2-({[(1S)-2-cyclohexyl-1-methylethyl]amino}methyl)phenyl]-4-(1,2,3-thiadiazol-4-yl)benzenesulfonamide (Compound No. 367), N-[2-({[(1S)-2-cyclohexyl-1-methylethyl]amino}methyl)phenyl]-4-(1,3-oxazol-5-yl)benzenesulfonamide (Compound No. 368), N-[3-({[2-({[(1S)-2-cyclohexyl-1-methylethyl]amino}methyl)phenyl]amino}sulfonyl)phenyl]thiophene-2-sulfonamide (Compound No. 369), N-[2-({[2-({[(1S)-2-cyclohexyl-1-methylethyl]amino}methyl)phenyl]amino}sulfonyl)phenyl]thiophene-2-sulfonamide (Compound No. 370), 3-amino-N-[2-({[(1S)-2-cyclohexyl-1-methylethyl]amino}methyl)phenyl]benzenesulfonamide (Compound No. 371), 2-amino-N-[2-({[(1S)-2-cyclohexyl-1-methylethyl]amino}methyl)phenyl]benzenesulfonamide (Compound No. 372), N-[3-({[2-({[(1S)-2-cyclohexyl-1-methylethyl]amino}methyl)phenyl]amino}sulfonyl)phenyl]-2,4-dimethyl-1,3-thiazole-5-sulfonamide (Compound No. 373), N-[3-({[2-({[(1S)-2-cyclohexyl-1-methylethyl]amino}methyl)phenyl]amino}sulfonyl)phenyl]-3,5-dimethylisoxazole-4-sulfonamide (Compound No. 374), N-[3-({[2-({[(1S)-2-cyclohexyl-1-methylethyl]amino}methyl)phenyl]amino}sulfonyl)phenyl]isoxazole-5-carboxamide (Compound No. 375), N-[3-({[2-({[(1S)-2-cyclohexyl-1-methylethyl]amino}methyl)phenyl]amino}sulfonyl)phenyl]thiophene-3-sulfonamide (Compound No. 376), ethyl 5-{[4-({[2-({[(1S)-2-cyclohexyl-1-methylethyl]amino}methyl)phenyl]amino}sulfonyl)phenyl]amino}-5-oxopentanoate (Compound No. 377), 2-amino-N-[2-({[(1S)-2-cyclohexyl-1-methylethyl]amino}methyl)phenyl]-1,3-benzothiazole-5-sulfonamide (Compound No. 378), 5-chloro-N-[3-({[2-({[(1S)-2-cyclohexyl-1-methylethyl]amino}methyl)phenyl]amino}sulfonyl)phenyl]-1,3-dimethyl-1H-pyrazole-4-sulfonamide (Compound No. 379), N-[2-({[2-({[(1S)-2-cyclohexyl-1-methylethyl]amino}methyl)phenyl]amino}sulfonyl)phenyl]-2,4-dimethyl-1,3-thiazole-5-sulfonamide (Compound No. 380), N-[4-({[2-({[(1S)-2-cyclopentyl-1-methylethyl]amino}methyl)phenyl]amino}sulfonyl)phenyl]thiophene-3-sulfonamide (Compound No. 381), N-(2-{[[(1S)-2-cyclohexyl-1-methylethyl](methylsulfonyl)amino]methyl}phenyl)-2-[(methylsulfonyl)amino]benzenesulfonamide (Compound No. 382), N-[2-({[(1S)-2-cyclopentyl-1-methylethyl]amino}methyl)phenyl]-4-(1H-pyrazol-1-yl)benzenesulfonamide (Compound No. 383), N-[2-({[(1S)-2-cyclohexyl-1-methylethyl]amino}methyl)phenyl]-4-(1H-pyrazol-1-yl)benzenesulfonamide (Compound No. 384), N-[2-({[(1S)-2-cyclohexyl-1-methylethyl]amino}methyl)phenyl]-3-fluoro-4-(1H-1,2,4-triazol-1-yl)benzenesulfonamide (Compound No. 385),

[5-(2-thienyl)isoxazol-3-yl]methyl[2-({[(1S)-2-cyclohexyl-1-methylethyl]amino}methyl)phenyl]carbamate (Compound No. 386), N-[(1S)-2-cyclopentyl-1-methylethyl]-2-[(2-thienylsulfonyl)amino]benzamide (Compound No. 387), N-[(1S)-2-cyclohexyl-1-methylethyl]-2-[(2-thienylsulfonyl)amino]benzamide (Compound No. 388), methyl[5-({[2-({[(1S)-2-cyclohexyl-1-methylethyl]amino}methyl)phenyl]amino}sulfonyl)-1H-benzimidazol-2-yl]carbamate (Compound No. 389), methyl[6-({[4-({[2-({[(1S)-2-cyclohexyl-1-methylethyl]amino}methyl)phenyl]amino}sulfonyl)phenyl]amino}sulfonyl)-1H-benzimidazol-2-yl]carbamate (Compound No. 390), N-[2-({[(1S)-2-cyclohexyl-1-methylethyl]amino}methyl)phenyl]-4-[(1E)-N-hydroxyethanimidoyl]benzenesulfonamide (Compound No. 391), N-[2-({[(1S)-2-cyclohexyl-1-methylethyl]amino}methyl)phenyl]-4-[(1E)-N-methoxyethanimidoyl]benzenesulfonamide (Compound No. 392), 4-{[amino(imino)methyl]amino}-N-[2-({[(1S)-2-cyclohexyl-1-methylethyl]amino}methyl)phenyl]benzenesulfonamide (Compound No. 393), N-[2-({[(1S)-2-cyclohexyl-1-methylethyl]amino}methyl)phenyl]sulfamide (Compound No. 394), N-[4-({[2-({[(1S)-2-cyclohexyl-1-methylethyl]amino}methyl)phenyl]amino}sulfonyl)phenyl]-4-[(1E)-N-hydroxyethanimidoyl]benzenesulfonamide (Compound No. 395), N-[2-({[(1S)-2-cyclohexyl-1-methylethyl]amino}methyl)phenyl]-3-{[(isopropylamino)carbonyl]amino}benzenesulfonamide (Compound No. 396), ethyl (2Z)-4-{[2-({[(1S)-2-cyclohexyl-1-methylethyl]amino}methyl)phenyl]amino}-4-oxobut-2-enoate (Compound No. 397), N-[2-({[(1S)-2-cyclohexyl-1-methylethyl]amino}methyl)phenyl]-1-benzofuran-2-sulfonamide (compound No. 398), N-[2-({[(1S)-2-cyclopentyl-1-methylethyl]amino}methyl)phenyl]-1-benzofuran-2-sulfonamide (compound No. 399), N-[3-({[2-cyclohexyl-1-methylethyl]amino}methyl)pyridin-4-yl]thiophene-2-sulfonamide (compound No. 400), 2-amino-N-[2-({[2-cyclohexyl-1-methylethyl]amino}methyl)phenyl]-1H-benzimidazole-5-sulfonamide (compound No. 401), N-[2-({[2-cyclohexyl-1-methylethyl]amino}methyl)phenyl] guanidine (compound No. 402), N-[2-({[2-cyclohexyl-1-methylethyl]amino}methyl)phenyl]-4-(5-oxo-1,5-dihydro-4H-1,2,4-triazol-4-yl)benzenesulfonamide (compound No. 403), N-[2-({[2-cyclohexyl-1-methylethyl]amino}methyl)phenyl]-4-(5-methyl-1,3,4-oxadiazol-2-yl)benzenesulfonamide (compound No. 404), N-[2-({[(1S)-2-cyclopentyl-1-methylethyl]amino}methyl)phenyl]-4-(1-methyl-1H-pyrazol-4-yl)benzenesulfonamide (compound No. 405), N-[2-({[2-cyclohexyl-1-methylethyl]amino}methyl)phenyl]-4-(3,5-dimethylisoxazol-4-yl)benzenesulfonamide (compound No. 406), N-[2-({[2-cyclohexyl-1-methylethyl]amino}methyl)phenyl]-5-(3,5-dimethylisoxazol-4-yl)thiophene-2-sulfonamide (compound No. 407), N-[2-({[(1S)-2-cyclopentyl-1-methylethyl]amino}methyl)phenyl]-5-(3,5-dimethylisoxazol-4-yl)thiophene-2-sulfonamide (compound No. 408), N-[2-({[2-cyclohexyl-1-methylethyl]amino}methyl)phenyl]-3-[(methylsulfonyl)amino]benzenesulfonamide (compound No. 409), N-[2-({[2-cyclohexyl-1-methylethyl]amino}methyl)phenyl]-4-{[(dimethylamino)sulfonyl]amino}benzenesulfonamide (compound No. 410), N-[3-({[2-cyclohexyl-1-methylethyl]amino}methyl)pyridin-4-yl]-1-benzothiophene-2-sulfonamide (compound No. 411), N-[2-({[2-cyclohexyl-1-methylethyl]amino}methyl)phenyl]-5-{[(1-methyl-1H-imidazol-4-yl)sulfonyl]amino}pyridine-2-sulfonamide (compound No. 412), N-[2-({[2-cyclohexyl-1-methylethyl]amino}methyl)phenyl]-5-[(methylsulfonyl)amino]pyridine-2-sulfonamide (compound No. 413), N-[2-({[2-cyclohexyl-1-methylethyl]amino}methyl)phenyl]-5-[(2-thienylsulfonyl)amino]pyridine-2-sulfonamide (compound No. 414), 5-bromo-N-[2-({[2-cyclohexyl-1-methylethyl]amino}methyl)phenyl]-1,3-thiazole-2-sulfonamide (compound No. 415),

[5-(2-thienyl)isoxazol-3-yl]methyl[2-({[(1S)-2-cyclopentyl-1-methylethyl]amino}methyl)phenyl]carbamate (compound No. 416), N-[2-({[2-cyclohexyl-1-methylethyl]amino}methyl)phenyl]-2-fluoro-5-(1H-pyrrol-1-yl)benzenesulfonamide (compound No. 417), 2-amino-N-[2-({[2-cyclohexyl-1-methylethyl]amino}methyl)phenyl]-1,3-benzothiazole-4-sulfonamide (compound No. 418), N-[2-({2-({[2-cyclohexyl-1-methylethyl]amino}methyl)phenyl]amino}sulfonyl)phenyl]thiophene-3-sulfonamide (compound No. 419), N-[2-({[(1S)-2-cyclopentyl-1-methylethyl]amino}methyl)phenyl]-3-fluoro-4-(1H-tetrazol-1-yl)benzenesulfonamide (compound No. 420), N-[2-({[(2S)-2-cyclohexyl-2-hydroxy-1-methylethyl]amino}methyl)phenyl]-4-(1H-pyrrol-1-yl)benzenesulfonamide (compound No. 421), N-[2-({[(1S)-2-cyclopentyl-1-methylethyl]amino}methyl)phenyl]-4-(1,3-oxazol-5-yl)benzenesulfonamide (compound No. 422), N-[2-({[(1S)-2-cyclopentyl-1-methylethyl]amino}methyl)phenyl]-6-(1H-1,2,4-triazol-1-yl)pyridine-3-sulfonamide (compound No. 423), N-[2-({[2-cyclohexyl-1-methylethyl]amino}methyl)pyridin-3-yl]thiophene-2-sulfonamide (compound No. 424), N-[2-({[(1S)-2-cyclopentyl-1-methylethyl]amino}methyl)phenyl]-3-fluoro-4-(1H-1,2,4-triazol-1-yl)benzenesulfonamide (compound No. 425), N-[2-({[2-cyclohexyl-1-methylethyl]amino}methyl)phenyl]-6-(1H-1,2,4-triazol-1-yl)pyridine-3-sulfonamide (compound No. 426), N-[2-({[2-cyclohexyl-1-methylethyl]amino}methyl)phenyl]-3-fluoro-4-(1H-tetrazol-1-yl)benzenesulfonamide (compound No. 427), N-[2-({[2-cyclohexyl-1-methylethyl]amino}methyl)phenyl]-6-(1H-pyrrol-1-yl)pyridine-3-sulfonamide (compound No. 428), N-[2-({[2-cyclohexyl-1-methylethyl]amino}methyl)pyridin-3-yl]-3-fluoro-4-(1H-1,2,4-triazol-1-yl)benzenesulfonamide (compound No. 429), N-[2-({[2-cyclohexyl-2-fluoro-1-methylethyl]amino}methyl)phenyl]thiophene-2-sulfonamide (compound No. 430), N-[2-({[(1S)-2-cyclopentyl-1-methylethyl]amino}methyl)phenyl]-6-(1H-pyrrol-1-yl)pyridine-3-sulfonamide (compound No. 431), N-[3-({[2-cyclohexyl-1-methylethyl]amino}methyl)pyridin-4-yl]-5-isoxazol-5-ylthiophene-2-sulfonamide hydrochloride (compound No. 432), 2-amino-N-[2-({[(1S)-2-cyclopentyl-1-methylethyl]amino}methyl)phenyl]-1,3-benzothiazole-6-sulfonamide (compound No. 433), 2-amino-N-[2-({[(1S)-2-cyclopentyl-1-methylethyl]amino}methyl)phenyl]-1H-benzimidazole-6-sulfonamide (compound No. 434), 5-{[amino(imino)methyl]amino}-N-[2-({[2-cyclohexyl-1-methylethyl]amino}methyl)phenyl]pyridine-2-sulfonamide (compound No. 435), N-[4-({[2-({[2-cyclohexyl-1-methylethyl]amino}methyl)phenyl]amino}sulfonyl)-3-methoxyphenyl]-1-methyl-1H-imidazole-4-sulfonamide (compound No. 436), N-[6-({[2-({[2-cyclohexyl-1-methylethyl]amino}methyl)phenyl]amino}sulfonyl)-1,3-benzothiazol-2-yl]acetamide (compound No. 437), N-[2-({[2-cyclohexyl-1-methylethyl]amino}methyl)phenyl]-5-methyl-1H-benzimidazole-2-sulfonamide (compound No. 438), 4-amino-N-[2-({[2-cyclohexyl-1-methylethyl]amino}methyl)phenyl]-2-fluorobenzene sulfonamide (compound No. 439), 4-amino-N-[2-({[2-cyclohexyl-1-methylethyl]amino}methyl)phenyl]-2-methoxybenzene sulfonamide (compound No. 440), N-[4-({[2-({[2-cyclohexyl-1-methylethyl]amino}methyl)phenyl]amino}sulfonyl)-3-methoxyphenyl]acetamide (compound No. 441), N-[2-({[2-cyclohexyl-1-methylethyl]amino}methyl)phenyl]-2-methoxy-4-[(methylsulfonyl)amino]benzenesulfonamide (compound No. 442), methyl[4-({[2-({[2-cyclohexyl-1-methylethyl]amino}methyl)phenyl]amino}sulfonyl)phenyl]carbamate (compound No. 443), N-[2-({[(1S)-2-cyclopentyl-1-methylethyl]amino}methyl)phenyl]-4-(1,2,3-thiadiazol-4-yl)benzenesulfonamide (compound No. 444), N-[2-({[2-cyclohexyl-1-methylethyl]amino}methyl)phenyl]-4-(2-methyl-2H-tetrazol-5-yl)benzenesulfonamide (compound No. 445), N-[2-({[(1S)-2-cyclopentyl-1-methylethyl]amino}methyl)phenyl]-4-(2-methyl-2H-tetrazol-5-yl)benzenesulfonamide (compound No. 446), N-[2-({[(1S)-2-cyclopentyl-1-methylethyl]amino}methyl)phenyl]-4-(5-methyl-1,3,4-oxadiazol-2-yl)benzenesulfonamide (compound No. 447), N-[2-({[2-cyclohexyl-1-methylethyl]amino}methyl)phenyl]-6-(2-furyl)pyridine-3-sulfonamide (compound No. 448), N-[2-({[(1S)-2-cyclopentyl-1-methylethyl]amino}methyl)phenyl]-6-(2-furyl)pyridine-3-sulfonamide (compound No. 449), N-[2-({[2-cyclohexyl-1-methylethyl]amino}methyl)phenyl]-6-(3-furyl)pyridine-3-sulfonamide (compound No. 450), N-[2-({[(1S)-2-cyclopentyl-1-methylethyl]amino}methyl)phenyl]-6-(3-furyl)pyridine-3-sulfonamide (compound No. 451), N-[2-({[2-cyclohexyl-1-methylethyl]amino}methyl)phenyl]-1-methyl-2-oxo-1,2-dihydroquinoline-6-sulfonamide (compound No. 452), N-[2-({[(1S)-2-cyclopentyl-1-methylethyl]amino}methyl)phenyl]-1-methyl-2-oxo-1,2-dihydroquinoline-6-sulfonamide (compound No. 453), N-[2-({[2-cyclohexyl-1-methylethyl]amino}methyl)phenyl]-6-(1H-tetrazol-1-yl)pyridine-3-sulfonamide (compound No. 454), N-[2-({[(1S)-2-cyclopentyl-1-methylethyl]amino}methyl)phenyl]-6-(1H-tetrazol-1-yl)pyridine-3-sulfonamide (compound No. 455), N-[2-({[2-cyclohexyl-1-methylethyl]amino}methyl)phenyl]-6-(2-thienyl)pyridine-3-sulfonamide (compound No. 456), N-[2-({[(1S)-2-cyclopentyl-1-methylethyl]amino}methyl)phenyl]-6-(2-thienyl)pyridine-3-sulfonamide (compound No. 457), N-[2-({[2-cyclohexyl-1-methylethyl]amino}methyl)phenyl]-6-(1H-imidazol-1-yl)pyridine-3-sulfonamide (compound No. 458), N-[2-({[(1S)-2-cyclopentyl-1-methylethyl]amino}methyl)phenyl]-6-(1H-imidazol-1-yl)pyridine-3-sulfonamide (compound No. 459), N-[2-({[2-cyclohexyl-1-methylethyl]amino}methyl)phenyl]-3-(2-methyl-1,3-thiazol-4-yl)benzenesulfonamide (compound No. 460), N-[2-({[(1S)-2-cyclopentyl-1-methylethyl]amino}methyl)phenyl]-3-(2-methyl-1,3-thiazol-4-yl)benzenesulfonamide (compound No. 461), N-[2-({[2-cyclohexyl-1-methylethyl]amino}methyl)phenyl]-5-fluoro-3-methyl-1-benzothiophene-2-sulfonamide (compound No. 462), N-[2-({[(1S)-2-cyclopentyl-1-methylethyl]amino}methyl)phenyl]-5-fluoro-3-methyl-1-benzothiophene-2-sulfonamide (compound No. 463), N-[2-({[2-cyclohexyl-2-fluoro-1-methylethyl]amino}methyl)phenyl]-2-(trifluoroacetyl)-1,2,3,4-tetrahydroisoquinoline-7-sulfonamide (compound No. 464), N-[4-({[2-({[2-cyclohexyl-2-fluoro-1-methylethyl]amino}methyl)phenyl]amino}sulfonyl)phenyl]thiophene-2-sulfonamide (compound No. 465), N-[2-({[2-cyclohexyl-2-fluoro-1-methylethyl]amino}methyl)phenyl]-4-(1H-pyrrol-1-yl)benzenesulfonamide (compound No. 466), N-(2-{[(3-cyclohexyl-2-fluoropropyl)amino]methyl}phenyl)-2-(trifluoroacetyl)-1,2,3,4-tetrahydroisoquinoline-7-sulfonamide (compound No. 467), N-(4-{[(2-{[(3-cyclohexyl-2-fluoropropyl)amino]methyl}phenyl)amino]sulfonyl}phenyl)thiophene-2-sulfonamide (compound No. 468), 5-amino-N-[2-({[2-cyclohexyl-1-methylethyl]amino}methyl)phenyl]pyridine-2-sulfonamide (compound No. 469), 5-chloro-N-[2-({[(1S)-2-cyclopentyl-1-methylethyl]amino}methyl)phenyl]-2,1,3-benzoxadiazole-4-sulfonamide (compound No. 470), N-[2-({[(1S)-2-cyclopentyl-1-methylethyl]amino}methyl)phenyl]-1-benzothiophene-2-carboxamide (compound No. 471), N-(2-{[(3-cyclohexyl-2-fluoropropyl)amino]methyl}phenyl)thiophene-2-sulfonamide (compound No. 472), N-[2-({[(1S)-2-cyclopentyl-1-methylethyl]amino}methyl)phenyl]-2,1,3-benzothiadiazole-5-sulfonamide (compound No. 473), N-[4-({[2-({[2-cyclohexyl-1-methylethyl]amino}methyl)phenyl]amino}sulfonyl)-3-methoxyphenyl]thiophene-2-sulfonamide (compound No. 474), N-[4-({[2-({[2-cyclohexyl-1-methylethyl]amino}methyl)phenyl]amino}sulfonyl)-3-hydroxyphenyl]thiophene-2-sulfonamide (compound No. 475), N-[4-({[2-({[2-cyclohexyl-1-methylethyl]amino}methyl)phenyl]amino}sulfonyl)-3-hydroxyphenyl]acetamide (compound No. 476), N-[2-({[2-cyclohexyl-1-methylethyl]amino}methyl)phenyl]-3-fluoro-4-(2-oxo-1,3-oxazolidin-3-yl)benzenesulfonamide (compound No. 477), N-[2-({[(1S)-2-cyclopentyl-1-methylethyl]amino}methyl)phenyl]-3-fluoro-4-(2-oxo-1,3-oxazolidin-3-yl)benzenesulfonamide (compound No. 478), N-[2-({[2-cyclohexyl-1-methylethyl]amino}methyl)phenyl]-3-fluoro-4-(1H-1,2,3-triazol-1-yl)benzenesulfonamide (compound No. 479), N-[2-({[(1S)-2-cyclopentyl-1-methylethyl]amino}methyl)phenyl]-3-fluoro-4-(1H-1,2,3-triazol-1-yl)benzenesulfonamide (compound No. 480), N-[2-({[2-cyclohexyl-1-methylethyl]amino}methyl)phenyl]-1-(trifluoroacetyl)indoline-5-sulfonamide (compound No. 481), N-[2-({[2-cyclohexyl-1-methylethyl]amino}methyl)phenyl]indoline-5-sulfonamide (compound No. 482), N-[2-({[2-cyclohexyl-1-methylethyl]amino}methyl)phenyl]-4-(1,2,4-oxadiazol-3-yl)benzenesulfonamide (compound No. 483), N-[2-({[(1S)-2-cyclopentyl-1-methylethyl]amino}methyl)phenyl]-4-(1,2,4-oxadiazol-3-yl)benzenesulfonamide (compound No. 484), N-[2-({[(1S)-2-cyclopentyl-1-methylethyl]amino}methyl)phenyl]-3,4-difluorobenzene sulfonamide (compound No. 485), N-[2-({[2-cyclohexyl-1-methylethyl]amino}methyl)pyridin-3-yl]-4-(5-methyl-1,3,4-oxadiazol-2-yl)benzenesulfonamide (compound No. 486), N-[2-({[(1S)-2-cyclopentyl-1-methylethyl]amino}methyl)phenyl]-4-(1H-1,2,3-triazol-1-yl)benzenesulfonamide (compound No. 487), N-[2-({[2-cyclohexyl-1-methylethyl]amino}methyl)phenyl]-3-fluoro-4-(1H-pyrazol-1-yl)benzenesulfonamide (compound No. 488), N-[2-({[(1S)-2-cyclopentyl-1-methylethyl]amino}methyl)phenyl]-3-fluoro-4-(1H-pyrazol-1-yl)benzenesulfonamide (compound No. 489), N-[2-({[2-cyclohexyl-1-methylethyl]amino}methyl)phenyl]-6-pyrrolidin-1-ylpyridine-3-sulfonamide (compound No. 490), N-[2-({[(1S)-2-cyclopentyl-1-methylethyl]amino}methyl)phenyl]-6-pyrrolidin-1-ylpyridine-3-sulfonamide (compound No. 491), N-[2-({[2-cyclohexyl-1-methylethyl]amino}methyl)phenyl]-6-morpholin-4-ylpyridine-3-sulfonamide (compound No. 492), N-[2-({[(1S)-2-cyclopentyl-1-methylethyl]amino}methyl)phenyl]-6-morpholin-4-ylpyridine-3-sulfonamide (compound No. 493), N-[2-({[2-cyclohexyl-1-methylethyl]amino}methyl)phenyl]-1-ethyl-2-oxo-1,2-dihydroquinoline-6-sulfonamide (compound No. 494), N-[2-({[(1S)-2-cyclopentyl-1-methylethyl]amino}methyl)phenyl]-1-ethyl-2-oxo-1,2-dihydroquinoline-6-sulfonamide (compound No. 495), N-[2-({[(1S)-2-cyclopentyl-1-methylethyl]amino}methyl)phenyl]-2-oxo-1,2-dihydroquinoline-6-sulfonamide (compound No. 496), 6-bromo-N-[2-({[2-cyclohexyl-1-methylethyl]amino}methyl)phenyl]pyridine-3-sulfonamide (compound No. 497), 2-amino-N-[2-({[2-cyclohexyl-1-methylethyl]amino}methyl)phenyl]pyrimidine-5-sulfonamide (compound No. 498), 6-amino-N-[2-({[2-cyclohexyl-1-methylethyl]amino}methyl)phenyl]pyridine-3-sulfonamide (compound No. 499), N-[2-({[2-cyclohexyl-1-methylethyl]amino}methyl)phenyl]-2-oxo-2,3-dihydro-1,3-benzoxazole-6-sulfonamide (compound No. 500), 5-chloro-N-[2-({[2-cyclohexyl-1-methylethyl]amino}methyl)phenyl]-1,3-benzothiazole-2-sulfonamide (compound No. 501), 5-chloro-N-[2-({[(1S)-2-cyclopentyl-1-methylethyl]amino}methyl)phenyl]-1,3-benzothiazole-2-sulfonamide (compound No. 502), N-[2-({[2-cyclohexyl-1-methylethyl]amino}methyl)phenyl]-2-(dimethylamino)-1,3-benzothiazole-6-sulfonamide (compound No. 503), N-[6-({[2-({[2-cyclohexyl-1-methylethyl]amino}methyl)phenyl]amino}sulfonyl)-1,3-benzothiazol-2-yl]-L-alaninamide (compound No. 504), N-[2-({[2-cyclohexyl-1-methylethyl]amino}methyl)phenyl]-4-oxo-3,4-dihydroquinazoline-2-sulfonamide (compound No. 505), N-[2-({[2-cyclohexyl-1-methylethyl]amino}methyl)phenyl]-2-(trifluoroacetyl)-1,2,3,4-tetrahydroisoquinoline-7-sulfonamide (compound No. 506), N-[2-({[2-cyclohexyl-1-methylethyl]amino}methyl)phenyl]-1,2,3,4-tetrahydroisoquinoline-7-sulfonamide (compound No. 507), N-[2-({[2-cyclohexyl-1-methylethyl]amino}methyl)phenyl]-2-oxo-1,2-dihydroquinoline-6-sulfonamide (compound No. 508), N-[2-({[2-cyclohexyl-1-methylethyl]amino}methyl)phenyl]-3-fluoro-4-(1H-imidazol-1-yl)benzenesulfonamide (compound No. 509), N-[2-({[(1S)-2-cyclohexyl-1-methylethyl]amino}methyl)phenyl]-5-fluoro-3-methyl-1-benzothiophene-2-sulfonamide (compound No. 510), N-[2-({[(1S)-2-cyclohexyl-1-methylethyl]amino}methyl)phenyl]-1-methyl-2-oxo-1,2-dihydroquinoline-6-sulfonamide (compound No. 511), N-[2-({[(1S)-2-cyclohexyl-1-methylethyl]amino}methyl)phenyl]-1-ethyl-2-oxo-1,2-dihydroquinoline-6-sulfonamide (compound No. 512), N-[2-({[(1S)-2-cyclohexyl-1-methylethyl]amino}methyl)phenyl]-6-(2-thienyl)pyridine-3-sulfonamide (compound No. 513), N-[2-({[(1S)-2-cyclohexyl-1-methylethyl]amino}methyl)phenyl]-6-(2-furyl)pyridine-3-sulfonamide (compound No. 514), N-[2-({[(1S)-2-cyclohexyl-1-methylethyl]amino}methyl)phenyl]-6-(1H-tetrazol-1-yl)pyridine-3-sulfonamide (compound No. 515), N-[2-({[(1S)-2-cyclohexyl-1-methylethyl]amino}methyl)phenyl]-6-pyrrolidin-1-ylpyridine-3-sulfonamide (compound No. 516), N-[2-({[(1S)-2-cyclohexyl-1-methylethyl]amino}methyl)phenyl]-3-(2-methyl-1,3-thiazol-4-yl)benzenesulfonamide (compound No. 517), N-[2-({[(1S)-2-cyclohexyl-1-methylethyl]amino}methyl)phenyl]-5-(3,5-dimethylisoxazol-4-yl)thiophene-2-sulfonamide (compound No. 518), N-[2-({[(1S)-2-cyclohexyl-1-methylethyl]amino}methyl)phenyl]-4-(5-methyl-1,3,4-oxadiazol-2-yl)benzenesulfonamide (compound No. 519), N-[2-({[(1S)-2-cyclohexyl-1-methylethyl]amino}methyl)phenyl]-4-(1,2,4-oxadiazol-3-yl)benzenesulfonamide (compound No. 520), N-[2-({[(1S)-2-cyclohexyl-1-methylethyl]amino}methyl)phenyl]-3-fluoro-4-(1H-pyrazol-1-yl)benzenesulfonamide (compound No. 521), N-(2-{[(2-cyclohexyl-1-methylethyl)amino]methyl}phenyl)-1-[(1-methyl-1H-imidazol-4-yl)sulfonyl]indoline-5-sulfonamide (compound No. 522), N-(2-{[(2-cyclohexyl-1-methylethyl)amino]methyl}phenyl)-1-(methylsulfonyl)indoline-5-sulfonamide (compound No. 523), N-[4-({[2-({[1-(cyclohexylmethyl)-2,2,2-trifluoroethyl]amino}methyl)phenyl]amino}sulfonyl)phenyl]-1-methyl-1H-imidazole-4-sulfonamide (compound No. 524), 1-acetyl-N-(2-{[(2-cyclohexyl-1-methylethyl)amino]methyl}phenyl)indoline-5-sulfonamide, (compound No. 525), N-[4-({[2-({[(1S)-2-cyclohexyl-1-methylethyl]amino}methyl)phenyl]amino}sulfonyl)phenyl]acetamide (compound No. 526), N-[2-({[(1S)-2-cyclohexyl-1-methylethyl]amino}methyl)phenyl]-3-fluoro-4-(2-oxo-1,3-oxazolidin-3-yl)benzenesulfonamide (compound No. 527), 2-amino-N-(2-{[(2-cyclohexyl-1-methylethyl)amino]methyl}phenyl)-1,3-benzoxazole-6-sulfonamide (compound No. 528), N-(2-{[(2-cyclohexyl-1-methylethyl)amino]methyl}phenyl)-1,3-benzothiazole-6-sulfonamide (compound No. 529), N-[2-({[(1S)-2-cyclopropyl-1-methylethyl]amino}methyl)phenyl]-1-benzothiophene-2-sulfonamide (compound No. 530), N-[2-({[(1S)-2-cyclopentyl-1-methylethyl]amino}methyl)phenyl]-1,3-benzothiazole-6-sulfonamide (compound No. 531), 2-amino-N-[2-({[(1S)-2-cyclopropyl-1-methylethyl]amino}methyl)phenyl]-1,3-benzothiazole-6-sulfonamide (compound No. 532), N-(4-{[(2-{[(2-cyclohexyl-1-methylethyl)amino]methyl}phenyl)amino]sulfonyl}phenyl)nonanamide (compound No. 533), 4-amino-N-(2-{[(2-cyclohexyl-1-methylethyl)amino]methyl}phenyl)-3-hydroxybenzene sulfonamide (compound No. 534), N-(4-{[(2-{[(2-cyclohexyl-1-methylethyl)amino]methyl}phenyl)amino]sulfonyl}-2-hydroxyphenyl)thiophene-2-sulfonamide (compound No. 535), N-[2-({[(1S)-2-cyclopentyl-1-methylethyl]amino}methyl)phenyl]-2-oxo-2,3-dihydro-1,3-benzoxazole-6-sulfonamide (compound No. 536), 2-amino-N-[2-({[(1S)-2-cyclopentyl-1-methylethyl]amino}methyl)phenyl]-1,3-benzoxazole-6-sulfonamide (compound No. 537), N-[2-({[(1S)-2-cyclopentyl-1-methylethyl]amino}methyl)phenyl]-2-oxoindoline-6-sulfonamide (compound No. 538), 5-chloro-N-(2-{[(2-cyclohexyl-1-methylethyl)amino]methyl}phenyl)-1-benzothiophene-2-sulfonamide (compound No. 539), 5-chloro-N-[2-({[(1S)-2-cyclopentyl-1-methylethyl]amino}methyl)phenyl]-1-benzothiophene-2-sulfonamide (compound No. 540), N-[2-({[(1S)-2-cyclopentyl-1-methylethyl]amino}methyl)phenyl]-5-methoxy-1-benzothiophene-2-sulfonamide (compound No. 541), N-[2-({[(1S)-2-cyclopentyl-1-methylethyl]amino}methyl)phenyl]-5-hydroxy-1-benzothiophene-2-sulfonamide (compound No. 542), N-(2-{[(2-cyclohexyl-1-methylethyl)amino]methyl}phenyl)-5-fluoro-1-benzothiophene-2-sulfonamide (compound No. 543), N-[2-({[(1S)-2-cyclopentyl-1-methylethyl]amino}methyl)phenyl]-5-fluoro-1-benzothiophene-2-sulfonamide (compound No. 544), N-[2-({[1-(cyclohexylmethyl)-2,2,2-trifluoroethyl]amino}methyl)phenyl]-1-benzothiophene-2-sulfonamide (compound No. 545), N-(2-{[(2-cyclohexyl-1-methylethyl)amino]methyl}phenyl)-2-oxoindoline-6-sulfonamide (compound No. 546), 4-amino-N-[2-({[1-(cyclohexylmethyl)-2,2,2-trifluoroethyl]amino}methyl)phenyl]benzenesulfonamide (compound No. 547), 5-(6-aminopyridin-3-yl)-N-[2-({[(1S)-2-cyclohexyl-1-methylethyl]amino}methyl)phenyl]thiophene-2-sulfonamide (compound No. 548), 5-(6-aminopyridin-3-yl)-N-[2-({[(1S)-2-cyclopentyl-1-methylethyl]amino}methyl)phenyl]thiophene-2-sulfonamide (compound No. 549), N-[2-({[(1S)-2-cyclopentyl-1-methylethyl]amino}methyl)phenyl]-4-(1,3-thiazol-2-yl)benzenesulfonamide (compound No. 550), N-[2-({[(1S)-2-cyclohexyl-1-methylethyl]amino}methyl)phenyl]-4-(1,3-thiazol-2-yl)benzenesulfonamide (compound No. 551), 2-amino-N-[2-({[(1S)-2-cyclohexyl-1-methylethyl]amino}methyl)phenyl]-1,3-benzothiazole-6-sulfonamide (compound No. 552), N-[2-({[(1S)-2-cyclohexyl-1-methylethyl]amino}methyl)phenyl]-1-benzothiophene-2-sulfonamide (compound No. 553), N-[2-({[(1S)-2-cyclohexyl-1-methylethyl]amino}methyl)phenyl]-2-oxo-2,3-dihydro-1,3-benzoxazole-6-sulfonamide (compound No. 554), N-[2-({[(1S)-2-cyclohexyl-1-methylethyl]amino}methyl)phenyl]-1-benzofuran-2-sulfonamide (compound No. 555), 2-amino-N-[2-({[(1S)-2-cyclohexyl-1-methylethyl]amino}methyl)phenyl]-1,3-benzoxazole-6-sulfonamide (compound No. 556), N-[2-({[(1S)-2-cyclopentyl-1-methylethyl]amino}methyl)phenyl]-5-methoxy-1-benzofuran-2-sulfonamide (compound No. 557), N-[2-({[(1S)-2-cyclohexyl-1-methylethyl]amino}methyl)phenyl]-5-methoxy-1-benzofuran-2-sulfonamide (compound No. 558), N-[2-({[(1S)-2-cyclohexyl-1-methylethyl]amino}methyl)phenyl]-5-hydroxy-1-benzofuran-2-sulfonamide (compound No. 559), N-[2-({[(1S)-2-cyclopentyl-1-methylethyl]amino}methyl)phenyl]-5-hydroxy-1-benzofuran-2-sulfonamide (compound No. 560), N-[2-({[1-(cyclohexylmethyl)-2,2,2-trifluoroethyl]amino}methyl)phenyl]-4-[(methylsulfonyl)amino]benzenesulfonamide (compound No. 561), N-[4-({[2-({[1-(cyclohexylmethyl)-2,2,2-trifluoroethyl]amino}methyl)phenyl]amino}sulfonyl)phenyl]thiophene-2-sulfonamide (compound No. 562), 2-amino-N-[2-({[1-(cyclohexylmethyl)-2,2,2-trifluoroethyl]amino}methyl)phenyl]-1,3-benzothiazole-6-sulfonamide (compound No. 563), N-[2-({[(1S)-2-cyclopentyl-1-methylethyl]amino}methyl)phenyl]-2-(1H-pyrrol-1-yl)-1,3-thiazole-5-sulfonamide (compound No. 564), N-[2-({[(1S)-2-cyclohexyl-1-methylethyl]amino}methyl)phenyl]-2-oxo-1,2,3,4-tetrahydroquinoline-6-sulfonamide (compound No. 565), N-[2-({[(1S)-2-cyclopentyl-1-methylethyl]amino}methyl)phenyl]-2-oxo-1,2,3,4-tetrahydroquinoline-6-sulfonamide (compound No. 566), N-[2-({[(1S)-2-cyclohexyl-1-methylethyl]amino}methyl)phenyl]-3,5-difluoro-4-(1H-tetrazol-1-yl)benzenesulfonamide (compound No. 567), N-[2-({[(1S)-2-cyclopentyl-1-methylethyl]amino}methyl)phenyl]-3,5-difluoro-4-(1H-tetrazol-1-yl)benzenesulfonamide (compound No. 568), N-(2-{[(2-cyclohexyl-1,1-dimethylethyl)amino]methyl}phenyl)-4-(1H-pyrrol-1-yl)benzenesulfonamide (compound No. 569), 2-amino-N-[2-({[(1S)-2-cyclohexyl-1-methylethyl]amino}methyl)phenyl]-1,3-thiazole-5-sulfonamide (compound No. 570), N-[2-({[(1S)-2-cyclohexyl-1-methylethyl]amino}methyl)phenyl]-6-(1,2,3-thiadiazol-4-yl)pyridine-3-sulfonamide (compound No. 571), N-[2-({[(1S)-2-cyclopentyl-1-methylethyl]amino}methyl)phenyl]-6-(1,2,3-thiadiazol-4-yl)pyridine-3-sulfonamide (compound No. 572), N-(2-{[(2-cyclohexyl-1-methylethyl)amino]methyl}phenyl)-3-oxo-3,4-dihydro-2H-1,4-benzoxazine-7-sulfonamide (compound No. 573), N-[2-({[(1S)-2-cyclohexyl-1-methylethyl]amino}methyl)phenyl]-2-hydroxy-1,3-benzothiazole-6-sulfonamide (compound No. 574), N-[2-({[(1S)-2-cyclopentyl-1-methylethyl]amino}methyl)phenyl]-2-hydroxy-1,3-benzothiazole-6-sulfonamide (compound No. 575), N-[2-({[(1S)-2-cyclohexyl-1-methylethyl]amino}methyl)phenyl]-3-oxo-3,4-dihydro-2H-1,4-benzothiazine-6-sulfonamide (compound No. 576), N-[2-({[(1S)-2-cyclopentyl-1-methylethyl]amino}methyl)phenyl]-3-oxo-3,4-dihydro-2H-1,4-benzothiazine-6-sulfonamide (compound No. 577), N-(2-{[(2-cyclohexyl-1-methylethyl)amino]methyl}phenyl)-2-mercapto-1,3-benzoxazole-6-sulfonamide (compound No. 578), N-[2-({[(1S)-2-cyclohexyl-1-methylethyl]amino}methyl)phenyl]benzene-1,4-disulfonamide (compound No. 579), N-[2-({[(1S)-2-cyclopentyl-1-methylethyl]amino}methyl)phenyl]benzene-1,4-disulfonamide (compound No. 580), N-[2-({[(1S)-2-cyclopentyl-1-methylethyl]amino}methyl)phenyl]-N'-pyrimidin-2-ylbenzene-1,4-disulfonamide (compound No. 581), N-[2-({[(1S)-2-cyclopentyl-1-methylethyl]amino}methyl)phenyl]-6-methoxypyridine-3-sulfonamide (compound No. 582), N-[2-({[(1S)-2-cyclohexyl-1-methylethyl]amino}methyl)phenyl]-6-methoxypyridine-3-sulfonamide (compound No. 583), N-[5-({[2-({[(1S)-2-cyclohexyl-1-methylethyl]amino}methyl)phenyl]amino}sulfonyl)-1,3,4-thiadiazol-2-yl]acetamide (compound No. 584), 5-amino-N-[2-({[(1S)-2-cyclohexyl-1-methylethyl]amino}methyl)phenyl]-1,3,4-thiadiazole-2-sulfonamide (compound No. 585), 5-amino-N-[2-({[(1S)-2-cyclopentyl-1-methylethyl]amino}methyl)phenyl]-1,3,4-thiadiazole-2-sulfonamide (compound No. 586), N-[2-({[(1S)-2-cyclohexyl-1-methylethyl]amino}methyl)phenyl]-5-fluoro-1-benzothiophene-2-sulfonamide (compound No. 587), 5-chloro-N-[2-({[(1S)-2-cyclohexyl-1-methylethyl]amino}methyl)phenyl]-1-benzofuran-2-sulfonamide (compound No. 588), N-[2-({[(1R)-2-cyclohexyl-1-methylethyl]amino}methyl)phenyl]-1-benzothiophene-2-sulfonamide (compound No. 589), N-[5-({[2-({[(1S)-2-cyclohexyl-1-methylethyl]amino}methyl)phenyl]amino}sulfonyl)-1,3-thiazol-2-yl]acetamide (compound No. 590), N-[2-({[(1R)-2-cyclohexyl-1-methylethyl]amino}methyl)phenyl]-2-oxo-2,3-dihydro-1,3-benzoxazole-6-sulfonamide (compound No. 591), N-[2-({[(1S)-2-cyclopentyl-1-methylethyl]amino}methyl)phenyl]-2,4-dioxo-1,2,3,4-tetrahydroquinazoline-6-sulfonamide (compound No. 592), N-[2-({[(1S)-2-cyclohexyl-1-methylethyl]amino}methyl)phenyl]-2,4-dioxo-1,2,3,4-tetrahydroquinazoline-6-sulfonamide (compound No. 593), N-[2-({[(1S)-2-cyclopentyl-1-methylethyl]amino}methyl)phenyl]-2,3-dihydroxyquinoxaline-6-sulfonamide (compound No. 594), N-[2-({[(1S)-2-cyclohexyl-1-methylethyl]amino}methyl)phenyl]-2,3-dihydroxyquinoxaline-6-sulfonamide (compound No. 595), N-[2-({[(1S)-2-cyclopentyl-1-methylethyl]amino}methyl)phenyl]-2-oxo-1,4-dihydro-2H-3,1-benzoxazine-6-sulfonamide (compound No. 596), N-[2-({[(1S)-2-cyclohexyl-1-methylethyl]amino}methyl)phenyl]-2-oxo-1,4-dihydro-2H-3,1-benzoxazine-6-sulfonamide (compound No. 597), N-[2-({[(1S)-2-cyclopentyl-1-methylethyl]amino}methyl)phenyl]-2-mercapto-1,3-benzoxazole-6-sulfonamide (compound No. 598), N-[2-({[(1S)-2-cyclohexyl-1-methylethyl]amino}methyl)phenyl]-2-mercapto-1,3-benzoxazole-6-sulfonamide (compound No. 599), N-[2-({[(1S)-2-cyclopentyl-1-methylethyl]amino}methyl)phenyl]-2-oxo-2,3-dihydro-1,3-benzoxazole-5-sulfonamide (compound No. 600), N-[2-({[(1S)-2-cyclohexyl-1-methylethyl]amino}methyl)phenyl]-2-oxo-2,3-dihydro-1,3-benzoxazole-5-sulfonamide (compound No. 601), N-(2-{[(2-cyclohexyl-1,1-dimethylethyl)amino]methyl}phenyl)-1-benzothiophene-2-sulfonamide (compound No. 602), 5-chloro-N-[2-({[(1S)-2-cyclopentyl-1-methylethyl]amino}methyl)phenyl]-1-benzofuran-2-sulfonamide (compound No. 603), 5-({[2-({[(1S)-2-cyclopentyl-1-methylethyl]amino}methyl)phenyl]amino}sulfonyl)-2-methyl-3-furoic acid (compound No. 604), 5-({[2-({[(1S)-2-cyclohexyl-1-methylethyl]amino}methyl)phenyl]amino}sulfonyl)-2-methyl-3-furoic acid (compound No. 605), methyl 5-({[2-({[(1S)-2-cyclohexyl-1-methylethyl]amino}methyl)phenyl]amino}sulfonyl)-2-methyl-3-furoate (compound No. 606), methyl 5-({[2-({[(1S)-2-cyclopentyl-1-methylethyl]amino}methyl)phenyl]amino}sulfonyl)-2-methyl-3-furoate, (compound No. 607), N-[2-({[(1S)-2-cyclopentyl-1-methylethyl]amino}methyl)phenyl]-4-(1H-pyrrol-1-ylsulfonyl)benzenesulfonamide (compound No. 608), methyl 5-({[4-({[2-({[(1S)-2-cyclopentyl-1-methylethyl]amino}methyl)phenyl]amino}sulfonyl)phenyl]amino}sulfonyl)-2-methyl-3-furoate (compound No. 609), 5-({[4-({[2-({[(1S)-2-cyclopentyl-1-methylethyl]amino}methyl)phenyl]amino}sulfonyl)phenyl]amino}sulfonyl)-2-methyl-3-furoic acid (compound No. 610), 5-({[4-({[2-({[(1S)-2-cyclopentyl-1-methylethyl]amino}methyl)phenyl]amino}sulfonyl)phenyl]amino}sulfonyl)-N,N,2-trimethyl-3-furamide (compound No. 611), 5-({[4-({[2-({[(1S)-2-cyclopentyl-1-methylethyl]amino}methyl)phenyl]amino}sulfonyl)phenyl]amino}sulfonyl)-2-methyl-3-furamide, (compound No. 612)

2-({[(1S)-2-cyclohexyl-1-methylethyl]amino}methyl)aniline (compound No. 613), 2-({[(1S)-2-cyclopentyl-1-methylethyl]amino}methyl)aniline (compound No. 614), 1-(cyanomethyl)-N-[2-({[(1S)-2-cyclopentyl-1-methylethyl]amino}methyl)phenyl]-2-oxo-1,2-dihydroquinoline-6-sulfonamide (compound No. 615), 4-amino-N-[2-({[(1S)-2-cyclopentyl-1-methylethyl]amino}methyl)phenyl]benzenesulfonamide (compound No. 616), N-[4-({[2-({[(1S)-2-cyclopentyl-1-methylethyl]amino}methyl)phenyl]amino}sulfonyl)phenyl]-1-methyl-1H-imidazole-2-sulfonamide (compound No. 617), N-[2-({[(1S)-2-cyclopentyl-1-methylethyl]amino}methyl)phenyl]-1-methyl-1H-imidazole-2-sulfonamide (compound No. 618), N-[2-({[(1S)-2-cyclopentyl-1-methylethyl]amino}methyl)phenyl]-4-oxochromane-6-sulfonamide (compound No. 619), N-[2-({[(1S)-2-cyclohexyl-1-methylethyl]amino}methyl)phenyl]-4-oxochromane-6-sulfonamide (compound No. 620), N-[2-({[1-methyl-2-(tetrahydro-2H-pyran-4-yl)ethyl]amino}methyl)phenyl]-1-benzothiophene-2-sulfonamide (compound No. 621).

Because of their antimicrobial activity, the compounds described herein may be administered to an animal for treatment orally, topically, rectally, internasally, or by a parenteral route. The pharmaceutical compositions of the present invention comprise a pharmaceutically effective amount of compounds described herein formulated together with one or more pharmaceutically acceptable carriers.

Solid form preparations for oral administration include capsules, tablets, pills, powders, granules, cachets and suppositories. For solid form preparations, the active compound can be mixed with at least one inert, pharmaceutically acceptable excipients or carrier, for example, sodium citrate, dicalcium phosphate and/or a filler or extenders, for example, starches, lactose, sucrose, glucose, mannitol and silicic acid; binders, for example, carboxymethylcellulose, alginates, gelatins, polyvinylpyrrolidinone, sucrose, or acacia; disintegrating agents, for example, agar-agar, calcium carbonate, potato starch, alginic acid, certain silicates and sodium carbonate; absorption acceletors, for example, quaternary ammonium compounds; wetting agents, for example, cetyl alcohol, or glycerol mono stearate; adsorbants, for example, Kaolin; lubricants, for example, talc, calcium stearate, magnesium stearate, solid polyethyleneglycol, sodium lauryl sulphate and mixture thereof. In the case of capsules, tablets, or pills, the dosage form may also comprise buffering agents.

The solid preparation of tablets, capsules, pills and granules can be prepared with coating and shells, for example, enteric coating and other coatings well known in the pharmaceutical formulating art.

Liquid form preparations for oral administration can include pharmaceutically acceptable emulsions, solutions, suspensions, syrups and elixirs. For liquid form preparations, the active compound can be mixed with water or other solvent, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, for example, cottonseed, groundnut, corn, germ, olive, castor and sesame oil), glycerol, and fatty acid esters of sorbitan and mixture thereof. Besides inert diluents, the oral composition can also include adjuvants, for example, wetting agents, emulsifying agents, suspending agents, sweetening agents, flavouring agents and perfuming agents.

Injectable preparations, for example, sterile injections, aqueous suspensions may be formulated according to the art using suitable dispersing or wetting and suspending agent. Among the acceptable vehicles and solvents that may be employed are water, Ringer's solution and isotonic sodium chloride.

Dosage forms for tropical or transdermal administration of compounds provided herein include ointments, pastes, creams, lotions, gels, powders, solutions, sprays, inhalants or patches. The active compound can be admixed under sterile condition with a pharmaceutically acceptable carrier and any needed preservatives or buffers as may be required. Ophthalmic formulations, eardrops, eye ointments, powder and solution are also contemplated as being within the scope of this invention.

The pharmaceutical preparation can be provided in a unit dosage form. In such forms, the preparation is subdivided into unit doses containing appropriate quantities of the active component. The unit dosage form can be packaged preparation, the package containing discrete capsules, powders, in vials or ampoules, and ointments capsule, sachet, tablet, gel, cream itself or it can be the appropriate number of any of these packaged forms.

Examples set forth below demonstrate general synthetic procedures for the preparation of representative compounds. The examples are provided to illustrate particular aspect of the disclosure and do not constrain the scope of the present invention as defined by the claims.

EXAMPLES

General Procedures

Example 1

Preparation of a Compound of Formula 4

To a solution of a compound of Formula 2 (1 equiv.) in pyridine, a compound of Formula 3 (1.2 equiv.) was added portion wise at about 0-5° C. The reaction mixture was allowed to come at an ambient temperature and stirred overnight. The solvent was evaporated under reduced pressure. Water was added to the residue, which was then extracted with ethyl acetate. The organic layer was washed with water, brine, and dried over anhydrous sodium sulfate. The solvent was evaporated under reduced pressure and the residue was purified by column chromatography to yield the required product.

Example 2

Preparation of Compound of Formula 5

To a solution of compound of Formula 4 (1.0 equiv.) in dichloromethane (20-30 mL) was added Dess Martin Periodinane (1.5 equiv.). The reaction mixture was stirred overnight at an ambient temperature, filtered, and the mother liquor was washed with aqueous sodium bicarbonate solution. The organic layer was dried and evaporated under reduced pressure. The residue was purified by column chromatography to give the desired product.

Example 3

Preparation of a Compound of Formula 9a

To a solution of a compound of Formula 9 (10.0 equiv., prepared according to Scheme I) in propanol (15 mL) was added a compound of Formula $R_8B(OH)_2$ (12.0 equiv.). The reaction mixture was degassed with argon for about 15 minutes. Tetrakis(triphenyl-phosphine) palladium (0) (1.0 equiv.) was added to the reaction mixture. Sodium carbonate (10.0 equiv.) in water was added to the reaction mixture. The reaction mixture was heated to about 100° C. and stirred for about 5 hours in dark under an argon atmosphere. The reaction mixture was filtered, the residue was concentrated and the product was purified by column chromatography.

Example 4

Preparation of a Compound of Formula 10

The compound of Formula 10 was prepared using the procedure described for compound of Formula 5.

Example 5

Preparation of a Compound of Formula 12

A compound of Formula 11 (1.0 equiv.) and a compound of Formula $R_6COOH$ (1.2 equiv.) were taken in dry dimethylformamide (3-10 mL) and cooled to 0° C. 1-hydroxybenzotriazole (1.2 equiv.) and N-Methylpyrrolidone (3.0 equiv.) were added and stirred for about 15 minutes. 1-Ethyl-3-[3-(dimethylamino)propyl]carbodimide (1.5 equiv.) was added and the resulting mixture was stirred at an ambient temperature for about 12 hours, quenched with water and extracted in dichloromethane. The organic layer was washed with water, brine and dried over anhydrous sodium sulphate. Solvent was removed under reduced pressure and the residue was purified over silica gel column.

Example 6

Preparation of a Compound of Formula 13

Compound of Formula 12 (1.0 equiv.) was taken in dry tetrahydrofuran and Tetrabutylammonium fluoride (1.2 equiv.) was added. After stirring for about 1 hour at an ambient temperature, solvent was removed under reduced pressure and the residue was extracted in ethyl acetate. Organic layer was washed with water, brine and dried over anhydrous sodium sulphate. Solvent was removed and the residue was purified over silica gel column.

Example 7

Preparation of Compound of Formula 14

The compound of Formula 14 was prepared using the procedure described for compound of Formula 5.

Example 8

Preparation of Compound of Formula 16

Compound II (1.0 equiv.) was taken in dry dichloromethane (5-10 mL) and imidazole (1.5 equiv.) and N,N'-carbonyldiimidazole (1.5 equiv.) were added. Resulting mixture was stirred at room temperature for about 2 hours, quenched with water and extracted in dichloromethane. The organic layer was washed with water, brine and dried over anhydrous sodium sulphate. The solvent was removed and the residue was dissolved in dichloromethane (5-10 mL) and imidazole (1.5 equiv.) and a compound of Formula $R_2CH_2OH$ (1.2 equiv.) were added. The resulting mixture was stirred at an ambient temperature for about 5 hours, quenched with water and extracted in dichloromethane. The organic layer was washed with water, brine and dried over anhydrous sodium sulphate. Solvent was removed under pressure and the residue was purified over silica gel column.

Example 9

Preparation of Compound of Formula 17

Compound of Formula 16 (1.0 equiv.) was taken in dry tetrahydrofuran and Tetrabutylammonium Fluoride (1.2 equiv.) was added. After stirring for about 1 hour at an ambient temperature, solvent was removed under reduced pressure and the residue was extracted in ethyl acetate. The organic layer was washed with water, brine and dried over anhydrous sodium sulphate. Solvent was removed and the residue was purified over silica gel column.

Example 10

Preparation of Compound of Formula 18

The compound of Formula 18 was prepared using the procedure described for compound of Formula 5.

Example 11

Preparation of a Compound of Formula 18b

The compound of Formula 18a (10.0 mmol) was added in portion wise to neat chlorosulfonic acid (10 mL) at about 0° C. After complete addition resulting mixture was slowly warm to about 50° C. for about 12 hours. The reaction mixture was poured into ice. Solid was filtered, washed thoroughly with cold water and dried in vacuum over phosphorus pentachloride to form the desired compound.

Example 12

Preparation of a Compound of Formula 18c

The compound of Formula 18b (1.0 equiv.) was added to a compound of Formula 2a (1.0 equiv.) in pyridine at an ambient temperature. After stirring for about 12 hours the mixture was evaporated to dryness and the residue partitioned between ethyl acetate and water. The organic layer was separated, washed with water, dried and evaporated to form the crude compound of Formula 18c, which was purified by silica gel column chromatography using methanol/dichloromethane as eluent.

Example 13

Preparation of a Compound of Formula 18d

Dess-Martin Periodinane (1.5 equiv.) was added to a solution of a compound of Formula 18c (1.0 equiv.) in dichloromethane (20-30 mL). The reaction mixture was stirred overnight at an ambient temperature, filtered and the mother liquor was washed with aqueous sodium bicarbonate solution. The organic layer was dried and evaporated under reduced pressure. The residue was purified by column chromatography to form the desired product.

Example 14

Preparation of a Compound of Formula 21

To a solution of L-alaniol (1.0 equiv.) in dichloromethane was added di-tert-Butyl dicarbonate (1.1 equiv.) slowly at about 0-5° C. The reaction mixture was stirred for about 3 hours at an ambient temperature. The reaction mixture was diluted with dichloromethane and washed with water, brine, dried over anhydrous sodium sulfate, and evaporated in vacuo. The residue was purified by column chromatography to give the desired product.

Example 15

Preparation of a Compound of Formula 22

To a solution of compound of Formula 21 (1.0 equiv.) in ether (20-30 mL) was added tosyl chloride (1.3 equiv.). The reaction mixture was stirred for about 15 hours and cooled to 0° C. Potassium hydroxide (about 1.25 equiv., powdered) was added and stirring was continued for about 15 minutes. Additional 1.25 equiv. of potassium hydroxide was added and again the reaction mixture was stirred for additional 15 minutes. The reaction mixture was refluxed at about 40-50° C. for about 3 hours. The reaction mixture was diluted with water and the compound was extracted with ethyl acetate. The organic layer was dried and evaporated under reduced pressure. The product was purified by column chromatography over silica gel to give the desired compound.

Example 16

Preparation of a Compound of Formula 23

In a two-necked round bottom flask Mg (50.3 equiv.) was suspended in ether (100-125 mL), cooled to 0° C., added slowly a compound of Formula Cy-Ha (50.3 equiv.), and diluted with tetrahydrofuran (100-110 mL). A crystal of iodine was added to titrate the reaction. The reaction mixture was stirred for about 2 hours. The reaction mixture was cooled to about −40° C. and $CuBr-Me_2S$ complex (1.0 equiv.) was added to it. Compound of Formula 22 (10.0 equiv.) dissolved in tetrahydrofuran was added slowly to the reaction mixture. The reaction mixture was stirred for about 2 hours and quenched by adding saturated ammonium chloride solution. The reaction mixture was stirred overnight and was extracted with ethyl acetate. The organic layer was dried and evaporated under reduced pressure. The product was purified by column chromatography.

Example 17

Preparation of a Compound of Formula 24

The deprotection of a compound of Formula 23 to give a compound of Formula 24 was carried out following the methods well known in the art.

Example 18

Preparation of a Compound of Formula 26

(S)-Amphetamine (3.5 equiv.) was dissolved in acetic acid (30-40 mL). Platinum oxide (1.0 equiv.) was added to it and the suspension was stirred at about 50 psi (Hz). After about 24 hours platinum oxide (2 g) was added and stirred at about 50 psi (Hz) pressure. The reaction mixture was filtered through celite pad. The mother liquor was evaporated to get the final component (10 gm) as the acetate salt. This was used as such for next step without further purification.

Example 19

Preparation of a Compound of Formula 28

Pyridine-4-carboxaldehyde (1 equiv.) and nitro ethane (6.0 equiv.) were taken in a round bottom flask fitted with a magnetic stirrer. To the vigorously stirred reaction mixture at an ambient temperature was added sodium hydroxide (2.0 equiv.) and kept at an ambient temperature for about 3 hours during which a yellowish white solid product separated out. It was filtered and collected for the next reaction as such without purification.

Example 20

Preparation of a Compound of Formula 29

Compound of Formula 28 (1.0 equiv.) was added to a stirred solution acetic anhydride (50-75 mL). The reaction mixture was stirred at an ambient temperature for about 1 hour during which the initially white suspension becomes deep yellow colored solution. Volatiles were removed in vacuo and the content was dissolved in dichloromethane (500-600 mL). Washed with aqueous saturated sodium bicarbonate solution. Dried over anhydrous sodium sulfate, column chromatography on silica gel (230-400 mesh) eluant dichloromethane afforded the product as yellowish thick liquid.

Example 21

Preparation of a Compound of Formula 30

Compound of Formula 29 (1.0 equiv.) and platinum oxide (0.32 equiv.) was suspended in glacial acetic acid (30-40 mL). The reaction mixture was subjected to about 55-psi hydrogen pressure for about 16 hours at an ambient temperature, filtered through a celite pad and volatiles were removed in vacuo to obtain the required product as colorless oil.

Example 22

Preparation of a Compound of Formula 31

Isobutyl methyl ketone (100-125 mL) was added to a flask containing the compound of Formula 30 (1.0 equiv.) and sodium carbonate (2.5 equiv.). The heterogeneous mixture was heated to reflux under nitrogen, and water was removed from the reaction mixture with a Dean-Stark trap. When the imine formation was complete, the flask was cooled to 0° C. di-tert-Butyl dicarbonate (1.0 equiv.) was added drop wise into the reaction mixture and kept stirring for about 1 hour. Reaction mixture was quenched with water. Isobutyl methyl ketone layer separated out was collected, volatiles were removed in vacuo to obtain the intermediate imine, which when subjected to heating at about 50° C. with water and n-butanol hydrolyses to the required product.

Example 23

Preparation of a Compound of Formula 31b

Potassium carbonate (2.0 equiv.) and benzyl bromide (2.0 equiv.) were added to a solution of compound of Formula 31a (1.0 equiv.) in dry acetonitrile (5 mL). The resulting mixture was heated at about 60° C. for about 8 hours. The reaction mixture was filtered and washed with dichloromethane. The filtrate was concentrated and the residue was purified over silica gel column to form the desired compound.

Example 24

Preparation of a Compound of Formula 31c

The compound of Formula 31b (1.0 equiv.) was taken in dry dichloromethane (5 mL) and cooled to about −20° C.

Diethylaminosulfur trifluoride (DAST, 1.5 equiv.) was added and the resulting mixture was slowly warm to about 0° C. and stirred for about 2 hours. The reaction mixture was quenched with saturated aqueous sodium bicarbonate and extracted in dichloromethane. The organic layer was washed with water, brine and dried over anhydrous sodium sulfate. The solvent was removed and the residue was purified over silica gel column to form the desired compound.

Example 25

Preparation of a Compound of Formula 31d

Palladium hydroxide (0.2 gm, 20% on carbon) was added to a compound of Formula 31c (1.0 gm, 2.95 mmol) in methanol (15 mL). The resulting mixture was stirred under hydrogen atmosphere for about 12 hours. The reaction mixture was filtered and washed thoroughly with methanol. The filtrate was concentrated to form the desired compound.

Example 26

Preparation of a Compound of Formula 31f

The compound of Formula 31f was prepared following the procedure described in Example 23.

Example 27

Preparation of a Compound of Formula 31g

The compound of Formula 31g was prepared following the procedure described in Example 24.

Example 28

Preparation of a Compound of Formula 31h

The compound of Formula 31h was prepared following the procedure described in Example 25.

Example 29

Preparation of a Compound of Formula 31j

The compound of Formula 31j was prepared following the procedure described in Example 18.

Example 30

Preparation of a Compound of Formula 32

To a solution of compound of Formula 5 (1.0 equiv.) in methanol (20-30 mL) was added compound of Formula 24 (2.45 equiv.). After stirring for about 1 hour, sodium cyanoborohydride (2.45 equiv.) was added to the reaction mixture. The reaction mixture was stirred overnight and then evaporated the solvent under reduced pressure. The residue was dissolved in dichloromethane, washed with water, brine and dried over anhydrous sodium sulfate. The product was purified by column chromatography.

Example 31

Preparation of Compound of Formula 33 and 34

To a solution of compound of Formula 14 (1.0 equiv.) or 18 (1.0 equiv.) in methanol (20-30 mL) was added compound of Formula 24 (2.45 equiv.). After stirring for about 1 hour, sodium cyanoborohydride (2.45 equiv.) was added to the reaction mixture. The reaction mixture was stirred overnight and then evaporated the solvent under reduced pressure. The residue was dissolved in dichloromethane, washed with water, brine and dried over anhydrous sodium sulfate. The product was purified by column chromatography.

Example 32

Preparation of a Compound of Formula 36

The compound of Formula 35 (1.0 equiv.) was taken in dichloromethane (75-100 mL) and to it triethylamine (1.5 equiv.) was added at an ambient temperature. It was cooled to 0° C. and di-tert-Butyl dicarbonate (1.2 equiv.) dissolved in 25 mL was added drop wise and the contents were stirred at an ambient temperature overnight, quenched with water and extracted in dichloromethane. Solvent was evaporated and the crude product was purified over silica gel column.

Example 33

Preparation of a Compound of Formula 37

The compound of Formula 36 (1.0 equiv.) was taken in methanol (10-15 mL) and cooled to 0° C. To this Raney Nickel (1.0 equiv.) was added, followed by drop wise addition of hydrazine hydrate (10-15 mL). The reaction mixture was stirred at an ambient temperature for about 1 hour and filtered through celite pad. Evaporation of filtrate gave the desired compound.

Example 34

Preparation of a Compound of Formula 39

The compound of Formula 37 (1.0 equiv.) was taken in dichloromethane (5-10 mL) and cooled to 0° C. To this $R_6NCO$ (1.2 equiv.) was added and the reaction mixture was stirred at room temperature overnight. It was then filtered and the filtrate was evaporated to give compound of Formula 38. Compound of Formula 38 (1.4 equiv.) was taken in a round bottom flask and cooled to 0° C. To this mixture, ethanolic hydrochloride (5-10 mL) was added and the reaction mixture was stirred overnight at an ambient temperature. Evaporation of the solvent gave the salt of the amine, which was taken in dichloromethane, cooled and basified using triethylamine to get the free amine. The crude product was purified on preparative thin layer chromatography.

Example 35

Preparation of a Compound of Formula 39c

The compound of Formula 39a (1.0 equiv.) was taken in a round bottom flask and to it acetonitrile (10 ml) was added followed by addition of the compound of Formula 39b (1.5 equiv.). The reaction mixture was heated at about 70° C. for about 10 hours, cooled to an ambient temperature and water was added. It was then extracted with ethyl acetate. The solvent was evaporated and the residue thus formed was purified by column chromatography.

Example 36

Preparation of a Compound of Formula 39d

The compound of Formula 39c (1.54 equiv.) was taken in a round bottom flask and cooled to about 0° C. To this ethanolic hydrochloride (5-10 mL) was added and the reaction mixture was stirred overnight at an ambient temperature. Evaporation of the solvent gave the salt of the amine, which was taken in dichloromethane, cooled and basified using triethylamine to get the free amine. The crude compound of Formula 39d was purified by preparative thin layer chromatography.

Example 37

Preparation of a Compound of Formula 39f

The compound of Formula 39a (1.0 equiv.) was dissolved in dichloromethane (10 ml) and cooled to about 0° C. Diisopropyl ethyl amine (Hunigs base) was added to it under argon atmosphere. The compound of Formula 39e (1.3 equiv.) was then added. The reaction mixture was stirred for about 2 hours from about 0° C. to an ambient temperature, and washed with water. The organic layer was dried over anhydrous sodium sulfate, concentrated in vacuo to form the desired compound.

Example 38

Preparation of a Compound of Formula 39g

The compound of Formula 39g was prepared following the procedure described in Example 36.

Example 39

Preparation of a Compound of Formula 41

The compound of Formula 37a (1.0 equiv.) was taken in pyridine (5-10 mL) and cooled to 0° C. To this mixture, $RxSO_2Cl$ (1.2 equiv.) was added in portion wise and the contents were stirred for about 1 hour at 0° C., quenched with water and extracted in dichloromethane. The organic layer was washed with dilute hydrochloric acid solution, water and brine, evaporated to form the crude product of Formula 40.

Compound of Formula 40 (1.54 equiv.) was taken in a round bottomed flask and cooled to 0° C. To this ethanolic hydrochloride (5-10 mL) was added and the reaction mixture was stirred overnight at an ambient temperature. Evaporation of the solvent gave the salt of the amine, which was taken in dichloromethane, cooled and basified using triethylamine to get the free amine. The crude product was purified on preparative thin layer chromatography.

Example 40

Preparation of a Compound of Formula 42

The compound of Formula 35 (1.0 equiv.) was taken in acetonitrile (10-20 mL) and to it cesium carbonate (4.0 equiv.) and thiophenol (3.0 equiv.) were added at an ambient temperature. The reaction mixture was heated at about 50° C. for about 4 hours, cooled to an ambient temperature, quenched with water and extracted with ethyl acetate. Evaporation of solvent gave the crude product, which was purified by silica gel column chromatography.

Example 41

Preparation of a Compound of Formula 44

The amine of Formula 42 (1.0 equiv.) was taken in pyridine (5-10 mL) and cooled to 0° C. To this a compound of Formula 42a (1.2 equiv.) was added in portion wise and the contents were stirred for about 1 hour at about 0° C., quenched with water and extracted in dichloromethane. The organic layer was washed with dilute hydrochloric acid solution, water and brine and evaporated to form compound of Formula 43.

Compound of Formula 43 (1.0 equiv.) was taken in a round bottom flask and cooled to 0° C. To this mixture, ethanolic hydrochloride (5-10 mL) was added and the reaction mixture was stirred overnight at room temperature. Evaporation of the solvent gave the salt of the amine, which was taken in dichloromethane, cooled and basified using triethylamine to get the free amine. The crude product was then purified by preparative thin layer chromatography.

Example 42

Preparation of a Compound of Formula 46

The amine of Formula 42 (1.0 equiv.) was taken in dichloromethane (5-10 mL) and cooled to 0° C. To this mixture, $R_6NCO$ (1.2 equiv.) was added and the reaction mixture was stirred at an ambient temperature overnight. It was then filtered and the filtrate was evaporated to get compound of Formula 45.

Compound of Formula 45 (1.0 equiv.) was taken in an round bottom and cooled to 0° C. To this mixture, ethanolic hydrochloride (10-15 mL) was added and the reaction mixture was stirred overnight at room temperature for about 5 hours. Evaporation of the solvent gave the salt of the amine, which was taken in dichloromethane, cooled and basified using triethylamine to get the free amine. The crude product was then purified by preparative thin layer chromatography.

Example 43

Preparation of a Compound of Formula 42b

The compound of Formula 42 (1.0 equiv.) was taken in dichloromethane (15-20 mL) and cooled to about 0° C. To this triethylamine (1.5 equiv.) was added followed by drop wise addition of phenyl chloroformate (1.2 equiv.). The reaction mixture was stirred at about 0° C. for about half an hour. The reaction mixture was then quenched with water and extracted with dichloromethane. The solvent was evaporated to form the desired compound.

Example 44

Preparation of a Compound of Formula 48

Compound of Formula 47 (3.0 equiv.) and compound of Formula 24 (1.0 equiv.) were taken in methanol containing about 1% acetic acid and stirred at an ambient temperature for about 24 hours. Sodium cyanoborohydride (1.5 equiv.) was added and the resulting mixture was stirred at room temperature for about 2 hours. Solvent was removed and the residue was extracted in dichloromethane. Organic layer was washed with aqueous sodium bicarbonate, water, brine and dried over anhydrous sodium sulphate. Solvent was removed and the residue was purified over silica gel column to get the desired compound.

Example 45

Preparation of a Compound of Formula 49

Compound of Formula 48 (1.0 equiv.) was taken in dry dichloromethane (5-10 mL) and di-tert-Butyl dicarbonate (1.2 equiv.) was added. The resulting mixture was stirred at an ambient temperature for about 12 hours. Solvent was removed and the residue was purified over silica gel column to get the desired compound.

Example 46

Preparation of a Compound of Formula 50

Compound of Formula 49 (1.0 equiv.) was taken in dry dichloromethane (5-10 mL) and cooled to 0° C. Triethylamine (2.0 equiv.) and a compound of Formula $R_6NCO$ (1.5 equiv.) were added. The resulting mixture was slowly warm to an ambient temperature and stirred for about 3 hours. Quenched with water and extracted in dichloromethane. Organic layer was washed with water, brine and dried over anhydrous sodium sulphate. Solvent was removed and the residue was purified over silica gel column.

Example 47

Preparation of a Compound of Formula 51

Compound of Formula 50 (1.0 equiv.) was dissolved in about 20% trifluoroacetic acid solution in dichloromethane (5-10 mL) and stirred for about 3 hours. Quenched with aqueous sodium bicarbonate and extracted in dichloromethane. Organic layer was washed with water, brine and dried over anhydrous sodium sulphate. Solvent was removed and the residue was purified over silica gel column.

Example 48

Preparation of a Compound of Formula 54

The compound of Formula 52 (1.0 equiv.) was taken in a round bottom flask and to it acetonitrile (10 mL) was added followed by addition of the compound of Formula 39b (1.5 equiv.). The reaction mixture was heated at about 70° C. for about 10 hours, cooled to an ambient temperature and water was added to it and extracted with ethyl acetate. The solvent was evaporated and the residue thus formed was purified by column chromatography to form a compound of Formula 53, which was deprotected following the procedure described above.

Example 49

Preparation of a Compound of Formula 56

Triethylamine (1.5 equiv.) and phenylchloroformate (1.2 equiv.) were added to a solution of compound of formula 55 (1.0 equiv.) in dichloromethane (30 mL), cooled to about 0° C. and stirred for about 2 hours. The reaction mixture was diluted with dichloromethane, washed with water, dried over anhydrous sodium sulfate and evaporated in vacuo to form the desired compound.

Example 50

Preparation of a Compound of Formula 57

A mixture of compound of formula 56 (1.0 equiv.), hydrazine hydrate (2.5 equiv.) and dioxane were stirred at about 80° C. for about 2 hours. The reaction mixture was evaporated in vacuo. The residue was diluted with dichloromethane, washed with water, dried over anhydrous sodium sulfate and evaporated in vacuo to form the desired compound.

Example 51

Preparation of a Compound of Formula 59

A mixture of a compound of formula 57 (1.0 equiv.), formamidine acetate (3 equiv.), acetic acid (3 equiv.) and dimethylformamide (20 mL) were stirred at about 80° C. for about 3 hours. The reaction mixture was diluted with ethyl acetate, washed with water dried over anhydrous sodium sulfate and evaporated in vacuo. The product was purified by column chromatography in ethyl acetate and hexane to form the compound of Formula 58, which was deprotected to form a compound of Formula 59.

The following compounds were prepared analogously, following the above general procedures:

Compound No. 1: N-[2-({[(1S)-2-cyclohexyl-1-methylethyl]amino}methyl)phenyl]-2,3,4,5,6-pentafluorobenzenesulfonamide, Mass (m/z): 477.3; m. pt.: 63-64;

Compound No. 2: N-[2-({[(1S)-2-cyclohexyl-1-methylethyl]amino}methyl)phenyl]-5-(3-methoxyphenyl)thiophene-2-sulfonamide, Mass (m/z): 499.3; m. pt.: Gummy;

Compound No. 3: 5-(1-benzothien-2-yl)-N-[2-({[(1S)-2-cyclohexyl-1-methylethyl]amino}methyl)phenyl]thiophene-2-sulfonamide, Mass (m/z): 525.2; m. pt.: 59-61;

Compound No. 4: N-[2-({[(1S)-2-cyclohexyl-1-methylethyl]amino}methyl)phenyl]-5-(3,4-dimethoxyphenyl)thiophene-2-sulfonamide, Mass (m/z): 529.3; m. pt.: 55-57;

Compound No. 5: N-[2-({[(1S)-2-cyclohexyl-1-methylethyl]amino}methyl)phenyl]-1-benzothiophene-2-sulfonamide, Mass (m/z): 443.1; m. pt.: 49-51;

Compound No. 6: N-[2-({[(1S)-2-cyclopentyl-1-methylethyl]amino}methyl)phenyl]-5-(2,5-dimethoxyphenyl)thiophene-2-sulfonamide, Mass (m/z): 515.2; m. pt.: Gummy;

Compound No. 7: N-[2-({[(1S)-2-cycloheptyl-1-methylethyl]amino}methyl)phenyl]-5-(2,5-dimethoxyphenyl)thiophene-2-sulfonamide, Mass (m/z): 543.2; m. pt.: Gummy;

Compound No. 8: 5-(3-acetylphenyl)-N-[2-({[(1S)-2-cyclopentyl-1-methylethyl]amino}methyl)phenyl]thiophene-2-sulfonamide, Mass (m/z): 497.1; m. pt.: Gummy;

Compound No. 9: N-[2-({[(1S)-2-cyclohexyl-1-methylethyl]amino}methyl)phenyl]-5-[3-(1-hydroxyethyl)phenyl]thiophene-2-sulfonamide, Mass (m/z): 513.1; m. pt.: 52-55;

Compound No. 10: 5-(3-acetylphenyl)-N-[2-({[(1S)-2-cycloheptyl-1-methylethyl]amino}methyl)phenyl]thiophene-2-sulfonamide, Mass (m/z): 525.2; m. pt.: Gummy;

Compound No. 11: N-[2-({[(1S)-2-cyclohexyl-1-methylethyl]amino}methyl)phenyl]-5-(2,5-dimethoxyphenyl)thiophene-2-sulfonamide, Mass (m/z): 529.1; m. pt.: Gummy;

Compound No. 12: N-[2-({[(1S)-2-cyclopentyl-1-methylethyl]amino}methyl)phenyl]-1-benzothiophene-2-sulfonamide, Mass (m/z): 429.2; m. pt.: Gummy;

Compound No. 13: N-[2-({[(1S)-2-cycloheptyl-1-methylethyl]amino}methyl)phenyl]-1-benzothiophene-2-sulfonamide, Mass (m/z): 457.2; m. pt.: Gummy;

Compound No. 14: N-[2-({[(1S)-2-cyclopentyl-1-methylethyl]amino}methyl)phenyl]-5-(3,4-dimethoxyphenyl)thiophene-2-sulfonamide, Mass (m/z): 515.3; m. pt.: 47-48;

Compound No. 15: 6-chloro-N-[2-({[(1S)-2-cyclohexyl-1-methylethyl]amino}methyl)phenyl]imidazo[2,1-b][1,3]thiazole-5-sulfonamide, Mass (m/z): 467.1; m. pt.: Gummy;

Compound No. 16: N-[2-({[(1S)-2-cyclohexyl-1-methylethyl]amino}methyl)phenyl]-5-[3-(trifluoromethyl)phenyl]thiophene-2-sulfonamide, Mass (m/z): 537.3; m. pt.: Gummy;

Compound No. 17: N-[2-({[(1S)-2-cyclohexyl-1-methylethyl]amino}methyl)phenyl]-5-[1-methyl-5-(trifluoromethyl)-1H-pyrazol-3-yl]thiophene-2-sulfonamide; Mass (m/z): 541.3; m. pt.: 69;

Compound No. 18: N-[2-({[(1S)-2-cyclohexyl-1-methylethyl]amino}methyl)phenyl]-5-[5-(trifluoromethyl)isoxazol-3-yl]thiophene-2-sulfonamide, Mass (m/z): 528.2; m. pt.: 110;

Compound No. 19: N-[2-({[(1S)-2-cyclohexyl-1-methylethyl]amino}methyl)phenyl]-5-[1-methyl-3-(trifluoromethyl)-1H-pyrazol-5-yl]thiophene-2-sulfonamide, Mass (m/z): 541.2; m. pt.: Gummy;

Compound No. 20: N-[2-({[(1S)-2-cyclopentyl-1-methylethyl]amino}methyl)phenyl]-5-[4-(trifluoromethoxy)phenyl]thiophene-2-sulfonamide, Mass (m/z): 539.1; m. pt.: Gummy;

Compound No. 21: N-[2-({[(1S)-2-cyclopentyl-1-methylethyl]amino}methyl)phenyl]-5-[5-(trifluoromethyl)isoxazol-3-yl]thiophene-2-sulfonamide, Mass (m/z): 514.0; m. pt.: Gummy;

Compound No. 22: N-[2-({[(1S)-2-cycloheptyl-1-methylethyl]amino}methyl)phenyl]-5-[5-(trifluoromethyl)isoxazol-3-yl]thiophene-2-sulfonamide, Mass (m/z): 542.1; m. pt.: Gummy;

Compound No. 23: N-[2-({[(1S)-2-cycloheptyl-1-methylethyl]amino}methyl)phenyl]-5-[1-methyl-3-(trifluoromethyl)-1H-pyrazol-5-yl]thiophene-2-sulfonamide, Mass (m/z): 555.1; m. pt.: Gummy;

Compound No. 24: N-[2-({[(1S)-2-cyclopentyl-1-methylethyl]amino}methyl)phenyl]-5-[1-methyl-3-(trifluoromethyl)-1H-pyrazol-5-yl]thiophene-2-sulfonamide, Mass (m/z): 527.0; m. pt.: Gummy;

Compound No. 25: N-[2-({[(1S)-2-cycloheptyl-1-methylethyl]amino}methyl)phenyl]-5-[1-methyl-5-(trifluoromethyl)-1H-pyrazol-3-yl]thiophene-2-sulfonamide, Mass (m/z): 555.1; m. pt.: Gummy;

Compound No. 26: N-[2-({[(1S)-2-cyclohexyl-1-methylethyl]amino}methyl)phenyl]-5-[4-(trifluoromethoxy)phenyl]thiophene-2-sulfonamide, Mass (m/z): 553.2; m. pt.: 59;

Compound No. 27: 5-chloro-N-[2-({[(1S)-2-cyclohexyl-1-methylethyl]amino}methyl)phenyl]-3-methyl-1-benzothiophene-2-sulfonamide, Mass (m/z): 491.2; m. pt.: 82-84;

Compound No. 28: methyl 5-({[2-({[(1S)-2-cyclohexyl-1-methylethyl]amino}methyl)phenyl]amino}sulfonyl)-4-methylthiophene-2-carboxylate, Mass (m/z): 465.2; m. pt.: Gummy;

Compound No. 29: methyl 4-({[2-({[(1S)-2-cyclohexyl-1-methylethyl]amino}methyl)phenyl]amino}sulfonyl)-2,5-dimethyl-3-furoate, Mass (m/z): 463.2; m. pt.: Gummy;

Compound No. 30: 5-chloro-N-[2-({[(1S)-2-cyclohexyl-1-methylethyl]amino}methyl)phenyl]-1,3-dimethyl-1H-pyrazole-4-sulfonamide, Mass (m/z): 439.4; m. pt.: Gummy;

Compound No. 31: N-[2-({[(1S)-2-cyclohexyl-1-methylethyl]amino}methyl)phenyl]-2,2'-bithiophene-5-sulfonamide, Mass (m/z): 475.2; m. pt.: Gummy;

Compound No. 32: N-[2-({[(1S)-2-cyclohexyl-1-methylethyl]amino}methyl)phenyl]-5-(3-furyl)thiophene-2-sulfonamide, Mass (m/z): 459.3; m. pt.: Gummy;

Compound No. 33: N-[2-({[(1S)-2-cyclohexyl-1-methylethyl]amino}methyl)phenyl]-5-phenylthiophene-2-sulfonamide, Mass (m/z): 469.3; m. pt.: 81-83;

Compound No. 34: N-[2-({[(1R)-2-cyclohexyl-1-(hydroxymethyl)ethyl]amino}methyl)phenyl]thiophene-2-sulfonamide, Mass (m/z): 409.3; m. pt.: 79-80;

Compound No. 35: methyl 5-({[2-({[(1S)-2-cycloheptyl-1-methylethyl]amino}methyl)phenyl]amino}sulfonyl)-4-methylthiophene-2-carboxylate, Mass (m/z): 479.2; m. pt.: Gummy;

Compound No. 36: 5-chloro-N-[2-({[(1S)-2-cycloheptyl-1-methylethyl]amino}methyl)phenyl]-3-methyl-1-benzothiophene-2-sulfonamide, Mass (m/z): 505.2; m. pt.: Gummy;

Compound No. 37: 5-chloro-N-[2-({[(1S)-2-cycloheptyl-1-methylethyl]amino}methyl)phenyl]-1,3-dimethyl-1H-pyrazole-4-sulfonamide, Mass (m/z): 453.2; m. pt.: Gummy;

Compound No. 38: N-[2-({[(1S)-2-cycloheptyl-1-methylethyl]amino}methyl)phenyl]-2,2'-bithiophene-5-sulfonamide, Mass (m/z): 489.2; m. pt.: Gummy;

Compound No. 39: N-[2-({[(1S)-2-cyclopentyl-1-methylethyl]amino}methyl)phenyl]-5-(3-furyl)thiophene-2-sulfonamide, Mass (m/z): 445.2; m. pt.: Gummy;

Compound No. 40: N-[2-({[(1S)-2-cycloheptyl-1-methylethyl]amino}methyl)phenyl]-5-(3-furyl)thiophene-2-sulfonamide, Mass (m/z): 473.2; m. pt.: Gummy;

Compound No. 41: N-[2-({[(1S)-2-cyclopentyl-1-methylethyl]amino}methyl)phenyl]-5-phenylthiophene-2-sulfonamide, Mass (m/z): 455.2; m. pt.: 61-62.5;

Compound No. 42: 5-bromo-N-[2-({[(1S)-2-cyclopentyl-1-methylethyl]amino}methyl)phenyl]thiophene-2-sulfonamide, Mass (m/z): 457.1; m. pt.: 135-136.5;

Compound No. 43: N-[2-({[(1S)-2-cyclopentyl-1-methylethyl]amino}methyl)phenyl]thiophene-2-sulfonamide, Mass (m/z): 379.2; m. pt.: Gummy;

Compound No. 44: N-[2-({[(1S)-2-cycloheptyl-1-methylethyl]amino}methyl)phenyl]thiophene-2-sulfonamide, Mass (m/z): 407.2; m. pt.: Gummy;

Compound No. 45: N-[2-({[(1S)-2-cyclohexyl-1-methylethyl]amino}methyl)phenyl]isonicotinamide, Mass (m/z): 352.3; m. pt.: Gummy;

Compound No. 46: N-[2-({[(1S)-2-cyclohexyl-1-methylethyl]amino}methyl)phenyl]nicotinamide, Mass (m/z): 352.3; m. pt.: 113-114;

Compound No. 47: N-[2-({[(1S)-2-cyclopentyl-1-methylethyl]amino}methyl)phenyl]-2,2'-bithiophene-5-sulfonamide, Mass (m/z): 461.2; m. pt.: Gummy;

Compound No. 48: N-[2-({[(1S)-2-cyclohexyl-1-methylethyl]amino}methyl)phenyl]-3,5-bis(trifluoromethyl)benzenesulfonamide, Mass (m/z): 523.3; m. pt.: 114-116;

Compound No. 49: 2-({[(1S)-2-cyclohexyl-1-methylethyl]amino}methyl)phenyl[(2-methylphenyl)sulfonyl]carbamate hydrochloride salt, Mass (m/z): 445.2; m. pt.: 151-152.5;

Compound No. 50: N-[2-({[(1S)-2-cyclohexyl-1-methylethyl]amino}methyl)phenyl]-6-phenoxypyridine-3-sulfonamide, Mass (m/z): 480.3; m. pt.: 58-60;

Compound No. 51: 5-bromo-N-[2-({[(1S)-2-cyclohexyl-1-methylethyl]amino}methyl)phenyl]-2-furamide, Mass (m/z): 419.2; m. pt.: 60-62;

Compound No. 52: N-[2-({[(1S)-2-cyclohexyl-1-methylethyl]amino}methyl)phenyl]-2-furamide, Mass (m/z): 341.2; m. pt.: 48-50;

Compound No. 53: N-[2-({[(1S)-2-cyclohexyl-1-methylethyl]amino}methyl)phenyl]-1-benzothiophene-3-sulfonamide, Mass (m/z): 443.2; m. pt.: 50-52;

Compound No. 54: N-[2-({[(1S)-2-cyclohexyl-1-methylethyl]amino}methyl)phenyl]thiophene-2-carboxamide, Mass (m/z): 357.2; m. pt.: 48-50;

Compound No. 55: N-[2-({[(1S)-2-cycloheptyl-1-methylethyl]amino}methyl)phenyl]thiophene-2-carboxamide hydrochloride salt, Mass (m/z): 371.3; m. pt.: 143-145;

Compound No. 56: N-[2-({[(1S)-2-cyclopentyl-1-methylethyl]amino}methyl)phenyl]-2-furamide hydrochloride salt, Mass (m/z): 327.3; m. pt.: 174-176;

Compound No. 57: 5-bromo-N-[2-({[(1S)-2-cyclopentyl-1-methylethyl]amino}methyl)phenyl]-2-furamide hydrochloride salt, Mass (m/z): 405.1; m. pt.: 84-86;

Compound No. 58: 5-(3-acetylphenyl)-N-[2-({[(1S)-2-cyclohexyl-1-methylethyl]amino}methyl)phenyl]thiophene-2-sulfonamide, Mass (m/z): 511.2; m. pt.: Gummy;

Compound No. 59: 5-(1,3-benzodioxol-5-yl)-N-[2-({[(1S)-2-cyclohexyl-1-methylethyl]amino}methyl)phenyl]thiophene-2-sulfonamide, Mass (m/z): 513.2; m. pt.: Gummy;

Compound No. 60: N-[2-({[(1S)-2-cyclohexyl-1-methylethyl]amino}methyl)phenyl]-3,3'-bithiophene-5-sulfonamide, Mass (m/z): 475.2; m. pt.: Gummy;

Compound No. 61: N-[2-({[(1S)-2-cycloheptyl-1-methylethyl]amino}methyl)phenyl]-5-(3-methoxyphenyl)thiophene-2-sulfonamide, Mass (m/z): 513.2; m. pt.: 34-35;

Compound No. 62: methyl 3-({[2-({[(1S)-2-cyclohexyl-1-methylethyl]amino}methyl)phenyl]amino}sulfonyl)-4-(isopropylsulfonyl)thiophene-2-carboxylate, Mass (m/z): 557.2; m. pt.: 111-112.5;

Compound No. 63: N-[2-({[(1S)-2-cyclohexyl-1-methylethyl]amino}methyl)phenyl]-5-(3-fluorophenyl)thiophene-2-sulfonamide, Mass (m/z): 487.2; m. pt.: 56-58;

Compound No. 64: N-[2-({[(1S)-2-cyclohexyl-1-methylethyl]amino}methyl)phenyl]-5-[3-(hydroxymethyl)phenyl]thiophene-2-sulfonamide, Mass (m/z): 499.0; m. pt.: 62-63;

Compound No. 65: N-[2-({[(1S)-2-cyclohexyl-1-methylethyl]amino}methyl)phenyl]-5-[4-(hydroxymethyl)phenyl]thiophene-2-sulfonamide, Mass (m/z): 199.0; m. pt.: 144-146;

Compound No. 66: methyl 5-({[2-({[(1S)-2-cyclopentyl-1-methylethyl]amino}methyl)phenyl]amino}sulfonyl)-4-methylthiophene-2-carboxylate, Mass (m/z): 451.3; m. pt.: 58-60;

Compound No. 67: methyl 4-({[2-({[(1S)-2-cycloheptyl-1-methylethyl]amino}methyl)phenyl]amino}sulfonyl)-2,5-dimethyl-3-furoate, Mass (m/z): 477.1; m. pt.: 135-136.5;

Compound No. 68: N-[2-({[(1S)-2-cycloheptyl-1-methylethyl]amino}methyl)phenyl]-5-[3-(trifluoromethyl)phenyl]thiophene-2-sulfonamide, Mass (m/z): 551.2; m. pt.: 40-41;

Compound No. 69: N-[2-({[(1S)-2-cyclopentyl-1-methylethyl]amino}methyl)phenyl]-5-(3-fluorophenyl)thiophene-2-sulfonamide, Mass (m/z): 473.2; m. pt.: 55-56;

Compound No. 70: N-[2-({[(1S)-2-cycloheptyl-1-methylethyl]amino}methyl)phenyl]-5-(3-fluorophenyl)thiophene-2-sulfonamide, Mass (m/z): 501.3; m. pt.: 62-63;

Compound No. 71: N-[2-({[(1S)-2-cyclopentyl-1-methylethyl]amino}methyl)phenyl]-5-isoxazol-3-ylthiophene-2-sulfonamide, Mass (m/z): 446.0; m. pt.: 81-82;

Compound No. 72: N-[2-({[(1S)-2-cyclohexyl-1-methylethyl]amino}methyl)phenyl]-5-methylthiophene-2-carboxamide, Mass (m/z): 371.3; m. pt.: 118-119;

Compound No. 73: N-[2-({[(1S)-2-cycloheptyl-1-methylethyl]amino}methyl)phenyl]-5-methylthiophene-2-carboxamide, Mass (m/z): 385.3; m. pt.: Gummy;

Compound No. 74: N-[2-({[(1S)-2-cyclopentyl-1-methylethyl]amino}methyl)phenyl]nicotinamide, Mass (m/z): 338.3; m. pt.: 80-82;

Compound No. 75: N-[2-({[(1S)-2-cycloheptyl-1-methylethyl]amino}methyl)phenyl]nicotinamide, Mass (m/z): 366.2; m. pt.: 105-107;

Compound No. 76: N-[3-({[(1S)-2-cycloheptyl-1-methylethyl]amino}methyl)pyridin-2-yl]thiophene-2-sulfonamide, Mass (m/z): 408.3; m. pt.: Gummy;

Compound No. 77: N-[3-({[(1S)-2-cyclohexyl-1-methylethyl]amino}methyl)pyridin-2-yl]thiophene-2-sulfonamide, Mass (m/z): 394.1; m. pt.: 172-173;

Compound No. 78: N-[3-({[(1S)-2-cyclohexyl-1-methylethyl]amino}methyl)pyridin-2-yl]-4-fluorobenzenesulfonamide, Mass (m/z): 406.3; m. pt.: 148-149;

Compound No. 79: N-[2-({[(1S)-2-cyclohexyl-1-methylethyl]amino}methyl)phenyl]-2-(trifluoroacetyl)-1,2,3,4-tetrahydroisoquinoline-6-sulfonamide, Mass (m/z): 538.1; m. pt.: 68;

Compound No. 80: N-[2-({[(1S)-2-cyclohexyl-1-methylethyl]amino}methyl)phenyl]-1,2,3,4-tetrahydroisoquinoline-6-sulfonamide, Mass (m/z): 442.1; m. pt.: Gummy;

Compound No. 81: methyl 5-({[2-({[(1S)-2-cycloheptyl-1-methylethyl]amino}methyl)phenyl]amino}sulfonyl)-1-methyl-1H-pyrrole-2-carboxylate, Mass (m/z): 462.1; m. pt.: Gummy;

Compound No. 82: methyl 5-({[2-({[(1S)-2-cyclopentyl-1-methylethyl]amino}methyl)phenyl]amino}sulfonyl)-1-methyl-1H-pyrrole-2-carboxylate, Mass (m/z): 434.1; m. pt.: Gummy;

Compound No. 83: N-[2-({[(1S)-2-cyclopentyl-1-methylethyl]amino}methyl)phenyl]-1-methyl-1H-imidazole-4-sulfonamide, Mass (m/z): 377.0; m. pt.: 42-44;

Compound No. 84: N-[2-({[(1S)-2-cycloheptyl-1-methylethyl]amino}methyl)phenyl]-1-methyl-1H-imidazole-4-sulfonamide, Mass (m/z): 405.2; m. pt.: 43-45;

Compound No. 85: 5-bromo-N-[2-({[(1S)-2-cycloheptyl-1-methylethyl]amino}methyl)phenyl]-2-furamide, Mass (m/z): 433.0; m. pt.: Gummy;

Compound No. 86: N-[2-({[(1S)-2-cyclopentyl-1-methylethyl]amino}methyl)phenyl]-3,5-bis(trifluoromethyl)benzenesulfonamide, Mass (m/z): 509.1; m. pt.: 97-98;

Compound No. 87: N-[2-({[(1S)-2-cyclohexyl-1-methylethyl]amino}methyl)phenyl]-5-isoxazol-3-ylthiophene-2-sulfonamide, Mass (m/z): 460.2; m. pt.: 68-69.5;

Compound No. 88: [2-({[(1S)-2-cycloheptyl-1-methylethyl]amino}methyl)phenyl]isonicotinamide, Mass (m/z): 366.2; m. pt.: Gummy;

Compound No. 89: Chloro-N-[2-({[(1S)-2-cyclopentyl-1-methylethyl]amino}methyl)phenyl]-1,3-dimethyl-1H-pyrazole-4-sulfonamide, Mass (m/z): 425.0; m. pt.: Gummy;

Compound No. 90: -benzothien-2-yl)-N-[2-({[(1S)-2-cycloheptyl-1-methylethyl]amino}methyl)phenyl]thiophene-2-sulfonamide, Mass (m/z): 539.2; m. pt.: 128-130;

Compound No. 91: (1-benzothien-2-yl)-N-[2-({[(1S)-2-cyclopentyl-1-methylethyl]amino}methyl)phenyl]thiophene-2-sulfonamide, Mass (m/z): 511.2; m. pt.: 124-126;

Compound No. 92: [2-({[(1S)-2-cycloheptyl-1-methylethyl]amino}methyl)phenyl]-5-(3,4-dimethoxyphenyl)thiophene-2-sulfonamide, Mass (m/z): 543.2; m. pt.: 45-46;

Compound No. 93: [2-({[(1S)-2-cyclopentyl-1-methylethyl]amino}methyl)phenyl]-5-(4-methoxyphenyl)thiophene-2-sulfonamide, Mass (m/z): 485.2; m. pt.: 101-102;

Compound No. 94: [2-({[(1S)-2-cyclopentyl-1-methylethyl]amino}methyl)phenyl]-3,3'-bithiophene-5-sulfonamide, Mass (m/z): 461.2; m. pt.: Gummy;

Compound No. 95: [2-({[(1S)-2-cycloheptyl-1-methylethyl]amino}methyl)phenyl]-3,3'-bithiophene-5-sulfonamide, Mass (m/z): 489.2; m. pt.: Gummy;

Compound No. 96: [2-({[(1S)-2-cyclopentyl-1-methylethyl]amino}methyl)phenyl]-2-(trifluoroacetyl)-1,2,3,4-tetrahydroisoquinoline-6-sulfonamide, Mass (m/z): 524.0; m. pt.: 55;

Compound No. 97: [2-({[(1S)-2-cyclopentyl-1-methylethyl]amino}methyl)phenyl]-1,2,3,4-tetrahydroisoquinoline-6-sulfonamide, Mass (m/z): 428.1; m. pt.: Gummy;

Compound No. 98: (1,3-benzodioxol-5-yl)-N-[2-({[(1S)-2-cyclopentyl-1-methylethyl]amino}methyl)phenyl]thiophene-2-sulfonamide, Mass (m/z): 499.0; m. pt.: Gummy;

Compound No. 99: [2-({[(1S)-2-cyclohexyl-1-methylethyl]amino}methyl)phenyl]-2-[4-(4-methoxyphenyl)piperazin-1-yl]acetamide; Mass (m/z): 479.2; m. pt.: Gummy;

Compound No. 100: 5-chloro-N-[2-({[(1S)-2-cyclopentyl-1-methylethyl]amino}methyl)phenyl]-3-methyl-1-benzothiophene-2-sulfonamide; Mass (m/z): 477.08; m. pt.: 74-76;

Compound No. 101: [2-({[(1S)-2-cycloheptyl-1-methylethyl]amino}methyl)phenyl]-5-isoxazol-3-ylthiophene-2-sulfonamide; Mass (m/z): 574.1; m. pt.: 148-150;

Compound No. 102: N-[2-({[(1S)-2-cyclopentyl-1-methylethyl]amino}methyl)phenyl]-5-(2-methyl-1,3-thiazol-4-yl)thiophene-2-sulfonamide; Mass (m/z): 476.00; m. pt.: 158-159;

Compound No. 103: N-[2-({[(1S)-2-cycloheptyl-1-methylethyl]amino}methyl)phenyl]-5-(2-methyl-1,3-thiazol-4-yl)thiophene-2-sulfonamide; Mass (m/z): 504.10; m. pt.: 80-82;

Compound No. 104: ethyl 3-[5-({[2-({[(1S)-2-cyclohexyl-1-methylethyl]amino}methyl)phenyl]amino}sulfonyl)-2-thienyl]-1,2,4-oxadiazole-5-carboxylate; Mass (m/z): 533.10; m. pt.: 40-41;

Compound No. 105: ethyl 3-[5-({[2-({[(1S)-2-cyclopentyl-1-methylethyl]amino}methyl)phenyl]amino}sulfonyl)-2-thienyl]-1,2,4-oxadiazole-5-carboxylate; Mass (m/z): 519.00; m. pt.: 56-58;

Compound No. 106: ethyl 3-[5-({[2-({[(1S)-2-cycloheptyl-1-methylethyl]amino}methyl)phenyl]amino}sulfonyl)-2-thienyl]-1,2,4-oxadiazole-5-carboxylate; Mass (m/z): 547.10; m. pt.: 54-56;

Compound No. 107: N-[2-({[(1S)-2-cyclohexyl-1-methylethyl]amino}methyl)phenyl]-2,4-dimethyl-1,3-thiazole-5-sulfonamide; Mass (m/z): 422.0479.2; m. pt.: 56-58;

Compound No. 108: N-[2-({[(1S)-2-cyclopentyl-1-methylethyl]amino}methyl)phenyl]-2,4-dimethyl-1,3-thiazole-5-sulfonamide; Mass (m/z): 408.1; m. pt.: 60-61;

Compound No. 109: N-[2-({[(1S)-2-cycloheptyl-1-methylethyl]amino}methyl)phenyl]-2,4-dimethyl-1,3-thiazole-5-sulfonamide; Mass (m/z): 436.0; m. pt.: 53-55;

Compound No. 110: N-[2-({[(1S)-2-cyclopentyl-1-methylethyl]amino}methyl)phenyl]-5-methylthiophene-2-carboxamide; Mass (m/z): 357.1; m. pt.: Gummy;

Compound No. 111: N-[2-({[(1S)-2-cyclopentyl-1-methylethyl]amino}methyl)phenyl]isonicotinamide; Mass (m/z): 338.2; m. pt.: 70-72;

Compound No. 112: N-[2-({[(1S)-2-cyclohexyl-1-methylethyl]amino}methyl)phenyl]-2-(4-pyrimidin-2-ylpiperazin-1-yl)acetamide; Mass (m/z): 451.2; m. pt.: Gummy;

Compound No. 113: methyl 3-({[2-({[(1S)-2-cyclopentyl-1-methylethyl]amino}methyl)phenyl]amino}sulfonyl)thiophene-2-carboxylate; Mass (m/z): 437.0; m. pt.: Gummy;

Compound No. 114: methyl 3-({[2-({[(1S)-2-cycloheptyl-1-methylethyl]amino}methyl)phenyl]amino}sulfonyl)thiophene-2-carboxylate; Mass (m/z): 465.1; m. pt.: 53-57;

Compound No. 115: N-[2-({[(1S)-2-cycloheptyl-1-methylethyl]amino}methyl)phenyl]-4-(1H-imidazol-1-yl)benzenesulfonamide; Mass (m/z): 467.1; m. pt.: 62-64;

Compound No. 116: N-[2-({[(1S)-2-cyclohexyl-1-methylethyl]amino}methyl)phenyl]-2-(2-thienylsulfonyl)-1,2,3,4-tetrahydroisoquinoline-6-sulfonamide; Mass (m/z): 588.0; m. pt.: 80-81;

Compound No. 117: N-[2-({[(1S)-2-cycloheptyl-1-methylethyl]amino}methyl)phenyl]-6-phenoxypyridine-3-sulfonamide; Mass (m/z): 494.1; m. pt.: Gummy;

Compound No. 118: N-[2-({[(1S)-2-cyclopentyl-1-methylethyl]amino}methyl)phenyl]-6-phenoxypyridine-3-sulfonamide; Mass (m/z): 466.1; m. pt.: Gummy;

Compound No. 119: N-[2-({[(1S)-2-cyclohexyl-1-methylethyl]amino}methyl)phenyl]-4-(1H-pyrrol-1-yl)benzenesulfonamide; Mass (m/z): 452.1; m. pt.: 207-209;

Compound No. 120: N-[2-({[(1S)-2-cyclopentyl-1-methylethyl]amino}methyl)phenyl]-4-(1H-pyrrol-1-yl)benzenesulfonamide; Mass (m/z): 438.1; m. pt.: 135-137;

Compound No. 121: N-[2-({[(1S)-2-cyclohexyl-1-methylethyl]amino}methyl)phenyl]-4-(1H-1,2,4-triazol-1-yl)benzenesulfonamide; Mass (m/z): 454.1; m. pt.: 110-112;

Compound No. 122: N-[2-({[(1S)-2-cyclohexyl-1-methylethyl]amino}methyl)phenyl]-1H-imidazole-4-sulfonamide; Mass (m/z): 377.1; m. pt.: 55-56;

Compound No. 123: N-[2-({[(1S)-2-cycloheptyl-1-methylethyl]amino}methyl)phenyl]-1H-imidazole-4-sulfonamide; Mass (m/z): 391.1; m. pt.: 51-52;

Compound No. 124: N-[2-({[(1S)-2-cyclopentyl-1-methylethyl]amino}methyl)phenyl]-2-(4-pyrimidin-2-ylpiperazin-1-yl)acetamide; Mass (m/z): 437.2; m. pt.: Gummy;

Compound No. 125: N-[2-({[(1S)-2-cycloheptyl-1-methylethyl]amino}methyl)phenyl]-2-(4-pyrimidin-2-ylpiperazin-1-yl)acetamide; Mass (m/z): 465.3; m. pt.: 115-117;

Compound No. 126: N-[2-({[(1S)-2-cyclohexyl-1-methylethyl]amino}methyl)phenyl]-5-{3-[(1E)-N-hydroxyethanimidoyl]phenyl}thiophene-2-sulfonamide; Mass (m/z): 526.1; m. pt.: 73-77;

Compound No. 127: N-[2-({[(1S)-2-cyclohexyl-1-methylethyl]amino}methyl)phenyl]-5-{3-[(1E)-N-methoxyethanimidoyl]phenyl}thiophene-2-sulfonamide; Mass (m/z): 540.1; m. pt.: 48-50;

Compound No. 128: N-[2-({[(1S)-2-cycloheptyl-1-methylethyl]amino}methyl)phenyl]-2-furamide; Mass (m/z): 355.2; m. pt.: Gummy;

Compound No. 129: 2-({[(1S)-2-cyclohexyl-1-methylethyl]amino}methyl)phenyl (4-methoxyphenyl)carbamate; Mass (m/z): 397.1; m. pt.: 56-57;

Compound No. 130: N-[2-({[(1S)-2-cycloheptyl-1-methylethyl]amino}methyl)phenyl]-5-(phenylsulfonyl)thiophene-2-sulfonamide; Mass (m/z): 547.0; m. pt.: 85-87;

Compound No. 131: N-[2-({[(1S)-2-cyclopentyl-1-methylethyl]amino}methyl)phenyl]-5-(phenylsulfonyl)thiophene-2-sulfonamide; Mass (m/z): 519; m. pt.: 50-52;

Compound No. 132: N-[2-({[(1S)-2-cyclohexyl-1-methylethyl]amino}methyl)phenyl]-5-(phenylsulfonyl)thiophene-2-sulfonamide; Mass (m/z): 533.0; m. pt.: 175-177;

Compound No. 133: N-[2-({[(1S)-2-cyclohexyl-1-methylethyl][(2,2-dimethylpropanoyl)oxy]amino}methyl)phenyl]-2-(2-thienylsulfonyl)-1,2,3,4-tetrahydroisoquinoline-6-sulfonamide; Mass (m/z): 688.1; m. pt.: 80;

Compound No. 134: N-[2-({[(1S)-2-cyclohexyl-1-methylethyl][(2,2-dimethylpropanoyl)oxy]amino}methyl)phenyl]-2-(trifluoroacetyl)-1,2,3,4-tetrahydroisoquinoline-6-sulfonamide; Mass (m/z): 638.1; m. pt.: 132;

Compound No. 135: N-[2-({[(1S)-2-cyclohexyl-1-methylethyl][(2,2-dimethylpropanoyl)oxy]amino}methyl)phenyl]-1,2,3,4-tetrahydroisoquinoline-6-sulfonamide; Mass (m/z): 542.1; m. pt.: 93;

Compound No. 136: 5-(1,3-benzodioxol-5-yl)-N-[2-({[(1S)-2-cycloheptyl-1-methylethyl]amino}methyl)phenyl]thiophene-2-sulfonamide; Mass (m/z): 527.1; m. pt.: 53;

Compound No. 137: N-[2-({[(1S)-2-cyclohexyl-1-methylethyl]amino}methyl)phenyl]-4-(1H-imidazol-1-yl)benzenesulfonamide; Mass (m/z): 453.1; m. pt.: 60-62;

Compound No. 138: N-[2-({[(1S)-2-cyclopentyl-1-methylethyl]amino}methyl)phenyl]-4-(1H-imidazol-1-yl)benzenesulfonamide; Mass (m/z): 439.1; m. pt.: 56-58;

Compound No. 139: N-[2-({[(1S)-2-cycloheptyl-1-methylethyl]amino}methyl)phenyl]-5-(1,3-oxazol-2-yl)thiophene-2-sulfonamide; Mass (m/z): 474.0; m. pt.: 48-50;

Compound No. 140: N-[2-({[(1S)-2-cyclopentyl-1-methylethyl]amino}methyl)phenyl]thiophene-2-carboxamide; Mass (m/z): 343.2; m. pt.: Gummy;

Compound No. 141: N-(4-acetylphenyl)-N'-[2-({[(1S)-2-cyclohexyl-1-methylethyl]amino}methyl)phenyl]urea; Mass (m/z): 408.1; m. pt.: 150-151° C.;

Compound No. 142: N-[2-({[(1S)-2-cyclopentyl-1-methylethyl]amino}methyl)phenyl]-1-benzothiophene-2-sulfonamide; Mass (m/z): 429.2; m. pt.: Gummy;

Compound No. 143: N-[2-({[(1S)-2-cyclohexyl-1-methylethyl]amino}methyl)phenyl]-5-pyridin-4-ylthiophene-2-sulfonamide; Mass (m/z): 470.0; m. pt.: 84-86° C.

Compound No. 144: N-[2-({[(1S)-2-cyclopentyl-1-methylethyl]amino}methyl)phenyl]-5-pyridin-3-ylthiophene-2-sulfonamide; Mass (m/z): 456.0; m. pt.: 78-80° C.

Compound No. 145: 2-({[(1S)-2-cyclohexyl-1-methylethyl]amino}methyl)phenyl (4-acetylphenyl)carbamate; Mass (m/z): 409.1; m. pt.: 63-65° C.

Compound No. 146: N-[2-({[(1S)-2-cyclopentyl-1-methylethyl]amino}methyl)phenyl]-4-(1H-1,2,4-triazol-1-yl)benzenesulfonamide; Mass (m/z): 440.0; m. pt.: 174-175° C.

Compound No. 147: N-[2-({[(1S)-2-cycloheptyl-1-methylethyl]amino}methyl)phenyl]-4-(1H-1,2,4-triazol-1-yl)benzenesulfonamide; Mass (m/z): 468.1; m. pt.: 177-178° C.

Compound No. 148: N-[2-({[(1S)-2-cyclopentyl-1-methylethyl]amino}methyl)phenyl]-2-(4-pyrimidin-2-ylpiperazin-1-yl)acetamide; Mass (m/z): 437.2; m. pt.: Gummy;

Compound No. 149: 6-({[2-({[(1S)-2-cyclopentyl-1-methylethyl]amino}methyl)phenyl]amino}sulfonyl)-N-(4-methoxyphenyl)-3,4-dihydroisoquinoline-2(1H)-carboxamide; Mass (m/z): 578.1; m. pt.: 96-98° C.

Compound No. 150: 6-({[2-({[(1S)-2-cyclopentyl-1-methylethyl]amino}methyl)phenyl]amino}sulfonyl)-N-isopropyl-3,4-dihydroisoquinoline-2(1H)-carboxamide; Mass (m/z): 513.1; m. pt.: 94-95° C.

Compound No. 151: N-[2-({[(1S)-2-cyclopentyl-1-methylethyl]amino}methyl)phenyl]-2-(1H-imidazol-1-ylcarbonyl)-1,2,3,4-tetrahydroisoquinoline-6-sulfonamide; Mass (m/z): 522.1; m. pt.: 79-81° C.

Compound No. 152: N-[2-({[(1S)-2-cyclohexyl-1-methylethyl]amino}methyl)phenyl]-4-({[(4-methoxyphenyl)amino]carbonyl}amino)benzenesulfonamide; Mass (m/z): 551.1; m. pt.: 97-98° C.

Compound No. 153: 4-({[(4-acetylphenyl)amino]carbonyl}amino)-N-[2-({[(1S)-2-cyclohexyl-1-methylethyl]amino}methyl)phenyl]benzenesulfonamide; Mass (m/z): 563.1; m. pt.: 155-156° C.

Compound No. 154: N-[4-({[2-({[(1S)-2-cyclohexyl-1-methylethyl]amino}methyl)phenyl]amino}sulfonyl)phenyl]thiophene-2-sulfonamide; Mass (m/z): 548.0; m. pt.: 82-83° C.

Compound No. 155: N-[2-({[(1S)-2-cyclohexyl-1-methylethyl]amino}methyl)phenyl]-1-pyrimidin-2-yl-1H-imidazole-4-sulfonamide; Mass (m/z): 455.1; m. pt.: 90-92° C.

Compound No. 156: N-[2-({[(1S)-2-cyclohexyl-1-methylethyl]amino}methyl)phenyl]-1-benzofuran-2-carboxamide; Mass (m/z): 391.0; m. pt.: 122-124° C.

Compound No. 157: N-[2-({[(1S)-2-cyclopentyl-1-methylethyl]amino}methyl)phenyl]-1-benzofuran-2-carboxamide; Mass (m/z): 377.1; m. pt.: 150-152° C.

Compound No. 158: N-[2-({[(1S)-2-cycloheptyl-1-methylethyl]amino}methyl)phenyl]-1-benzofuran-2-carboxamide; Mass (m/z): 405.2; m. pt.: 133-134° C.

Compound No. 159: N-{3-[5-({[2-({[(1S)-2-cyclohexyl-1-methylethyl]amino}methyl)phenyl]amino}sulfonyl)-2-thienyl]phenyl}acetamide; Mass (m/z): 526.1; m. pt.: 95-98° C.

Compound No. 160: N-{3-[5-({[2-({[(1S)-2-cyclopentyl-1-methylethyl]amino}methyl)phenyl]amino}sulfonyl)-2-thienyl]phenyl}acetamide; Mass (m/z): 512.0; m. pt.: 84-87° C.

Compound No. 161: N-[2-({[(1S)-2-cyclohexyl-1-methylethyl]amino}methyl)phenyl]-5-(2,3,4-trimethoxyphenyl)thiophene-2-sulfonamide; Mass (m/z): 559.1; m. pt.: Gummy;

Compound No. 162: N-[2-({[(1S)-2-cyclopentyl-1-methylethyl]amino}methyl)phenyl]-5-(2,3,4-trimethoxyphenyl)thiophene-2-sulfonamide; Mass (m/z): 545.1; m. pt.: Gummy;

Compound No. 163: N-[2-({[(1S)-2-cyclopentyl-1-methylethyl]amino}methyl)phenyl]-4-fluorobenzamide; Mass (m/z): 355.2; m. pt.: 103-105° C.

Compound No. 164: N-[2-({[(1S)-2-cyclohexyl-1-methylethyl]amino}methyl)phenyl]-4-fluorobenzamide; Mass (m/z): 369.1; m. pt.: 118-120° C.

Compound No. 165: 4-amino-N-[2-({[(1S)-2-cyclohexyl-1-methylethyl]amino}methyl)phenyl]benzamide; Mass (m/z): 366.2; m. pt.: 116-118° C.

Compound No. 166: N-[2-({[(1S)-2-cyclohexyl-1-methylethyl]amino}methyl)phenyl]-N'-isopropylurea; Mass (m/z): 332.2; m. pt.: 61-62° C.

Compound No. 167: N-[2-({[(1S)-2-cyclohexyl-1-methylethyl]amino}methyl)phenyl]-N'-isopropylthiourea; Mass (m/z): ; m. pt.: 167-169° C.

Compound No. 168: N-[2-({[(1S)-2-cyclohexyl-1-methylethyl]amino}methyl)phenyl]-N'-(4-methoxyphenyl)urea; Mass (m/z): 396.1; m. pt.: 52-54° C.

Compound No. 169: N-(4-acetylphenyl)-6-({[2-({[(1S)-2-cyclopentyl-1-methylethyl]amino}methyl)phenyl]amino}sulfonyl)-3,4-dihydroisoquinoline-2(1H)-carboxamide; Mass (m/z): 589.2 m. pt.: 92-97° C.

Compound No. 170: N-[2-({[(1S)-2-cycloheptyl-1-methylethyl]amino}methyl)phenyl]-1,2,3,4-tetrahydroisoquinoline-6-sulfonamide; Mass (m/z): 456.1; m. pt.: 88-90° C.

Compound No. 171: N-[2-({[(1S)-2-cycloheptyl-1-methylethyl]amino}methyl)phenyl]-N'-isopropylurea; Mass (m/z): 346.2; m. pt.: Gummy;

Compound No. 172: N-[2-({[(1S)-2-cyclohexyl-1-methylethyl]amino}methyl)phenyl]isoxazole-5-carboxamide; Mass (m/z): 342.1; m. pt.: not done Compound No. 173: N-[2-({[(1S)-2-cyclohexyl-1-methylethyl]amino}methyl)phenyl]-5-isoxazol-5-ylthiophene-2-carboxamide; Mass (m/z): 460.0; m. pt.: 65-67° C.

Compound No. 174: N-[2-({[(1S)-2-cycloheptyl-1-methylethyl]amino}methyl)phenyl]-4-fluorobenzamide; Mass (m/z): 383.2; m. pt.: 73-74° C.

Compound No. 175: tert-butyl 4-(2-{[2-(2-furoylamino)benzyl]amino}propyl)piperidine-1-carboxylate; Mass (m/z): 442.2; m. pt.: 65-67° C.

Compound No. 176: N-[2-({[(1S)-2-cyclohexyl-1-methylethyl]amino}methyl)phenyl]-4-nitrobenzamide; Mass (m/z): 396.1; m. pt.: 76-77° C.

Compound No. 177: tert-butyl 4-[2-({2-[(4-fluorobenzoyl)amino]benzyl}amino)propyl]piperidine-1-carboxylate; Mass (m/z): 470.1; m. pt.: 40-42° C.

Compound No. 178: tert-butyl 4-[2-({2-[(2-thienylcarbonyl)amino]benzyl}amino)propyl]piperidine-1-carboxylate; Mass (m/z): 458.1; m. pt.: 48-49° C.

Compound No. 179: N-[2-({[(1S)-2-cyclohexyl-1-methylethyl]amino}methyl)phenyl]-1-pyrazin-2-yl-1H-imidazole-4-sulfonamide; Mass (m/z): 455.1; m. pt.: 90-92° C.

Compound No. 180: N-[2-({[(1S,2R)-2-cyclohexyl-2-hydroxy-1-methylethyl]amino}methyl)phenyl]thiophene-2-sulfonamide; Mass (m/z): 409.0; m. pt.: 74-76° C.

Compound No. 181: N-[2-({[(1S,2R)-2-cyclohexyl-2-hydroxy-1-methylethyl]amino}methyl)phenyl]-1-benzofuran-2-carboxamide; Mass (m/z): 407.1; m. pt.: 146-147° C.

Compound No. 182: tert-butyl 4-{2-[(2-{[(5-isoxazol-5-yl-2-thienyl)carbonyl]amino}benzyl)amino]propyl}piperidine-1-carboxylate; Mass (m/z): 561.1; m. pt.: 75-80° C.

Compound No. 183: N-[2-({[(1S)-2-cyclopentyl-1-methylethyl]amino}methyl)phenyl]-5-isoxazol-5-ylthiophene-2-sulfonamide; Mass (m/z): 446.1; m. pt.: 51-55° C.

Compound No. 183a: N-(2-{[(2-cyclohexyl-1-methylethyl)amino]methyl}phenyl)-N'-[4-(1,3-oxazol-5-yl)phenyl]urea; Mass (m/z) 433.2; m. pt.: 72-74° C.;

Compound No. 183b: N-(2-{[(2-cyclohexyl-1-methylethyl)amino]methyl}phenyl)-4-[(methylsulfonyl)amino]benzenesulfonamide The following compounds can be prepared following the above general procedures Compound No. 184: N-(4-chlorophenyl)-N'-(2-{[(2-cyclohexyl-1-methylethyl)amino]methyl}phenyl)urea;

Compound No. 185: N-(2-{[(2-cyclohexyl-1-methylethyl)amino]methyl}phenyl)-N'-phenylurea;

Compound No. 186: N-(2-{[(2-cyclohexyl-1-methylethyl)amino]methyl}phenyl)-N'-(3,4-dichlorophenyl)urea;

Compound No. 187: N-(2-{[(2-cyclohexyl-1-methylethyl)amino]methyl}phenyl)-N'-(3,4,5-trichlorophenyl)urea;

Compound No. 188: N-(2-{[(2-cyclohexyl-1-methylethyl)amino]methyl}phenyl)-N'-(2,4-dichlorophenyl)urea;

Compound No. 189: N-(2-{[(2-cyclohexyl-1-methylethyl)amino]methyl}phenyl)-N'-(4-fluorophenyl)urea;

Compound No. 190: N-(2-{[(2-cyclohexyl-1-methylethyl)amino]methyl}phenyl)-N'-1-naphthylurea;

Compound No. 191: N-(2-{[(2-cyclohexyl-1-methylethyl)amino]methyl}phenyl)-N'-isopropyl urea;

Compound No. 192: N-(2-{[(2-cyclohexyl-1-methylethyl)amino]methyl}phenyl)-N'-isopropylthiourea;

Compound No. 193: N-(2-{[(2-cyclohexyl-1-methylethyl)amino]methyl}phenyl)-N'-1-naphthylthiourea;

Compound No. 194: N-(2-{[(2-cyclohexyl-1-methylethyl)amino]methyl}phenyl)-N'-(trichloromethyl)thiourea;

Compound No. 195: N-(2-{[(2-cyclohexyl-1-methylethyl)amino]methyl}phenyl)-4-phenylpiperazine-1-carboxamide;

Compound No. 196: 4-benzyl-N-(2-{[(2-cyclohexyl-1-methylethyl)amino]methyl}phenyl)piperazine-1-carboxamide;

Compound No. 197: N-(2-{[(2-cyclohexyl-1-methylethyl)amino]methyl}phenyl)piperazine-1-carboxamide;

Compound No. 198: 4-(4-chlorophenyl)-N-(2-{[(2-cyclohexyl-1-methylethyl)amino]methyl}phenyl)piperazine-1-carboxamide;

Compound No. 199: N-(2-{[(2-cyclohexyl-1-methylethyl)amino]methyl}phenyl)-4-methyl piperazine-1-carboxamide;

Compound No. 200: N-(2-{[(2-cyclohexyl-1-methylethyl)amino]methyl}phenyl)morpholine-4-carboxamide;

Compound No. 201: N-(2-{[(2-cyclohexyl-1-methylethyl)amino]methyl}phenyl)-4-pyrimidin-4-ylpiperazine-1-carboxamide;

Compound No. 202: 4-chloro-N-{[(2-{[(2-cyclohexyl-1-methylethyl)amino]methyl}phenyl)amino]carbonyl}benzenesulfonamide;

Compound No. 203: N-{[(2-{[(2-cyclohexyl-1-methylethyl)amino]methyl}phenyl)amino]carbonyl}-4-methylbenzenesulfonamide;

Compound No. 204: N-{[(2-{[(2-cyclohexyl-1-methylethyl)amino]methyl}phenyl)amino]carbonyl}benzamide;

Compound No. 205: N-{[(2-{[(2-cyclohexyl-1-methylethyl)amino]methyl}phenyl)amino]carbonyl}benzenecarbothioamide;

Compound No. 206: 4-[(4-chlorophenyl)sulfonyl]-N-(2-{[(2-cyclohexyl-1-methylethyl)amino]methyl}phenyl)piperazine-1-carboxamide;

Compound No. 207: N-(2-{[(2-cyclohexyl-1-methylethyl)amino]methyl}phenyl)-4-(phenylsulfonyl)piperazine-1-carboxamide;

Compound No. 208: N-(2-{[(2-cyclohexyl-1-methylethyl)amino]methyl}phenyl)-4-[(4-methylphenyl)sulfonyl]piperazine-1-carboxamide;

Compound No. 209: N-(2-{[(2-cyclohexyl-1-methylethyl)amino]methyl}phenyl)-4-(2-thienylsulfonyl)piperazine-1-carboxamide;

Compound No. 210: N-{(1E)-amino[(2-{[(2-cyclohexyl-1-methylethyl)amino]methyl}phenyl)amino]methylene}-4-chlorobenzenesulfonamide;

Compound No. 211: N-{(1E)-amino[(2-{[(2-cyclohexyl-1-methylethyl)amino]methyl}phenyl)amino]methylene}-4-methylbenzenesulfonamide;

Compound No. 212: N-{(1E)-amino[(2-{[(2-cyclohexyl-1-methylethyl)amino]methyl}phenyl)amino]methylene}methanesulfonamide;

Compound No. 213: N-{(1E)-amino[(2-{[(2-cyclohexyl-1-methylethyl)amino]methyl}phenyl)amino]methylene}thiophene-2-sulfonamide;
Compound No. 214: N-(2-{[(1-methyl-2-piperazin-1-ylethyl)amino]methyl}phenyl)benzenesulfonamide;
Compound No. 215: 4-methyl-N-(2-{[(1-methyl-2-piperazin-1-ylethyl)amino]methyl}phenyl)benzenesulfonamide;
Compound No. 216: 4-chloro-N-(2-{[(1-methyl-2-piperazin-1-ylethyl)amino]methyl}phenyl)benzenesulfonamide;
Compound No. 217: N-(2-{[(1-methyl-2-piperazin-1-ylethyl)amino]methyl}phenyl)thiophene-2-sulfonamide;
Compound No. 218: 5-bromo-N-(2-{[(1-methyl-2-piperazin-1-ylethyl)amino]methyl}phenyl)thiophene-2-sulfonamide;
Compound No. 219: 4-methyl-N-[2-({[1-methyl-2-(4-phenylpiperazin-1-yl)ethyl]amino}methyl)phenyl]benzenesulfonamide;
Compound No. 220: N-[2-({[1-methyl-2-(4-phenylpiperazin-1-yl)ethyl]amino}methyl)phenyl]benzenesulfonamide;
Compound No. 221: N-[2-({[1-methyl-2-(4-phenylpiperazin-1-yl)ethyl]amino}methyl)phenyl]thiophene-2-sulfonamide;
Compound No. 222: 5-bromo-N-[2-({[1-methyl-2-(4-phenylpiperazin-1-yl)ethyl]amino}methyl)phenyl]thiophene-2-sulfonamide;
Compound No. 223: 4-methyl-N-[2-({[1-methyl-2-(4-methylpiperazin-1-yl)ethyl]amino}methyl)phenyl]benzenesulfonamide;
Compound No. 224: 4-chloro-N-[2-({[1-methyl-2-(4-methylpiperazin-1-yl)ethyl]amino}methyl)phenyl]benzenesulfonamide;
Compound No. 225: N-[2-({[1-methyl-2-(4-methylpiperazin-1-yl)ethyl]amino}methyl)phenyl]thiophene-2-sulfonamide;
Compound No. 226: N-(4-chlorophenyl)-N'-[2-({[1-methyl-2-(4-methylpiperazin-1-yl)ethyl]amino}methyl)phenyl]urea;
Compound No. 227: N-(4-chlorophenyl)-N'-[2-({[1-methyl-2-(4-phenylpiperazin-1-yl)ethyl]amino}methyl)phenyl]urea;
Compound No. 228: N-{2-[({[(2-cyclohexyl-1-methylethyl)amino]carbonyl}amino)methyl]phenyl}methanesulfonamide;
Compound No. 229: N-{2-[({[(2-cyclohexyl-1-methylethyl)amino]carbonyl}amino)methyl]phenyl}benzenesulfonamide;
Compound No. 230: {2-[({[(2-cyclohexyl-1-methylethyl)amino]carbonyl}amino)methyl]phenyl}-4-methylbenzenesulfonamide;
Compound No. 231: N-{2-[({[(2-cyclohexyl-1-methylethyl)amino]carbonyl}amino)methyl]phenyl}thiophene-2-sulfonamide;
Compound No. 232: 5-bromo-N-{2-[({[(2-cyclohexyl-1-methylethyl)amino]carbonyl}amino)methyl]phenyl}thiophene-2-sulfonamide;
Compound No. 233: 4-chloro-N-{2-[({[(2-cyclohexyl-1-methylethyl)amino]carbonyl}amino)methyl]phenyl}benzenesulfonamide;
Compound No. 234: N-(2-{[(2-cyclohexyl-1-methylethyl)amino]methyl}phenyl)-3-methoxy-4-piperazin-1-ylbenzenesulfonamide;
Compound No. 235: N-(2-{[(2-cycloheptyl-1-methylethyl)amino]methyl}phenyl)-5-(phenylsulfonyl)thiophene-2-sulfonamide;
Compound No. 236: N-(2-{[(2-cyclohexyl-1-methylethyl)amino]methyl}phenyl)-1-benzofuran-2-carboxamide;
Compound No. 237: N-(2-{[(2-cyclopentyl-1-methylethyl)amino]methyl}phenyl)-2-(1,3-dioxo-1,3-dihydro-2H-isoindol-2-yl)acetamide;
Compound No. 238: 2-{[(2-cyclohexyl-1-methylethyl)amino]methyl}phenyl (4-methoxyphenyl)carbamate;
Compound No. 239: N-(2-{[(2-cycloheptyl-1-methylethyl)amino]methyl}phenyl)-6-(1H-imidazol-1-yl)nicotinamide;
Compound No. 240: N-(4-{[(2-{[(2-cyclopropyl-1-methylethyl)amino]methyl}phenyl)amino]sulfonyl}phenyl)thiophene-2-sulfonamide;
Compound No. 241: N-(2-{[(2-cyclopentyl-1-methylethyl)amino]methyl}phenyl)-2-(1H-1,2,4-triazol-1-yl)acetamide;
Compound No. 242: N-(2-{[(2-cycloheptyl-1-methylethyl)amino]methyl}phenyl)-2-(4-pyrimidin-2-ylpiperazin-1-yl)acetamide;
Compound No. 243: 2-{[(2-cyclopentyl-1-methylethyl)amino]methyl}phenyl (4-acetylphenyl)carbamate;
Compound No. 244: N-(2-{[(2-cycloheptyl-1-methylethyl)amino]methyl}phenyl)isonicotinamide;
Compound No. 245: N-(2-{[(2-cycloheptyl-1-methylethyl)amino]methyl}phenyl)-4-fluorobenzenesulfonamide;
Compound No. 246: N-(2-{[(2-cyclohexyl-1-methylethyl)amino]methyl}phenyl)-6-(3-furyl)nicotinamide;
Compound No. 247: N-(2-{[(2-cyclopentyl-1-methylethyl)amino]methyl}phenyl)-4-(1H-1,2,3-triazol-1-yl)benzenesulfonamide;
Compound No. 248: N-(3-{[(2-cycloheptyl-1-methylethyl)amino]methyl}pyridin-2-yl)-2-furamide;
Compound No. 249: N-(2-{[(2-cyclopentyl-1-methylethyl)amino]methyl}phenyl)isonicotinamide;
Compound No. 250: N-(2-{[(2-cyclohex-1-en-1-yl-1-methylethyl)amino]methyl}phenyl)-5-(1,3-oxazol-5-yl)furan-2-sulfonamide;
Compound No. 251: N-(2-{[(2-cyclopropyl-1-methylethyl)amino]methyl}phenyl)-N'-(3-methylisoxazol-5-yl)urea;
Compound No. 252: 2-{[(2-cyclohexyl-1-methylethyl)amino]methyl}phenyl[4-(1H-imidazol-1-yl)phenyl]carbamate;
Compound No. 253: N-(2-{[(2-cyclohexyl-1-methylethyl)amino]methyl}phenyl)-5-(3-furyl)nicotinamide;
Compound No. 254: 1-benzofuran-2-ylmethyl (2-{[(2-cyclohexyl-1-methylethyl)amino]methyl}phenyl)carbamate;
Compound No. 255: N-[2-({[1-methyl-2-(4-methylpiperazin-1-yl)ethyl]amino}methyl)phenyl]thiophene-2-sulfonamide;
Compound No. 256: N-1-benzothien-2-yl-N'-[2-({[1-methyl-2-(tetrahydro-2H-pyran-4-yl)ethyl]amino}methyl)phenyl]urea;
Compound No. 257: 2-{[(2-cyclohexyl-1-methylethyl)amino]methyl}phenyl[4-(1H-pyrazol-1-yl)phenyl]carbamate;
Compound No. 258: 2-{[(2-cyclohexyl-1-methylethyl)amino]methyl}phenyl[4-(2-furyl)phenyl]carbamate;
Compound No. 259: 3,3'-bipyridin-6-yl (2-{[(2-cyclohexyl-1-methylethyl)amino]methyl}phenyl)carbamate;
Compound No. 260: Pyridin-4-yl (2-{[(2-cyclohexyl-1-methylethyl)amino]methyl}phenyl)carbamate;
Compound No. 261: N-1-benzothien-2-yl-N'-(4-{[(2-cyclohexyl-1-methylethyl)amino]methyl}pyridin-3-yl)urea;
Compound No. 262: N-1-benzothien-2-yl-N'-(2-{[(2-cyclohexyl-1-methylethyl)amino]methyl}pyridin-3-yl)urea;
Compound No. 263: 3-{[(2-cyclohexyl-1-methylethyl)amino]methyl}pyridin-4-yl 1-benzothien-2-ylcarbamate;

Compound No. 264: 3-{[(2-cyclohexyl-1-methylethyl)amino]methyl}pyridin-2-yl 1-benzothien-2-ylcarbamate;
Compound No. 265: N-1-benzothien-2-yl-N'-(3-{[(2-cyclohexyl-1-methylethyl)amino]methyl}pyridin-2-yl)urea;
Compound No. 266: N-1-benzothien-2-yl-N'-(3-{[(2-cyclohexyl-1-methylethyl)amino]methyl}pyridin-4-yl)urea;
Compound No. 267: 2-{[(2-cyclohexyl-1-methylethyl)amino]methyl}pyridin-3-yl 1-benzothien-2-ylcarbamate;
Compound No. 268: 4-{[(2-cyclohexyl-1-methylethyl)amino]methyl}pyridin-3-yl 1-benzothien-2-ylcarbamate;
Compound No. 269: 1-benzothien-2-yl (3-{[(2-cyclohexyl-1-methylethyl)amino]methyl}pyridin-2-yl)carbamate;
Compound No. 270: 1-benzothien-2-yl (4-{[(2-cyclohexyl-1-methylethyl)amino]methyl}pyridin-3-yl)carbamate;
Compound No. 271: 1-benzothien-2-yl (2-{[(2-cyclohexyl-1-methylethyl)amino]methyl}pyridin-3-yl)carbamate;
Compound No. 272: 2-{[(2-cyclopropyl-1-methylethyl)amino]methyl}phenyl[4-(2-furyl)phenyl]carbamate;
Compound No. 273: 2-{[(2-cyclopropyl-1-methylethyl)amino]methyl}phenyl 1-benzothien-2-ylcarbamate;
Compound No. 274: 1-benzothien-2-yl[2-({[1-methyl-2-(tetrahydro-2H-pyran-4-yl)ethyl]amino}methyl)phenyl]carbamate;
Compound No. 275: 1-benzothien-2-yl (3-{[(2-cyclohexyl-1-methylethyl)amino]methyl}pyridin-4-yl)carbamate;
Compound No. 276: 1-benzothien-2-yl (2-{[(2-cyclopropyl-1-methylethyl)amino]methyl}phenyl)carbamate;
Compound No. 277: N-(2-{[(2-cyclopropyl-1-methylethyl)amino]methyl}phenyl)-2-(1,3-dioxo-1,3-dihydro-2H-isoindol-2-yl)acetamide;
Compound No. 278: 1-benzothien-2-yl[2-({[1-methyl-2-(tetrahydro-2H-pyran-4-yl)ethyl]amino}methyl)pyridin-3-yl]carbamate;
Compound No. 279: N-(2-{[(2-cyclopentyl-1-methylethyl)amino]methyl}phenyl)-2-(1H-1,2,4-triazol-1-yl)acetamide;
Compound No. 280: 1-benzothien-2-yl (2-{[(1-methyl-2-piperidin-4-ylethyl)amino]methyl}phenyl)carbamate;
Compound No. 281: 3-{[(1-methyl-2-piperidin-4-ylethyl)amino]methyl}pyridin-4-yl 1-benzothien-2-ylcarbamate;
Compound No. 282: N-1-benzothien-2-yl-N'-(2-{[(1-methyl-2-piperidin-4-ylethyl)amino]methyl}phenyl)urea;
Compound No. 283: N-(2-{[(1-methyl-2-piperidin-4-ylethyl)amino]methyl}phenyl)thiophene-2-sulfonamide;
Compound No. 284: N-(2-{[(1-methyl-2-piperidin-4-ylethyl)amino]methyl}phenyl)-2-(1H-pyrazol-1-yl)acetamide;
Compound No. 285: N-(2-{[(1-methyl-2-piperidin-4-ylethyl)amino]methyl}phenyl)isonicotinamide.
Compound No. 286: 4-chloro-N-({[2-({[(1S)-2-cyclohexyl-1 methylethyl]amino}methyl)phenyl]amino}carbonyl)benzenesulfonamide, Mass (m/z): 464.1; m. pt.: 162-163;
Compound No. 287: N-[2-({[(1S)-2-cyclohexyl-1-methylethyl]amino}methyl)phenyl]-N'-(4-morpholin-4-ylphenyl)urea, Mass (m/z): 451.3; m. pt.: 68-70;
Compound No. 288: N-[2-({[(1S)-2-cyclohexyl-1-methylethyl]amino}methyl)phenyl]-N'-[3-(2-furyl)-1H-pyrazol-5-yl]urea, Mass (m/z): 422.2; m. pt.: 103-105;
Compound No. 289: N-[2-({[(1S)-2-cyclohexyl-1-methylethyl]amino}methyl)phenyl]-N'-(5-oxo-1-phenyl-4,5-dihydro-1H-pyrazol-3-yl)urea, Mass (m/z): 448.2; m. pt.: 162-164;
Compound No. 290: N-[2-({[(1S)-2-cyclohexyl-1-methylethyl]amino}methyl)phenyl]-N'-(4-methoxy-1,2-benzisoxazol-3-yl)urea, Mass (m/z): 437.2; m. pt.: 70-71;
Compound No. 291: N-[2-({[(1S)-2-cyclohexyl-1-methylethyl]amino}methyl)phenyl]-N'-(3,4-dimethylisoxazol-5-yl)urea, Mass (m/z): 385.2; m. pt.: 53-55;
Compound No. 292: N-[2-({[(1S)-2-cyclohexyl-1-methylethyl]amino}methyl)phenyl]-N'-[1-methyl-3-(2-thienyl)-1H-pyrazol-5-yl]urea, Mass (m/z): 452.2; m. pt.: 105-107;
Compound No. 293: N-[2-({[(1S)-2-cyclohexyl-1-methylethyl]amino}methyl)phenyl]-1H-imidazole-4-sulfonamide, Mass (m/z): 376.50; m. pt.: 55-56;
Compound No. 294: N-[2-({[(1S)-2-cyclopentyl-1-methylethyl]amino}methyl)phenyl]-1H-imidazole-4-sulfonamide, Mass (m/z): 363.1; m. pt.: 120-122;
Compound No. 295: N-[4-({[2-({[(1S)-2-cyclohexyl-1-methylethyl]amino}methyl)phenyl]amino}sulfonyl)phenyl]acetamide, Mass (m/z): 444.3; m. pt.: 69-72;
Compound No. 296: 4-amino-N-[2-({[(1S)-2-cyclohexyl-1-methylethyl]amino}methyl)phenyl]benzenesulfonamide, Mass (m/z): 402.3; m. pt.: 74-76;
Compound No. 297: N-[4-({[2-({[(1S)-2-cyclopentyl-1-methylethyl]amino}methyl)phenyl]amino}sulfonyl)phenyl]thiophene-2-sulfonamide, Mass (m/z): 534.1; m. pt.: 93.8-95;
Compound No. 298: 2-thienylmethyl[2-({[(1S)-2-cyclohexyl-1-methylethyl]amino}methyl)phenyl]carbamate, Mass (m/z): 387.2;
Compound No. 299: 2-thienylmethyl[2-({[(1S)-2-cyclopentyl-1-methylethyl]amino}methyl)phenyl]carbamate, Mass (m/z): 373.2;
Compound No. 300: N-[2-({[(1S)-2-cyclopentyl-1-methylethyl]amino}methyl)phenyl]-5-(2,3,4-trimethoxyphenyl)thiophene-2-sulfonamide, Mass (m/z): 545.1;
Compound No. 301: N-[2-({[(1S)-2-cyclohexyl-1-methylethyl]amino}methyl)phenyl]-4-{3-[(E)-(hydroxyimino)methyl]-1H-pyrrol-1-yl}benzenesulfonamide, Mass (m/z): 495.1; m. pt.: 150-152;
Compound No. 302: N-[2-({[(1S)-2-cyclohexyl-1-methylethyl]amino}methyl)phenyl]-4-(3-formyl-1H-pyrrol-1-yl)benzamide, Mass (m/z): 444.2; m. pt.: 84-86;
Compound No. 303: N-[2-({[(1S)-2-cyclohexyl-1-methylethyl]amino}methyl)phenyl]-N'-[4-(1,2,3-thiadiazol-4-yl)phenyl]urea, Mass (m/z): 450.2; m. pt.: 158-159;
Compound No. 304: N-[2-({[(1S)-2-cyclohexyl-1-methylethyl]amino}methyl)phenyl]-1-benzofuran-6-carboxamide, Mass (m/z): 391.2;
Compound No. 305: N-[2-({[(1S)-2-cyclohexyl-1-methylethyl]amino}methyl)phenyl]-3,5-dimethylisoxazole-4-sulfonamide, Mass (m/z): 406.2; m. pt.: 104-106;
Compound No. 306: N-[4-({[2-({[(1S)-2-cyclohexyl-1-methylethyl]amino}methyl)phenyl]amino}sulfonyl)phenyl]isoxazole-5-carboxamide, Mass (m/z): 497.1;
Compound No. 307: N-[4-({[2-({[(1S)-2-cyclohexyl-1-methylethyl]amino}methyl)phenyl]amino}sulfonyl)phenyl]-3,5-dimethylisoxazole-4-sulfonamide, Mass (m/z): 561.0; m. pt.: 82-84;
Compound No. 308: N-[4-({[2-({[(1S)-2-cyclohexyl-1-methylethyl]amino}methyl)phenyl]amino}sulfonyl)phenyl]-1-methyl-1H-imidazole-4-sulfonamide, Mass (m/z): 546.1; m. pt.: 175-177;
Compound No. 309: N-[2-({[(1S)-2-cyclohexyl-1-methylethyl]amino}methyl)phenyl]-4-(1-hydroxyethyl)benzenesulfonamide, Mass (m/z): 431.1; m. pt.: 42-44;
Compound No. 310: pyridin-3-ylmethyl[2-({[(1S)-2-cyclohexyl-1methylethyl]amino}methyl)phenyl]carbamate, Mass (m/z): 382.3;
Compound No. 311: pyridin-3-ylmethyl[2-({[(1S)-2-cyclopentyl-1-methylethyl]amino}methyl)phenyl]carbamate, Mass (m/z): 368.2;

Compound No. 312: pyridin-3-ylmethyl[2-({[(1S,2R)-2-cyclohexyl-2-hydroxy-1-methylethyl]amino}methyl)phenyl]carbamate, Mass (m/z): 398.1;

Compound No. 313: N-[2-({[(1S)-2-cyclopentyl-1-methylethyl]amino}methyl)phenyl]-1-pyrazin-2-yl-1H-imidazole-4-sulfonamide, Mass (m/z): 441.2; m. pt.: 85-87;

Compound No. 314: 5-chloro-N-[2-({[(1S,2R)-2-cyclohexyl-2-hydroxy-1-methylethyl]amino}methyl)phenyl]-3-methyl-1-benzothiophene-2-sulfonamide, Mass (m/z): 507.1; m. pt.: 110-112;

Compound No. 315: ethyl 3-[5-({[2-({[(1S)-2-cyclopentyl-1-methylethyl]amino}methyl)phenyl]amino}sulfonyl)-2-thienyl]benzoate, Mass (m/z): 527.1;

Compound No. 316: 4-acetyl-N-[4-({[2-({[(1S)-2-cyclohexyl-1-methylethyl]amino}methyl)phenyl]amino}sulfonyl)phenyl]benzenesulfonamide, Mass (m/z): 584.2; m. pt.: 117-119;

Compound No. 317: N-[4-({[2-({[(1S)-2-cyclohexyl-1-methylethyl]amino}methyl)phenyl]amino}sulfonyl)phenyl]-2,4-dimethyl-1,3-thiazole-5-sulfonamide, Mass (m/z): 577.1; m. pt.: 72-73;

Compound No. 318: N-1,3-benzothiazol-2-yl-N'-[2-({[(1S)-2-cyclohexyl-1methylethyl]amino}methyl)phenyl]urea, Mass (m/z): 423.1; m. pt.: 74-75;

Compound No. 319: N-[2-({[(1S)-2-cyclohexyl-1-methylethyl]amino}methyl)phenyl]-N'-[4-(1,3-oxazol-5-yl)phenyl]urea, Mass (m/z): 433.2; m. pt.: 133-135;

Compound No. 320: N-[2-({[(1S)-2-cyclohexyl-1-methylethyl]amino}methyl)phenyl]-4-(1,3-dioxo-1,3-dihydro-2H-isoindol-2-yl)benzenesulfonamide, Mass (m/z): 532.1; m. pt.: 142-144;

Compound No. 321: N-[2-({[(1S,2S)-2-cyclohexyl-2-hydroxy-1-methylethyl]amino}methyl)phenyl]-1,2,3,4-tetrahydroisoquinoline-6-sulfonamide, Mass (m/z): 458.2; m. pt.: 127.2-129.1;

Compound No. 322: N-[2-({[(1S,2S)-2-cyclohexyl-2-hydroxy-1-methylethyl]amino}methyl)phenyl]-1-benzothiophene-2-sulfonamide, Mass (m/z): 459.0; m. pt.: 78.8-82.1;

Compound No. 323: N-[2-({[(1S,2S)-2-cyclohexyl-2-hydroxy-1-methylethyl]amino}methyl)phenyl]-5-isoxazol-5-ylthiophene-2-sulfonamide, Mass (m/z): 476.0; m. pt.: 89.3-93.8;

Compound No. 324: N-[2-({[(1S,2S)-2-cyclohexyl-2-hydroxy-1-methylethyl]amino}methyl)phenyl]-2-(trifluoroacetyl)-1,2,3,4-tetrahydroisoquinoline-6-sulfonamide, Mass (m/z): 554.1; m. pt.: 73.6-75.8;

Compound No. 325: N-[2-({[(1S)-2-cyclohexyl-1-methylethyl]amino}methyl)phenyl]-4-(3-formyl-1H-pyrrol-1-yl)benzenesulfonamide, Mass (m/z): 480.1; m. pt.: 53-54;

Compound No. 326: N-[3-({[(1S)-2-cyclohexyl-1-methylethyl]amino}methyl)pyridin-2-yl]-5-isoxazol-5-ylthiophene-2-sulfonamide, Mass (m/z): 461.0; m. pt.: 107-108;

Compound No. 327: N-[3-({[(1S)-2-cyclopentyl-1-methylethyl]amino}methyl)pyridin-2-yl]-5-isoxazol-3-ylthiophene-2-sulfonamide, Mass (m/z): 447.0; m. pt.: 97-99;

Compound No. 328: N-[3-({[(1S)-2-cyclohexyl-1-methylethyl]amino}methyl)pyridin-2-yl]-4-(1H-pyrrol-1-yl)benzenesulfonamide, Mass (m/z): 453.2; m. pt.: 179-180;

Compound No. 329: N-[2-({[(1S)-2-cyclopentyl-1-methylethyl]amino}methyl)phenyl]-4-(3-formyl-1H-pyrrol-1-yl)benzenesulfonamide, Mass (m/z): 466.0; m. pt.: 76-78;

Compound No. 330: N-[2-({[(1S)-2-cyclohexyl-1-methylethyl]amino}methyl)phenyl]-4-(2-oxo-1,3-oxazolidin-3-yl)benzenesulfonamide, Mass (m/z): 472.2; m. pt.: 75-77;

Compound No. 331: N-[4-({[2-({[(1S)-2-cyclohexyl-1-methylethyl]amino}methyl)phenyl]amino}sulfonyl)phenyl]thiophene-3-sulfonamide, Mass (m/z): 548.2; m. pt.: 162-165;

Compound No. 332: N-[2-({[(1S)-2-cyclohexyl-1-methylethyl]amino}methyl)phenyl]-5-(1-methyl-1H-pyrazol-4-1)thiophene-2-sulfonamide, Mass (m/z): 473.1; m. pt.: 85-87;

Compound No. 333: N-[2-({[(1S)-2-cyclohexyl-1-methylethyl]amino}methyl)phenyl]-1-(2-thienylsulfonyl)-1H-imidazole-4-sulfonamide, Mass (m/z): 523.0; m. pt.: 67-69;

Compound No. 334: N-[2-({[(1S)-2-cyclopentyl-1-methylethyl]amino}methyl)phenyl]-2,1,3-benzothiadiazole-4-sulfonamide, Mass (m/z): 431.0; m. pt.: 72-74;

Compound No. 335: N-[4-({[2-({[(1S)-2-cyclopentyl-1-methylethyl]amino}methyl)phenyl]amino}sulfonyl)phenyl]-1-methyl-1H-imidazole-4-sulfonamide, Mass (m/z): 532.1; m. pt.: 114.6-116.2;

Compound No. 336: N-[2-({[(1S)-2-cyclopentyl-1-methylethyl]amino}methyl)phenyl]-4-[(methylsulfonyl)amino]benzenesulfonamide, Mass (m/z): 466.1; m. pt.: 78.6-80.9;

Compound No. 337: 4-[(butylsulfonyl)amino]-N-[2-({[(1S)-2-cyclohexyl-1-methylethyl]amino}methyl)phenyl]benzenesulfonamide, Mass (m/z): 522.2; m. pt.: 53-56;

Compound No. 338: N-[2-({[(1S)-2-cyclohexyl-1-methylethyl]amino}methyl)phenyl]-4-[(ethylsulfonyl)amino]benzenesulfonamide, Mass (m/z): 494.1; m. pt.: 65-67;

Compound No. 339: 5-chloro-N-[4-({[2-({[(1S)-2-cyclohexyl-1-methylethyl]amino}methyl)phenyl]amino}sulfonyl)phenyl]-1,3-dimethyl-1H-pyrazole-4-sulfonamide, Mass (m/z): 594.2; m. pt.: 75-78;

Compound No. 340: methyl 4-({[4-({[2-({[(1S)-2-cyclohexyl-1-methylethyl]amino}methyl)phenyl]amino}sulfonyl)phenyl]amino}sulfonyl)-2,5-dimethyl-3-furoate, Mass (m/z): 618.2; m. pt.: 65-67;

Compound No. 341: methyl 5-({[4-({[2-({[(1S)-2-cyclohexyl-1-methylethyl]amino}methyl)phenyl]amino}sulfonyl)phenyl]amino}sulfonyl)-3-methylthiophene-2-carboxylate, Mass (m/z): 620.2; m. pt.: 93-95;

Compound No. 342: methyl 5-({[4-({[2-({[(1S)-2-cyclohexyl-1-methylethyl]amino}methyl)phenyl]amino}sulfonyl)phenyl]amino}sulfonyl)-2-furoate, Mass (m/z): 590.2; m. pt.: 109-111;

Compound No. 343: N-[2-({[(1S)-2-cyclohexyl-1-methylethyl]amino}methyl)phenyl]-N'-(3-oxo-1,3-dihydro-2-benzofuran-5-yl)urea, Mass (m/z): 422.2; m. pt.: 169-172;

Compound No. 344: 2-[({[2-({[(1S)-2-cyclohexyl-1-methylethyl]amino}methyl)phenyl]amino}carbonyl)amino]benzamide, Mass (m/z): 392.2 (M-16); m. pt.: 51-54;

Compound No. 345: N-[2-({[(1S)-2-cyclohexyl-1-methylethyl]amino}methyl)phenyl]-N'-isoquinolin-5-ylurea, Mass (m/z): 417.2; m. pt.: 156-158;

Compound No. 346: N-[2-({[(1S)-2-cyclohexyl-1-methylethyl]amino}methyl)phenyl]-N'-morpholin-4-ylurea, Mass (m/z): 375.2; m. pt.: 132-134;

Compound No. 347: N-1,3-benzothiazol-6-yl-N'-[2-({[(1S)-2-cyclohexyl-1-methylethyl]amino}methyl)phenyl]urea, Mass (m/z): 423.1; m. pt.: 150-153;

Compound No. 348: N-[2-({[(1S)-2-cyclohexyl-1-methylethyl]amino}methyl)phenyl]-N'-1,3-thiazol-2-ylurea, Mass (m/z): 373.2; m. pt.: 51-54;

Compound No. 349: ethyl 3-[5-({[2-({[(1S)-2-cyclohexyl-1-methylethyl]amino}methyl)phenyl]amino}sulfonyl)-2-thienyl]benzoate, Mass (m/z): 541.1;

Compound No. 350: N-[2-({[(1S)-2-cyclohexyl-1-methylethyl]amino}methyl)phenyl]-1,3-benzothiazole-2-sulfonamide, Mass (m/z): 444.1; m. pt.: 80-82;

Compound No. 351: N-[2-({[(1S,2R)-2-cyclohexyl-2-hydroxy-1-methylethyl]amino}methyl)phenyl]-4-(1H-1,2,4-triazol-1-yl)benzenesulfonamide, Mass (m/z): 470.1; m. pt.: 92-94;

Compound No. 352: N-[2-({[(1S,2R)-2-cyclohexyl-2-hydroxy-1-methylethyl]amino}methyl)phenyl]-4-(1H-pyrrol-1-yl)benzenesulfonamide, Mass (m/z): 468.2; m. pt.: 88-90;

Compound No. 353: N-[4-({[2-({[(1S)-2-cyclohexyl-1-methylethyl]amino}methyl)phenyl]amino}sulfonyl)phenyl]-2-(trifluoroacetyl)-1,2,3,4-tetrahydroisoquinoline-7-sulfonamide, Mass (m/z): 693.2; m. pt.: 114-116;

Compound No. 354: N-[2-({[(1S)-2-cyclohexyl-1-methylethyl]amino}methyl)phenyl]-4-pyridin-3-ylbenzenesulfonamide, Mass (m/z): 464.2; m. pt.: 60-62;

Compound No. 355: N-[2-({[(1S)-2-cyclopentyl-1-methylethyl]amino}methyl)phenyl]-4-pyridin-3-ylbenzenesulfonamide, Mass (m/z): 450.2; m. pt.: 135-137;

Compound No. 356: N-[2-({[(1S)-2-cyclohexyl-1-methylethyl]amino}methyl)phenyl]-4-pyrimidin-5-ylbenzenesulfonamide, Mass (m/z): 465.2; m. pt.: 63-64;

Compound No. 357: N-[2-({[(1S)-2-cyclopentyl-1-methylethyl]amino}methyl)phenyl]-4-pyrimidin-5-ylbenzenesulfonamide, Mass (m/z): 451.2; m. pt.: 120-122;

Compound No. 358: N-[2-({[(1S)-2-cyclohexyl-1-methylethyl]amino}methyl)phenyl]-4-(1-methyl-1H-pyrazol-4-yl)benzenesulfonamide, Mass (m/z): 467.2; m. pt.: 75-77;

Compound No. 359: N-[2-({[(1S)-2-cyclopentyl-1-methylethyl]amino}methyl)phenyl]-4-(1-methyl-1H-pyrazol-4-yl)benzenesulfonamide, Mass (m/z): 453.2; m. pt.: 65-67;

Compound No. 360: N-[2-({[(1S,2R)-2-cyclohexyl-2-hydroxy-1-methylethyl]amino}methyl)phenyl]-1,2,3,4-tetrahydroisoquinoline-6-sulfonamide, Mass (m/z): 458.2; m. pt.: 142.5-145;

Compound No. 361: N-[2-({[(1S,2R)-2-cyclohexyl-2-hydroxy-1-methylethyl]amino}methyl)phenyl]-5-isoxazol-5-ylthiophene-2-sulfonamide, Mass (m/z): 476.2; m. pt.: 117.6-121.8;

Compound No. 362: N-[2-({[(1S,2R)-2-cyclohexyl-2-hydroxy-1-methylethyl]amino}methyl)phenyl]-1-benzothiophene-2-sulfonamide, Mass (m/z): 459.2; m. pt.: 79.4-80.5;

Compound No. 363: N-[2-({[2-({[(1S)-2-cyclohexyl-1-methylethyl]amino}methyl)phenyl]amino}sulfonyl)phenyl]-1-methyl-1H-imidazole-4-sulfonamide, Mass (m/z): 546.2; m. pt.: 115-118;

Compound No. 364: N-[3-({[2-({[(1S)-2-cyclohexyl-1-methylethyl]amino}methyl)phenyl]amino}sulfonyl)phenyl]-1-methyl-1H-imidazole-4-sulfonamide, Mass (m/z): 546.2; m. pt.: 92-95;

Compound No. 365: 5-chloro-N-[4-({[2-({[(1S)-2-cyclopentyl-1-methylethyl]amino}methyl)phenyl]amino}sulfonyl)phenyl]-1,3-dimethyl-1H-pyrazole-4-sulfonamide, Mass (m/z): 580.1; m. pt.: 78.7-84.3;

Compound No. 366: N'-[2-({[(1S)-2-cyclohexyl-1-methylethyl]amino}methyl)phenyl]-N,N-dimethylsulfamide, Mass (m/z): 354.2;

Compound No. 367: N-[2-({[(1S)-2-cyclohexyl-1-methylethyl]amino}methyl)phenyl]-4-(1,2,3-thiadiazol-4-yl)benzenesulfonamide, Mass (m/z): 471.2; m. pt.: 122-123;

Compound No. 368: N-[2-({[(1S)-2-cyclohexyl-1-methylethyl]amino}methyl)phenyl]-4-(1,3-oxazol-5-yl)benzenesulfonamide, Mass (m/z): 454.1; m. pt.: 50-52;

Compound No. 369: N-[3-({[2-({[(1S)-2-cyclohexyl-1-methylethyl]amino}methyl)phenyl]amino}sulfonyl)phenyl]thiophene-2-sulfonamide, Mass (m/z): 548.1; m. pt.: 75-77;

Compound No. 370: N-[2-({[2-({[(1S)-2-cyclohexyl-1-methylethyl]amino}methyl)phenyl]amino}sulfonyl)phenyl]thiophene-2-sulfonamide, Mass (m/z): 548.1; m. pt.: 75-77;

Compound No. 371: 3-amino-N-[2-({[(1S)-2-cyclohexyl-1-methylethyl]amino}methyl)phenyl]benzenesulfonamide, Mass (m/z): 402.2;

Compound No. 372: 2-amino-N-[2-({[(1S)-2-cyclohexyl-1-methylethyl]amino}methyl)phenyl]benzenesulfonamide, Mass (m/z): 402.1;

Compound No. 373: N-[3-({[2-({[(1S)-2-cyclohexyl-1-methylethyl]amino}methyl)phenyl]amino}sulfonyl)phenyl]-2,4-dimethyl-1,3-thiazole-5-sulfonamide, Mass (m/z): 577.1; m. pt.: 77-78;

Compound No. 374: N-[3-({[2-({[(1S)-2-cyclohexyl-1-methylethyl]amino}methyl)phenyl]amino}sulfonyl)phenyl]-3,5-dimethylisoxazole-4-sulfonamide, Mass (m/z): 561.1; m. pt.: 63-66;

Compound No. 375: N-[3-({[2-({[(1S)-2-cyclohexyl-1-methylethyl]amino}methyl)phenyl]amino}sulfonyl)phenyl]isoxazole-5-carboxamide, Mass (m/z): 497.1; m. pt.: 97-99;

Compound No. 376: N-[3-({[2-({[(1S)-2-cyclohexyl-1-methylethyl]amino}methyl)phenyl]amino}sulfonyl)phenyl]thiophene-3-sulfonamide, Mass (m/z): 548.1; m. pt.: 68-70;

Compound No. 377: ethyl 5-{[4-({[2-({[(1S)-2-cyclohexyl-1-methylethyl]amino}methyl)phenyl]amino}sulfonyl)phenyl]amino}-5-oxopentanoate, Mass (m/z): 544.2;

Compound No. 378: 2-amino-N-[2-({[(1S)-2-cyclohexyl-1-methylethyl]amino}methyl)phenyl]-1,3-benzothiazole-5-sulfonamide, Mass (m/z): 459.1; m. pt.: 64-66;

Compound No. 379: 5-chloro-N-[3-({[2-({[(1S)-2-cyclohexyl-1-methylethyl]amino}methyl)phenyl]amino}sulfonyl)phenyl]-1,3-dimethyl-1H-pyrazole-4-sulfonamide, Mass (m/z): 594.1; m. pt.: 65-67;

Compound No. 380: N-[2-({[2-({[(1S)-2-cyclohexyl-1-methylethyl]amino}methyl)phenyl]amino}sulfonyl)phenyl]-2,4-dimethyl-1,3-thiazole-5-sulfonamide, Mass (m/z): 577.2; m. pt.: 71-74;

Compound No. 381: N-[4-({[2-({[(1S)-2-cyclopentyl-1-methylethyl]amino}methyl)phenyl]amino}sulfonyl)phenyl]thiophene-3-sulfonamide, Mass (m/z): 534.1; m. pt.: 137.8-141.2;

Compound No. 382: N-(2-{[[(1S)-2-cyclohexyl-1-methylethyl](methylsulfonyl)amino]methyl}phenyl)-2-[(methylsulfonyl)amino]benzenesulfonamide, Mass (m/z): 558.1; m. pt.: 78-80° C.;

Compound No. 383: N-[2-({[(1S)-2-cyclopentyl-1-methylethyl]amino}methyl)phenyl]-4-(1H-pyrazol-1-yl)benzenesulfonamide, Mass (m/z): 439.1; m. pt.: 147-148;

Compound No. 384: N-[2-({[(1S)-2-cyclohexyl-1-methylethyl]amino}methyl)phenyl]-4-(1H-pyrazol-1-yl)benzenesulfonamide, Mass (m/z): 453.1;

Compound No. 385: N-[2-({[(1S)-2-cyclohexyl-1-methylethyl]amino}methyl)phenyl]-3-fluoro-4-(1H-1,2,4-triazol-1-yl)benzenesulfonamide, Mass (m/z): 472.2; m. pt.: 136-137;

Compound No. 386: [5-(2-thienyl)isoxazol-3-yl]methyl[2-({[(1S)-2-cyclohexyl-1-methylethyl]amino}methyl)phenyl carbamate, Mass (m/z): 454.2;

Compound No. 387: N-[(1S)-2-cyclopentyl-1-methylethyl]-2-[(2-thienylsulfonyl)amino]benzamide, Mass (m/z): 393.1;

Compound No. 388: N-[(1S)-2-cyclohexyl-1-methylethyl]-2-[(2-thienylsulfonyl)amino]benzamide, Mass (m/z): 407.1;

Compound No. 389: methyl[5-({[2-({[(1S)-2-cyclohexyl-1-methylethyl]amino}methyl)phenyl]amino}sulfonyl)-1H-benzimidazol-2-yl]carbamate, Mass (m/z): 500.1; m. pt.: 122-124;

Compound No. 390: methyl[6-({[4-({[2-({[(1S)-2-cyclohexyl-1-methylethyl]amino}methyl)phenyl]amino}sulfonyl)phenyl]amino}sulfonyl)-1H-benzimidazol-2-yl]carbamate, Mass (m/z): 655.2; m. pt.: 160-163;

Compound No. 391: N-[2-({[(1S)-2-cyclohexyl-1-methylethyl]amino}methyl)phenyl]-4-[(1E)-N-hydroxyethanimidoyl]benzenesulfonamide, Mass (m/z): 444.1; m. pt.: 144-147;

Compound No. 392: N-[2-({[(1S)-2-cyclohexyl-1-methylethyl]amino}methyl)phenyl]-4-[(1E)-N-methoxyethanimidoyl]benzenesulfonamide, Mass (m/z): 458.1;

Compound No. 393: 4-{[amino(imino)methyl]amino}-N-[2-({[(1S)-2-cyclohexyl-1-methylethyl]amino}methyl)phenyl]benzenesulfonamide, Mass (m/z): 445.1; m. pt.: 94-96;

Compound No. 394: N-[2-({[(1S)-2-cyclohexyl-1-methylethyl]amino}methyl)phenyl]sulfamide, Mass (m/z): 326.2;

Compound No. 395: N-[4-({[2-({[(1S)-2-cyclohexyl-1-methylethyl]amino}methyl)phenyl]amino}sulfonyl)phenyl]-4-[(1E)-N-hydroxyethanimidoyl]benzenesulfonamide, Mass (m/z): 599.2; m. pt.: 120-122;

Compound No. 396: N-[2-({[(1S)-2-cyclohexyl-1-methylethyl]amino}methyl)phenyl]-3-{[(isopropylamino)carbonyl]amino}benzenesulfonamide, Mass (m/z): 487.2;

Compound No. 397: ethyl (2Z)-4-{[2-({[(1S)-2-cyclohexyl-1-methylethyl]amino}methyl)phenyl]amino}-4-oxobut-2-enoate, Mass (m/z): 373.2; m. pt.: 65-68.

Compound No. 398: N-[2-({[2-cyclohexyl-1-methylethyl]amino}methyl)phenyl]-1-benzofuran-2-sulfonamide, Mass (m/z): 427.5; m.pt: Gummy;

Compound No. 399: N-[2-({[(1S)-2-cyclopentyl-1-methylethyl]amino}methyl)phenyl]-1-benzofuran-2-sulfonamide, Mass (m/z): 413.00; m.pt: 58-61° C.;

Compound No. 400: N-[3-({[2-cyclohexyl-1-methylethyl]amino}methyl)pyridin-4-yl]thiophene-2-sulfonamide, Mass (m/z): 394.5; m.pt: Gummy;

Compound No. 401: 2-amino-N-[2-({[2-cyclohexyl-1-methylethyl]amino}methyl)phenyl]-1H-benzimidazole-5-sulfonamide, Mass (m/z): 442.04; m.pt: 83-85° C.;

Compound No. 402: N-[2-({[2-cyclohexyl-1-methylethyl]amino}methyl)phenyl]guanidine, Mass (m/z): 290.40; m.pt: Gummy;

Compound No. 403: N-[2-({[2-cyclohexyl-1-methylethyl]amino}methyl)phenyl]-4-(5-oxo-1,5-dihydro-4H-1,2,4-triazol-4-yl)benzenesulfonamide, Mass (m/z): 470.4; m.pt: Gummy;

Compound No. 404: N-[2-({[2-cyclohexyl-1-methylethyl]amino}methyl)phenyl]-4-(5-methyl-1,3,4-oxadiazol-2-yl)benzenesulfonamide, Mass (m/z): 469.04; m.pt: 62-64° C.;

Compound No. 405: N-[2-({[(1S)-2-cyclopentyl-1-methylethyl]amino}methyl)phenyl]-4-(1-methyl-1H-pyrazol-4-yl)benzenesulfonamide, Mass (m/z): 453.2; m.pt: 65-67° C.;

Compound No. 406: N-[2-({[2-cyclohexyl-1-methylethyl]amino}methyl)phenyl]-4-(3,5-dimethylisoxazol-4-yl)benzenesulfonamide, Mass (m/z): 482.1; m.pt: Gummy;

Compound No. 407: N-[2-({[2-cyclohexyl-1-methylethyl]amino}methyl)phenyl]-5-(3,5-dimethylisoxazol-4-yl)thiophene-2-sulfonamide, Mass (m/z): 488.0; m.pt: Gummy;

Compound No. 408: N-[2-({[(1S)-2-cyclopentyl-1-methylethyl]amino}methyl)phenyl]-5-(3,5-dimethylisoxazol-4-yl)thiophene-2-sulfonamide, Mass (m/z): 473.9; m.pt: 61-62° C.;

Compound No. 409: N-[2-({[2-cyclohexyl-1-methylethyl]amino}methyl)phenyl]-3-[(methylsulfonyl)amino]benzenesulfonamide, Mass (m/z): 480.3; m.pt: 55-57° C.;

Compound No. 410: N-[2-({[2-cyclohexyl-1-methylethyl]amino}methyl)phenyl]-4-{[(dimethylamino)sulfonyl]amino}benzenesulfonamide, Mass (m/z): 509.20; m.pt: 53-56° C.;

Compound No. 411: N-[3-({[2-cyclohexyl-1-methylethyl]amino}methyl)pyridin-4-yl]-1-benzothiophene-2-sulfonamide, Mass (m/z): 444.6; m.pt: 89.9-94.3° C.;

Compound No. 412: N-[2-({[2-cyclohexyl-1-methylethyl]amino}methyl)phenyl]-5-{[(1-methyl-1H-imidazol-4-yl)sulfonyl]amino}pyridine-2-sulfonamide, Mass (m/z): 546.97; m.pt: Gummy;

Compound No. 413: N-[2-({[2-cyclohexyl-1-methylethyl]amino}methyl)phenyl]-5-[(methylsulfonyl)amino]pyridine-2-sulfonamide, Mass (m/z): 546.97; m.pt: Gummy;

Compound No. 414: N-[2-({[2-cyclohexyl-1-methylethyl]amino}methyl)phenyl]-5-[(2-thienylsulfonyl)amino]pyridine-2-sulfonamide, Mass (m/z): 548.93; m.pt: 123-126° C.;

Compound No. 415: 5-bromo-N-[2-({[2-cyclohexyl-1-methylethyl]amino}methyl)phenyl]-1,3-thiazole-2-sulfonamide, Mass (m/z): 472.1; m.pt: 74-75° C.;

Compound No. 416: [5-(2-thienyl)isoxazol-3-yl]methyl[2-({[(1S)-2-cyclopentyl-1-methylethyl]amino}methyl)phenyl]carbamate, Mass (m/z): 440.2; m.pt: Gummy;

Compound No. 417: N-[2-({[2-cyclohexyl-1-methylethyl]amino}methyl)phenyl]-2-fluoro-5-(1H-pyrrol-1-yl)benzenesulfonamide, Mass (m/z): 470.3; m.pt: 65-66° C.;

Compound No. 418: 2-amino-N-[2-({[2-cyclohexyl-1-methylethyl]amino}methyl)phenyl]-1,3-benzothiazole-4-sulfonamide, Mass (m/z): 459.30; m.pt: 58-60° C.;

Compound No. 419: N-[2-({[2-({[2-cyclohexyl-1-methylethyl]amino}methyl)phenyl]amino}sulfonyl)phenyl]thiophene-3-sulfonamide, Mass (m/z): 548.30; m.pt: 85-87° C.;

Compound No. 420: N-[2-({[(1S)-2-cyclopentyl-1-methylethyl]amino}methyl)phenyl]-3-fluoro-4-(1H-tetrazol-1-yl)benzenesulfonamide, Mass (m/z): 394.2; m.pt: 146-148° C.;

Compound No. 421: N-[2-({[(2S)-2-cyclohexyl-2-hydroxy-1-methylethyl]amino}methyl)phenyl]-4-(1H-pyrrol-1-yl)benzenesulfonamide, Mass (m/z): 468.3; m.pt: 106-108° C.;

Compound No. 422: N-[2-({[(1S)-2-cyclopentyl-1-methylethyl]amino}methyl)phenyl]-4-(1,3-oxazol-5-yl)benzenesulfonamide, Mass (m/z): 440.4; m.pt: 58-60° C.;

Compound No. 423: N-[2-({[(1S)-2-cyclopentyl-1-methylethyl]amino}methyl)phenyl]-6-(1H-1,2,4-triazol-1-yl)pyridine-3-sulfonamide, Mass (m/z): 441.2; m.pt: 153-155° C.;

Compound No. 424: N-[2-({[2-cyclohexyl-1-methylethyl]amino}methyl)pyridin-3-yl]thiophene-2-sulfonamide, Mass (m/z): 394.2; m.pt: 56-58° C.;

Compound No. 425: N-[2-({[(1S)-2-cyclopentyl-1-methylethyl]amino}methyl)phenyl]-3-fluoro-4-(1H-1,2,4-triazol-1-yl)benzenesulfonamide, Mass (m/z): 458.4; m.pt: 122-124° C.;

Compound No. 426: N-[2-({[2-cyclohexyl-1-methylethyl]amino}methyl)phenyl]-6-(1H-1,2,4-triazol-1-yl)pyridine-3-sulfonamide, Mass (m/z): 455.3; m.pt: 108-109° C.;

Compound No. 427: N-[2-({[2-cyclohexyl-1-methylethyl]amino}methyl)phenyl]-3-fluoro-4-(1H-tetrazol-1-yl)benzenesulfonamide, Mass (m/z): 445.3; m.pt: 175-176° C.;

Compound No. 428: N-[2-({[2-cyclohexyl-1-methylethyl]amino}methyl)phenyl]-6-(1H-pyrrol-1-yl)pyridine-3-sulfonamide, Mass (m/z): 453.3; m.pt: 98-100° C.;

Compound No. 429: N-[2-({[2-cyclohexyl-1-methylethyl]amino}methyl)pyridin-3-yl]-3-fluoro-4-(1H-1,2,4-triazol-1-yl)benzenesulfonamide, Mass (m/z): 473.6; m.pt: 62-64° C.;

Compound No. 430: N-[2-({[2-cyclohexyl-2-fluoro-1-methylethyl]amino}methyl)phenyl]thiophene-2-sulfonamide, Mass (m/z): 411.0; m.pt: Gummy;

Compound No. 431: N-[2-({[(1S)-2-cyclopentyl-1-methylethyl]amino}methyl)phenyl]-6-(1H-pyrrol-1-yl)pyridine-3-sulfonamide, Mass (m/z): 439.0; m.pt: 149-151° C.;

Compound No. 432: N-[3-({[2-cyclohexyl-1-methylethyl]amino}methyl)pyridin-4-yl]-5-isoxazol-5-ylthiophene-2-sulfonamide hydrochloride, Mass (m/z): 497.62; m.pt: 146-150° C.;

Compound No. 433: 2-amino-N-[2-({[(1S)-2-cyclopentyl-1-methylethyl]amino}methyl)phenyl]-1,3-benzothiazole-6-sulfonamide, Mass (m/z): 444.94; m.pt: 61-63° C.;

Compound No. 434: 2-amino-N-[2-({[(1S)-2-cyclopentyl-1-methylethyl]amino}methyl)phenyl]-1H-benzimidazole-6-sulfonamide, Mass (m/z): 427.96; m.pt: 109-110° C.;

Compound No. 435: 5-{[amino(imino)methyl]amino}-N-[2-({[2-cyclohexyl-1-methylethyl]amino}methyl)phenyl]pyridine-2-sulfonamide, Mass (m/z): 446.00; m.pt: Gummy;

Compound No. 436: N-[4-({2-({[2-cyclohexyl-1-methylethyl]amino}methyl)phenyl]amino}sulfonyl)-3-methoxyphenyl]-1-methyl-1H-imidazole-4-sulfonamide, Mass (m/z): 576.5; m.pt: Gummy;

Compound No. 437: N-[6-({2-({[2-cyclohexyl-1-methylethyl]amino}methyl)phenyl]amino}sulfonyl)-1,3-benzothiazol-2-yl]acetamide, Mass (m/z): 501.2; m.pt: 78-80° C.;

Compound No. 438: N-[2-({[2-cyclohexyl-1-methylethyl]amino}methyl)phenyl]-5-methyl-1H-benzimidazole-2-sulfonamide, Mass (m/z): 441.03; m.pt: 129-131° C.;

Compound No. 439: 4-amino-N-[2-({[2-cyclohexyl-1-methylethyl]amino}methyl)phenyl]-2-fluorobenzenesulfonamide, Mass (m/z): 420; m.pt: 58.4-60.2° C.;

Compound No. 440: 4-amino-N-[2-({[2-cyclohexyl-1-methylethyl]amino}methyl)phenyl]-2-methoxybenzenesulfonamide, Mass (m/z): 432.5; m.pt: Gummy;

Compound No. 441: N-[4-({2-({[2-cyclohexyl-1-methylethyl]amino}methyl)phenyl]amino}sulfonyl)-3-methoxyphenyl]acetamide, Mass (m/z): 474.02; m.pt: 82-85° C.;

Compound No. 442: N-[2-({[2-cyclohexyl-1-methylethyl]amino}methyl)phenyl]-2-methoxy-4-[(methylsulfonyl)amino]benzenesulfonamide, Mass (m/z): 510; m.pt: Gummy;

Compound No. 443: Methyl[4-({2-({[2-cyclohexyl-1-methylethyl]amino}methyl)phenyl]amino}sulfonyl)phenyl]carbamate, Mass (m/z): 460.00; m.pt: 44-46° C.;

Compound No. 444: N-[2-({[(1S)-2-cyclopentyl-1-methylethyl]amino}methyl)phenyl]-4-(1,2,3-thiadiazol-4-yl)benzenesulfonamide, Mass (m/z): 456.90; m.pt: 142-144° C.;

Compound No. 445: N-[2-({[2-cyclohexyl-1-methylethyl]amino}methyl)phenyl]-4-(2-methyl-2H-tetrazol-5-yl)benzenesulfonamide, Mass (m/z): 468.99; m.pt: 58-60° C.;

Compound No. 446: N-[2-({[(1S)-2-cyclopentyl-1-methylethyl]amino}methyl)phenyl]-4-(2-methyl-2H-tetrazol-5-yl)benzenesulfonamide, Mass (m/z): 454.94; m.pt: 55-57° C.;

Compound No. 447: N-[2-({[(1S)-2-cyclopentyl-1-methylethyl]amino}methyl)phenyl]-4-(5-methyl-1,3,4-oxadiazol-2-yl)benzenesulfonamide, Mass (m/z): 455.01; m.pt: 83-85° C.;

Compound No. 448: N-[2-({[2-cyclohexyl-1-methylethyl]amino}methyl)phenyl]-6-(2-furyl)pyridine-3-sulfonamide, Mass (m/z): 453.9; m.pt: 94-95° C.;

Compound No. 449: N-[2-({[(1S)-2-cyclopentyl-1-methylethyl]amino}methyl)phenyl]-6-(2-furyl)pyridine-3-sulfonamide, Mass (m/z): 439.9; m.pt: 64-65° C.;

Compound No. 450: N-[2-({[2-cyclohexyl-1-methylethyl]amino}methyl)phenyl]-6-(3-furyl)pyridine-3-sulfonamide, Mass (m/z): 454.0; m.pt: 70-72° C.;

Compound No. 451: N-[2-({[(1S)-2-cyclopentyl-1-methylethyl]amino}methyl)phenyl]-6-(3-furyl)pyridine-3-sulfonamide, Mass (m/z): 439.9; m.pt: 68-70° C.;

Compound No. 452: N-[2-({[2-cyclohexyl-1-methylethyl]amino}methyl)phenyl]-1-methyl-2-oxo-1,2-dihydroquinoline-6-sulfonamide, Mass (m/z): 468.0; m.pt: 55-57° C.;

Compound No. 453: N-[2-({[(1S)-2-cyclopentyl-1-methylethyl]amino}methyl)phenyl]-1-methyl-2-oxo-1,2-dihydroquinoline-6-sulfonamide, Mass (m/z): 454.0; m.pt: 68-69° C.;

Compound No. 454: N-[2-({[2-cyclohexyl-1-methylethyl]amino}methyl)phenyl]-6-(1H-tetrazol-1-yl)pyridine-3-sulfonamide, Mass (m/z): 455.9; m.pt: 119-121° C.;

Compound No. 455: N-[2-({[(1S)-2-cyclopentyl-1-methylethyl]amino}methyl)phenyl]-6-(1H-tetrazol-1-yl)pyridine-3-sulfonamide, Mass (m/z): 442.0; m.pt: 142-144° C.;

Compound No. 456: N-[2-({[2-cyclohexyl-1-methylethyl]amino}methyl)phenyl]-6-(2-thienyl)pyridine-3-sulfonamide, Mass (m/z): 469.9; m.pt: 91-92° C.;

Compound No. 457: N-[2-({[(1S)-2-cyclopentyl-1-methylethyl]amino}methyl)phenyl]-6-(2-thienyl)pyridine-3-sulfonamide, Mass (m/z): 455.9; m.pt: 62-64° C.;

Compound No. 458: N-[2-({[2-cyclohexyl-1-methylethyl]amino}methyl)phenyl]-6-(1H-imidazol-1-yl)pyridine-3-sulfonamide, Mass (m/z): 454.0; m.pt: 119-120° C.;

Compound No. 459: N-[2-({[(1S)-2-cyclopentyl-1-methylethyl]amino}methyl)phenyl]-6-(1H-imidazol-1-yl)pyridine-3-sulfonamide, Mass (m/z): 440.0; m.pt: 68-69° C.;

Compound No. 460: N-[2-({[2-cyclohexyl-1-methylethyl]amino}methyl)phenyl]-3-(2-methyl-1,3-thiazol-4-yl)benzenesulfonamide, Mass (m/z): 484.0; m.pt: 88-89° C.;

Compound No. 461: N-[2-({[(1S)-2-cyclopentyl-1-methylethyl]amino}methyl)phenyl]-3-(2-methyl-1,3-thiazol-4-yl)benzenesulfonamide, Mass (m/z): 470.0; m.pt: Gummy;

Compound No. 462: N-[2-({[2-cyclohexyl-1-methylethyl]amino}methyl)phenyl]-5-fluoro-3-methyl-1-benzothiophene-2-sulfonamide, Mass (m/z): 474.9; m.pt: 131-132° C.;

Compound No. 463: N-[2-({[(1S)-2-cyclopentyl-1-methylethyl]amino}methyl)phenyl]-5-fluoro-3-methyl-1-benzothiophene-2-sulfonamide, Mass (m/z): 461.0; m.pt: 64-65° C.;

Compound No. 464: N-[2-({[2-cyclohexyl-2-fluoro-1-methylethyl]amino}methyl)phenyl]-2-(trifluoroacetyl)-1,2,3,4-tetrahydroisoquinoline-7-sulfonamide, Mass (m/z): 556.0; m.pt: Gummy;

Compound No. 465: N-[4-({[2-({[2-cyclohexyl-2-fluoro-1-methylethyl]amino}methyl)phenyl]amino}sulfonyl)phenyl]thiophene-2-sulfonamide, Mass (m/z): 565.9; m.pt: 85-86° C.;

Compound No. 466: N-[2-({[2-cyclohexyl-2-fluoro-1-methylethyl]amino}methyl)phenyl]-4-(1H-pyrrol-1-yl)benzenesulfonamide, Mass (m/z): 470.1; m.pt: 80-81° C.;

Compound No. 467: N-(2-{[(3-cyclohexyl-2-fluoropropyl)amino]methyl}phenyl)-2-(trifluoroacetyl)-1,2,3,4-tetrahydroisoquinoline-7-sulfonamide, Mass (m/z): 556.0; m.pt: 65-66° C.;

Compound No. 468: N-(4-{[(2-{[(3-cyclohexyl-2-fluoropropyl)amino]methyl}phenyl)amino]sulfonyl}phenyl)thiophene-2-sulfonamide, Mass (m/z): 565.9; m.pt: 69-70° C.;

Compound No. 469: 5-amino-N-[2-({[2-cyclohexyl-1-methylethyl]amino}methyl)phenyl]pyridine-2-sulfonamide, Mass (m/z): 403.01; m.pt: Gummy;

Compound No. 470: 5-chloro-N-[2-({[(1S)-2-cyclopentyl-1-methylethyl]amino}methyl)phenyl]-2,1,3-benzoxadiazole-4-sulfonamide, Mass (m/z): 462.89; m.pt: Gummy;

Compound No. 471: N-[2-({[(1S)-2-cyclopentyl-1-methylethyl]amino}methyl)phenyl]-1-benzothiophene-2-carboxamide, Mass (m/z): 407.08; m.pt: Gummy;

Compound No. 472: N-(2-{[(3-cyclohexyl-2-fluoropropyl)amino]methyl}phenyl)thiophene-2-sulfonamide, Mass (m/z): 435.1; m.pt: Gummy;

Compound No. 473: N-[2-({[(1S)-2-cyclopentyl-1-methylethyl]amino}methyl)phenyl]-2,1,3-benzothiadiazole-5-sulfonamide, Mass (m/z): 430.95; m.pt: Gummy;

Compound No. 474: N-[4-({[2-({[2-cyclohexyl-1-methylethyl]amino}methyl)phenyl]amino}sulfonyl)-3-methoxyphenyl]thiophene-2-sulfonamide, Mass (m/z): 577.93; m.pt: 101-103° C.;

Compound No. 475: N-[4-({[2-({[2-cyclohexyl-1-methylethyl]amino}methyl)phenyl]amino}sulfonyl)-3-hydroxyphenyl]thiophene-2-sulfonamide, Mass (m/z): 563.94; m.pt: 147-150° C.;

Compound No. 476: N-[4-({[2-({[2-cyclohexyl-1-methylethyl]amino}methyl)phenyl]amino}sulfonyl)-3-hydroxyphenyl]acetamide, Mass (m/z): 459.97; m.pt: 118-120° C.;

Compound No. 477: N-[2-({[2-cyclohexyl-1-methylethyl]amino}methyl)phenyl]-3-fluoro-4-(2-oxo-1,3-oxazolidin-3-yl)benzenesulfonamide, Mass (m/z): 489.98; m.pt: 141-142° C.;

Compound No. 478: N-[2-({[(1S)-2-cyclopentyl-1-methylethyl]amino}methyl)phenyl]-3-fluoro-4-(2-oxo-1,3-oxazolidin-3-yl)benzenesulfonamide, Mass (m/z): 475.94; m.pt: 130-131° C.;

Compound No. 479: N-[2-({[2-cyclohexyl-1-methylethyl]amino}methyl)phenyl]-3-fluoro-4-(1H-1,2,3-triazol-1-yl)benzenesulfonamide, Mass (m/z): 471.99; m.pt: 124-125° C.;

Compound No. 480: N-[2-({[(1S)-2-cyclopentyl-1-methylethyl]amino}methyl)phenyl]-3-fluoro-4-(1H-1,2,3-triazol-1-yl)benzenesulfonamide, Mass (m/z): 457.96; m.pt: 110-111° C.;

Compound No. 481: N-[2-({[2-cyclohexyl-1-methylethyl]amino}methyl)phenyl]-1-(trifluoroacetyl)indoline-5-sulfonamide, Mass (m/z): 524.6; m.pt: 94.2-103° C.;

Compound No. 482: N-[2-({[2-cyclohexyl-1-methylethyl]amino}methyl)phenyl]indoline-5-sulfonamide, Mass (m/z): 428.2; m.pt: 92.8-94.5° C.;

Compound No. 483: N-[2-({[2-cyclohexyl-1-methylethyl]amino}methyl)phenyl]-4-(1,2,4-oxadiazol-3-yl)benzenesulfonamide, Mass (m/z): 455.01; m.pt: 52-54° C.;

Compound No. 484: N-[2-({[(1S)-2-cyclopentyl-1-methylethyl]amino}methyl)phenyl]-4-(1,2,4-oxadiazol-3-yl)benzenesulfonamide, Mass (m/z): 441.02; m.pt: 128-130° C.;

Compound No. 485: N-[2-({[(1S)-2-cyclopentyl-1-methylethyl]amino}methyl)phenyl]-3,4-difluorobenzenesulfonamide, Mass (m/z): 409.01; m.pt: 78-80° C.;

Compound No. 486: N-[2-({[2-cyclohexyl-1-methylethyl]amino}methyl)pyridin-3-yl]-4-(5-methyl-1,3,4-oxadiazol-2-yl)benzenesulfonamide, Mass (m/z): 470.03; m.pt: 64-66° C.;

Compound No. 487: N-[2-({[(1S)-2-cyclopentyl-1-methylethyl]amino}methyl)phenyl]-4-(1H-1,2,3-triazol-1-yl)benzenesulfonamide, Mass (m/z): 440.04; m.pt: 149-150° C.;

Compound No. 488: N-[2-({[2-cyclohexyl-1-methylethyl]amino}methyl)phenyl]-3-fluoro-4-(1H-pyrazol-1-yl)benzenesulfonamide, Mass (m/z): 471.01; m.pt: 62-63° C.;

Compound No. 489: N-[2-({[(1S)-2-cyclopentyl-1-methylethyl]amino}methyl)phenyl]-3-fluoro-4-(1H-pyrazol-1-yl)benzenesulfonamide, Mass (m/z): 456.97; m.pt: 123-124° C.;

Compound No. 490: N-[2-({[2-cyclohexyl-1-methylethyl]amino}methyl)phenyl]-6-pyrrolidin-1-ylpyridine-3-sulfonamide, Mass (m/z): 457.1; m.pt: 110-111° C.;

Compound No. 491: N-[2-({[(1S)-2-cyclopentyl-1-methylethyl]amino}methyl)phenyl]-6-pyrrolidin-1-ylpyridine-3-sulfonamide, Mass (m/z): 443.0; m.pt: 104-106° C.;

Compound No. 492: N-[2-({[2-cyclohexyl-1-methylethyl]amino}methyl)phenyl]-6-morpholin-4-ylpyridine-3-sulfonamide, Mass (m/z): 473.0; m.pt: Gummy;

Compound No. 493: N-[2-({[(1S)-2-cyclopentyl-1-methylethyl]amino}methyl)phenyl]-6-morpholin-4-ylpyridine-3-sulfonamide, Mass (m/z): 459.0; m.pt: Gummy;

Compound No. 494: N-[2-({[2-cyclohexyl-1-methylethyl]amino}methyl)phenyl]-1-ethyl-2-oxo-1,2-dihydroquinoline-6-sulfonamide, Mass (m/z): 482.0; m.pt: 81-82° C.;

Compound No. 495: N-[2-({[(1S)-2-cyclopentyl-1-methylethyl]amino}methyl)phenyl]-1-ethyl-2-oxo-1,2-dihydroquinoline-6-sulfonamide, Mass (m/z): 468.0; m.pt: 70-71° C.;

Compound No. 496: N-[2-({[(1S)-2-cyclopentyl-1-methylethyl]amino}methyl)phenyl]-2-oxo-1,2-dihydroquinoline-6-sulfonamide, Mass (m/z): 440.0; m.pt: 83-84° C.;

Compound No. 497: 6-bromo-N-[2-({[2-cyclohexyl-1-methylethyl]amino}methyl)phenyl]pyridine-3-sulfonamide, Mass (m/z): 465.9; m.pt: 120-121° C.;

Compound No. 498: 2-amino-N-[2-({[2-cyclohexyl-1-methylethyl]amino}methyl)phenyl]pyrimidine-5-sulfonamide, Mass (m/z): 404.00; m.pt: 142-144° C.;

Compound No. 499: 6-amino-N-[2-({[2-cyclohexyl-1-methylethyl]amino}methyl)phenyl]pyridine-3-sulfonamide, Mass (m/z): 403.00; m.pt: 54-56° C.;

Compound No. 500: N-[2-({[2-cyclohexyl-1-methylethyl]amino}methyl)phenyl]-2-oxo-2,3-dihydro-1,3-benzoxazole-6-sulfonamide, Mass (m/z): 443.9; m.pt: 167-169° C.;

Compound No. 501: 5-chloro-N-[2-({[2-cyclohexyl-1-methylethyl]amino}methyl)phenyl]-1,3-benzothiazole-2-sulfonamide, Mass (m/z): 477.83; m.pt: 79-82° C.;

Compound No. 502: 5-chloro-N-[2-({[(1S)-2-cyclopentyl-1-methylethyl]amino}methyl)phenyl]-1,3-benzothiazole-2-sulfonamide, Mass (m/z): 463.82; m.pt: 69-72° C.;

Compound No. 503: N-[2-({[2-cyclohexyl-1-methylethyl]amino}methyl)phenyl]-2-(dimethylamino)-1,3-benzothiazole-6-sulfonamide, Mass (m/z): 486.88; m.pt: Gummy;

Compound No. 504: N-[6-({[2-({[2-cyclohexyl-1-methylethyl]amino}methyl)phenyl]amino}sulfonyl)-1,3-benzothiazol-2-yl]-L-alaninamide, Mass (m/z): 456.00; m.pt: 93-95° C.;

Compound No. 505: N-[2-({[2-cyclohexyl-1-methylethyl]amino}methyl)phenyl]-4-oxo-3,4-dihydroquinazoline-2-sulfonamide, Mass (m/z): 529.93; m.pt: Gummy;

Compound No. 506: N-[2-({[2-cyclohexyl-1-methylethyl]amino}methyl)phenyl]-2-(trifluoroacetyl)-1,2,3,4-tetrahydroisoquinoline-7-sulfonamide, Mass (m/z): 537.9; m.pt: 55-56° C.;

Compound No. 507: N-[2-({[2-cyclohexyl-1-methylethyl]amino}methyl)phenyl]-1,2,3,4-tetrahydroisoquinoline-7-sulfonamide, Mass (m/z): 441.9; m.pt: 116-117° C.;

Compound No. 508: N-[2-({[2-cyclohexyl-1-methylethyl]amino}methyl)phenyl]-2-oxo-1,2-dihydroquinoline-6-sulfonamide, Mass (m/z): 454.0; m.pt: 107-108° C.;

Compound No. 509: N-[2-({[2-cyclohexyl-1-methylethyl]amino}methyl)phenyl]-3-fluoro-4-(1H-imidazol-1-yl)benzenesulfonamide, Mass (m/z): 471.06; m.pt: 70-72° C.

Compound No. 510: N-[2-({[(1S)-2-cyclohexyl-1-methylethyl]amino}methyl)phenyl]-5-fluoro-3-methyl-1-benzothiophene-2-sulfonamide, Mass (m/z): 475.0; m.pt: 81-82° C.;

Compound No. 511: N-[2-({[(1S)-2-cyclohexyl-1-methylethyl]amino}methyl)phenyl]-1-methyl-2-oxo-1,2-dihydroquinoline-6-sulfonamide, Mass (m/z): 467.9; m.pt: 84-86° C.;

Compound No. 512: N-[2-({[(1S)-2-cyclohexyl-1-methylethyl]amino}methyl)phenyl]-1-ethyl-2-oxo-1,2-dihydroquinoline-6-sulfonamide, Mass (m/z): 481.9; m.pt: 87-88° C.;

Compound No. 513: N-[2-({[(1S)-2-cyclohexyl-1-methylethyl]amino}methyl)phenyl]-6-(2-thienyl)pyridine-3-sulfonamide, Mass (m/z): 469.8; m.pt: 85-87° C.;

Compound No. 514: N-[2-({[(1S)-2-cyclohexyl-1-methylethyl]amino}methyl)phenyl]-6-(2-furyl)pyridine-3-sulfonamide, Mass (m/z): 453.9; m.pt: 66-67° C.;

Compound No. 515: N-[2-({[(1S)-2-cyclohexyl-1-methylethyl]amino}methyl)phenyl]-6-(1H-tetrazol-1-yl)pyridine-3-sulfonamide, Mass (m/z): 455.8; m.pt: 158-159° C.;

Compound No. 516: N-[2-({[(1S)-2-cyclohexyl-1-methylethyl]amino}methyl)phenyl]-6-pyrrolidin-1-ylpyridine-3-sulfonamide, Mass (m/z): 456.9; m.pt: 108-109° C.;

Compound No. 517: N-[2-({[(1S)-2-cyclohexyl-1-methylethyl]amino}methyl)phenyl]-3-(2-methyl-1,3-thiazol-4-yl)benzenesulfonamide, Mass (m/z): 483.9; m.pt: Gummy;

Compound No. 518: N-[2-({[(1S)-2-cyclohexyl-1-methylethyl]amino}methyl)phenyl]-5-(3,5-dimethylisoxazol-4-yl)thiophene-2-sulfonamide, Mass (m/z): 487.8; m.pt: 84-86° C.;

Compound No. 519: N-[2-({[(1S)-2-cyclohexyl-1-methylethyl]amino}methyl)phenyl]-4-(5-methyl-1,3,4-oxadiazol-2-yl)benzenesulfonamide, Mass (m/z): 468.89; m.pt: 94-96° C.;

Compound No. 520: N-[2-({[(1S)-2-cyclohexyl-1-methylethyl]amino}methyl)phenyl]-4-(1,2,4-oxadiazol-3-yl)benzenesulfonamide, Mass (m/z): 454.93; m.pt: 106-108° C.;

Compound No. 521: N-[2-({[(1S)-2-cyclohexyl-1-methylethyl]amino}methyl)phenyl]-3-fluoro-4-(1H-pyrazol-1-yl)benzenesulfonamide, Mass (m/z): 470.91; m.pt: 60-62° C.;

Compound No. 522: N-(2-{[(2-cyclohexyl-1-methylethyl)amino]methyl}phenyl)-1-[(1-methyl-1H-imidazol-4-yl)sulfonyl]indoline-5-sulfonamide, Mass (m/z): 571.90; m.pt: 78-83° C., Compound No. 523: N-(2-{[(2-cyclohexyl-1-methylethyl)amino]methyl}phenyl)-1-(methylsulfonyl)indoline-5-sulfonamide, Mass (m/z): 506.07; m.pt: 74-76° C., Compound No. 524: N-[4-({[2-({[1-(cyclohexylmethyl)-2,2,2-trifluoroethyl]amino}methyl)phenyl]amino}sulfonyl)phenyl]-1-methyl-1H-imidazole-4-sulfonamide, Mass (m/z): 599.91; m.pt: 67-68° C., Compound No. 525: 1-acetyl-N-(2-{[(2-cyclohexyl-1-methylethyl)amino]methyl}phenyl)indoline-5-sulfonamide, Mass (m/z): 469.91; m.pt: 76-78° C., Compound No. 526: N-[4-({[2-({[(1S)-2-cyclohexyl-1-methylethyl]amino}methyl)phenyl]amino}sulfonyl)phenyl]acetamide, Mass (m/z): 444; m.pt: Gummy, Compound No. 527: N-[2-({[(1S)-2-cyclohexyl-1-methylethyl]amino}methyl)phenyl]-3-fluoro-4-(2-oxo-1,3-oxazolidin-3-yl)benzenesulfonamide, Mass (m/z): 490; m.pt: 111° C., Compound No. 528: 2-amino-N-(2-{[(2-cyclohexyl-1-methylethyl)amino]methyl}phenyl)-1,3-benzoxazole-6-sulfonamide, Mass (m/z): 442.91; m.pt: Gummy, Compound No. 529: N-(2-{[(2-cyclohexyl-1-methylethyl)amino]methyl}phenyl)-1,3-benzothiazole-6-sulfonamide, Mass (m/z): 443.85; m.pt: Gummy, Compound No. 530: N-[2-({[(1S)-2-cyclopropyl-1-methylethyl]amino}methyl)phenyl]-1-benzothiophene-2-sulfonamide, Mass (m/z): 400.83; m.pt: Gummy, Compound No. 531: N-[2-({[(1S)-2-cyclopentyl-1-methylethyl]amino}methyl)phenyl]-1,3-benzothiazole-6-sulfonamide, Mass (m/z): 429.89; m.pt: Gummy, Compound No. 532: 2-amino-N-[2-({[(1S)-2-cyclopropyl-1-methylethyl]amino}methyl)phenyl]-1,3-benzothiazole-6-sulfonamide, Mass (m/z): 416.56; m.pt: Gummy, Compound No. 533: N-(4-{[(2-{[(2-cyclohexyl-1-methylethyl)amino]methyl}phenyl)amino]sulfonyl}phenyl)nonanamide, Mass (m/z): 541.95; m.pt: 72° C., Compound No. 534: 4-amino-N-(2-{[(2-cyclohexyl-1-methylethyl)amino]methyl}phenyl)-3-hydroxybenzenesulfonamide, Mass (m/z): 417.94; m.pt: 65-67° C., Compound No. 535: N-(4-{[(2-{[(2-cyclohexyl-1-methylethyl)amino]methyl}phenyl)amino]sulfonyl}-2-hydroxyphenyl)thiophene-2-sulfonamide, Mass (m/z): 563.71; m.pt: 103-106° C., Compound No. 536: N-[2-({[(1S)-2-cyclopentyl-1-methylethyl]amino}methyl)phenyl]-2-oxo-2,3-dihydro-1,3-benzoxazole-6-sulfonamide, Mass (m/z): 430.33; m.pt: 168-170° C., Compound No. 537: 2-amino-N-[2-({[(1S)-2-cyclopentyl-1-methylethyl]amino}methyl)phenyl]-1,3-benzoxazole-6-sulfonamide, Mass (m/z): 428.88; m.pt: 146-149° C., Compound No. 538: N-[2-({[(1S)-2-cyclopentyl-1-methylethyl]amino}methyl)phenyl]-2-oxoindoline-6-sulfonamide, Mass (m/z): 427.88; m.pt: 75-78° C., Compound No. 539: 5-chloro-N-(2-{[(2-cyclohexyl-1-methylethyl)amino]methyl}phenyl)-1-benzothiophene-2-sulfonamide, Mass (m/z): 477.23; m.pt: 65-67° C., Compound No. 540: 5-chloro-N-[2-({[(1S)-2-cyclopentyl-1-methylethyl]amino}methyl)phenyl]-1-benzothiophene-2-sulfonamide, Mass (m/z): 463.2; m.pt: 54-55° C., Compound No. 541: N-[2-({[(1S)-2-cyclopentyl-1-methylethyl]amino}methyl)phenyl]-5-methoxy-1-benzothiophene-2-sulfonamide, Mass (m/z): 459.24; m.pt: Gummy, Compound No. 542: N-[2-({[(1S)-2-cyclopentyl-1-methylethyl]amino}methyl)phenyl]-5-hydroxy-1-benzothiophene-2-sulfonamide, Mass (m/z): 445.29; m.pt: 92-95° C., Compound No. 543: N-(2-{[(2-cyclohexyl-1-methylethyl)amino]methyl}phenyl)-5-fluoro-1-benzothiophene-2-sulfonamide, Mass (m/z): 460.84; m.pt: 67-69° C., Compound No. 544: N-[2-({[(1S)-2-cyclopentyl-1-methylethyl]amino}methyl)phenyl]-5-fluoro-1-benzothiophene-2-sulfonamide, Mass (m/z): 446.81; m.pt: 55-56° C., Compound No. 545: N-[2-({[1-(cyclohexylmethyl)-2,2,2-trifluoroethyl]amino}methyl)phenyl]-1-benzothiophene-2-sulfonamide, Mass (m/z): 496.76; m.pt: Gummy, Compound No. 546: N-(2-{[(2-cyclohexyl-1-methylethyl)amino]methyl}phenyl)-2-oxoindoline-6-sulfonamide, Mass (m/z): 441.91; m.pt: Gummy, Compound No. 547: 4-amino-N-[2-({[1-(cyclohexylmethyl)-2,2,2-trifluoroethyl]amino}methyl)phenyl]benzenesulfonamide, Mass (m/z): 455.87; m.pt: Gummy, Compound No. 548: 5-(6-aminopyridin-3-yl)-N-[2-({[(1S)-2-cyclohexyl-1-methylethyl]amino}methyl)phenyl]thiophene-2-sulfonamide, Mass (m/z): 484.91; m.pt: 68-70° C., Compound No. 549: 5-(6-aminopyridin-3-yl)-N-[2-({[(1S)-2-cyclopentyl-1-methylethyl]amino}methyl)phenyl]thiophene-2-sulfonamide, Mass (m/z): 470.92; m.pt: 72-73° C., Compound No. 550: N-[2-({[(1S)-2-cyclopentyl-1-methylethyl]amino}methyl)phenyl]-4-(1,3-thiazol-2-yl)benzenesulfonamide, Mass (m/z): 456.06; m.pt: 147° C., Compound No. 551: N-[2-({[(1S)-2-cyclohexyl-1-methylethyl]amino}methyl)phenyl]-4-(1,3-thiazol-2-yl)benzenesulfonamide, Mass (m/z): 470; m.pt: 82° C., Compound No. 552: 2-amino-N-[2-({[(1S)-2-cyclohexyl-1-methylethyl]amino}methyl)phenyl]-1,3-benzothiazole-6-sulfonamide, Mass (m/z): 459.15; m.pt: Gummy, Compound No. 553: N-[2-({[(1S)-2-cyclohexyl-1-methylethyl]amino}methyl)phenyl]-1-benzothiophene-2-sulfonamide, Mass (m/z): 443.05; m.pt: 55-59° C., Compound No. 554: N-[2-({[(1S)-2-cyclohexyl-1-methylethyl]amino}methyl)phenyl]-2-oxo-2,3-dihydro-1,3-benzoxazole-6-sulfonamide, Mass (m/z): 444.1; m.pt: 167-169° C., Compound No. 555: N-[2-({[(1S)-2-cyclohexyl-1-methylethyl]amino}methyl)phenyl]-1-benzofuran-2-sulfonamide, Mass (m/z): 427.11; m.pt: 50-52° C., Compound No. 556: 2-amino-N-[2-({[(1S)-2-cyclohexyl-1-methylethyl]amino}methyl)phenyl]-1,3-benzoxazole-6-sulfonamide, Mass (m/z): 443.14; m.pt: 169-171° C., Compound No. 557: N-[2-({[(1S)-2-cyclopentyl-1-methylethyl]amino}methyl)phenyl]-5-methoxy-1-benzofuran-2-sulfonamide, Mass (m/z): 443.11; m.pt: 58-60° C., Compound No. 558: N-[2-({[(1S)-2-cyclohexyl-1-methylethyl]amino}methyl)phenyl]-5-methoxy-1-benzofuran-2-sulfonamide, Mass (m/z): 457.14; m.pt: 48-50° C., Compound No. 559: N-[2-({[(1S)-2-cyclohexyl-1-methylethyl]amino}methyl)phenyl]-5-hydroxy-1-benzofuran-2-sulfonamide, Mass (m/z): 443.16; m.pt: 180-182° C., Compound No. 560: N-[2-({[(1S)-2-cyclopentyl-1-methylethyl]amino}methyl)phenyl]-5-hydroxy-1-benzofuran-2-sulfonamide, Mass (m/z): 429.12; m.pt: 158-160° C., Compound No. 561: N-[2-({[1-(cyclohexylmethyl)-2,2,2-trifluoroethyl]amino}methyl)phenyl]-4-[(methylsulfonyl)amino]benzenesulfonamide, Mass (m/z): 534.06; m.pt: 120-124° C., Compound No. 562: N-[4-({[2-({[1-(cyclohexylmethyl)-2,2,2-trifluoroethyl]amino}methyl)phenyl]amino}sulfonyl)phenyl]thiophene-2-sulfonamide, Mass (m/z): 602.12; m.pt: 109-111° C., Compound No. 563: 2-amino-N-[2-({[1-(cyclohexylmethyl)-2,2,2-trifluoroethyl]amino}methyl)phenyl]-1,3-benzothiazole-6-sulfonamide, Mass (m/z): 513.10; m.pt: 149-153° C., Compound No. 564: N-[2-({[(1S)-2-cyclopentyl-1-methylethyl]amino}methyl)phenyl]-2-(1H-pyrrol-1-yl)-1,3-thiazole-5-sulfonamide, Mass (m/z): 445.04; m.pt: 124-125° C., Compound No. 565: N-[2-({[(1S)-2-cyclohexyl-1-methylethyl]amino}methyl)phenyl]-2-oxo-1,2,3,4-tetrahydroquinoline-6-sulfonamide, Mass (m/z): 456.11; m.pt: 85-87° C., Compound No. 566: N-[2-({[(1S)-2-cyclopentyl-1-methylethyl]amino}methyl)phenyl]-2-oxo-1,2,3,4-tetrahydroquinoline-6-sulfonamide, Mass (m/z): 442.09; m.pt: 78-80° C., Compound No. 567: N-[2-({[(1S)-2-cyclohexyl-1-methylethyl]amino}methyl)phenyl]-3,5-difluoro-4-(1H-tetrazol-1-yl)benzenesulfonamide, Mass (m/z): 491.06; m.pt: 186-187° C., Compound No. 568: N-[2-({[(1S)-2-cyclopentyl-1-methylethyl]amino}methyl)phenyl]-3,5-difluoro-4-(1H-tetrazol-1-yl)benzenesulfonamide, Mass (m/z): 477.09; m.pt: 83-85° C., Compound No. 569: N-(2-{[(2-cyclohexyl-1,1-dimethylethyl)amino]methyl}phenyl)-4-(1H-pyrrol-1-yl)benzenesulfonamide, Mass (m/z): 466.14; m.pt: Gummy, Compound No. 570: 2-amino-N-[2-({[(1S)-2-cyclohexyl-1-methylethyl]amino}methyl)phenyl]-1,3-thiazole-5-sulfonamide, Mass (m/z): 409.11; m.pt: 121-122° C., Compound No. 571: N-[2-({[(1S)-2-cyclohexyl-1-methylethyl]amino}methyl)phenyl]-6-(1,2,3-thiadiazol-4-yl)pyridine-3-sulfonamide, Mass (m/z): 472.20; m.pt: 112-114° C., Compound No. 572: N-[2-({[(1S)-2-cyclopentyl-1-methylethyl]amino}methyl)phenyl]-6-(1,2,3-thiadiazol-4-yl)pyridine-3-sulfonamide, Mass (m/z): 458.18; m.pt: 95-97° C., Compound No. 573: N-(2-{[(2-cyclohexyl-1-methylethyl)amino]methyl}phenyl)-3-oxo-3,4-dihydro-2H-1,4-benzoxazine-7-sulfonamide, Mass (m/z): 458.25; m.pt: 86-89° C., Compound No. 574: N-[2-({[(1S)-2-cyclohexyl-1-methylethyl]amino}methyl)phenyl]-2-hydroxy-1,3-benzothiazole-6-sulfonamide, Mass (m/z): 460.19; m.pt: 118-121° C., Compound No. 575: N-[2-({[(1S)-2-cyclopentyl-1-methylethyl]amino}methyl)phenyl]-2-hydroxy-1,3-benzothiazole-6-sulfonamide, Mass (m/z): 446.17; m.pt: 135-137° C., Compound No. 576: N-[2-({[(1S)-2-cyclohexyl-1-methylethyl]amino}methyl)phenyl]-3-oxo-3,4-dihydro-2H-1,4-benzothiazine-6-sulfonamide, Mass (m/z): 474.13; m.pt: 171-174° C., Compound No. 577: N-[2-({[(1S)-2-cyclopentyl-1-methylethyl]amino}methyl)phenyl]-3-oxo-3,4-dihydro-2H-1,4-benzothiazine-6-sulfonamide, Mass (m/z): 460.19; m.pt: 163-165° C., Compound No. 578: N-(2-{[(2-cyclohexyl-1-methylethyl)amino]methyl}phenyl)-2-mercapto-1,3-benzoxazole-6-sulfonamide, Mass (m/z): 460.19; m.pt: 250-252° C., Compound No. 579: N-[2-({[(1S)-2-cyclohexyl-1-methylethyl]amino}methyl)phenyl]benzene-1,4-disulfonamide, Mass (m/z): 466; m.pt: 134.4° C., Compound No. 580: N-[2-({[(1S)-2-cyclopentyl-1-methylethyl]amino}methyl)phenyl]benzene-1,4-disulfonamide, Mass (m/z): 552; m.pt: 152.9° C., Compound No. 581: N-[2-({[(1S)-2-cyclopentyl-1-methylethyl]amino}methyl)phenyl]-N'-pyrimidin-2-ylbenzene-1,4-disulfonamide, Mass (m/z): 530; m.pt: 204.9° C., Compound No. 582: N-[2-({[(1S)-2-cyclopentyl-1-methylethyl]amino}methyl)phenyl]-6-methoxypyridine-3-sulfonamide, Mass (m/z): 404; m.pt: 126.6° C., Compound No. 583: N-[2-({[(1S)-2-cyclohexyl-1-methylethyl]amino}methyl)phenyl]-6-methoxypyridine-3-sulfonamide, Mass (m/z): 418; m.pt: Gummy, Compound No. 584: N-[5-({[2-({[(1S)-2-cyclohexyl-1-methylethyl]amino}methyl)phenyl]amino}sulfonyl)-1,3,4-thiadiazol-2-yl]acetamide, Mass (m/z): 452.21; m.pt: Gummy, Compound No. 585: 5-amino-N-[2-({[(1S)-2-cyclohexyl-1-methylethyl]amino}methyl)phenyl]-1,3,4-thiadiazole-2-sulfonamide, Mass (m/z): 410.22; m.pt: Gummy, Compound No. 586: 5-amino-N-[2-({[(1S)-2-cyclopentyl-1-methylethyl]amino}methyl)phenyl]-1,3,4-thiadiazole-2-sulfonamide, Mass (m/z): 396.17; m.pt: Gummy, Compound No. 587: N-[2-({[(1S)-2-cyclohexyl-1-methylethyl]amino}methyl)phenyl]-5-fluoro-1-benzothiophene-2-sulfonamide, Mass (m/z): 461.08; m.pt: 70-72° C., Compound No. 588: 5-chloro-N-[2-({[(1S)-2-cyclohexyl-1-methylethyl]amino}methyl)phenyl]-1-benzofuran-2-sulfonamide, Mass (m/z): 461.20; m.pt: gummy, Compound No. 589: N-[2-({[(1R)-2-cyclohexyl-1-methylethyl]amino}methyl)phenyl]-1-benzothiophene-2-sulfonamide, Mass (m/z): 443.22; m.pt: 65-67° C., Compound No. 590: N-[5-({[2-({[(1S)-2-cyclohexyl-1-methylethyl]amino}methyl)phenyl]amino}sulfonyl)-1,3-thiazol-2-yl]acetamide, Mass (m/z): 451.20; m.pt: 70-72° C., Compound No. 591: N-[2-({[(1R)-2-cyclohexyl-1-methylethyl]amino}methyl)phenyl]-2-oxo-2,3-dihydro-1,3-benzoxazole-6-sulfonamide, Mass (m/z): 444; m.pt: 80-82° C., Compound No. 592: N-[2-({[(1S)-2-cyclohexyl-1-methylethyl]amino}methyl)phenyl]-2,4-dioxo-1,2,3,4-tetrahydroquinazoline-6-sulfonamide, Mass (m/z): 457; m.pt: 239-241° C., Compound No. 593: N-[2-({[(1S)-2-cyclohexyl-1-methylethyl]amino}methyl)phenyl]-2,4-dioxo-1,2,3,4-tetrahydroquinazoline-6-sulfonamide, Mass (m/z): 471; m.pt: 208-210° C., Compound No. 594: N-[2-({[(1S)-2-cyclopentyl-1-methylethyl]amino}methyl)phenyl]-2,3-dihydroxyquinoxaline-6-sulfonamide, Mass (m/z): 457; m.pt: 244-246° C., Compound No. 595: N-[2-({[(1S)-2-cyclohexyl-1-methylethyl]amino}methyl)phenyl]-2,3-dihydroxyquinoxaline-6-sulfonamide, Mass (m/z): 471; m.pt: 243-245° C., Compound No. 596: N-[2-({[(1S)-2-cyclopentyl-1-methylethyl]amino}methyl)phenyl]-2-oxo-1,4-dihydro-2H-3,1-benzoxazine-6-sulfonamide, Mass (m/z): 444; m.pt: 158-160° C., Compound No. 597: N-[2-({[(1S)-2-cyclohexyl-1-methylethyl]amino}methyl)phenyl]-2-oxo-1,4-dihydro-2H-3,1-benzoxazine-6-sulfonamide, Mass (m/z): 458; m.pt: 93-95° C., Compound No. 598: N-[2-({[(1S)-2-cyclopentyl-1-methylethyl]amino}methyl)phenyl]-2-mercapto-1,3-benzoxazole-6-sulfonamide, Mass (m/z): 446; m.pt: 244-246° C., Compound No. 599: N-[2-({[(1S)-2-cyclohexyl-1-methylethyl]amino}methyl)phenyl]-2-mercapto-1,3-benzoxazole-6-sulfonamide, Mass (m/z): 460; m.pt: 244-246° C., Compound No. 600: N-[2-({[(1S)-2-cyclopentyl-1-methylethyl]amino}methyl)phenyl]-2-oxo-2,3-dihydro-1,3-benzoxazole-5-sulfonamide, Mass (m/z): 430; m.pt: 194-195° C., Compound No. 601: N-[2-({[(1S)-2-cyclohexyl-1-methylethyl]amino}methyl)phenyl]-2-oxo-2,3-dihydro-1,3-benzoxazole-5-sulfonamide, Mass (m/z): 444; m.pt: 107-109° C., Compound No. 602: N-(2-{[(2-cyclohexyl-1,1-dimethylethyl)amino]methyl}phenyl)-1-benzothiophene-2-sulfonamide, Mass (m/z): 457.24; m.pt: 81-83° C., Compound No. 603: 5-chloro-N-[2-({[(1S)-2-cyclopentyl-1-methylethyl]amino}methyl)phenyl]-1-benzofuran-2-sulfonamide, Mass (m/z): 447; m.pt: Gummy, Compound No. 604: 5-({[2-({[(1S)-2-cyclopentyl-1-methylethyl]amino}methyl)phenyl]amino}sulfonyl)-2-methyl-3-furoic acid, Mass (m/z): 421; m.pt: 195.9° C., Compound No. 605: 5-({[2-({[(1S)-2-cyclohexyl-1-methylethyl]amino}methyl)phenyl]amino}sulfonyl)-2-methyl-3-furoic acid, Mass (m/z): 435; m.pt: 219.4° C., Compound No. 606: methyl 5-({[2-({[(1S)-2-cyclohexyl-1-methylethyl]amino}methyl)phenyl]amino}sulfonyl)-2-methyl-3-furoate, Mass (m/z): 449; m.pt: Gummy, Compound No. 607: methyl 5-({[2-({[(1S)-2-cyclopentyl-1-methylethyl]amino}methyl)phenyl]amino}sulfonyl)-2-methyl-3-furoate, Mass (m/z): 435; m.pt: Gummy, Compound No. 608: N-[2-({[(1S)-2-cyclopentyl-1-methylethyl]amino}methyl)phenyl]-4-(1H-pyrrol-1-ylsulfonyl)benzenesulfonamide, Mass (m/z): 502; m.pt: 139° C., Compound No. 609: methyl 5-({[4-({[2-({[(1S)-2-cyclopentyl-1-methylethyl]amino}methyl)phenyl]amino}sulfonyl)phenyl]amino}sulfonyl)-2-methyl-3-furoate, Mass (m/z): 590; m.pt: 144-146° C., Compound No. 610: 5-({[4-({[2-({[(1S)-2-cyclopentyl-1-methylethyl]amino}methyl)phenyl]amino}sulfonyl)phenyl]amino}sulfonyl)-2-methyl-3-furoic acid, Mass (m/z): 576; m.pt: 226-228° C., Compound No. 611: 5-({[4-({[2-({[(1S)-2-cyclopentyl-1-methylethyl]amino}methyl)phenyl]amino}sulfonyl)phenyl]amino}sulfonyl)-N,N,2-trimethyl-3-furamide, Mass (m/z): 603; m.pt: 143-145° C., Compound No. 612: 5-({[4-({[2-({[(1S)-2-cyclopentyl-1-methylethyl]amino}methyl)phenyl]amino}sulfonyl)phenyl]amino}sulfonyl)-2-methyl-3-furamide, Mass (m/z): 575; m.pt: 203-205° C., Compound No. 613: 2-({[(1S)-2-cyclohexyl-1-methylethyl]amino}methyl)aniline, Mass (m/z): 247; m.pt: Gummy, Compound No. 614: 2-({[(1S)-2-cyclopentyl-1-methylethyl]amino}methyl)aniline, Mass (m/z): 233; m.pt: Gummy, Compound No. 615: 1-(cyanomethyl)-N-[2-({[(1S)-2-cyclopentyl-1-methylethyl]amino}methyl)phenyl]-2-oxo-1,2-dihydroquinoline-6-sulfonamide, Mass (m/z): 479; m.pt: 98-100° C., Compound No. 616: 4-amino-N-[2-({[(1S)-2-cyclopentyl-1-methylethyl]amino}methyl)phenyl]benzenesulfonamide, Mass (m/z): 399; m.pt: 114.8-117° C., Compound No. 617: N-[4-({[2-({[(1S)-2-cyclopentyl-1-methylethyl]amino}methyl)phenyl]amino}sulfonyl)phenyl]-1-methyl-1H-imidazole-2-sulfonamide, Mass (m/z): 532.0; m.pt: 148.2-150° C., Compound No. 618: N-[2-({[(1S)-2-cyclopentyl-1-methylethyl]amino}methyl)phenyl]-1-methyl-1H-imidazole-2-sulfonamide, Mass (m/z): 377; m.pt: 158-160° C., Compound No. 619: N-[2-({[(1S)-2-cyclopentyl-1-methylethyl]amino}methyl)phenyl]-4-oxochromane-6-sulfonamide, Mass (m/z): 443; m.pt: 124.7-126° C., Compound No. 620: N-[2-({[(1S)-2-cyclohexyl-1-methylethyl]amino}methyl)phenyl]-4-oxochromane-6-sulfonamide, Mass (m/z): 457; m.pt: Gummy, Compound No. 621: N-[2-({[1-methyl-2-(tetrahydro-2H-pyran-4-yl)ethyl]amino}methyl)phenyl]-1-benzothiophene-2-sulfonamide, Mass (m/z): 445; m.pt: 178.4-150° C., While the present invention has been described in terms of its specific embodiments, certain modifications and equivalents will be apparent to those skilled in the art and are included within the scope of the present invention.

Microbiological Activity

Microbroth minimum inhibitory concentration (MIC) was performed using NCCLS method in Cation adjusted Mueller Hinton broth for facultative cultures (*S. aureus, Enterococcus*) and Cation adjusted Mueller Hinton broth +2.5% lysed horse blood for *S. pneumoniae*. MIC against *H. influenzae* strains was performed by NCCLS broth dilution method using HTM broth. Overnight grown cultures were adjusted to 0.5 Mcfarland using normal saline and diluted 100 times. 1 mg/ml concentration of stock solution of drug in DMSO/ distilled water/solvent given in NCCLS manual were prepared. NCCLS double dilutions were done to get the required concentration range of the drugs in the 96 well microtiter plates using the respective media. 100 µl of culture broth was added in wells already containing 100 µl of broth containing antibiotic to get approximately $3-7\times10^5$ CFU/ml. The plates were incubated at 37° C. for about 18-24 hours. The concentration of drug at which there was complete disappearance of growth was considered as MIC.

Compounds described herein have shown good activity against microbial strains. Some of the compounds specifically mentioned herein (Nos. 1-183b) have shown very good activity against microbial strains, for example, *Streptococcus pneumoniae* (49619 and 6303), *Haemophilus influenzae* (49247), *Streptococcus pyogenes* (19615) or *Staphylococcus aureus* (25923). The compounds tested exhibited MIC values against *Streptococcus pneumoniae* (49619) in the range between about 2 µg/mL to greater than 64 µg/mL, between about 2 µg/mL to about 64 µg/mL, and even between about 2 µg/mL to about 32 µg/mL. The compounds tested exhibited MIC values against *Streptococcus pneumoniae* (6303) in the range between about 2 µg/mL to greater than 64 µg/mL, between about 2 µg/mL to about 64 µg/mL, and even between about 2 µg/mL to about 32 µg/mL. The compounds tested exhibited MIC values against *Haemophilus influenzae* (49247) in the range between about 1 µg/mL to greater than 64 µg/mL, between about 1 µg/mL to about 64 µg/mL, and even between about 1 µg/mL to about 32 µg/mL. The compounds tested exhibited MIC values against *Streptococcus pyogenes* (19615) in the range between about 2 µg/mL to greater than 64 µg/mL, between about 2 µg/mL to about 64 µg/mL, and even between about 2 µg/mL to about 32 µg/mL. The compounds tested exhibited MIC values against *Staphylococcus aureus* 25923 in the range between about 1 µg/mL to greater than 64 µg/mL, between about 1 µg/mL to about 64 µg/mL, and even between about 1 µg/mL to about 32 µg/mL.

Compounds described herein have shown good activity against microbial strains. Some of the compounds specifically mentioned herein (Nos. 286-397) have shown very good activity against microbial strains, for example, *Streptococcus pneumoniae* (3579, AB34, 49619 and 6303), *Haemophilus influenzae* (49247and β lac), *Streptococcus pyogenes* (19615) or *Staphylococcus aureus* (25923). The compounds tested exhibited MIC values against *Streptococcus pneumoniae* 3579 in the range between about 1µg/mL to greater than 32µg/mL, and between about 1µg/mL to about 16µg/mL. The compounds tested exhibited MIC values against *Streptococcus pneumoniae* AB34 in the range between about 2 µg/mL to greater than 32 µg/mL, and between about 2 µg/mL to about 16 µg/mL. The compounds tested exhibited MIC values against *Streptococcus pneumoniae* ATCC 49619 in the range between about 1 µg/mL to greater than 32 µg/mL, and between about 1 µg/mL to about 16 µg/mL. The compounds tested exhibited MIC values against *Streptococcus pneumoniae* 6303 in the range between about 1 µg/mL to greater than 32 µg/mL, and between about 1 µg/mL to about 16 µg/mL. The compounds tested exhibited MIC values against *Haemophilus influinzae* ATCC 49247 in the range between less than about 1 µg/mL to greater than 32 µg/mL, and between less than about 1 µg/mL to about 16 µg/mL. The compounds tested exhibited MIC values against *Haemophilus influenzae* β-lac in the range between less than 1 µg/mL to greater than 32 µg/mL, and between less than about 1 µg/mL to about 16 µg/mL. The compounds tested exhibited MIC values against *Streptococcus pyogenes* 19615 in the range between about 4 µg/mL to greater than 32 µg/mL, and between about 4 µg/mL to about 16 µg/mL. The compounds tested exhibited MIC values against *Streptococcus aureus* ATCC 25923 in the range between about 8 µg/mL to greater than 32 µg/mL, and between about 8 µg/mL to about 16 µg/mL.

Compounds described herein have shown good activity againsts microbial strains. Some of the compounds specifically mentioned herein (Nos. 398-521) have shown very good activity against microbial strains, for example, *Streptococcus pneumoniae* (49619 and 6303), *Haemophilius influenzae* (49247), *Streptococcus pyogenes* (19615), *Staphylococcus aureus* (25923), or MRSA 562. The compounds tested exhibited MIC values against *Streptococcus pneumoniae* 3579 in the range between less than about 1 µg/mL to greater than 16 µg/mL, and between less than about 1 µg/mL to about 16 µg/mL. The compounds tested exhibited MIC values against *Streptococcus pneumoniae* AB34 in the range between less than about 1 µg/mL to greater than 16 µg/mL, and between less than about 1 µg/mL to about 16 µg/mL. The compounds tested exhibited MIC values against *Streptococcus pneumoniae* ATCC 49619 in the range between less than about 1 µg/mL to greater than 16 µg/mL, and between less than about 1 µg/mL to about 16 µg/mL. The compounds tested exhibited MIC values against *Streptococcus pneumoniae* 6303 in the range between less than about 1 µg/mL to greater than 16 µg/mL, and between less than about 1 µg/mL to about 16 µg/mL. The compounds tested exhibited MIC values against *Haemophilus influinzae* 49247 in the range between about 2 µg/mL to greater than 16 µg/mL, and between about 2 µg/mL to about 16 µg/mL. The compounds tested exhibited MIC values against *Haemophilus influinzae* β-lac in the range between about 1 µg/mL to greater than 16 µg/mL, and between about 1 µg/mL to about 16 µg/mL. The compounds tested exhibited MIC values against *Streptococcus pyogenes* 19615 in the range between less than about 1 µg/mL to greater than 16 µg/mL, and between less than about 1 µg/mL to about 16 µg/mL. The compounds tested exhibited MIC values against *Streptococcus aureus* ATCC 25923 in the range between less than about 1 µg/mL to greater than 16 µg/mL, and between less than about 1 µg/mL to about 16 µg/mL. The compounds tested exhibited MIC values against MRSA562 in the range between less than about 1 µg/mL to greater than 16 µg/mL, and between less than about 1 µg/mL to about 16 µg/mL.

Some of the compounds specifically mentioned herein (Nos. 398-521) were also tested for their $IC_{50}$ values in Rat FRS, *Streptococcus aureus* FRS, *Streptococcus pneumoniae* FRS and *Haemophilus influinzae* FRS.

The $IC_{50}$ values of the compounds described herein are as follows:

The $IC_{50}$ values against Rat FRS were in the range of between about 5000 nM to greater than 10000 nM. The $IC_{50}$ values against *Streptococcus aureus* FRS were in the range of between about 5 nM to greater than 1000 nM, for example, between about 5 nM to about 700 nM, and, for example, between about 5 nM to about 50 nM. The $IC_{50}$ values against *Streptococcus pneumoniae* FRS were in the range of between about 5 nM to greater than 1000 nM, for example, between about 5 nM to about 200 nM, and, for example, between about 5 nM to about 50 nM. The $IC_{50}$ values against *Haemophilus influenzae* FRS were in the range of between about 4 nM to greater than 1000 nM, for example, between about 4 nM to about 100 nM, and, for example, between about 4 nM to about 50 nM.

Compounds of this invention have shown good activity againsts microbial strains. Some of the compounds specifically mentioned herein (Nos. 522-621) have shown very good activity against microbial strains, for example, *Streptococcus pneumoniae* (3579, AB34, 49f19 and 6303), *Haemophilus influenzae* (49247 and β-lac), *Streptococcus pyogenes* (19615) or *Staphylococcus aureus* (25923).

The compounds tested exhibited MIC values against *Streptococcus pneumoniae* 3579 in the range between about 0.5 µg/mL to greater than 16 µg/mL, and between about 0.5 µg/mL to about 16 µg/mL. The compounds tested exhibited MIC values against *Streptococcus pneumoniae* AB34 in the range between about 0.25 µg/mL to greater than 16 µg/mL, and between about 0.25 µg/mL to about 16 µg/mL. The compounds tested exhibited MIC values against *Streptococcus pneumoniae* ATCC 49619 in the range between about 0.25 µg/mL to greater than 16 µg/mL, and between about 0.25 µg/mL to about 16m/mL. The compounds tested exhibited MIC values against *Streptococcus pneumoniae* 6303 in the range between less than about 1 µg/mL to greater than 16 µg/mL, and between less than about 1 µg/mL to about 16 µg/mL. The compounds tested exhibited MIC values against *Haemophilus influinzae* ATCC 49247 in the range between less than about 1 µg/mL to greater than 16 µg/mL, and between less than about 1 µg/mL to about 16 µg/mL. The compounds tested exhibited MIC values against *Haemophilus influenzae* β-lac in the range between less than about 1 µg/mL to greater than 16 µg/mL, and between less than about 1 µg/mL to 16 µg/mL. The compounds tested exhibited MIC values against *Streptococcus pyogenes* 19615 in the range between less than about 1 µg/mL to greater than 16 µg/mL, and between less than about 1 µg/mL to about 16 µg/mL. The compounds tested exhibited MIC values against *Streptococcus aureus* ATCC 25923 in the range between about 0.5 µg/mL to greater than 16 µg/mL, and between about 0.5 µg/mL to about 16 µg/mL.

We claim:
1. A compound having the structure of Formula Ib,

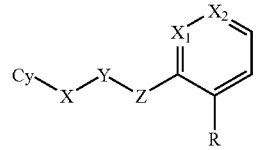

Formula Ib pharmaceutically acceptable salts or stereoisomers thereof, wherein:
Cy is cyclohexyl or cyclopentyl;
X is $CH_2CH(CH_3)$, $CH(F)CH(CH_3)$, $CH(OH)CH(CH_3)$ or $CH_2CH(F)CH_2$;
Y is NH;
Z is $CH_2$;
$X_1$ and $X_2$ are CH or N;
R is $NHC(NH)NH_2$, $NHCOOCH_2R_6$ or $NHSO_2R_6$;
$R_6$ is aryl, heteroaryl or heterocyclyl.

2. A compound as claimed in claim 1, which is:
N-[2-({[(1S)-2-cyclohexyl-1-methylethyl]amino}methyl)phenyl]-2,3,4,5,6-pentafluoro benzenesulfonamide,
N-[2-({[(1S)-2-cyclohexyl-1-methylethyl]amino}methyl)phenyl]-5-(3-methoxyphenyl)thiophene-2-sulfonamide),
5-(1-benzothien-2-yl)-N-[2-({[(1S)-2-cyclohexyl-1-methylethyl]amino}methyl)phenyl]thiophene-2-sulfonamide,
N-[2-({[(1S)-2-cyclohexyl-1-methylethyl]amino}methyl)phenyl]-5-(3,4-dimethoxyphenyl)thiophene-2-sulfonamide,
N-[2-({[(1S)-2-cyclohexyl-1-methylethyl]amino}methyl)phenyl]-1-benzothiophene-2-sulfonamide,
N-[2-({[(1S)-2-cyclopentyl-1-methylethyl]amino}methyl)phenyl]-5-(2,5-dimethoxyphenyl)thiophene-2-sulfonamide,
N-[2-({[(1S)-2-cycloheptyl-1-methylethyl]amino}methyl)phenyl]-5-(2,5-dimethoxyphenyl)thiophene-2-sulfonamide,
5-(3-acetylphenyl)-N-[2-({[(1S)-2-cyclopentyl-1-methylethyl]amino}methyl)phenyl]thiophene-2-sulfonamide,
N-[2-({[(1S)-2-cyclohexyl-1-methylethyl]amino}methyl)phenyl]-5-[3-(1-hydroxyethyl)phenyl]thiophene-2-sulfonamide,
N-[2-({[(1S)-2-cyclohexyl-1-methylethyl]amino}methyl)phenyl]-5-(2,5-dimethoxyphenyl)thiophene-2-sulfonamide,
N-[2-({[(1S)-2-cyclopentyl-1-methylethyl]amino}methyl)phenyl]-1-benzothiophene-2-sulfonamide,
N-[2-({[(1S)-2-cyclopentyl-1-methylethyl]amino}methyl)phenyl]-5-(3,4-dimethoxyphenyl)thiophene-2-sulfonamide,
6-chloro-N-[2-({[(1S)-2-cyclohexyl-1-methylethyl]amino}methyl)phenyl]imidazo[2,1-b][1,3]thiazole-5-sulfonamide,
N-[2-({[(1S)-2-cyclohexyl-1-methylethyl]amino}methyl)phenyl]-5-[3-(trifluoromethyl)phenyl]thiophene-2-sulfonamide,
N-[2-({[(1S)-2-cyclohexyl-1-methylethyl]amino}methyl)phenyl]-5-[1-methyl-5-(trifluoromethyl)-1H-pyrazol-3-yl]thiophene-2-sulfonamide, N-[2-({[(1S)-2-cyclohexyl-1-methylethyl]amino}methyl)phenyl]-5-[5-(trifluoromethyl)isoxazol-3-yl]thiophene-2-sulfonamide, N-[2-({[(1S)-2-cyclohexyl-1-methylethyl]amino}methyl)phenyl]-5-[1-methyl-3-(trifluoromethyl)-1H-pyrazol-5-yl]thiophene-2-sulfonamide, N-[2-({[(1S)-2-cyclopentyl-1-methylethyl]amino}methyl)phenyl]-5-[4-(trifluoromethoxy)phenyl]thiophene-2-sulfonamide, N-[2-({[(1S)-2-cyclopentyl-1-methylethyl]amino}methyl)phenyl]-5-[5-(trifluoromethyl)isoxazol-3yl]thiophene-2-sulfonamide, N-[2-({[(1S)-2-cyclopentyl-1-methylethyl]amino}methyl)phenyl]-5-[1-methyl-3-(trifluoromethyl)-1H-pyrazol-5-yl]thiophene-2-sulfonamide, N-[2-({[(1S)-2-cyclohexyl-1-methylethyl]amino}methyl)phenyl]-5-[4-(trifluoromethoxy)phenyl]thiophene-2-sulfonamide, 5-chloro-N-[2-({[(1S)-2-cyclohexyl-1-methylethyl]amino}methyl)phenyl]-3-methyl-1-benzo thiophene-2-sulfonamide, methyl 5-({[2-({[(1S)-2-cyclohexyl-1-methylethyl]amino}methyl)phenyl]amino}sulfonyl)-4-methylthiophene-2-carboxylate, methyl 4-({[2-({[(1S)-2-cyclohexyl-1-methylethyl]amino}methyl)phenyl]amino}sulfonyl)-2,5-dimethyl-3-furoate, 5-chloro-N-[2-({[(1S)-2-cyclohexyl-1-methylethyl]amino}methyl)phenyl]-1,3-dimethyl-1H-pyrazole-4-sulfonamide, N-[2-({[(1S)-2-cyclohexyl-1-methylethyl]amino}methyl)phenyl]-2,2'-bithiophene-5-sulfonamide, N-[2-({[(1S)-2-cyclohexyl-1-methylethyl]amino}methyl)phenyl]-5-(3-furyl)thiophene-2-sulfonamide, N-[2-({[(1S)-2-cyclohexyl-1-methylethyl]amino}methyl)phenyl]-5-phenylthiophene-2-sulfonamide, N-[2-({[(1S)-2-cyclopentyl-1-methylethyl]amino}methyl)phenyl]-5-(3-furyl)thiophene-2-sulfonamide, N-[2-({[(1S)-2-cyclopentyl-1-methylethyl]amino}methyl)phenyl]-5-phenylthiophene-2-sulfonamide, 5-bromo-N-[2-({[(1S)-2-cyclopentyl-1-methylethyl]amino}methyl)phenyl]thiophene-2-sulfonamide, N-[2-({[(1S)-2-cyclopentyl-1-methylethyl]amino}methyl)phenyl]thiophene-2-sulfonamide, N-[2-({[(1S)-2-cyclopentyl-1-methylethyl]amino}methyl)phenyl]-2,2'-bithiophene-5-sulfonamide, N-[2-({[(1S)-2-cyclohexyl-1-methylethyl]amino}methyl)phenyl]-3,5-bis(trifluoromethyl)benzenesulfonamide, N-[2-({[(1S)-2-cyclohexyl-1-methylethyl]amino}methyl)phenyl]-6-phenoxypyridine-3-sulfonamide, N-[2-({[(1S)-2-cyclohexyl-1-methylethyl]amino}methyl)phenyl]-1-benzothiophene-3-sulfonamide, 5-(3-acetylphenyl)-N-[2-({[(1S)-2-cyclohexyl-1-methylethyl]amino}methyl)phenyl]thiophene-2-sulfonamide, 5-(1,3-benzodioxo-1-5-yl)-N-[2-({[(1S)-2-cyclohexyl-1-methylethyl]amino}methyl)phenyl]thiophene-2-sulfonamide, N-[2-({[(1S)-2-cyclohexyl-1-methylethyl]amino}methyl)phenyl]-3,3'-bithiophene-5-sulfonamide, methyl 3-({[2-({[(1S)-2-cyclohexyl-1-methylethyl]amino}methyl)phenyl]amino}sulfonyl)-4-(isopropylsulfonyl)thiophene -2-carboxylate, N-[2-({[(1S)-2-cyclohexyl-1-methylethyl]amino}methyl)phenyl]-5-(3-fluorophenyl)thiophene-2-sulfonamide, N-[2-({[(1S)-2-cyclohexyl-1-methylethyl]amino}methyl)phenyl]-5-[3-(hydroxymethyl)phenyl]thiophene-2-sulfonamide, N-[2-({[(1S)-2-cyclohexyl-1-methylethyl]amino}methyl)phenyl]-5-[4-(hydroxymethyl)phenyl]thiophene-2-sulfonamide, methyl 5-({[2-({[(1S)-2-cyclopentyl-1-methylethyl]amino}methyl)phenyl]amino}sulfonyl)-4-methylthiophene-2-carboxylate, N-[2-({[(1S)-2-cyclopentyl-1-methylethyl]amino}methyl)phenyl]-5-(3-fluorophenyl)thiophene-2-sulfonamide, N-[2-({[(1S)-2-cyclopentyl-1-methylethyl]amino}methyl)phenyl]-5-isoxazol-3-ylthiophene-2-sulfonamide, N-[2-({[(1S)-2-cyclohexyl-1-methylethyl]amino}methyl)phenyl]-2-(trifluoroacetyl)-1,2,3,4-tetrahydroisoquinoline-6-sulfonamide, N-[2-({[(1S)-2-cyclohexyl-1-methylethyl]amino}methyl)phenyl]-1,2,3,4-tetrahydroisoquinoline-6-sulfonamide, methyl 5-({[2-({[(1S)-2-cyclopentyl-1-methylethyl]amino}methyl)phenyl]amino}sulfonyl)-1-methyl-1H-pyrrole-2-carboxylate, N-[2-({[(1S)-2-cyclopentyl-1-methylethyl]amino}methyl)phenyl]-1-methyl-1H -imidazole-4-sulfonamide, N-[2-({[(1S)-2-cyclopentyl-1-methylethyl]amino}methyl)phenyl]-3,5-bis(trifluoromethyl)benzenesulfonamide, N-[2-({[(1S)-2-cyclohexyl-1-methylethyl]amino}methyl)phenyl]-5-isoxazol-3-ylthiophene-2-sulfonamide, 5-chloro-N-[2-({[(1S)-2-cyclopentyl-1-methylethyl]amino}methyl)phenyl]-1,3-dimethyl-1H-pyrazole-4-sulfonamide, 5-(1-benzothien-2-yl)-N-[2-({[(1S)-2-cyclopentyl-1-methylethyl]amino}methyl)phenyl]thiophene-2-sulfonamide, N-[2-({[(1S)-2-cyclopentyl-1-methylethyl]amino}methyl)phenyl]-5-(4-methoxyphenyl)thiophene-2-sulfonamide, N-[2-({[(1S)-2-cyclopentyl-1-methylethyl]amino}methyl)phenyl]-3,3'-bithiophene-5-sulfonamide, N-[2-({[(1S)-2-cyclopentyl-1-methylethyl]amino}methyl)phenyl]-2-(trifluoroacetyl)-1,2,3,4-tetrahydroisoquinoline-6-sulfonamide, N-[2-({[(1S)-2-cyclopentyl-1-methylethyl]amino}methyl)phenyl]-1,2,3,4-tetrahydroisoquinoline-6-sulfonamide, 5-(1,3-benzodioxo-5-yl)-N-[2-({[(1S)-2-cyclopentyl-1-methylethyl]amino}methyl)phenyl]thiophene-2-sulfonamide, 5-chloro-N-[2-({[(1S)-2-cyclopentyl-1-methylethyl]amino}methyephenyl]-3-methyl-1-benzothiophene-2-sulfonamide, N-[2-({[(1S)-2-cyclopentyl-1-methylethyl]amino}methyl)phenyl]-5-(2-methyl-1,3-thiazol-4-yl)thiophene-2-sulfonamide, ethyl 3-[5-({[2-({[(1S)-2-cyclohexyl-1-methylethyl]amino}methyl)phenyl]amino}sulfonyl)-2-thienyl]-1,2,4-oxadiazole-5-carboxylate, ethyl 3-[5-({[2-({[(1S)-2-cyclopentyl-1-methylethyl]amino}methyl)phenyl]amino}sulfonyl)-2-thienyl]-1,2,4-oxadiazole-5-carboxylate, N-[2-({[(1S)-2-cyclohexyl-1-methylethyl]amino}methyl)phenyl]-2,4-dimethyl-1,3-thiazole-5-sulfonamide, N-[2-({[(1S)-2-cyclopentyl-1-methylethyl]amino}methyl)phenyl]-2,4-dimethyl-1,3-thiazole-5-sulfonamide, methyl 3-({[2-([(1S)-2-cyclopentyl-1-methylethyl]amino}methyl)phenyl]amino}sulfonyl)thiophene-2-carboxylate, N-[2-({[(1S)-2-cyclohexyl-1-methylethyl]amino}methyl)phenyl]-2-(2-thienylsulfonyl)-1,2,3,4-tetrahydroisoquinoline-6-sulfonamide, N-[2-({[(1S)-2-cyclopentyl-1-methylethyl]amino}methyl)phenyl]-6-phenoxypyridine-3-sulfonamide, N-[2-([(1S)-2-cyclohexyl-1-methylethyl]amino}methyl)phenyl]-4-(1H-pyrrol-1-yl)benzenesulfonamide, N-[2-({[(1S)-2-cyclopentyl-1-methylethyl]amino}methyl)phenyl]-4-(1H-pyrrol-1-yl)benzenesulfonamide, N-[2-({[(1S)-2-cyclohexyl-1-methylethyl]amino}methyl)phenyl]-4-(1H-1,2,4-triazol-1-yl)benzenesulfonamide, N-[2-({[(1S)-2-cyclohexyl-1-methylethy]amino}methyl)phenyl]-1H-imidazole-4-sulfonamide, N-[2-({[(1S)-2-cyclohexyl-1-methylethyl]amino}methyl)phenyl]-5-{3-[(1E)-N-hydroxy ethanimidoyl]phenyl}thiophene-2-sulfonamide, N-[2-({[(1S)-2-cyclohexyl-1-methylethyl]amino}methyl)phenyl]-5-{3-[(1E)-N-methoxy ethanimidoyl]phenyl}thiophene-2-sulfonamide, N-[2-({[(1S)-2-cyclopentyl-1-methylethyl]amino}methyl)phenyl]-5-(phenylsulfonyl)thiophene-2-sulfonamide, N-[2-({[(1S)-2-cyclohexyl-1-methylethyl]amino}methyl)phenyl]-5-(phenylsulfonyl)thiophene-2-sulfonamide, N-[2-({[(1S)-2-cyclohexyl-1-methylethyl]amino}methyl)phenyl]-4-(1H-imidazol-1-yl)benzenesulfonamide, N-[2-({[(1S)-2-cyclopentyl-1-methylethyl]amino}methyl)phenyl]-4-(1H-imidazol-1-yl)benzenesulfonamide, N-[2-({[(1S)-2-cyclopentyl-1-methylethyl]amino}methyl)phenyl]-1-benzothiophene-2-sulfonamide, N-[2-({[(1S)-2-cyclohexyl-1-methylethyl]amino}methyl)phenyl]-5-pyridin-4-ylthiophene-2-sulfonamide, N-[2-({[(1S)-2-cyclopentyl-1-methylethyl]amino}methyl)phenyl]-5-pyridin-3-ylthiophene-2-sulfonamide, N-[2-({[(1S)-2-cyclopentyl-1-methylethyl]amino}methyl)phenyl]-4-(1H-1,2,4-triazol-1-yl)benzenesulfonamide, 6-({[2-({[(1S)-2-cyclopentyl-1-methylethyl]amino}methyl)phenyl]amino}sulfonyl)-N-(4-methoxyphenyl)-3,4-dihydroisoquinoline-2(1H)-carboxamide, 6-({[2-({[(1S)-2-cyclopentyl-1-methylethyl]amino}methyl)phenyl]amino}sulfonyl)-N-isopropyl-3,4-dihydroisoquinoline-2(1H)-carboxamide, N-[2-({[(1S)-2-cyclopentyl-1-methylethyl]amino}methyl)phenyl]-2-(1H-imidazol-1-ylcarbonyl)-1,2,3,4-tetrahydroisoquinoline-6-sulfonamide, N-[2-({[(1S)-2-cyclohexyl-1-methylethyl]amino}methyl)phenyl]-4-({[(4-methoxyphenyl)amino]carbonyl}amino)benzenesulfonamide, 4-{[(4-acetylphenyl)amino]carbonyl}amino)-N-[2-{[(1S)-2-cyclohexyl-1-methylethyl]amino}methyl)phenyl]benzenesulfonamide, N-[4-({[2-({[(1S)-2-cyclohexyl-1-methylethyl]amino}methyl)phenyl]amino}sulfonyl)phenyl]thiophene-2-sulfonamide, N-[2-({[(1S)-2-cyclohexyl-1-methylethyl]amino}methyl)phenyl]-1-pyrimidin-2-yl-1H-imidazole-4-sulfonamide, N-{3-[5-({[2-({[(1S)-2-cyclohexyl-1-methylethyl]amino}methyl)phenyl]amino}sulfonyl)-2-thienyl]phenyl}acetamide, N-{3-[5-({[2-({[(1S)-2-cyclopentyl-1-methylethyl]amino}methyl)phenyl]amino}sulfonyl)-2-thienyl]phenyl}acetamide, N-[2-({[(1S)-2-cyclohexyl-1-methylethyl]amino}methyl)phenyl]-5-(2,3,4-trimethoxy phenyl)thiophene-2-sulfonamide, N-[2-({[(1S)-2-cyclopentyl-1-methylethyl]amino}methyl)phenyl]-5-(2,3,4-trimethoxy phenyl)thiophene-2-sulfonamide, N-(4-acetylphenyl)-6-({[2-({[(1S)-2-cyclopentyl-1-methylethyl]amino}methyl)phenyl]amino}sulfonyl)-3,4-dihydroisoquinoline-2(1H)-carboxamide, N-[2-({[(1S)-2-cyclohexyl-1-methylethyl]amino}methyl)phenyl1-pyrazin-2-yl-1H-imidazole-4-sulfonamide, N-[2-({[(1S,2R)-2-cyclohexyl-2-hydroxy-1-methylethyl]amino}methyl)phenyl]thiophene-2-sulfonamide, N-[2-({[(1S)-2-cyclopentyl-1-methylethyl]amino}methyl)phenyl]-5-isoxazol-5-ylthiophene-2-sulfonamide, N-(2-{[(2-cyclohexyl-1-methylethyl)amino]methyl}phenyl)-4-[(methylsulfonyl)amino]benzenesulfonamide, N-(2-{[(2-cyclohexyl-1-methylethyl)amino]methyl}phenyl)-3-methoxy-4-piperazin-1-ylbenzenesulfonamide, N-(2-{[(2-cyclopentyl-1-methylethyl)amino]methyl}phenyl)-4-(1H-1,2,3-triazol-1-yl)benzenesulfonamide, N-[2-({[(1S)-2-cyclohexyl-1-methylethyl]amino}methyl)phenyl]-1H-imidazole-4-sulfonamide, N-[2-({[(1S)-2-cyclopentyl-1-methylethyl]amino}methyl)phenyl]-1H-imidazole-4-sulfonamide, N-[4-({[2-({[(1S)-2-cyclohexyl-1-methylethyl]amino}methyl)phenyl]amino}sulfonyl)phenyl]acetamide, 4-amino-N-[2-({[(1S)-2-cyclohexyl-1-methylethyl]amino}methyl)phenyl]Benzenesulfonamide, N-[4-({[2-({[(1S)-2-cyclopentyl-1-methylethyl]amino}methyl)phenyl]amino}sulfonyl)phenyl]thiophene-2-sulfonamide, N-[2-({[(1S)-2-cyclopentyl-1-methylethyl]amino}methyl)phenyl]-5-(2,3,4-trimethoxyphenyl)thiophene-2-sulfonamide, N-[2-({[(1S)-2-cyclohexyl-1-methylethyl]amino}methyl)phenyl]-4-{3-[(E)-(hydroxyimino)methyl]-1H-pyrrol-1-yl}benzenesulfonamide, N-[2-({[(1S)-2-cyclohexyl-1-methylethyl]amino}methyl)phenyl]-3,5-dimethylisoxazole-4-sulfonamide, N-[4-({[2-({[(1S)-2-cyclohexyl-1-methylethyl]amino}methyl)phenyl]amino}sulfonyl)phenyl]isoxazole-5-carboxamide, N-[4-({[2-({[(1S)-2-cyclohexyl-1-methylethyl]amino}methyl)phenyl]amino}sulfonyl)phenyl]-3,5-dimethylisoxazole-4-sulfonamide, N-[4-({[2-({[(1S)-2-cyclohexyl-1-methylethyl]amino}methyl)phenyl]amino}sulfonyl)phenyl]-1-methyl-1H-imidazole-4-sulfonamide, N-[2-({[(1S)-2-cyclohexyl-1-methylethyl]amino}methyl)phenyl]-4-(1-hydroxyethyl)Benzenesulfonamide, pyridin-3-ylmethyl[2-({[(1S)-2-cyclohexyl-1-methylethyl]amino}methyl)phenyl]carbamate, pyridin-3-ylmethyl[2-({[(1S)-2-cyclopentyl-1-methylethyl]amino}methyl)phenyl]carbamate,
pyridin-3-ylmethyl[2-({[(1S,2R)-2-cyclohexyl-2-hydroxy-1-methylethyl]amino}methyl)phenyl]carbamate,
N-[2-({[(1S)-2-cyclopentyl-1-methylethyl]amino}methyl)phenyl]-1-pyrazin-2-yl-1H-imidazole-4-sulfonamide,
5-chloro-N-[2-({[(1S,2R)-2-cyclohexyl-2-hydroxy-1-methylethyl]amino}methyl)phenyl]-3-methyl-1-benzothiophene-2-sulfonamide,
ethyl 3-({[2-({[(1S)-2-cyclopentyl-1-methylethyl]amino}methyl)phenyl]amino}sulfonyl)-2-thienyl]benzoate,
4-acetyl-N-[4-({[2-({[(1S)-2-cyclohexyl-1-methylethyl]amino}methyl)phenyl]amino}sulfonyl)phenyl]benzenesulfonamide,
N-[4-({[2-({[(1S)-2-cyclohexyl-1-methylethyl]amino}methyl)phenyl]amino}sulfonyl)phenyl]-2,4-dimethyl-1,3-thiazole-5-sulfonamide,
N-[2-({[(1S)-2-cyclohexyl-1-methylethyl]amino}methyl)phenyl]-4-(1,3-dioxo-1,3-dihydro-2H-isoindol-2-yl)benzenesulfonamide,
N-[2-({[(1S,2S)-2-cyclohexyl-2-hydroxy-1-methylethyl]amino}methyl)phenyl]-1,2,3,4-tetrahydroisoquinoline-6-sulfonamide,
N-[2-({[(1S,2S)-2-cyclohexyl-2-hydroxy-1-methylethyl]amino}methyl)phenyl]-1-benzothiophene-2-sulfonamide,
N-[2-({[(1S,2S)-2-cyclohexyl-2-hydroxy-1-methylethyl]amino}methyl)phenyl]-5-isoxazol-5-ylthiophene-2-sulfonamide,
N-[2-({[(1S,2S)-2-cyclohexyl-2-hydroxy-1-methylethyl]amino}methyl)phenyl]-2-(trifluoroacetyl)-1,2,3,4-tetrahydroisoquinoline-6-sulfonamide,
N-[2-({[(1S)-2-cyclohexyl-1-methylethyl]amino}methyl)phenyl]-4-(3-formyl-1H-pyrrol-1-yl)benzenesulfonamide,
N-[2-({[(1S)-2-cyclopentyl-1-methylethyl]amino}methyl)phenyl]-4-(3-formyl-1H-pyrrol-1-yl)benzenesulfonamide,
N-[2-({[(1S)-2-cyclohexyl-1-methylethyl]amino}methyl)phenyl]-4-(2-oxo-1,3-oxazolidin-3-yl)benzenesulfonamide,
N-[4-({[2-(1S)-2-cyclohexyl-1-methylethyl]amino}methyl)phenyl]amino}sulfonyl)phenyl]thiophene-3-sulfonamide,
N-[2-({[(1S)-2-cyclohexyl-1-methylethyl]amino}methyl)phenyl]-5-(1-methyl-1H-pyrazol-4-yl)thiophene-2-sulfonamide,
N-[2-({[(1S)-2-cyclohexyl-1-methylethyl]amino}methyl)phenyl]1-1-(2-thienylsulfonyl)-1H-imidazole-4-sulfonamide,
N-[2-([(1S)-2-cyclopentyl-1-methylethyl]amino}methyl)phenyl]-2,1,3-benzothiadiazole-4-sulfonamide,
N-[4-({[2-({[(1S)-2-cyclopentyl-1-methylethyl]amino}methyl)phenyl]amino}sulfonyl)phenyl]-1-methyl-1H-imidazole-4-sulfonamide,
N-[2-({[(1S)-2-cyclopentyl-1-methylethyl]amino}methyl)phenyl]-4-[(methylsulfonyl)amino]benzenesulfonamide,
4-[(butylsulfonyl)amino]-N-[2-({[(1S)-2-cyclohexyl-1-methylethyl]amino}methyl)phenyl]benzenesulfonamide,
N-[2-({[(1S)-2-cyclohexyl-1-methylethyl]amino}methyl)phenyl]-4-[(ethylsulfonyl)amino]benzenesulfonamide,
5-chloro-N-[4-({[2-({[(1S)-2-cyclohexyl-1-methylethyl]amino}methyl)phenyl]amino}sulfonyl)phenyl]-1,3-dimethyl-1H-pyrazole-4-sulfonamide,
methyl 4-({[4-({[2-({[(1S)-2-cyclohexyl-1-methylethyl]amino}methyl)phenyl]amino}sulfonyl)phenyl]amino}sulfonyl)-2,5-dimethyl-3-furoate, methyl 5-([4-([2-({[(1S)-2-cyclohexyl-1-methylethyl]amino}methyl)phenyl]amino}sulfonyl)phenyl]amino}sulfonyl)-3-methylthiophene-2-carboxylate,
methyl 5-({[4-({[2-({[(1S)-2-cyclohexyl-1-methylethyl]amino}methyl)phenyl]amino}sulfonyl)phenyl]amino}sulfonyl)-2-furoate,
ethyl 3-[5-({[2-({[(1S)-2-cyclohexyl-1-methylethyl]amino}methyl)phenyl]amino}sulfonyl)-2-thienyl]benzoate,
N-[2-({[(1S)-2-cyclohexyl-1-methylethyl]amino}methyl)phenyl]-1,3-benzothiazole-2-sulfonamide,
N-[2-({[(1S,2R)-2-cyclohexyl-2-hydroxy-1-methylethyl]amino}methyl)phenyl]-4-(1H-1,2,4-triazol-1-yl)benzenesulfonamide,
N-[2-({[(1S,2R)-2-cyclohexyl-2-hydroxy-1-methylethyl]amino}methyl)phenyl]-4-(1H-pyrrol-1-yl)benzenesulfonamide,
N-[4-({[2-({[(1S)-2-cyclohexyl-1-methylethyl]amino}methyl)phenyl]amino}sulfonyl)phenyl]-2-(trifluoroacetyl)-1,2,3,4-tetrahydroisoquinoline-7-sulfonamide,
N-[2-({[(1S)-2-cyclohexyl-1-methylethyl]amino}methyl)phenyl]-4-pyridin-3-ylbenzenesulfonamide,
N-[2-({[(1S)-2-cyclopentyl-1-methylethyl]amino}methyl)phenyl]-4-pyridin-3-ylbenzenesulfonamide,
N-[2-({[(1S)-2-cyclohexyl-1-methylethyl]amino}methyl)phenyl]-4-pyrimidin-5-ylbenzenesulfonamide,
N-[2-({[(1S)-2-cyclopentyl-1-methylethyl]amino}methyl)phenyl]-4-pyrimidin-5-ylbenzenesulfonamide,
N-[2-({[(1S)-2-cyclohexyl-1-methylethyl]amino}methyl)phenyl]-4-(1-methyl-1H-pyrazol-4-yl)benzenesulfonamide,
N-[2-({[(1S)-2-cyclopentyl-1-methylethyl]amino}methyl)phenyl]-4-(1-methyl-1H-pyrazol-4-yl)benzenesulfonamide,
N-[2-({[(1S,2R)-2-cyclohexyl-2-hydroxy-1-methylethyl]amino}methyl)phenyl]-1,2,3,4-tetrahydroisoquinoline-6-sulfonamide,
N-[2-({[(1S,2R)-2-cyclohexyl-2-hydroxy-1-methylethyl]amino}methyl)phenyl]-5-isoxazol-5-ylthiophene-2-sulfonamide,
N-[2-({[(1S,2R)-2-cyclohexyl-2-hydroxy-1-methylethyl]amino}methyl)phenyl]-1-benzothiophene-2-sulfonamide,
N-[2-({[2-({[(1S)-2-cyclohexyl-1-methylethyl]amino}methyl)phenyl]amino}sulfonyl)phenyl]-1-methyl-1H-imidazole-4- sulfonamide,
N-[3-({[2-({[(1S)-2-cyclohexyl-1-methylethyl]amino}methyl)phenyl]amino}sulfonyl)phenyl]-1-methyl-1H-imidazole-4-sulfonamide,
5-chloro-N-[4-({[2-({[(1S)-2-cyclopentyl-1-methylethyl]amino}methyl)phenyl]amino}sulfonyl)phenyl]-1,3-dimethyl-1H-pyrazole-4-sulfonamide,
N-[2-({[(1S)-2-cyclohexyl-1-methylethyl]amino}methyl)phenyl]-4-(1,2,3-thiadiazol-4-yl)benzenesulfonamide,
N-[2-({[(1S)-2-cyclohexyl-1-methylethyl]amino}methyl)phenyl]-4-(1,3-oxazol-5-yl)benzenesulfonamide, N-[3-({[2-({[(1S)-2-cyclohexyl-1-methylethyl] amino}methyl)phenyl]amino}sulfonyl)phenyl] thiophene-2-sulfonamide,
N-[2-({[2-({[(1S)-2-cyclohexyl-1-methylethyl] amino}methyl)phenyl]amino}sulfonyl)phenyl] thiophene-2-sulfonamide,
3-amino-N-[2-({[(1S)-2-cyclohexyl-1-methylethyl] amino}methyl)phenyl]benzenesulfonamide,
2-amino-N-[2-({[(1S)-2-cyclohexyl-1-methylethyl] amino}methyl)phenyl]benzenesulfonamide,
N-[3-({[2-({[(1S)-2-cyclohexyl-1-methylethyl] amino}methyl)phenyl]amino}sulfonyl)phenyl]-2,4-dimethyl-1,3-thiazole-5-sulfonamide,
N-[3-({[2-({[(1S)-2-cyclohexyl-1-methylethyl] amino}methyl)phenyl]amino}sulfonyl)phenyl]-3,5-dimethylisoxazole-4-sulfonamide,
N-[3-({[2-({[(1S)-2-cyclohexyl-1-methylethyl] amino}methyl)phenyl]amino}sulfonyl)phenyl]isoxazole-5-carboxamide,
N-[3-({[2-({[(1S)-2-cyclohexyl-1-methylethyl] amino}methyl)phenyl]amino}sulfonyl)phenyl] thiophene-3-sulfonamide,
ethyl 5-{[4-({[2-({[(1S)-2-cyclohexyl-1-methylethyl] amino}methyl)phenyl]amino}sulfonyl)phenyl] amino}-5-oxopentanoate,
2-amino-N-[2-({[(1S)-2-cyclohexyl-1-methylethyl] amino}methyl)phenyl]-1,3-benzothiazole-5-sulfonamide,
5-chloro-N-[3-({[2-({[(1S)-2-cyclohexyl-1-methylethyl] amino}methyl)phenyl]amino}sulfonyl)phenyl]-1,3-dimethyl-1H-pyrazole-4-sulfonamide,
N-[2-({[2-({[(1S)-2-cyclohexyl-1-methylethyl] amino}methyl)phenyl]amino}sulfonyl)phenyl]-2,4-dimethyl-1,3-thiazole-5-sulfonamide,
N-[4-({[2-({[(1S)-2-cyclopentyl-1-methylethyl] amino}methyl)phenyl]amino}sulfonyl)phenyl] thiophene-3-sulfonamide,
N-(2-{[[(1S)-2-cyclohexyl-1-methylethyl](methylsulfonyl)amino]methyl}phenyl)-2-[(methylsulfonyl)amino] benzenesulfonamide,
N-[2-({[(1S)-2-cyclopentyl-1-methylethyl] amino}methyl)phenyl]-4-(1H-pyrazol-1-yl)benzenesulfonamide,
N-[2-({[(1S)-2-cyclohexyl-1-methylethyl]amino}methyl) phenyl]-4-(1H-pyrazol-1-yl)benzenesulfonamide,
N-[2-({[(1S)-2-cyclohexyl-1-methylethyl]amino}methyl) phenyl]-fluoro-4-(1H-1,2,4-triazol-1-yl)benzenesulfonamide,
[5 -(2-thienyl)isoxazol-3-yl]methyl[2-({[(1S)-2-cyclohexyl-1-methylethyl]amino}methyl)phenyl]carbamate,
N-[(1S)-2-cyclopentyl-1-methylethyl]-2-[(2-thienylsulfonyl)amino]benzamides,
N-[(1S)-2-cyclohexyl-1-methylethyl]-2-[(2-thienylsulfonyl)amino]benzamides,
methyl [5 -({[2-({[(1S)-2-cyclohexyl-1-methylethyl] amino}methyl)phenyl]amino}sulfonyl)-1H-benzimidazol-2-yl]carbamate,
methyl [6-({[4-({[2-({[(1S)-2-cyclohexyl-1 -methylethyl] amino}methyl)phenyl]amino}sulfonyl)phenyl] amino}sulfonyl)-1H-benzimidazol-2-yl]carbamate,
N-[2-({[(1S)-2-cyclohexyl-1-methylethyl]amino}methyl) phenyl]-4-[(1E)-N-hydroxyeth animidoyl]benzenesulfonamide,
N-[2-({[(1S)-2-cyclohexyl-1-methylethyl]amino}methyl) phenyl]-4-[(1E)-N-methoxyethanimidoyl]benzenesulfonamide,
4-{[amino(imino)methyl]amino}-N-[2-({[(1S)-2-cyclohexyl-1-methylethyl]amino}methyl)phenyl]benzenesulfonamide,
N-[2-({[(1S)-2-cyclohexyl-1-methylethyl]amino}methyl) phenyl]sulfamide,
N-[4-({[2-({[(1S)-2-cyclohexyl-1-methylethyl] amino}methyl)phenyl]amino}sulfonyl)phenyl]-4-[(1E)-N-hydroxyethanimidoyl]benzenesulfonamide,
N-[2-({[(1S)-2-cyclohexyl-1-methylethyl]amino}methyl) phenyl]-3-{[(isopropylamino)carbonyl] amino}benzenesulfonamide,
N-[2-({[(1S)-2-cyclopentyl-1-methylethyl] amino}methyl)phenyl]-1-benzofuran-2-sulfonamide,
N-[3-({[2-cyclohexyl-1-methylethyl]amino}methyl)pyridin-4-yl]thiophene-2-sulfonamide (compound No. 400),
2-amino-N-[2-({[2-cyclohexyl-1-methylethyl] amino}methyl)phenyl]-1H-benzimidazole-5-sulfonamide,
N-[2-({[2-cyclohexyl-1-methylethyl]amino}methyl)phenyl]-4-(5-oxo-1,5-dihydro-4H-1,2,4-triazol-4-yl)benzenesulfonamide,
N-[2-({[2-cyclohexyl-1-methylethyl]amino}methyl)phenyl]-4-(5-methyl-1,3,4-oxadiazol-2-yl)benzenesulfonamide,
N-[2-({[(1S)-2-cyclopentyl-1-methylethyl] amino}methyl)phenyl]-4-(1-methyl-1H-pyrazol-4-yl) benzenesulfonamide,
N-[2-({[2-cyclohexyl-1-methylethyl]amino}methyl)phenyl]-4-(3,5-dimethylisoxazol-4-yl)benzenesulfonamide,
N-[2-({[2-cyclohexyl-1-methylethyl]amino}methyl)phenyl]-5-(3,5-dimethylisoxazol-4-yl)thiophene-2-sulfonamide,
N-[2-({[(1S)-2-cyclopentyl-1-methylethyl] amino}methyl)phenyl]-5-(3,5-dimethylisoxazol-4-yl) thiophene-2-sulfonamide,
N-[2-({[2-cyclohexyl-1-methylethyl]amino}methyl)phenyl]-3 -[(methylsulfonyl)amino]benzenesulfonamide,
N-[2-({[2-cyclohexyl-1-methylethyl]amino}methyl)phenyl]-4-{[(dimethylamino)sulfonyl] amino}benzenesulfonamide,
N-[3-({[2-cyclohexyl-1-methylethyl]amino}methyl)pyridin-4-yl]-1-benzothiophene-2-sulfonamide,
N-[2-({[2-cyclohexyl-1-methylethyl]amino}methyl)phenyl]-5-{[(1-methyl-1H-imidazol-4-yl)sulfonyl] amino}pyridine-2-sulfonamide,
N-[2-({[2-cyclohexyl-1-methylethyl]amino}methyl)phenyl]-5-[(methylsulfonyl)amino]pyridine-2-sulfonamide,
N-[2-({[2-cyclohexyl-1-methylethyl]amino}methyl)phenyl]-5- [(2-thienylsulfonyl)amino]pyridine-2-sulfonamide,
5-bromo-N-[2-({[2-cyclohexyl-1-methylethyl] amino}methyl)phenyl]-1,3-thiazole-2-sulfonamide,
[5-(2-thienyl)isoxazol-3-yl]methyl[2-({[(1S)-2-cyclopentyl-1-methylethyl]amino}methyl)phenyl]carbamate,
N-[2-({[2-cyclohexyl-1-methylethyl]amino}methyl)phenyl]-2-fluoro-5-(1H-pyrrol-1-yl)benzenesulfonamide,
2-amino-N-[2-({[2-cyclohexyl-1-methylethyl] amino}methyl)phenyl]-1,3-benzothiazole-4-sulfonamide,
N-[2-({[2-({[2-cyclohexyl-1-methylethyl]amino}methyl) phenyl]amino}sulfonyl)phenyl]thiophene-3-sulfonamide, N-[2-({[(1S)-2-cyclopentyl-1-methylethyl]amino}methyl)phenyl]-3-fluoro-4-H-tetrazol-1-yl)benzenesulfonamide,
N-[2-({[(2S)-2-cyclohexyl-2-hydroxy-1-methylethyl]amino}methyl)phenyl]-4-H-pyrrol-1-yl)benzenesulfonamide,
N-[2-({[(1S)-2-cyclopentyl-1-methylethyl]amino}methyl)phenyl]-4-(1,3-oxazol-5-yl)benzenesulfonamide,
N-[2-({[(1S)-2-cyclopentyl-1-methylethyl]amino}methyl)phenyl]-6-H-1,2,4-triazol-1-yl)pyridine-3-sulfonamide,
N-[2-({[2-cyclohexyl-1-methylethyl]amino}methyl)pyridin-3-yl]thiophene-2-sulfonamide,
N-[2-{[(1S)-2-cyclopentyl-1-methylethyl]amino}methyl)phenyl]-3-fluoro-4-H-1,2,4-triazol-1-yl)benzenesulfonamide,
N-[2-({[2-cyclohexyl-1-methylethyl]amino}methyl)phenyl]-6-(1H-1,2,4-triazol-1-yl)pyridine-3-sulfonamide,
N-[2-({[2-cyclohexyl-1-methylethyl]amino}methyl)phenyl]-3-fluoro-4-(1H-tetrazol-1-yl)benzenesulfonamide,
N-[2-({[2-cyclohexyl-1-methylethyl]amino}methyl)phenyl]-6-(1H-pyrrol-1-yl)pyridine-3-sulfonamide,
N-[2-({[2-cyclohexyl-1-methylethyl]amino}methyl)pyridin-3-yl]-3-fluoro-4-(1H-1,2,4-triazol-1-yl)benzenesulfonamide,
N-[2-({[2-cyclohexyl-2-fluoro-1-methylethyl]amino}methyl)phenyl]thiophene-2-sulfonamide,
N-[2-({[(1S)-2-cyclopentyl-1-methylethyl]amino}methyl)phenyl]-6-(1H-pyrrol-1-yl)pyridine-3-sulfonamide,
N-[3-({[2-cyclohexyl-1-methylethyl]amino}methyl)pyridin-4-yl]-5-isoxazol-5-ylthiophene-2-sulfonamide hydrochloride,
2-amino-N-[2-({[(1S)-2-cyclopentyl-1-methylethyl]amino}methyl)phenyl]-1,3-benzothiazole-6-sulfonamide,
2-amino-N-[2-({[(1S)-2-cyclopentyl-1-methylethyl]amino}methyl)phenyl]-1H-benzimidazole-6-sulfonamide,
5-{[amino(imino)methyl]amino}-N-[2-({[2-cyclohexyl-1-methylethyl]amino}methyl)phenyl]pyridine-2-sulfonamide,
N-[4-({[2-({[2-cyclohexyl-1-methylethyl]amino}methyl)phenyl]amino}sulfonyl)-3-methoxyphenyl]-1-methyl-1H-imidazole-4-sulfonamide,
N-[6-({[2-({[2-cyclohexyl-1-methylethyl]amino}methyl)phenyl]amino}sulfonyl)-1,3-benzothiazol-2-yl]acetamide,
N-[2-({[2-cyclohexyl-1-methylethyl]amino}methyl)phenyl]-5-methyl-1H-benzimidazole-2-sulfonamide,
4-amino-N-[2-({[2-cyclohexyl-1-methylethyl]amino}methyl)phenyl]-2-fluorobenzene sulfonamide,
4-amino-N-[2-({[2-cyclohexyl-1-methylethyl]amino}methyl)phenyl]-2-methoxybenzene sulfonamide,
N-[4-({[2-({[2-cyclohexyl-1-methylethyl]amino}methyl)phenyl]amino}sulfonyl)-3-methoxyphenyl]acetamide,
N-[2-({[2-cyclohexyl-1-methylethyl]amino}methyl)phenyl]-2-methoxy-4-[(methylsulfonyl)amino]benzenesulfonamide,
methyl[4-({[2-({[2-cyclohexyl-1-methylethyl]amino}methyl)phenyl]amino}sulfonyl)phenyl]carbamate,
N-[2-({[(1S)-2-cyclopentyl-1-methylethyl]amino}methyl)phenyl]-4-(1,2,3-thiadiazol-4-yl)benzenesulfonamide,
N-[2-({[2-cyclohexyl-1-methylethyl]amino}methyl)phenyl]-4-(2-methyl-2H-tetrazol-5-yl)benzenesulfonamide,
N-[2-({[(1S)-2-cyclopentyl-1-methylethyl]amino}methyl)phenyl]-4-(2-methyl-2H-tetrazol-5-yl)benzenesulfonamide,
N-[2-({[(1S)-2-cyclopentyl-1-methylethyl]amino}methyl)phenyl]-4-(5-methyl-1,3,4-oxadiazol-2-yl)benzenesulfonamide,
N-[2-({[2-cyclohexyl-1-methylethyl]amino}methyl)phenyl]-6-(2-furyl)pyridine-3-sulfonamide,
N-[2-({[(1S)-2-cyclopentyl-1-methylethyl]amino}methyl)phenyl]-6-(2-furyl)pyridine-3-sulfonamide,
N-[2-({[2-cyclohexyl-1-methylethyl]amino}methyl)phenyl]-6-(3-furyl)pyridine-3-sulfonamide,
N-[2-({[(1S)-2-cyclopentyl-1-methylethyl]amino}methyl)phenyl]-6-(3-furyl)pyridine-3-sulfonamide,
N-[2-({[2-cyclohexyl-1-methylethyl]amino}methyl)phenyl]-1-methyl-2-oxo-1,2-dihydroquinoline-6-sulfonamide,
N-[2-({[(1S)-2-cyclopentyl-1-methylethyl]amino}methyl)phenyl]-1-methyl-2-oxo-1,2-dihydroquinoline-6-sulfonamide,
N-[2-({[2-cyclohexyl-1-methylethyl]amino}methyl)phenyl]-6-(1H-tetrazol-1-yl)pyridine-3-sulfonamide,
N-[2-({[(1S)-2-cyclopentyl-1-methylethyl]amino}methyl)phenyl]-6-(1H-tetrazol-1-yl)pyridine-3-sulfonamide,
N-[2-({[2-cyclohexyl-1-methylethyl]amino}methyl)phenyl]-6-(2-thienyl)pyridine-3-sulfonamide,
N-[2-({[(1S)-2-cyclopentyl-1-methylethyl]amino}methyl)phenyl]-6-(2-thienyl)pyridine-3-sulfonamide,
N-[2-({[2-cyclohexyl-1-methylethyl]amino}methyl)phenyl]-6-(1H-imidazol-1-yl)pyridine-3-sulfonamide,
N-[2-({[(1S)-2-cyclopentyl-1-methylethyl]amino}methyl)phenyl]-6-(1H-imidazol-1-yl)pyridine-3-sulfonamide,
N-[2-({[2-cyclohexyl-1-methylethyl]amino}methyl)phenyl]-3-(2-methyl-1,3-thiazol-4-yl)benzenesulfonamide,
N-[2-({[(1S)-2-cyclopentyl-1-methylethyl]amino}methyl)phenyl]-3-(2-methyl-1,3-thiazol-4-yl)benzenesulfonamide,
N-[2-({[2-cyclohexyl-1-methylethyl]amino}methyl)phenyl]-5-fluoro-3-methyl-1-benzothiophene-2-sulfonamide,
N-[2-({[(1S)-2-cyclopentyl-1-methylethyl]amino}methyl)phenyl-5-fluoro-3-methyl-1-benzothiophene-2-sulfonamide,
N-[2-({[2-cyclohexyl-2-fluoro-1-methylethyl]amino}methyl)phenyl]-2-(trifluoroacetyl)-1,2,3,4-tetrahydroisoquinoline-7-sulfonamide,
N-[4-({[2-({[2-cyclohexyl-2-fluoro-1-methylethyl]amino}methyl)phenyl]amino}sulfonyl)phenyl]thiophene-2-sulfonamide,
N-[2-({[2-cyclohexyl-2-fluoro-1-methylethyl]amino}methyl)phenyl]-4-(1H-pyrrol-1-yl)benzenesulfonamide,
N-(2-{[(3-cyclohexyl-2-fluoropropyl)amino}methyl)phenyl]-2-(trifluoroacetyl)-1,2,3,4-tetrahydroisoquinoline-7-sulfonamide,
N-(4-{[(2-{[(3-cyclohexyl-2-fluoropropyl)amino]methyl}phenyl)amino]sulfonyl}phenyl)thiophene-2-sulfonamide, 5-amino-N-[2-({[2-cyclohexyl-1-methylethyl]amino}methyl)phenyl]pyridine-2-sulfonamide, 5-chloro-N-[2-({[(1S)-2-cyclopentyl-1-methylethyl]amino}methyl)phenyl]-2,1,3-benzoxadiazole-4-sulfonamide, N-[2-({[(1S)-2-cyclopentyl-1-methylethyl]amino}methyl)phenyl]-1-benzothiophene-2-carboxamide, N-(2-{[(3-cyclohexyl-2-fluoropropyl)amino]methyl}phenyl)thiophene-2-sulfonamide, N-[2-({[(1S)-2-cyclopentyl-1-methylethyl]amino}methyl)phenyl]-2,1,3-benzothiadiazole-5-sulfonamide, N-[4-({2-({[2-cyclohexyl-1-methylethyl]amino}methyl)phenyl]amino}sulfonyl)-3-methoxyphenyl]thiophene-2-sulfonamide, N-[4-({2-({[2-cyclohexyl-1-methylethyl]amino}methyl)phenyl]amino}sulfonyl)-3-hydroxyphenyl]thiophene-2-sulfonamide, N-[4-({2-({[2-cyclohexyl-1-methylethyl]amino}methyl)phenyl]amino}sulfonyl)-3-hydroxyphenyl]acetamide, N-[2-({[2-cyclohexyl-1-methylethyl]amino}methyl)phenyl]-3-fluoro-4-(2-oxo-1,3-oxazolidin-3-yl)benzenesulfonamide, N-[2-({[(1S)-2-cyclopentyl-1-methylethyl]amino}methyl)phenyl]-3-fluoro-4-(2-oxo-1,3-oxazolidin-3-yl)benzenesulfonamide, N-[2-({[2-cyclohexyl-1-methylethyl]amino}methyl)phenyl]-3-fluoro-4-(1H-1,2,3-triazol-1-yl)benzenesulfonamide, N-[2-({[(1S)-2-cyclopentyl-1-methylethyl]amino}methyl)phenyl]-3-fluoro-4-(1H-1,2,3-triazol-1-yl)benzenesulfonamide, N-[2-({[2-cyclohexyl-1-methylethyl]amino}methyl)phenyl]-1-(trifluoroacetyl)indoline-5-sulfonamide, N-[2-({[2-cyclohexyl-1-methylethyl]amino}methyl)phenyl]indoline-5-sulfonamide, N-[2-({[2-cyclohexyl-1-methylethyl]amino}methyl)phenyl]-4-(1,2,4-oxadiazol-3-yl)benzenesulfonamide, N-[2-({[(1S)-2-cyclopentyl-1-methylethyl]amino}methyl)phenyl]-4-(1,2,4-oxadiazol-3-yl)benzenesulfonamide, N-[2-({[(1S)-2-cyclopentyl-1-methylethyl]amino}methyl)phenyl]-3,4-difluorobenzene sulfonamide, N-[2-({[2-cyclohexyl-1-methylethyl]amino}methyl)pyridin-3-yl]-4-(5-methyl-1,3,4-oxadiazol-2-yl)benzenesulfonamide, N-[2-({[(1S)-2-cyclopentyl-1-methylethyl]amino}methyl)phenyl]-4-(1H-1,2,3-triazol-1-yl)benzenesulfonamide, N-[2-({[2-cyclohexyl-1-methylethyl]amino}methyl)phenyl]-3-fluoro-4-(1H-pyrazol-1-yl)benzenesulfonamide, N-[2-({[(1S)-2-cyclopentyl-1-methyl ethyl]amino}methyl)phenyl]-3-fluoro-4-(1H-pyrazol-1-yl)benzenesulfonamide, N-[2-({[2-cyclohexyl-1-methylethyl]amino}methyl)phenyl]-6-pyrrolidin-1-ylpyridine-3-sulfonamide, N-[2-({[(1S)-2-cyclopentyl-1-methylethyl]amino}methyl)phenyl]-6-pyrrolidin-1-ylpyridine-3-sulfonamide, N-[2-({[2-cyclohexyl-1-methylethyl]amino}methyl)phenyl]-6-morpholin-4-ylpyridine-3-sulfonamide, N-[2-({[(1S)-2-cyclopentyl-1-methylethyl]amino}methyl)phenyl]-6-morpholin-4-ylpyridine-3-sulfonamide, N-[2-({[2-cyclohexyl-1-methylethyl]amino}methyl)phenyl]-1-ethyl-2-oxo-1,2-dihydroquinoline-6-sulfonamide, N-[2-({[(1S)-2-cyclopentyl-1-methylethyl]amino}methyl)phenyl]-1-ethyl-2-oxo-1,2-dihydroquinoline-6-sulfonamide, N-[2-({[(1S)-2-cyclopentyl-1-methylethyl]amino}methyl)phenyl]-2-oxo-1,2-dihydroquinoline-6-sulfonamide, 6-bromo-N-[2-({[2-cyclohexyl-1-methylethyl]amino}methyl)phenyl]pyridine-3-sulfonamide, 2-amino-N-[2-({[2-cyclohexyl-1-methylethyl]amino}methyl)phenyl]pyrimidine-5-sulfonamide, 6-amino-N-[2-({[2-cyclohexyl-1-methylethyl]amino}methyl)phenyl]pyridine-3-sulfonamide, N-[2-({[2-cyclohexyl-1-methylethyl]amino}methyl)phenyl]-2-oxo-2,3-dihydro-1,3-benzoxazole-6-sulfonamide, 5-chloro-N-[2-({[2-cyclohexyl-1-methylethyl]amino}methyl)phenyl -1,3-benzothiazole-2-sulfonamide, 5-chloro-N-[2-({[(1S)-2-cyclopentyl-1-methylethyl]amino}methyl)phenyl]-1,3-benzothiazole-2-sulfonamide, N-[2-({[2-cyclohexyl-1-methylethyl]amino}methyl)phenyl]-2-(dimethylamino)-1,3-benzothiazole-6-sulfonamide, N-[6-({2-({[2-cyclohexyl-1-methylethyl]amino}methyl)phenyl]amino sulfonyl)-1,3-benzothiazol-2-yl]-L-alaninamide, N-[2-({[2-cyclohexyl-1-methylethyl]amino}methyl)phenyl]-4-oxo-3,4-dihydroquinazoline-2-sulfonamide, N-[2-({[2-cyclohexyl-1-methylethyl]amino}methyl)phenyl -2-(trifluoroacetyl)-1,2,3,4-tetrahydroisoquinoline-7-sulfonamide, N-[2-({[2-cyclohexyl-1-methylethyl]amino}methyl)phenyl]-1,2,3,4-tetrahydroisoquinoline-7 -sulfonamide, N-[2-({[2-cyclohexyl-1-methylethyl]amino}methyl)phenyl]-2-oxo-1,2-dihydroquinoline-6-sulfonamide, N-[2-({[2-cyclohexyl-1-methylethyl]amino}methyl)phenyl]-3-fluoro-4-(1H-imidazol-1-yl)benzenesulfonamide, N-[2-({[(1S)-2-cyclohexyl-1-methylethyl]amino}methyl)phenyl]-5-fluoro-3-methyl-1-benzothiophene-2-sulfonamide, N-[2-({[(1S)-2-cyclohexyl-1-methylethyl]amino}methyl)phenyl]-1-methyl-2-oxo-1,2-dihydroquinoline-6-sulfonamide, N-[2-({[(1S)-2-cyclohexyl-1-methylethyl]amino}methyl)phenyl]-1-ethyl-2-oxo-1,2-dihydroquinoline-6-sulfonamide, N-[2-({[(1S)-2-cyclohexyl-1-methylethyl]amino}methyl)phenyl]-6-(2-thienyl)pyridine-3-sulfonamide, N-[2-({[(1S)-2-cyclohexyl-1-methylethyl]amino}methyl)phenyl]-6-(2-furyl)pyridine-3-sulfonamide, N-[2-({[(1S)-2-cyclohexyl-1-methylethyl]amino}methyl)phenyl]-6-(1H-tetrazol-1-yl)pyridine-3-sulfonamide, N-[2-({[(1S)-2-cyclohexyl-1-methylethyl]amino}methyl)phenyl]-6-pyrrolidin-1-ylpyridine-3-sulfonamide, N-[2-({[(1S)-2-cyclohexyl-1-methylethyl]amino}methyl)phenyl]-3-(2-methyl-1,3-thiazol-4-yl)benzenesulfonamide, N-[2-({[(1S)-2-cyclohexyl-1-methylethyl]amino}methyl)phenyl]-5-(3,5-dimethylisoxazol-4-yl)thiophene-2-sulfonamide, N-[2-(1 [(1S)-2-cyclohexyl-1-methylethyl] amino}methyl)phenyl]-4-(5-methyl-1,3,4-oxadiazol-2-yl)benzenesulfonamide,
N-[2-(1 [(1S)-2-cyclohexyl-1-methylethyl] amino}methyl)phenyl]-4-(1,2,4-oxadiazol-3-yl)benzenesulfonamide,
N-[2-({[(1S)-2-cyclohexyl-1-methylethyl]amino}methyl)phenyl]-3-fluoro-4-(1H-pyrazol-1-yl)benzenesulfonamide,
N-(2-{[(2-cyclohexyl-1-methylethyl)amino]methyl}phenyl)-1-[(1-methyl-1H-imidazol-4-yl)sulfonyl]indoline-5-sulfonamide,
N-(2-{[(2-cyclohexyl-1-methylethyl)amino]methyl}phenyl)-1-(methylsulfonyl)indoline-5-sulfonamide,
1-acetyl-N-(2-{[(2-cyclohexyl-1-methylethy pamino]methyl}phenyl)indoline-5-sulfonamide,
N-[4-({[2-({[(1S)-2-cyclohexyl-1-methylethyl]amino}methyl)phenyl]amino}sulfonyl)phenyl]acetamide,
N-[2-({[(1S)-2-cyclohexyl-1-methylethyl]amino}methyl)phenyl]-3-fluoro-4-(2-oxo-1,3-oxazolidin-3-yl)benzenesulfonamide,
2-amino-N-(2-{[(2-cyclohexyl-1-methylethy pamino]methyl}phenyl)-1,3-benzoxazole-6-sulfonamide,
N-(2-{[(2-cyclohexyl-1-methylethyl)amino]methyl}phenyl)-1,3-benzothiazole-6-sulfonamide,
N-[2-({[(1S)-2-cyclopentyl-1-methylethyl]amino}methyl)phenyl]-1,3-benzothiazole-6-sulfonamide,
N-(4-{[(2-{[(2-cyclohexyl-1-methylethyl)amino]methyl}phenyl)amino]sulfonyl}phenyl)nonanamide,
4-amino-N-(2-{[(2-cyclohexyl-1-methylethyl)amino]methyl}phenyl)-3-hydroxybenzene sulfonamide,
N-(4-{[(2-{[(2-cyclohexyl-1-methylethy pamino]methyl}phenyl)amino]sulfonyl}-2-hydroxyphenyl)thiophene-2-sulfonamide,
N-[2-({[(1S)-2-cyclopentyl-1-methylethyl]amino}methyl)phenyl]-2-oxo-2,3-dihydro-1,3-benzoxazole-6-sulfonamide,
2-amino-N-[2-({[(1S)-2-cyclopentyl-1-methylethyl]amino}methyl)phenyl]-1,3-benzoxazole-6-sulfonamide,
N-[2-({[(1S)-2-cyclopentyl-1-methylethyl]amino}methyl)phenyl]-2-oxoindoline-6-sulfonamide,
5-chloro-N-(2-{[(2-cyclohexyl-1-methylethyl)amino]methy}phenyl)-1-benzothiophene-2-sulfonamide,
5-chloro-N-[2-({[(1S)-2-cyclopentyl-1-methylethyl]amino}methyl)phenyl]-1-benzothiophene-2-sulfonamide,
N-[2-({[(1S)-2-cyclopentyl-1-methylethyl]amino}methyl)phenyl]-5-methoxy-1-benzothiophene-2-sulfonamide,
N-[2-({[(1S)-2-cyclopentyl-1-methylethyl]amino}methyl)phenyl]-5-hydroxy-1-benzothiophene-2-sulfonamide,
N-(2-{[(2-cyclohexyl-1-methylethyl)amino]methyl}phenyl)-5-fluoro-1-benzothiophene-2-sulfonamide,
N-[2-({[(1S)-2-cyclopentyl-1-methylethyl]amino}methyl)phenyl]-5-fluoro-1-benzothiophene-2-sulfonamide,
N-(2-{[(2-cyclohexyl-1-methylethyl)amino]methyl}phenyl)-2-oxoindoline-6-sulfonamide,
5-(6-aminopyridin-3-yl)-N-({[(1S)-2-cyclohexyl-1-methylethyl]amino}methyl)phenyl]thiophene-2-sulfonamide,
5-(6-aminopyridin-3-yl)-N-[2-({[(1S)-2-cyclopentyl-1-methylethyl]amino}methyl)phenyl]thiophene-2-sulfonamide,
N-[2-({[(1S)-2-cyclopentyl-1-methylethyl]amino}methyl)phenyl]-4-(1,3-thiazol-2-yl)benzenesulfonamide,
N-[2-({[(1S)-2-cyclohexyl-1-methylethyl]amino}methyl)phenyl -4-(1,3-thiazol-2-yl)benzenesulfonamide,
2-amino-N-[2-({[(1S)-2-cyclohexyl-1-methylethyl]amino }methyl)phenyl]-1,3-benzothiazole-6-sulfonamide,
N-[2-({[(1S)-2-cyclohexyl-1-methylethyl]amino}methyl)phenyl]-1-benzothiophene-2-sulfonamide,
N-[2-({[(1S)-2-cyclohexyl-1-methylethyl]amino}methyl)phenyl]-2-oxo-2,3-dihydro-1,3-benzoxazole-6-sulfonamide,
N-[2-({[(1S)-2-cyclohexyl-1-methylethyl]amino}methyl)phenyl]-1-benzofuran-2-sulfonamide,
2-amino-N-[2-({[(1S)-2-cyclohexyl-1-methylethyl]amino}methyl)phenyl]-1,3-benzoxazole-6-sulfonamide,
N-[2-({[(1S)-2-cyclopentyl-1-methylethyl]amino}methyl)phenyl]-5-methoxy-1-benzofuran-2-sulfonamide,
N-[2-({[(1S)-2-cyclohexyl-1-methylethyl]amino}methyl)phenyl]-5-methoxy-1-benzofuran-2-sulfonamide,
N-[2-({[(1S)-2-cyclohexyl-1-methylethyl]amino}methyl)phenyl]-5-hydroxy-1-benzofuran-2-sulfonamide,
N-[2-({[(1S)-2-cyclopentyl-1-methylethyl]amino}methyl)phenyl]-5-hydroxy-1-benzofuran-2-sulfonamide,
N-[2-([(1S)-2-cyclopentyl-1-methylethyl]amino}methyl)phenyl]-2-(1H-pyrrol-1-yl)-1,3-thiazole-5-sulfonamide,
N-[2-({[(1S)-2-cyclohexyl-1-methylethyl]amino}methyl)phenyl]-2-oxo-1,2,3,4-tetrahydroquinoline-6-sulfonamide,
N-[2-({[(1S)-2-cyclopentyl-1-methylethyl]amino}methyl)phenyl]-2-oxo-1,2,3,4-tetrahydroquinoline-6-sulfonamide,
N-[2-([(1S)-2-cyclohexyl-1-methylethyl ]amino}methyl)phenyl]1-3,5-difluoro-4-(1H-tetrazol-1-yl)benzenesulfonamide,
N-[2-([(1S)-2-cyclopentyl-1-methylethyl]amino}methyl)phenyl]-3,5-difluoro-4-(1H-tetrazol-1-yl)benzenesulfonamide,
2-amino-N-[2-({[(1S)-2-cyclohexyl-1-methylethyl]amino }methyl)phenyl -1,3-thiazole-5-sulfonamide,
N-[2-({[(1S)-2-cyclohexyl-1-methylethyl]amino}methyl)phenyl]-6-(1,2,3-thiadiazol-4-yl)pyridine-3-sulfonamide,
N-[2-({[(1S)-2-cyclopentyl-1-methylethyl]amino}methyl)phenyl]-6-(1,2,3-thiadiazol-4-yl)pyridine-3-sulfonamide,
N-(2-{[(2-cyclohexyl-1-methylethyl)amino]methyl}phenyl)-3-oxo-3,4-dihydro-2H-1,4-benzoxazine-7-sulfonamide,
N-[2-({[(1S)-2-cyclohexyl-1-methylethyl]amino}methyl)phenyl]-2-hydroxy-1,3-benzothiazole-6-sulfonamide,
N-[2-({[(1S)-2-cyclopentyl-1-methylethyl]amino}methyl)phenyl]-2-hydroxy-1,3-benzothiazole-6-sulfonamide,
N-[2-({[(1S)-2-cyclohexyl-1-methylethyl]amino}methyl)phenyl]-3-oxo-3,4-dihydro-2H-1,4-benzothiazine-6-sulfonamide, N-[2-({[(1S)-2-cyclopentyl-1-methylethyl]
amino}methyl)phenyl]-3-oxo-3,4-dihydro-2H-1,4-
benzothiazine-6-sulfonamide,
N-(2-{[(2-cyclohexyl-1-methylethyl)amino]
methyl}phenyl)-2-mercapto-1,3-benzoxazole-6-sulfonamide,
N-[2-({[(1S)-2-cyclohexyl-1-methylethyl]amino}methyl)
phenyl]benzene-1,4-disulfonamide,
N-[2-({[(1S)-2-cyclopentyl-1-methylethyl]
amino}methyl)phenyl]benzene-1,4-disulfonamide,
N-[2-({[(1S)-2-cyclopentyl-1-methylethyl]
amino}methyl)phenyl]-N-pyrimidin-2-ylbenzene-1,4-
disulfonamide,
N-[2-({[(1S)-2-cyclopentyl-1-methylethyl]
amino}methyl)phenyl]-6-methoxypyridine-3-sulfonamide,
N-[2-({[(1S)-2-cyclohexyl-1-methylethyl]amino}methyl)
phenyl]-6-methoxypyridine-3-sulfonamide,
N-[5-([2-({[(1S)-2-cyclohexyl-1-methylethyl]
amino}methyl)phenyl]amino}sulfonyl)-1,3,4-thiadiazol-2-yl]acetamide,
5-amino-N-[2-({[(1S)-2-cyclohexyl-1-methylethyl]
amino}methyl)phenyl]-1,3,4-thiadiazole-2-sulfonamide,
5-amino-N-[2-({[(1 5)-2-cyclopentyl-1-methylethyl]
amino}methyl)phenyl]-1,3,4-thiadiazole-2-sulfonamide,
N-[2-({[(1S)-2-cyclohexyl-1-methylethyl]amino}methyl)
phenyl]-5-fluoro-1-benzothiophene-2-sulfonamide,
5-chloro-N-[2-({[(1S)-2-cyclohexyl-1-methylethyl]
amino}methyl)phenyl]-1-benzofuran-2-sulfonamide,
N-[2-({[(1S)-2-cyclohexyl-1-methylethyl]amino}methyl)
phenyl]-1-benzothiophene-2-sulfonamide,
N-[5-({[2-({[(1S)-2-cyclohexyl-1-methylethyl]
amino}methyl)phenyl]amino}sulfonyl)-1,3-thiazol-2-yl]acetamide,
N-[2-({[(1S)-2-cyclohexyl-1-methylethyl]amino}methyl)
phenyl]-2-oxo-2,3-dihydro -1,3-benzoxazole-6-sulfonamide,
N-[2-({[(1S)-2-cyclopentyl-1-methylethyl]
amino}methyl)phenyl]-2,4-dioxo-1,2,3,4-tetrahydroquinazoline-6-sulfonamide,
N-[2-({[(1S)-2-cyclohexyl-1-methylethyl]amino}methyl)
phenyl-2,4-dioxo-1,2,3,4-tetrahydroquinazoline-6-sulfonamide,
N-[2-({[(1S)-2-cyclopentyl-1-methylethyl]
amino}methyl)phenyl]-2,3-dihydroxyquinoxaline-6-sulfonamide,
N-[2-({[(1S)-2-cyclohexyl-1-methylethyl]amino}methyl)
phenyl]-2,3-dihydroxyquinoxaline-6-sulfonamide,
N-[2-({[(1S)-2-cyclopentyl-1-methylethyl]
amino}methyl)phenyl]-2-oxo-1,4-dihydro-2H-3,1-
benzoxazine-6-sulfonamide,
N-[2-({[(1S)-2-cyclohexyl-1-methylethyl]amino}methyl)
phenyl]-2-oxo-1,4-dihydro-2H-3,1-benzoxazine-6-sulfonamide,
N-[2-({[(1S)-2-cyclopentyl-1-methylethyl]
amino}methyl)phenyl]-2-mercapto-1,3-benzoxazole-6-sulfonamide,
N-[2-({[(1S)-2-cyclohexyl-1-methylethyl]amino}methyl)
phenyl -2-mercapto-1,3-benzoxazole-6-sulfonamide,
N-[2-({[(1S)-2-cyclopentyl-1-methylethyl]
amino}methyl)phenyl]-2-oxo-2,3-dihydro-1,3-benzoxazole-5-sulfonamide,
N-[2-({[(1S)-2-cyclohexyl-1-methylethyl]amino}methyl)
phenyl]-2-oxo-2,3-dihydro-1,3-benzoxazole-5-sulfonamide,
N-(2-{[(2-cyclohexyl-1,1 -dimethylethyl)amino]
methyl}phenyl)-1-benzothiophene-2-sulfonamide,
5-chloro-N-[2-({[(1S)-2-cyclopentyl-1-methylethyl]
amino}methyl)phenyl]-1-benzofuran-2-sulfonamide,
5-({[2-({[(1S)-2-cyclopentyl-1-methylethyl]
amino}methyl)phenyl]amino}sulfonyl)-2-methyl-3-furoic acid,
5-({[2-({[(1S)-2-cyclohexyl-1-methylethyl]
amino}methyl)phenyl]amino}sulfonyl)-2-methyl-3-furoic acid,
methyl 5-({[2-({[(1 5)-2-cyclohexyl-1-methylethyl]
amino}methyl)phenyl]amino}sulfonyl)-2-methyl-3-furoate,
methyl 5-({[2-({[(1S)-2-cyclopentyl-1-methylethyl]
amino}methyl)phenyl]amino}sulfonyl)-2-methyl-3-furoate,
N-[2-({[(1S)-2-cyclopentyl-1-methylethyl]
amino}methyl)phenyl]-4-(1H-pyrrol-1-ylsulfonyl)benzenesulfonamide,
methyl 5-({[4-({[2-({[(1S)-2-cyclopentyl-1-methylethyl]
amino}methyl)phenyl]amino}sulfonyl)phenyl]
amino}sulfonyl)-2-methyl-3-furoate,
5-({[4-({[2-({[(1S)-2-cyclopentyl-1-methylethyl]
amino}methyl)phenyl]amino}sulfonyl)phenyl]
amino}sulfonyl)-2-methyl-3-furoic acid,
5-({[4-({[2-({[(1S)-2-cyclopentyl-1-methylethyl]
amino}methyl)phenyl]amino}sulfonyl)phenyl]
amino}sulfonyl)-N,N,2-trimethyl-3-furamide,
5-({[4-({[2-({[(1S)-2-cyclopentyl-1-methylethyl]
amino}methyl)phenyl]amino}sulfonyl)phenyl]
amino}sulfonyl)-2-methyl-3-furamide,
1-(cyanomethyl)-N[2-({[(1S)-2-cyclopentyl-1-methylethyl]amino}methyl)phenyl]-2-oxo-1,2-dihydroquinoline-6-sulfonamide,
4-amino-N-[2-({[(1S)-2-cyclopentyl-1-methylethyl]
amino}methyl)phenyl]benzenesulfonamide,
N-[4-({[2-({[(1S)-2-cyclopentyl-1-methylethyl]
amino}methyl)phenyl]amino}sulfonyl)phenyl]-1-methyl-1H-imidazole-2-sulfonamide,
N-[2-({[(1S)-2-cyclopentyl-1-methylethyl]
amino}methyl)phenyl]-1-methyl-1H-imidazole-2-sulfonamide,
N-[2-({[(1S)-2-cyclopentyl-1-methylethyl]
amino}methyl)phenyl]-4-oxochromane-6-sulfonamide,
N-[2-({[(1S)-2-cyclohexyl-1-methylethyl]amino}methyl)
phenyl]-4-oxochromane-6-sulfonamide, and
pharmaceutically acceptable salts or mixtures thereof.

3. A pharmaceutical composition comprising therapeutically effective amounts of one or more compounds of claim 1 together with pharmaceutically acceptable carrier, excipients, diluents or mixture thereof.

4. A method for treating a subject suffering from a condition caused by or contributed to by bacterial infection comprising administering to the subject therapeutically effective amounts of one or more compounds of claim 1.

5. The method according to claim 4 wherein bacterial infection arises from contact with an organism selected from *Staphylococci, Enterococci, Streptococci, Haemophilus, Propionibacterium, Moraxalla, Escherichia, Chlamydia, Rickettsiae, Mycoplasm, Legionella, Mycobacterium, Helicobacter, Clostridium, Bacteroides, Corynebacterium, Bacillus* or *Enterobactericeae*.

6. The method according to claim 4 wherein the condition is selected from community acquired pneumonia, upper and lower respiratory tract infections, skin and soft tissue infections, hospital acquired lung infections or bone and joint infections, mastitis, catheter infection, foreign body, acne vulgaris, prosthesis infections and peptic ulcer disease.

* * * * *